US012383292B2

(12) United States Patent
Lee

(10) Patent No.: US 12,383,292 B2
(45) Date of Patent: *Aug. 12, 2025

(54) SURGICAL INSTRUMENT

(71) Applicant: LIVSMED INC., Seongnam-si (KR)

(72) Inventor: Jung Joo Lee, Seoul (KR)

(73) Assignee: LIVSMED INC., Seongnam-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/954,512

(22) Filed: Nov. 20, 2024

(65) Prior Publication Data

US 2025/0072923 A1  Mar. 6, 2025

Related U.S. Application Data

(60) Continuation of application No. 18/215,955, filed on Jun. 29, 2023, now Pat. No. 12,171,450, which is a
(Continued)

(30) Foreign Application Priority Data

Nov. 23, 2011  (KR) .......................... 10-2011-0123071
Nov. 23, 2011  (KR) .......................... 10-2011-0123074
Nov. 23, 2011  (KR) .......................... 10-2011-0123075

(51) Int. Cl.
A61B 17/29    (2006.01)
A61B 34/00    (2016.01)
A61B 34/30    (2016.01)

(52) U.S. Cl.
CPC .......... *A61B 17/29* (2013.01); *A61B 17/2909* (2013.01); *A61B 2017/2902* (2013.01);
(Continued)

(58) Field of Classification Search
CPC ............. A61B 34/30; A61B 2034/301; A61B 2034/305; A61B 34/70; A61B 34/71; A61B 2034/715; A61B 34/74; A61B 17/28; A61B 17/2804; A61B 17/282; A61B 17/2816; A61B 17/2812; A61B 17/2841; A61B 17/29; A61B 2017/2901; A61B 2017/2902; A61B 32/71; A61B 2043/715; A61B 17/2909; A61B 2017/291; A61B 2017/2918; A61B 2017/2924; A61B 2017/2925; A61B 1/0052; B25B 23/10; B25B 23/101; A61M 25/0136
See application file for complete search history.

(56) References Cited

U.S. PATENT DOCUMENTS 3,273,408 A    9/1966  Nagel et al.
3,529,481 A    9/1970  Budzyn
(Continued)

FOREIGN PATENT DOCUMENTS

CN    102131469 A    7/2011
JP    S59102587 A    6/1984
(Continued)

*Primary Examiner* — Melanie R Tyson
*Assistant Examiner* — Mikail A Mannan
(74) *Attorney, Agent, or Firm* — Bridgeway IP Law Group, PLLC; Sang Ho Lee; Hyun Woo Shin

(57) ABSTRACT

Provided are surgical instruments, and more particularly, surgical instruments that may be manually operated to perform laparoscopic operations or various surgical operations.

15 Claims, 43 Drawing Sheets

Related U.S. Application Data continuation of application No. 16/999,520, filed on Aug. 21, 2020, now Pat. No. 11,723,736, which is a division of application No. 16/722,676, filed on Dec. 20, 2019, now Pat. No. 11,628,027, which is a continuation of application No. 14/360,586, filed as application No. PCT/KR2012/009364 on Nov. 8, 2012, now Pat. No. 10,695,141.

(52) U.S. Cl.
CPC ............ *A61B 2017/2911* (2013.01); *A61B 2017/2927* (2013.01); *A61B 2034/305* (2016.02); *A61B 34/70* (2016.02); *A61B 34/71* (2016.02); *F04C 2270/0421* (2013.01)

(56) References Cited

U.S. PATENT DOCUMENTS

| | | |
|---|---|---|
| 5,478,347 A | 12/1995 | Aranyi |
| 5,539,987 A | 7/1996 | Zennyoji |
| 5,792,165 A | 8/1998 | Klieman et al. |
| 5,797,900 A | 8/1998 | Madhani et al. |
| 5,807,377 A | 9/1998 | Madhani et al. |
| 5,908,436 A | 6/1999 | Cuschieri et al. |
| 5,954,731 A | 9/1999 | Yoon |
| 6,191,017 B1 | 2/2001 | Chittipeddi et al. |
| 6,394,998 B1 * | 5/2002 | Wallace ............ A61B 34/35 901/29 |
| 6,432,112 B2 | 8/2002 | Brock et al. |
| 6,554,844 B2 | 4/2003 | Lee et al. |
| 6,676,684 B1 | 1/2004 | Morley et al. |
| 6,692,485 B1 | 2/2004 | Brock et al. |
| 6,889,116 B2 | 5/2005 | Jinno |
| 6,936,042 B2 | 8/2005 | Wallace et al. |
| 6,969,385 B2 | 11/2005 | Moreyra |
| 6,994,716 B2 | 2/2006 | Jinno et al. |
| 7,101,363 B2 | 9/2006 | Nishizawa et al. |
| 7,338,513 B2 | 3/2008 | Lee et al. |
| 7,364,582 B2 | 4/2008 | Lee |
| 7,540,867 B2 | 6/2009 | Jinno et al. |
| 7,648,519 B2 | 1/2010 | Lee et al. |
| 7,686,826 B2 | 3/2010 | Lee et al. |
| 7,914,522 B2 | 3/2011 | Morley et al. |
| 7,942,895 B2 | 5/2011 | Jinno et al. |
| 8,100,824 B2 | 1/2012 | Rho et al. |
| 8,465,475 B2 | 6/2013 | Isbell, Jr. |
| 8,801,731 B2 | 8/2014 | Jeong |
| 8,821,480 B2 | 9/2014 | Burbank |
| 9,033,998 B1 | 5/2015 | Schaible et al. |
| 9,179,927 B2 | 11/2015 | Stefanchik et al. |
| 9,695,916 B2 | 7/2017 | Lee |
| 9,737,302 B2 | 8/2017 | Shelton, IV et al. |
| 10,105,128 B2 | 10/2018 | Cooper et al. |
| 10,166,082 B1 | 1/2019 | Hariri et al. |
| 10,405,936 B2 | 9/2019 | Awtar et al. |
| 2003/0036748 A1 | 2/2003 | Cooper et al. |
| 2004/0199147 A1 | 10/2004 | Nishizawa et al. |
| 2005/0096694 A1 | 5/2005 | Lee |
| 2006/0020287 A1 | 1/2006 | Lee |
| 2006/0025811 A1 | 2/2006 | Shelton, IV |
| 2006/0190034 A1 | 8/2006 | Nishizawa et al. |
| 2006/0219065 A1 | 10/2006 | Jinno et al. |
| 2007/0208375 A1 | 9/2007 | Nishizawa et al. |
| 2007/0265502 A1 | 11/2007 | Minosawa et al. |
| 2008/0000317 A1 | 1/2008 | Patton et al. |
| 2008/0039255 A1 | 2/2008 | Jinno et al. |
| 2008/0065116 A1 | 3/2008 | Lee et al. |
| 2008/0245175 A1 | 10/2008 | Jinno et al. |
| 2009/0112230 A1 | 4/2009 | Jinno |
| 2010/0198253 A1 | 8/2010 | Jinno et al. |
| 2010/0249818 A1 | 9/2010 | Jinno et al. |
| 2010/0286480 A1 | 11/2010 | Peine et al. |
| 2011/0106145 A1 | 5/2011 | Jeong |
| 2011/0112517 A1 | 5/2011 | Willliam et al. |
| 2012/0004648 A1 | 1/2012 | Choi et al. |
| 2012/0143173 A1 | 6/2012 | Steege et al. |
| 2012/0330287 A1 | 12/2012 | Yim |
| 2013/0012958 A1 | 1/2013 | Marczyk et al. |
| 2013/0012959 A1 | 1/2013 | Jinno |
| 2013/0085494 A1 | 4/2013 | Weisenburgh, II et al. |
| 2013/0144274 A1 | 6/2013 | Stefanchik et al. |
| 2014/0114293 A1 | 4/2014 | Jeong et al. |
| 2014/0194893 A1 | 7/2014 | Jeong et al. |
| 2014/0318288 A1 | 10/2014 | Lee |
| 2014/0350570 A1 | 11/2014 | Lee |
| 2015/0032125 A1 | 1/2015 | Jeong et al. |
| 2015/0150635 A1 | 6/2015 | Kilroy et al. |
| 2016/0008068 A1 | 1/2016 | Hyodo et al. |
| 2016/0256232 A1 | 9/2016 | Awtar et al. |
| 2017/0042560 A1 | 2/2017 | Lee et al. |
| 2018/0110577 A1 | 4/2018 | Lee et al. |
| 2018/0228506 A1 | 8/2018 | Lee et al. |
| 2019/0336230 A1 | 11/2019 | Awtar et al. |

FOREIGN PATENT DOCUMENTS

| | | |
|---|---|---|
| JP | 64-49739 A | 2/1989 |
| JP | H06-311984 A | 11/1994 |
| JP | H08173442 A | 7/1996 |
| JP | 2002-503976 A | 2/2002 |
| JP | 2004-122286 A | 4/2004 |
| JP | 2006-061364 A | 3/2006 |
| JP | 2006-062019 A | 3/2006 |
| JP | 2006-116194 A | 5/2006 |
| JP | 2008-521485 A | 6/2008 |
| JP | 2010-220786 A | 10/2010 |
| JP | 4701433 B2 | 6/2011 |
| JP | 2011-200593 A | 10/2011 |
| JP | 2011-200666 A | 10/2011 |
| KR | 10-2006-0093060 A | 8/2006 |
| KR | 10-0695471 B1 | 3/2007 |
| KR | 10-2009-0119366 A | 11/2009 |
| KR | 10-2009-0124828 A | 12/2009 |
| KR | 10-0956760 B1 | 5/2010 |
| KR | 10-2010-0099818 A | 9/2010 |
| KR | 10-2010-0118573 A | 11/2010 |
| KR | 10-2011-0005671 A | 1/2011 |
| KR | 10-2011-0014534 A | 2/2011 |
| KR | 10-2011-0028613 A | 3/2011 |
| KR | 101064825 B1 | 9/2011 |
| KR | 10-1075294 B1 | 10/2011 |
| KR | 10-2012-0003091 A | 1/2012 |
| KR | 10-2013-0023311 A | 3/2013 |
| KR | 10-2013-0023755 A | 3/2013 |
| KR | 10-2013-0057250 A | 5/2013 |
| KR | 10-1301783 B1 | 8/2013 |
| KR | 10-1364970 B1 | 2/2014 |
| KR | 10-2014-0113893 A | 9/2014 |
| WO | 2009-100366 A2 | 8/2009 |
| WO | 2009/158115 A1 | 12/2009 |
| WO | 2010/030114 A2 | 3/2010 |
| WO | 2011/115311 A1 | 9/2011 |
| WO | 2012074564 A1 | 6/2012 |
| WO | 2013/077571 A1 | 11/2012 |
| WO | 2013082220 A2 | 6/2013 |
| WO | 2014-123390 A1 | 8/2014 |
| WO | 2014/156219 A1 | 10/2014 |

* cited by examiner

SURGICAL INSTRUMENT

CROSS-REFERENCE TO RELATED APPLICATIONS

This application is a continuation application of U.S. application Ser. No. 18/215,955, filed on Jun. 29, 2023, which is a continuation application of U.S. application Ser. No. 16/999,520, filed on Aug. 21, 2020 (issued as U.S. Pat. No. 11,723,736 on Aug. 15, 2023), which is a divisional application of U.S. application Ser. No. 16/722,676 filed on Dec. 20, 2019 (issued as U.S. Pat. No. 11,628,027 on Apr. 18, 2023), which is a continuation application of U.S. application Ser. No. 14/360,586 filed on May 23, 2014 (issued as U.S. Pat. No. 10,695,141 on Jun. 30, 2020), which in turn is a national-stage application under 35 USC § 371 of international application No. PCT/KR2012/009364 filed on Nov. 8, 2012, and claims priority under 35 U.S.C. § 119 (a) to Korean Patent Application Nos. 10-2011-0123071, 10-2011-0123074, and 10-2011-0123075 filed on Nov. 23, 2011, the contents of which are hereby incorporated by reference in their entirety.

TECHNICAL FIELD

The present invention relates to surgical instruments, and more particularly, to surgical instruments that may be manually operated to perform laparoscopic operations or various surgical operations.

BACKGROUND ART

A surgical operation is an operation for curing a disease by cutting, incising, and processing skin, membranes, or other tissues by using medical instruments. However, open surgery, which cuts and opens the skin of a surgical region and cures, shapes, or removes an organ therein, may cause bleeding, side effects, pain, scars, or the like. Therefore, a surgical operation, which is performed by forming a hole through the skin and inserting a medical instrument, for example, a laparoscope, a surgical instrument, or a surgical microscope thereinto, or a robotic surgical operation have recently become popular alternatives.

The surgical instrument is an instrument for performing, by a surgeon, an operation on a surgical region by operating an end tool, which is installed at one end of a shaft inserted into a hole formed through the skin, by using an operator or by using a robotic arm. The end tool provided in the surgical instrument performs a rotating operation, a gripping operation, a cutting operation, or the like through a predetermined structure.

However, since a conventional surgical instrument uses an unbendable end tool, it is not suitable for accessing a surgical region and performing various surgical operations. In order to solve this problem, a surgical instrument having a bendable end tool has been developed.

However, an operation of an operator for bending the end tool to perform a surgical operation is not intuitively identical to an actual bending operation of the end tool for performing the surgical operation. Therefore, for surgical operators, it is difficult to perform an intuitive operation and it takes a long time to learn how to use the surgical instrument.

Information disclosed in this Background section was already known to the inventors of the present invention before achieving the present invention or is technical information acquired in the process of achieving the present invention. Therefore, it may contain information that does not form the prior art that is already known in this country to a person of ordinary skill in the art.

DETAILED DESCRIPTION OF THE INVENTION

Technical Problem

The present invention provides a surgical instrument that is configured to intuitively match an actual operation of bending an end tool or performing a surgical operation with a corresponding operation of an operator. More particularly, to this end, the present invention provides an end tool having various degrees of freedom, an operator configured to intuitively control an operation of the end tool, and an operating force transmitter configured to transmit an operating force of the operator so that the end tool may operate in accordance with an operation of the operator.

Technical Solution

According to an aspect of the present invention, there is provided a surgical instrument including: an end tool formed to rotate in two or more directions; an operator controlling an operation of the end tool; an operating force transmitter including one or more wires and one or more pulleys transmitting an operation of the operator to the end tool; and a connector having one end portion coupled to the end tool and the other end portion coupled to the operator to connect the operator and the end tool, wherein at least a portion of the operator is formed to extend toward the end tool, and when the operator is rotated in the two or more directions, the end tool rotates in substantially the same direction as an operation direction of the operator.

According to another aspect of the present invention, there is provided an end tool of a surgical instrument, including: a first jaw and a second jaw operating independently of each other; and an end tool control member including: a J11 pulley coupled with the first jaw and formed to rotate around a first axis; a J12 pulley and a J14 pulley formed to rotate around an axis making a predetermined angle with the first axis and formed to face each other; a J13 pulley and a J15 pulley formed to rotate around an axis making a predetermined angle with the first axis and formed to face each other; a J21 pulley coupled with the second jaw and formed to face the J11 pulley; a J22 pulley and a J24 pulley formed to rotate around an axis making a predetermined angle with the first axis and formed to face each other; and a J23 pulley and a J25 pulley formed to rotate around an axis making a predetermined angle with the first axis and formed to face each other, wherein at least a portion of a first jaw operating wire sequentially contacts the J13 pulley, the J12 pulley, the J11 pulley, the J14 pulley, and the J15 pulley to rotate the J11 pulley and the J15 pulley, and at least a portion of a second jaw operating wire sequentially contacts the J23 pulley, the J22 pulley, the J21 pulley, the J24 pulley, and the J25 pulley to rotate the J21 pulley and the J25 pulley.

According to another aspect of the present invention, there is provided a surgical instrument including: an end tool including a first jaw and a second jaw operating independently of each other; an operator controlling operations of the first and second jaws of the end tool; an operating force transmitter including a first jaw operating wire connected with the operator to transmit a rotation of the operator to the first jaw and a second jaw operating wire connected with the operator to transmit a rotation of the operator to the second jaw; and a connector having one end portion coupled to the end tool and the other end portion coupled to the operator to connect the operator and the end tool, wherein at least a portion of the operator is formed to extend toward the end tool, and an operation direction of the operator and an operation direction of the end tool are intuitively identical to each other.

According to another aspect of the present invention, there is provided a surgical instrument including: an end tool including a first jaw and a second jaw operating independently of each other; an operator controlling operations of the first and second jaws of the end tool; an operating force transmitter including a pitch wire connected with the operator to transmit a pitch motion of the operator to the end tool, a yaw wire connected with the operator to transmit a yaw motion of the operator to the end tool, and an actuation wire connected with the operator to transmit an actuation motion of the operator to the end tool; and a connector having one end portion coupled to the end tool and the other end portion coupled to the operator to connect the operator and the end tool, wherein at least a portion of the operator is formed to extend toward the end tool, and an operation direction of the operator and an operation direction of the end tool are intuitively identical to each other.

According to another aspect of the present invention, there is provided a surgical instrument including: an end tool including a first jaw and a second jaw operating independently of each other; an operator controlling operations of the first and second jaws of the end tool; an operating force transmitter including a pitch wire connected with the operator to transmit a pitch motion of the operator to the end tool, a first jaw operating wire connected with the operator to transmit a rotation of the operator to the first jaw, and a second jaw operating wire connected with the operator to transmit a rotation of the operator to the second jaw; and a connector having one end portion coupled to the end tool and the other end portion coupled to the operator to connect the operator and the end tool, wherein at least a portion of the operator is formed to extend toward the end tool, and an operation direction of the operator and an operation direction of the end tool are intuitively identical to each other.

Advantageous Effects

According to the present invention, since an operation direction of the operator by a surgical operator and an operation direction of the end tool are intuitively identical to each other, the convenience of the surgical operator may be improved, and the accuracy, reliability, and the quickness of a surgical operation may be improved.

BEST MODE

Figure 1:
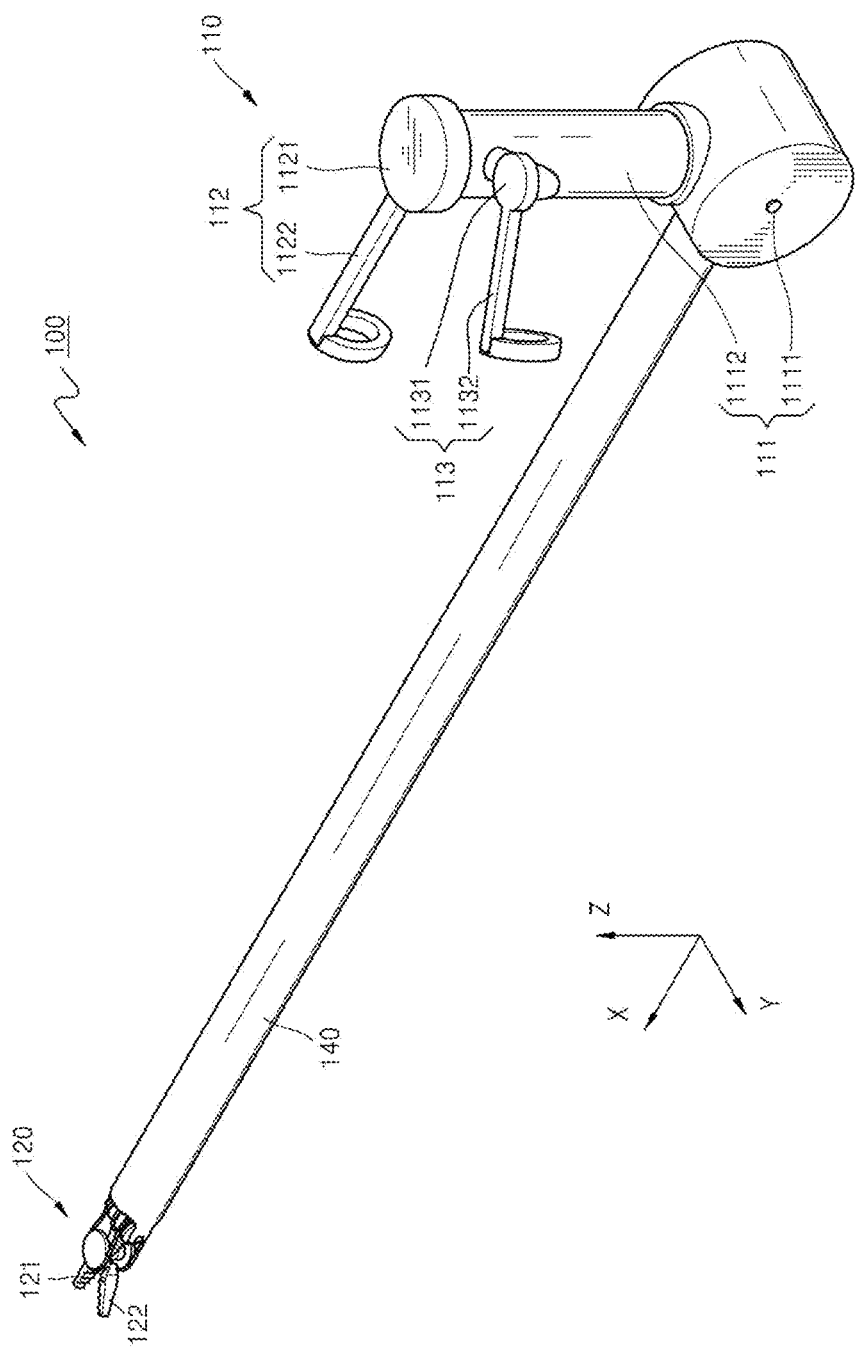
FIG. 1 is a view illustrating a surgical instrument according to a first embodiment of the present invention.

The present invention may include various embodiments and modifications, and exemplary embodiments thereof are illustrated in the drawings and will be described herein in detail. However, it will be understood that the present invention is not limited to the exemplary embodiments and includes all modifications, equivalents and substitutions falling within the spirit and scope of the present invention. In the following description, detailed descriptions of well-known functions or configurations will be omitted since they would unnecessarily obscure the subject matters of the present invention.

Although terms such as "first" and "second" may be used herein to describe various elements or components, these elements or components should not be limited by these terms. These terms are only used to distinguish one element or component from another element or component.

The terminology used herein is for the purpose of describing particular embodiments only and is not intended to be limiting of the inventive concept. As used herein, the singular forms "a", "an", and "the" are intended to include the plural forms as well, unless the context clearly indicates otherwise. It will be understood that terms such as "comprise", "include", and "have", when used herein, specify the presence of stated features, integers, steps, operations, elements, components, or combinations thereof, but do not preclude the presence or addition of one or more other features, integers, steps, operations, elements, components, or combinations thereof.

Hereinafter, embodiments of the present invention will be described in detail with reference to the accompanying drawings. In the following description, like reference numerals denote like elements, and redundant descriptions thereof will be omitted.

Also, it will be understood that various embodiments of the present invention may be interpreted or implemented in combination, and technical features of each embodiment may be interpreted or implemented in combination with technical features of other embodiments.

<First Embodiment of Surgical Instrument>
(E3+H1+D3)

Figure 2:
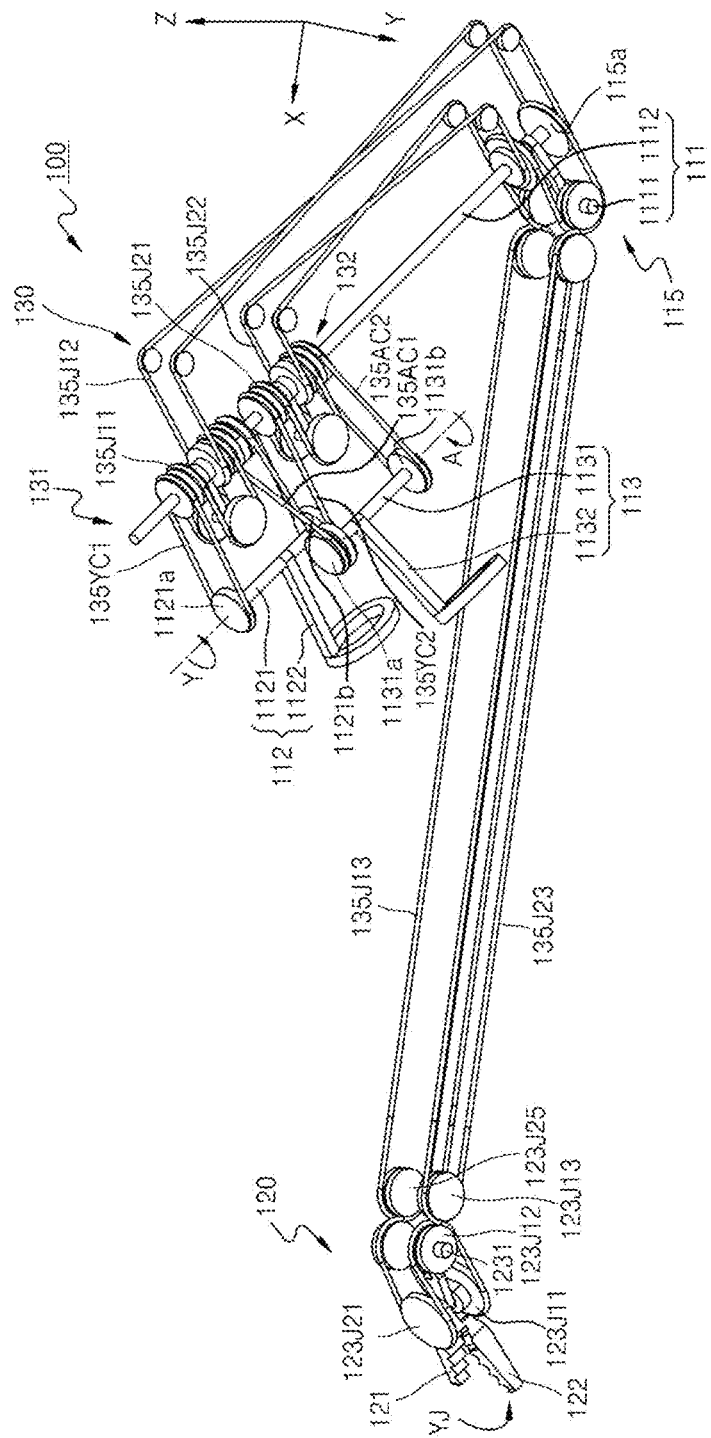
FIG. 2 is a detailed internal view of the surgical instrument of FIG. 1.

FIG. 1 is a view illustrating a surgical instrument 100 according to a first embodiment of the present invention, and FIG. 2 is a detailed internal view of the surgical instrument 100 of FIG. 1.

Referring to FIGS. 1 and 2, the surgical instrument 100 according to a first embodiment of the present invention includes an operator 110, an end tool 120, an operating force transmitter 130, and a connector 140. Herein, the connector 140 may be formed to have a shape of a hollow shaft, so that one or more wires (which will be described later) may be accommodated therein. The operator 110 may be coupled to one end portion of the connector 140, and the end tool 120 may be coupled to the other end portion of the connector 140, so that the connector 140 may connect the operator 110 and the end tool 120.

In detail, the operator 110 is formed at one end portion of the connector 140 and is provided as an interface having, for example, a tweezers shape, a stick shape, or a lever shape, which may be directly operated by a surgical operator. When a surgical operator operates the operator 110, the end tool 120, which is connected to the interface and is inserted into the body of a surgical patient, performs an operation, thereby performing a surgical operation. Although FIG. 1 illustrates that the operator 110 is formed to have a tweezers shape, the present invention is not limited thereto, and the operator 110 may have various shapes that may be connected with the end tool 120 to operate the end tool 120.

The end tool 120 is formed at the other end portion of the connector 140 and is inserted into a surgical region to perform a necessary surgical operation. As an example of the end tool 120, a pair of jaws, namely, first and second jaws 121 and 122, may be used to perform a grip operation, as illustrated in FIG. 1. However, the present invention is not limited thereto, and various surgical devices may be used as the end tool 120. For example, a one-armed cautery may be used as the end tool 120. The end tool 120 is connected with the operator 110 by the operating force transmitter 130 to receive an operating force of the operator 110 through the operating force transmitter 130, thereby performing a necessary surgical operation such as a grip, cutting, or suturing. Herein, the end tool 120 of the surgical instrument 100 according to the first embodiment of the present invention is formed to rotate in two or more directions. For example, the end tool 120 may be formed to perform a pitch motion around a Y axis of FIG. 1 and also perform a yaw motion and an actuation motion around a Z axis of FIG. 1. This will be described later in detail.

The operating force transmitter 130 connects the operator 110 and the end tool 120 to transmit an operating force of the operator 110 to the end tool 120 and may include a plurality of wires and pulleys.

Hereinafter, the operator 110, the end tool 120, and the operating force transmitter 130 of the surgical instrument 100 of FIG. 1 will be described in more detail.

(Operator)

Figure 3:
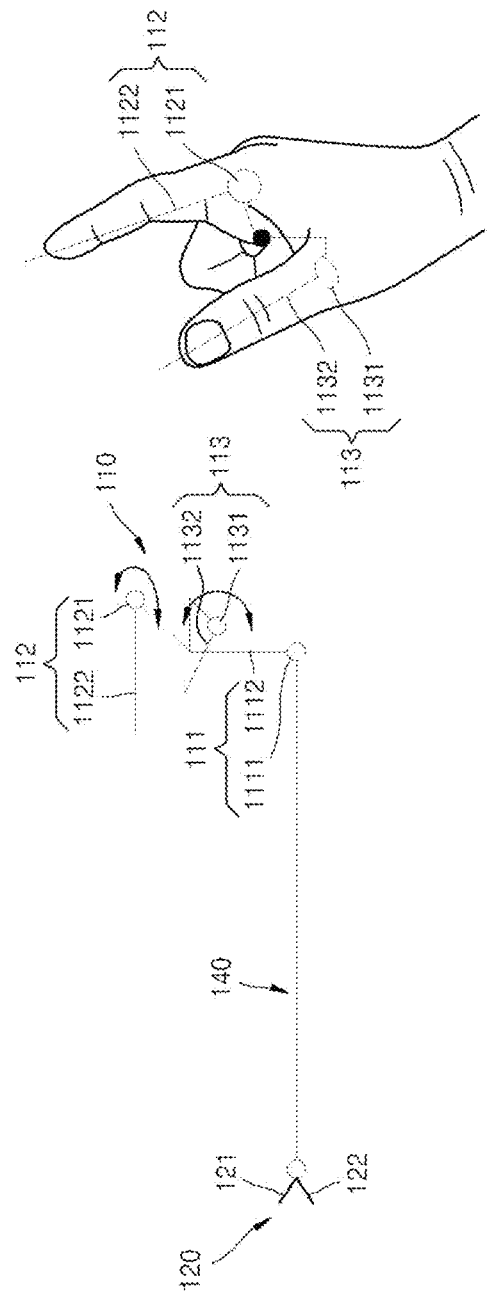
FIG. 3 is a schematic view of an operator of the surgical instrument of FIG. 2.

FIG. 3 is a schematic view of the operator 110 of the surgical instrument 100 of FIG. 2. Referring to FIGS. 1, 2, and 3, the operator 110 of the surgical instrument 100 according to the first embodiment of the present invention includes a pitch operator 111 controlling a pitch motion of the end tool 120, a yaw operator 112 controlling a yaw motion of the end tool 120, and an actuation operator 113 controlling an actuation motion of the end tool 120.

A pitch operation, a yaw operation, and an actuation operation used in the present invention are summarized as follows:

First, the pitch operation refers to a vertical motion with respect to an extension direction (an X-axis direction of FIG. 1) of the connector 140, that is, an operation of rotating around the Y axis of FIG. 1. In other words, the pitch operation refers to a vertical rotation of the end tool 120, which is formed to extend in the extension direction (the X-axis direction of FIG. 1) of the connector 140, around the Y axis. The yaw operation refers to a horizontal motion with respect to the extension direction (the X-axis direction of FIG. 1) of the connector 140, that is, an operation of rotating around the Z axis of FIG. 1. In other words, the yaw operation refers to a horizontal rotation of the end tool 120, which is formed to extend in the extension direction (the X-axis direction of FIG. 1) of the connector 140, around the Z axis. The actuation operation refers a folding or unfolding operation of the first and second jaws 121 and 122 when the first and second jaws 121 and 122 rotate in opposite directions while rotating around the same rotating axis as the yaw operation. That is, the actuation operation refers to rotations of the first and second jaws 121 and 122, which is formed at the end tool 120, in opposite directions around the Z axis.

Herein, when the operator 110 of the surgical instrument 100 is rotated in one direction, the end tool 120 rotates in a direction that is intuitively identical to an operation direction of the operator 110. In other words, when the pitch operator 111 of the operator 110 rotates in one direction, the end tool 120 rotates in a direction intuitively identical to the one direction to perform a pitch operation, and the end tool 120 rotates in the direction intuitively identical to the one direction to perform a yaw operation. Herein, it may be said that the intuitively identical direction refers to a case where a movement direction of an index finger of a user gripping the operator 110 is substantially identical to a movement direction of the end portion of the end tool 120. In addition, the identical direction may not be an exactly identical direction on a three-dimensional coordinate system. For example, the identical direction may refer to a case where when the index finger of the user moves to the left, the end portion of the end tool 120 also moves to the left, and when the index finger of the user moves to the right, the end portion of the end tool 120 also moves to the right.

To this end, in the surgical instrument 100, the operator 110 and the end tool 120 are formed in the same direction with respect to a plane perpendicular to an extension axis (X axis) of the connector 140. That is, in view of a YZ plane of FIG. 1, the operator 110 is formed to extend in a +X-axis direction, and the end tool 120 is also formed to extend in the +X-axis direction. In other words, it may be said that a formation direction of the end tool 120 at one end portion of the connector 140 may be identical to a formation direction of the operator 110 at the other end portion of the connector 140 in view of the YZ plane. In other words, it may be said that the operator 110 is formed to extend away from a body of the user gripping the operator 110, that is, the operator 110 is formed to extend toward the end tool 120.

In detail, in the case of a surgical instrument of the related art, an operation direction of an operator by a user is different from and is not intuitively identical to an actual operation direction of an end tool. Therefore, a surgical operator has difficulty in performing an intuitive operation and it takes a long time to skillfully move the end tool in a desired direction. Also, in some cases, a faulty operation may occur, thus damaging a surgical patient.

In order to solve such problems, the surgical instrument 100 according to the first embodiment of the present invention is configured such that an operation direction of the operator 110 is intuitively identical to an operation direction of the end tool 120. To this end, the operator 110 and the end tool 120 are formed on the same side in view of the YZ plane including a pitch operating axis 1111. This will be described below in more detail.

Referring to FIGS. 1, 2, and 3, the operator 110 of the surgical instrument 100 according to the first embodiment of the present invention includes the pitch operator 111 controlling a pitch motion of the end tool 120, a yaw operator 112 controlling a yaw motion of the end tool 120, and an actuation operator 113 controlling an actuation motion of the end tool 120.

The pitch operator 111 includes the pitch operating axis 1111 and a pitch operating bar 1112. Herein, the pitch operating axis 1111 may be formed in a direction parallel to the Y axis, and the pitch operating bar 1112 may be connected with the pitch operating axis 1111 to rotate along with the pitch operating axis 1111. For example, when the user grips and rotates the pitch operating bar 1112, the pitch operating axis 1111 connected with the pitch operating bar 1112 rotates along with the pitch operating bar 1112. Then, the resulting rotating force is transmitted to the end tool 120 through the operating force transmitter 130, so that the end tool 120 rotates in the same direction as the rotation direction of the pitch operating axis 1111. That is, when the pitch operator 111 rotates in the clockwise direction around the pitch operating axis 1111, the end tool 120 also rotates in the clockwise direction around an axis parallel to the pitch operating axis 1111, and when the pitch operator 111 rotates in the counterclockwise direction around the pitch operating axis 1111, the end tool 120 also rotates in the counterclockwise direction around the axis parallel to the pitch operating axis 1111.

The yaw operator 112 and the actuation operator 113 are formed on one end portion of the pitch operating bar 1112 of the pitch operator 111. Thus, when the pitch operator 111 rotates around the pitch operating axis 1111, the yaw operator 112 and the actuation operator 113 also rotate along with the pitch operator 111. FIGS. 1 and 3 illustrate a state in which the pitch operating bar 1112 of the pitch operator 111 is perpendicular to the connector 140, while FIG. 2 illustrates a state in which the pitch operating bar 1112 of the pitch operator 111 is at an angle to the connector 140.

Therefore, a coordinate system of the yaw operator 112 and the actuation operator 113 is not fixed, but relatively changes according to the rotation of the pitch operator 111. As illustrated in FIG. 1, since a yaw operating axis 1121 of the yaw operator 112 and an actuation operating axis 1131 of the actuation operator 113 are parallel to the Z axis, the yaw operator 112 and the actuation operator 113 rotate around an axis parallel to the Z axis. However, as illustrated in FIG. 2, when the pitch operator 111 rotates, the yaw operating axis 1121 of the yaw operator 112 and the actuation operating axis 1131 of the actuation operator 113 are not parallel to the Z axis. That is, the coordinate system of the yaw operator 112 and the actuation operator 113 change according to the rotation of the pitch operator 111. However, for convenience of description, the coordinate system of the yaw operator 112 and the actuation operator 113 will be described on the assumption that the pitch operating bar 1112 is perpendicular to the connector 140 as illustrated in FIG. 1.

The yaw operator 112 includes the yaw operating axis 1121 and a yaw operating bar 1122. Herein, the yaw operating axis 1121 may be formed to be at a predetermined angle to an XY plane where the connector 140 is formed. For example, the yaw operating axis 1121 may be formed in a direction parallel to the Z axis as illustrated in FIG. 1, and when the pitch operator 111 rotates, the coordinate system of the yaw operator 112 may relatively change as described above. However, the present invention is not limited thereto, and the yaw operating axis 1121 may be formed in various directions by ergonomic design according to the structure of a hand of the user gripping the yaw operator 112. The yaw operating bar 1122 is connected with the yaw operating axis 1121 to rotate along with the yaw operating axis 1121. For example, when the user holds and rotates the yaw operating bar 1122 with the index finger, the yaw operating axis 1121 connected with the yaw operating bar 1122 rotates along with the yaw operating bar 1122. Then, the resulting rotating force is transmitted to the end tool 120 through the operating force transmitter 130, so that the first and second jaws 121 and 122 of the end tool 120 horizontally rotate in the same direction as the rotation direction of the yaw operating axis 1121.

A first pulley 1121a and a second pulley 1121b may be formed respectively at both end portions of the yaw operating axis 1121. A YC1 wire 135YC1 may be connected to the first pulley 1121a, and a YC2 wire 135YC2 may be connected to the second pulley 1121b.

The actuation operator 113 includes the actuation operating axis 1131 and an actuation operating bar 1132. Herein, the actuation operating axis 1131 may be formed to be at a predetermined angle to the XY plane where the connector 140 is formed. For example, the actuation operating axis 1131 may be formed in a direction parallel to the Z axis as illustrated in FIG. 1, and when the pitch operator 111 rotates, the coordinate system of the actuation operator 113 may relatively change as described above. However, the present invention is not limited thereto, and the actuation operating axis 1131 may be formed in various directions by ergonomic design according to the structure of the hand of the user gripping the actuation operator 113. The actuation operating bar 1132 is connected with the actuation operating axis 1131 to rotate along with the actuation operating axis 1131. For example, when the user holds and rotates the actuation operating bar 1132 with the thumb finger, the actuation operating axis 1131 connected with the actuation operating bar 1132 rotates along with the actuation operating bar 1132. Then, the resulting rotating force is transmitted to the end tool 120 through the operating force transmitter 130, so that the first and second jaws 121 and 122 of the end tool 120 perform an actuation operation. Herein, as described above, the actuation operation refers to an operation of folding or unfolding the first and second jaws 121 and 122 by rotating the first and second jaws 121 and 122 in opposite directions. That is, when the actuation operator 113 is rotated in one direction, as the first jaw 121 rotates in the counterclockwise direction and the second jaw 122 rotates in the clockwise direction, the end tool 120 is folded; and when the actuation operator 113 is rotated in the opposite direction, as the first jaw 121 rotates in the clockwise direction and the second jaw 122 rotates in the counterclockwise direction, the end tool 120 is unfolded.

A first pulley 1131a and a second pulley 1131b may be formed respectively at both end portions of the actuation operating axis 1131. An AC1 wire 135AC1 may be connected to the first pulley 1131a, and an AC2 wire 135AC2 may be connected to the second pulley 1131b.

Referring to FIG. 3, the pitch operator 111 and the end tool 120 are formed on the same or parallel axis (X axis) in the surgical instrument 100 according to the first embodiment of the present invention. That is, the pitch operating axis 1111 of the pitch operator 111 is formed at one end portion of the connector 140, and the end tool 120 is formed at the other end portion of the connector 140. Although it is illustrated that the connector 140 is formed to have a shape of a straight line, the present invention is not limited thereto. For example, the connector 140 may be curved with a predetermined curvature, or may be bent one or more times. Also in this case, it may be said that the pitch operator 111 and the end tool 120 are formed on substantially the same or parallel axis. Although FIG. 3 illustrates that the pitch operator 111 and the end tool 120 are formed on the same axis (X axis), the present invention is not limited thereto. For example, the pitch operator 111 and the end tool 120 may be formed on different axes. This will be described later in detail.

The operator 110 of the surgical instrument 100 according to the first embodiment of the present invention further includes an operator control member 115 engaged with the pitch operating axis 1111 of the pitch operator 111. The operator control member 115 may include a relay pulley 115a. Since the configuration of the operator control member 115 is substantially identical to the configuration of the end tool 120, the relations between the operator control member 115 and other elements of the operator 110 and an end tool control member 123 will be described later.

Figure 3A:
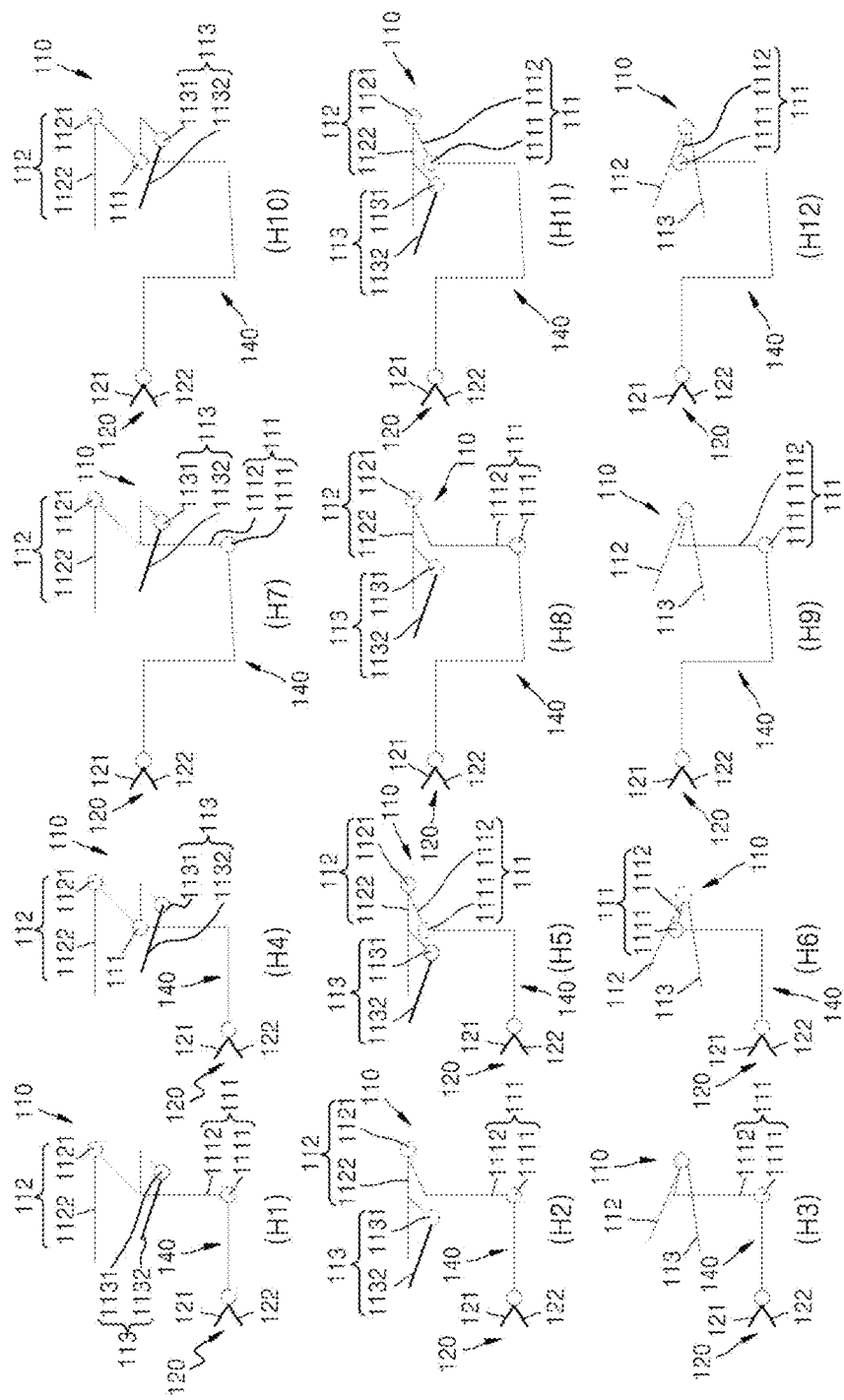
FIG. 3A illustrates various modifications of the operator of the surgical instrument according to the first embodiment of the present invention.

FIG. 3A illustrates various modifications of the operator 110 of the surgical instrument 100 according to the first embodiment of the present invention.

As for H1 of FIG. 3A, as described with reference to FIG. 3, (1) since the yaw operator 112 and the actuation operator 113 of the operator 110 are formed independently of each other, the rotation of one of the yaw operator 112 and the actuation operator 113 does not affect the rotation of the other of the yaw operator 112 and the actuation operator 113, (2) the pitch operator 111 is disposed under the plane formed by the yaw operator 112 and the actuation operator 113, and (3) the yaw operator 112 and the actuation operator 113 are formed over an extension line of the end tool 120. H1 may be seen in the first, fourth, and seventh embodiments of the present invention.

As for H2 of FIG. 3A, (1) since the actuation operator 113 of the operator 110 is formed on the yaw operator 112, when the yaw operator 112 rotates, the actuation operator 113 also rotates, (2) the pitch operator 111 is disposed under the plane formed by the yaw operator 112 and the actuation operator 113, and (3) the yaw operator 112 and the actuation operator 113 are formed over the extension line of the end tool 120. H2 may be seen in the second, fifth, and eighth embodiments of the present invention.

As for H3 of FIG. 3A, (1) a first jaw operator 112 and a second jaw operator 113, which rotate independently of each other, are formed in the operator 110, (2) the pitch operator 111 is disposed under the plane formed by the yaw operator 112 and the actuation operator 113, and (3) the yaw operator 112 and the actuation operator 113 are formed over the extension line of the end tool 120. H3 may be seen in the third, sixth, and ninth embodiments of the present invention.

As for H4 of FIG. 3A, (1) since the yaw operator 112 and the actuation operator 113 of the operator 110 are formed independently of each other, the rotation of one of the yaw operator 112 and the actuation operator 113 does not affect the rotation of the other of the yaw operator 112 and the actuation operator 113, (2) the pitch operator 111 is disposed on a plane identical to or adjacent to the plane formed by the yaw operator 112 and the actuation operator 113 such that the pitch operator 111 is more adjacent to the yaw operator 112 and the actuation operator 113 as compared to the H1 case, and (3) the yaw operator 112 and the actuation operator 113 are formed over the extension line of the end tool 120. H4 may be seen in detail in FIG. 9.

As for H5 of FIG. 3A, (1) since the actuation operator 113 of the operator 110 is formed on the yaw operator 112, when the yaw operator 112 rotates, the actuation operator 113 also rotates, (2) the pitch operator 111 is disposed on a plane identical to or adjacent to the plane formed by the yaw operator 112 and the actuation operator 113 such that the pitch operator 111 is more adjacent to the yaw operator 112 and the actuation operator 113 as compared to the H2 case, and (3) the yaw operator 112 and the actuation operator 113 are formed over the extension line of the end tool 120.

As for H6 of FIG. 3A, (1) a first jaw operator 112 and a second jaw operator 113, which rotate independently of each other, are formed in the operator 110, (2) the pitch operator 111 is disposed on a plane identical to or adjacent to the plane formed by the yaw operator 112 and the actuation operator 113 such that the pitch operator 111 is more adjacent to the yaw operator 112 and the actuation operator 113 as compared to the H3 case, and (3) the yaw operator 112 and the actuation operator 113 are formed over the extension line of the end tool 120.

As for H7 of FIG. 3A, (1) since the yaw operator 112 and the actuation operator 113 of the operator 110 are formed independently of each other, the rotation of one of the yaw operator 112 and the actuation operator 113 does not affect the rotation of the other of the yaw operator 112 and the actuation operator 113, (2) the pitch operator 111 is disposed under the plane formed by the yaw operator 112 and the actuation operator 113, and (3) the yaw operator 112 and the actuation operator 113 are formed on the extension line of the end tool 120.

As for H8 of FIG. 3A, (1) since the actuation operator 113 of the operator 110 is formed on the yaw operator 112, when the yaw operator 112 rotates, the actuation operator 113 also rotates, (2) the pitch operator 111 is disposed under the plane formed by the yaw operator 112 and the actuation operator 113, and (3) the yaw operator 112 and the actuation operator 113 are formed on the extension line of the end tool 120.

As for H9 of FIG. 3A, (1) a first jaw operator 112 and a second jaw operator 113, which rotate independently of each other, are formed in the operator 110, (2) the pitch operator 111 is disposed under the plane formed by the yaw operator 112 and the actuation operator 113, and (3) the yaw operator 112 and the actuation operator 113 are formed on the extension line of the end tool 120.

As for H10 of FIG. 3A, (1) since the yaw operator 112 and the actuation operator 113 of the operator 110 are formed independently of each other, the rotation of one of the yaw operator 112 and the actuation operator 113 does not affect the rotation of the other of the yaw operator 112 and the actuation operator 113, (2) the pitch operator 111 is disposed on a plane identical to or adjacent to the plane formed by the yaw operator 112 and the actuation operator 113 such that the pitch operator 111 is more adjacent to the yaw operator 112 and the actuation operator 113 as compared to the H7 case, and (3) the yaw operator 112 and the actuation operator 113 are formed on the extension line of the end tool 120.

As for H11 of FIG. 3A, (1) since the actuation operator 113 of the operator 110 is formed on the yaw operator 112, when the yaw operator 112 rotates, the actuation operator 113 also rotates, (2) the pitch operator 111 is disposed on a plane identical to or adjacent to the plane formed by the yaw operator 112 and the actuation operator 113 such that the pitch operator 111 is more adjacent to the yaw operator 112 and the actuation operator 113 as compared to the H8 case, and (3) the yaw operator 112 and the actuation operator 113 are formed on the extension line of the end tool 120.

As for H12 of FIG. 3A, (1) a first jaw operator 112 and a second jaw operator 113, which rotate independently of each other, are formed in the operator 110, (2) the pitch operator 111 is disposed on a plane identical to or adjacent to the plane formed by the yaw operator 112 and the actuation operator 113 such that the pitch operator 111 is more adjacent to the yaw operator 112 and the actuation operator 113 as compared to the H9 case, and (3) the yaw operator 112 and the actuation operator 113 are formed on the extension line of the end tool 120.

In addition to the above modifications, various other modifications of the operator 110 may be applicable to the surgical instrument of the present invention.

(Operating Force Transmitter)

Figure 4A:
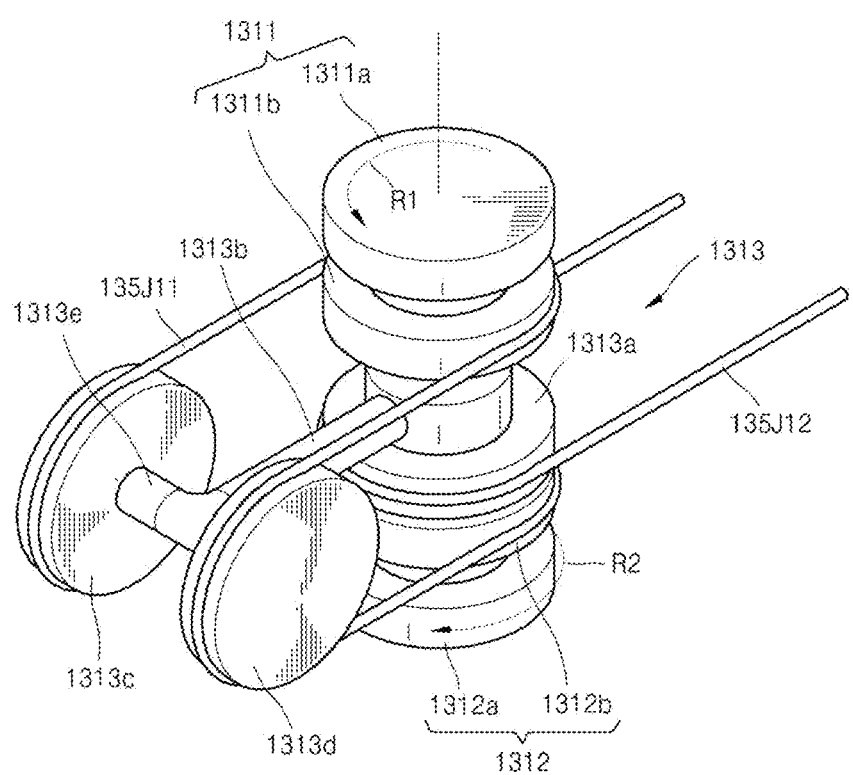
FIG. 4A is a detailed view of a first differential pulley of the surgical instrument of FIG. 2.
Figure 4B:
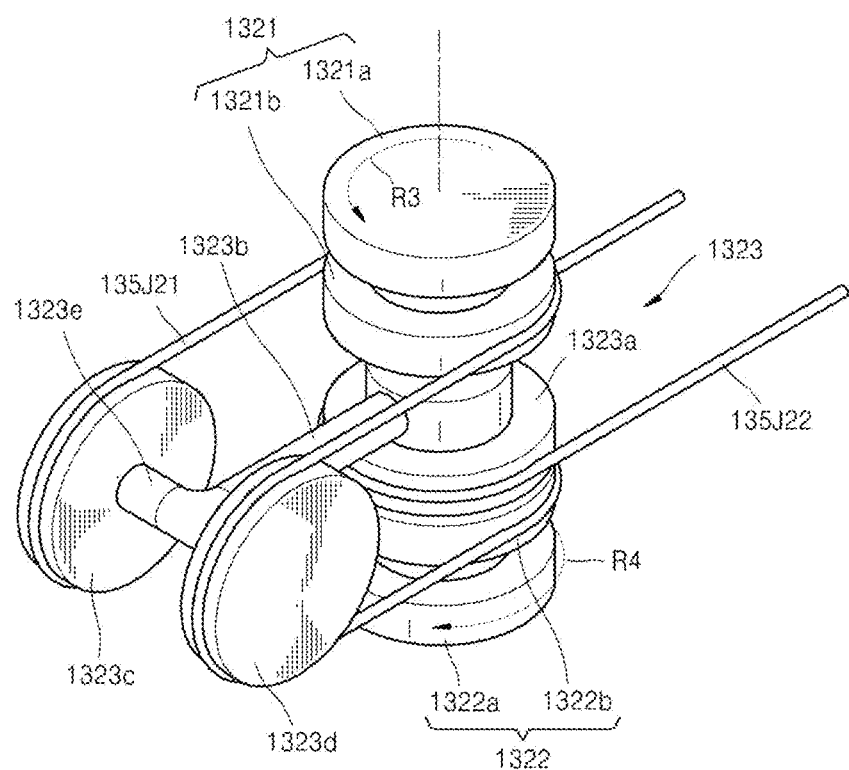
FIG. 4B is a detailed view of a second differential pulley of the surgical instrument of FIG. 2.

FIG. 4A is a detailed view of a first differential pulley 131 of the surgical instrument 100 of FIG. 2, and FIG. 4B is a detailed view of a second differential pulley of the surgical instrument 100 of FIG. 2.

Referring to FIGS. 1, 2, 4A, and 4B, the operating force transmitter 130 of the surgical instrument 100 according to the first embodiment of the present invention includes first and second differential pulleys 131 and 132, a plurality of pulleys, and a plurality of wires 135YC1, 135YC2, 135J11, 135J12, 135J13, 135J21, 135J22, and 135J23.

First, the first differential pulley 131 of the operating force transmitter 130 will be described below.

As described above, the yaw operator 112 and the actuation operator 113 are formed on one end portion of the pitch operating bar 1112 of the pitch operator 111. Thus, when the pitch operator 111 rotates around the pitch operating axis 1111, the yaw operator 112 and the actuation operator 113 also rotate along with the pitch operator 111. Also, the yaw operator 112 is connected with the first jaw 121 and the second jaw 122 to operate the first jaw 121 and the second jaw 122, and the actuation operator 113 is connected with the first jaw 121 and the second jaw 122 to operate the first jaw 121 and the second jaw 122. However, when the yaw operator 112 is rotated, the first jaw 121 and the second jaw 122 have to rotate in the same direction; and when the actuation operator 113 is rotated, the first jaw 121 and the second jaw 122 have to rotate in opposite directions. In order to implement this operation, a separate structure is required.

Thus, two rotation inputs of the yaw operator 112 and the actuation operator 113 have to be applied to one jaw. Accordingly, a structure for receiving two or more inputs and outputting a rotation of one jaw is required. In this case, two rotation inputs have to be independent of each other.

To this end, the surgical instrument 100 according to the first embodiment of the present invention includes a differential member including two or more input units and one output unit to receive an input of rotating forces from two or more input units from the two input units, extract a desired rotating force through the sum of or the difference between the two rotating forces, and output the desired rotating force through the output unit. The differential member may include a differential pulley using pulleys and wires, and a differential gear using gears, and a differential pulley is illustrated as an example of the differential member in FIGS. 1, 2, 4A, and 4B. Various embodiments of the differential member are illustrated in FIGS. 15 to 27.

In detail, the first differential pulley 131 includes a first input unit 1311, a second input unit 1312, and an output unit 1313.

The first input unit 1311 includes a first pulley 1311a and a second pulley 1311b. The first pulley 1311a and the second pulley 1311b rotate together around the same rotating axis. Herein, the first pulley 1311a of the first input unit 1311 is connected with the first pulley 1121a of the yaw operator 112 by the YC1 wire 135YC1 to transmit a rotation of the yaw operator 112 to the first input unit 1311. Also, the second pulley 1311b of the first input unit 1311 is connected with the output unit 1313 by the differential control wire 135J11 to transmit a rotation of the first input unit 1311 to the output unit 1313.

The second input unit 1312 includes a first pulley 1312a and a second pulley 1312b. The first pulley 1312a and the second pulley 1312b rotate together around the same rotating axis. Herein, the first pulley 1312a of the second input unit 1312 is connected with the first pulley 1131a of the actuation operator 113 by the AC1 wire 135AC1 to transmit a rotation of the actuation operator 113 to the second input unit 1312. Also, the second pulley 1312b of the second input unit 1312 is connected with the output unit 1313 by the differential control wire 135J11 to transmit a rotation of the second input unit 1312 to the output unit 1313.

The output unit 1313 includes an output pulley 1313a, an extension portion 1313b, a first differential control pulley 1313c, and a second differential control pulley 1313d. Herein, the output pulley 1313a of the output unit 1313 is connected with the operator control member 115 by the J12 wire 135J12 to transmit a rotation of the output unit 1313 to the first jaw 121 of the end tool 120 through the operator control member 115. The extension portion 1313b extends in one direction from a rotating axis of the output pulley 1313a to rotate along with the output pulley 1313a. The first differential control pulley 1313c and the second differential control pulley 1313d are formed at one end portion of the extension portion 1313b to face each other and rotate around both end portions of an axis 1313e that is formed at a predetermined angle to the rotating axis of the output pulley 1313a.

Herein, the first input unit 1311, the second input unit 1312, and the output unit 1313 rotate independently around independent axes.

The differential control wire 135J11 is wound along the second pulley 1311b of the first input unit 1311, the first differential control pulley 1313c of the output unit 1313, the second pulley 1312b of the second input unit 1312, and the second differential control pulley 1313d of the output unit 1313 to transmit a rotation of the first input unit 1311 and the second input unit 1312 to the output unit 1313.

Herein, the first differential pulley 131 includes the first input unit 1311, the second input unit 1312, and the output unit 1313, receives an input of rotation amounts from the first input unit 1311 and the second input unit 1312, and outputs the sum of the rotation amounts through the output unit 1313. That is, when only the first input unit 1311 rotates, the rotation of the first input unit 1311 is output through the output unit 1313; when only the second input unit 1312 rotates, the rotation of the second input unit 1312 is output through the output unit 1313; when the first input unit 1311 and the second input unit 1312 rotate in the same direction, the sum of the rotations of the first input unit 1311 and the second input unit 1312 is output through the output unit 1313; and when the first input unit 1311 and the second input unit 1312 rotate in opposite directions, the difference between the rotations of the first input unit 1311 and the second input unit 1312 is output through the output unit 1313. This may be expressed as the following equation:

$$C = A + B$$

(where C denotes a rotation of an output unit, A denotes a rotation of a first input unit, and B denotes a rotation of a second input unit.)

The operation of the first differential pulley 131 will be described later in detail.

Like the first differential pulley 131, the second differential pulley 132 includes a first input unit 1321, a second input unit 1322, and an output unit 1323.

Herein, a first pulley 1321a of the first input unit 1321 is connected with the second pulley 1121b of the yaw operator 112 by the YC2 wire 135YC2 to transmit a rotation of the yaw operator 112 to the first input unit 1321. Also, a second pulley 1321b of the first input unit 1321 is connected with the output unit 1323 by a differential control wire 135J21 to transmit a rotation of the first input unit 1321 to the output unit 1323.

A first pulley 1322a of the second input unit 1322 is connected with the second pulley 1131b of the actuation operator 113 by the AC2 wire 135AC2 to transmit a rotation of the actuation operator 113 to the second input unit 1322. Also, the second pulley 1322b of the second input unit 1322 is connected with the output unit 1323 by the differential control wire 135J21 to transmit a rotation of the second input unit 1322 to the output unit 1323.

The output unit 1323 includes an output pulley 1323a, an extension portion 1323b, a first differential control pulley 1323c, and a second differential control pulley 1323d. Herein, the output pulley 1323a of the output unit 1323 is connected with the operator control member 115 by the J22 wire 135J22 to transmit a rotation of the output unit 1323 to the second jaw 122 of the end tool 120 through the operator control member 115.

Herein, the second differential pulley 132 includes the first input unit 1321, the second input unit 1322, and the output unit 1323, receives an input of rotation amounts from the first input unit 1321 and the second input unit 1322, and outputs the sum of the rotation amounts through the output unit 1323. That is, when only the first input unit 1321 rotates, the rotation of the first input unit 1321 is output through the output unit 1323; when only the second input unit 1322 rotates, the rotation of the second input unit 1322 is output through the output unit 1323; when the first input unit 1321 and the second input unit 1322 rotate in the same direction, the sum of the rotations of the first input unit 1321 and the second input unit 1322 is output through the output unit 1323; and when the first input unit 1321 and the second input unit 1322 rotate in opposite directions, the difference between the rotations of the first input unit 1321 and the second input unit 1322 is output through the output unit 1323.

The operations of the first differential pulley 131 and the second differential pulley 132 will be described below.

First, a case where only the yaw operator 112 rotates and the actuation operator 113 does not rotate will be described below.

When the yaw operator 112 rotates in the direction of an arrow Y of FIG. 2, the first pulley 1121a of the yaw operator 112, the YC1 wire 135YC1 wound around the first pulley 1121a, the first pulley 1311a of the first input unit 1311 of the first differential pulley 131 around which the YC1 wire 135YC1 is wound, and the second pulley 1311b connected with the first pulley 1311a rotate together. However, the second input unit 1312 of the first differential pulley 131 connected with the actuation operator 113 does not rotate. In this manner, when the first input unit 1311 of the first differential pulley 131 rotates in the direction of an arrow R1 of FIG. 4A and the second input unit 1312 does not rotate, a portion wound around the first input unit 1311 of the differential control wire 135J11 rotates but a portion wound around the second input unit 1312 of the differential control wire 135J11 does not rotate. Accordingly, the wire wound around the second input unit 1312 is unwound as much as the rotation of the portion wound around the first input unit 1311 of the differential control wire 135J11, and the differential control wire 135J11 moves as much. Concurrently, the second differential control pulley 1313d rotates in the clockwise direction, and the first differential control pulley 1313c rotates in the counterclockwise direction. At the same time, the output unit 1313, which includes the output pulley 1313a, the extension portion 1313b, the first differential control pulley 1313c, and the second differential control pulley 1313d, rotates in the direction of the arrow R1 of FIG. 4A around the rotating axis of the output pulley 1313a. Then, the rotation of the output unit 1313 is transmitted to the first jaw 121 of the end tool 120 through the operator control member 115, so that the first jaw 121 rotates in the direction of an arrow YJ of FIG. 2.

Also, when the yaw operator 112 rotates in the direction of the arrow Y of FIG. 2, the second pulley 1121b of the yaw operator 112, the YC2 wire 135YC2 wound around the second pulley 1121b, the first pulley 1321a of the first input unit 1321 of the second differential pulley 132 around which the YC2 wire 135YC2 is wound, and the second pulley 1321b connected with the first pulley 1321a rotate together. However, the second input unit 1322 of the second differential pulley 132 connected with the actuation operator 113 does not rotate. In this manner, when the first input unit 1321 of the second differential pulley 132 rotates in the direction of an arrow R3 of FIG. 4B and the second input unit 1322 does not rotate, a portion wound around the first input unit 1321 of the differential control wire 135J21 rotates but a portion wound around the second input unit 1322 of the differential control wire 135J21 does not rotate. Accordingly, the wire wound around the second input unit 1322 is unwound as much as the rotation of the portion wound around the first input unit 1321 of the differential control wire 135J21, and the differential control wire 135J21 moves as much. Concurrently, the second differential control pulley 1323d rotates in the clockwise direction, and the first differential control pulley 1323c rotates in the counterclockwise direction. At the same time, the output unit 1323, which includes the output pulley 1323a, the extension portion 1323b, the first differential control pulley 1323c, and the second differential control pulley 1323d, rotates around the rotating axis of the output pulley 1323a in the direction of the arrow R3 of FIG. 4B. Then, the rotation of the output unit 1323 is transmitted to the second jaw 122 of the end tool 122 through the operator control member 115, so that the second jaw 122 rotates in the direction of the arrow YJ of FIG. 2.

A case where only the actuation operator 113 rotates and the yaw operator 112 does not rotate will be described below.

When the actuation operator 113 rotates in the direction of an arrow A of FIG. 2, the first pulley 1131a of the actuation operator 113, the AC1 wire 135AC1 wound around the first pulley 1131a, the first pulley 1312a of the second input unit 1312 of the first differential pulley 131 around which the AC1 wire 135AC1 is wound, and the second pulley 1312b connected with the first pulley 1312a rotate together. Herein, since the AC1 wire 135AC1 is twisted one time, the rotating force of the actuation operator 113 is reversed and transmitted to the first differential pulley 131. However, the first input unit 1311 of the first differential pulley 131 that is connected with the yaw operator 112 does not rotate. In this manner, when the second input unit 1312 of the first differential pulley 131 rotates in a direction opposite to the direction of an arrow R2 of FIG. 4A and the first input unit 1311 does not rotate, a portion wound around the second input unit 1312 of the differential control wire 135J11 rotates but a portion wound around the first input unit 1311 of the differential control wire 135J11 does not rotate. Accordingly, the wire wound around the first input unit 1311 is unwound as much as the rotation of the portion wound around the second input unit 1312 of the differential control wire 135J11, and the differential control wire 135J11 moves as much. Concurrently, the second differential control pulley 1313d rotates in the counterclockwise direction, and the first differential control pulley 1313c rotates in the clockwise direction. At the same time, the output unit 1313, which includes the output pulley 1313a, the extension portion 1313b, the first differential control pulley 1313c, and the second differential control pulley 1313d, rotates around the rotating axis of the output pulley 1313a in a direction opposite to the direction of the arrow R2 of FIG. 4A. Then, the rotation of the output unit 1313 is transmitted to the first jaw 121 of the end tool 120 through the operator control member 115, so that the first jaw 121 rotates in the direction of the arrow YJ of FIG. 2.

Also, when the actuation operator 113 rotates in the direction of the arrow A of FIG. 2, the second pulley 1131b of the actuation operator 113, the AC2 wire 135AC2 wound around the second pulley 1131b, the first pulley 1322a of the second input unit 1322 of the second differential pulley 132 around which the AC2 wire 135AC2 is wound, and the second pulley 1322b connected with the first pulley 1322a rotate together. However, the first input unit 1321 of the second differential pulley 132 that is connected with the yaw operator 112 does not rotate. In this manner, when the second input unit 1322 of the second differential pulley 132 rotates in the direction of an arrow R4 of FIG. 4B and the first input unit 1321 does not rotate, a portion wound around the second input unit 1322 of the differential control wire 135J21 rotates but a portion wound around the first input unit 1321 of the differential control wire 135J21 does not rotate. Accordingly, the wire wound around the first input unit 1321 is unwound as much as the rotation of the portion wound around the second input unit 1322 of the differential control wire 135J21, and the differential control wire 135J21 moves as much. Concurrently, the second differential control pulley 1323d rotates in the clockwise direction, and the first differential control pulley 1323c rotates in the counterclockwise direction. At the same time, the output unit 1323, which includes the output pulley 1323a, the extension portion 1323b, the first differential control pulley 1323c, and the second differential control pulley 1323d, rotates around the rotating axis of the output pulley 1323a in the direction of the arrow R4 of FIG. 4B. Then, the rotation of the output unit 1323 is transmitted to the second jaw 122 of the end tool 122 through the operator control member 115, so that the second jaw 122 rotates in a direction opposite to the direction of the arrow YJ of FIG. 2.

That is, when the first jaw 121 rotates in the direction of the arrow YJ of FIG. 2 and the second jaw 122 rotates in a direction opposite to the direction of the arrow YJ of FIG. 2, an actuation operation of the end tool 120 is performed.

There is a case where, in a differential pulley including two input units and one output unit, the rotation of one input unit does not generate the rotation of the output unit and generates the rotation of another input unit. In order to prevent this case, according to the present invention, in a situation where two operators are connected respectively to two differential pulleys, when one operator is connected with two input units of each of two differential pulleys, one of the wires connecting the operator and the input unit is twisted, thereby preventing a situation where the input of one operator causes another operator to rotate.

In order to describe this in more detail, a case where the second input unit 1312 of the first differential pulley 131 and the second input unit 1322 of the second differential pulley 132 also rotate in the same direction as a rotation input of the yaw operator 112 by the rotation input of the yaw operator 112 connected to the first input unit 1311 of the first differential pulley 131 and the first input unit 1321 of the second differential pulley 132 is assumed. In this case, the actuation operator 113 and the second input unit 1312 of the first differential pulley 131 are connected by the AC1 wire 135AC1 that is twisted one time, and the actuation operator 113 and the second input unit 1322 of the second differential pulley 132 are connected by the AC2 wire 135AC2 that is not twisted. Thus, rotations of the second input units 1312 and 1322 of the first and second differential pulleys 131 and 132 rotate the actuation operator 113 in opposite directions by the AC1 wire 135AC1 and the AC2 wire 135AC2. Therefore, the rotations offset each other and do not rotate the actuation operator 113, and the remaining rotation is transmitted to each of the output units 1313 and 1323 to rotate each of the output units 1313 and 1323. This is also applied to the rotation input of the actuation operator 113. Thus, the rotation input of the actuation operator 113 does not cause the yaw operator 112 to rotate and is transmitted to each of the output units 1313 and 1323 to rotate each of the output units 1313 and 1323.

In summary, according to this configuration, the rotation input of one operator does not cause another operator to rotate and is transmitted to each output unit to rotate each output unit.

By this operational principle, even when the yaw operator 112 and the actuation operator 113 rotate simultaneously, the sum of (or the difference between) the rotation inputs of the yaw operator 112 and the actuation operator 113 is transmitted to the output units 1313 and 1323 of the first and second differential pulleys 131 and 132 through the first and second differential pulleys 131 and 132 to rotate the output units 1313 and 1323, and the rotations of the output units 1313 and 1323 are transmitted to the first and second jaws 121 and 122 of the end tool 120 through the operation control member 115, thus causing the first and second jaws 121 and 122 to rotate according to the operations of the yaw operator 112 and the actuation operator 113.

(End Tool)

Figure 5:
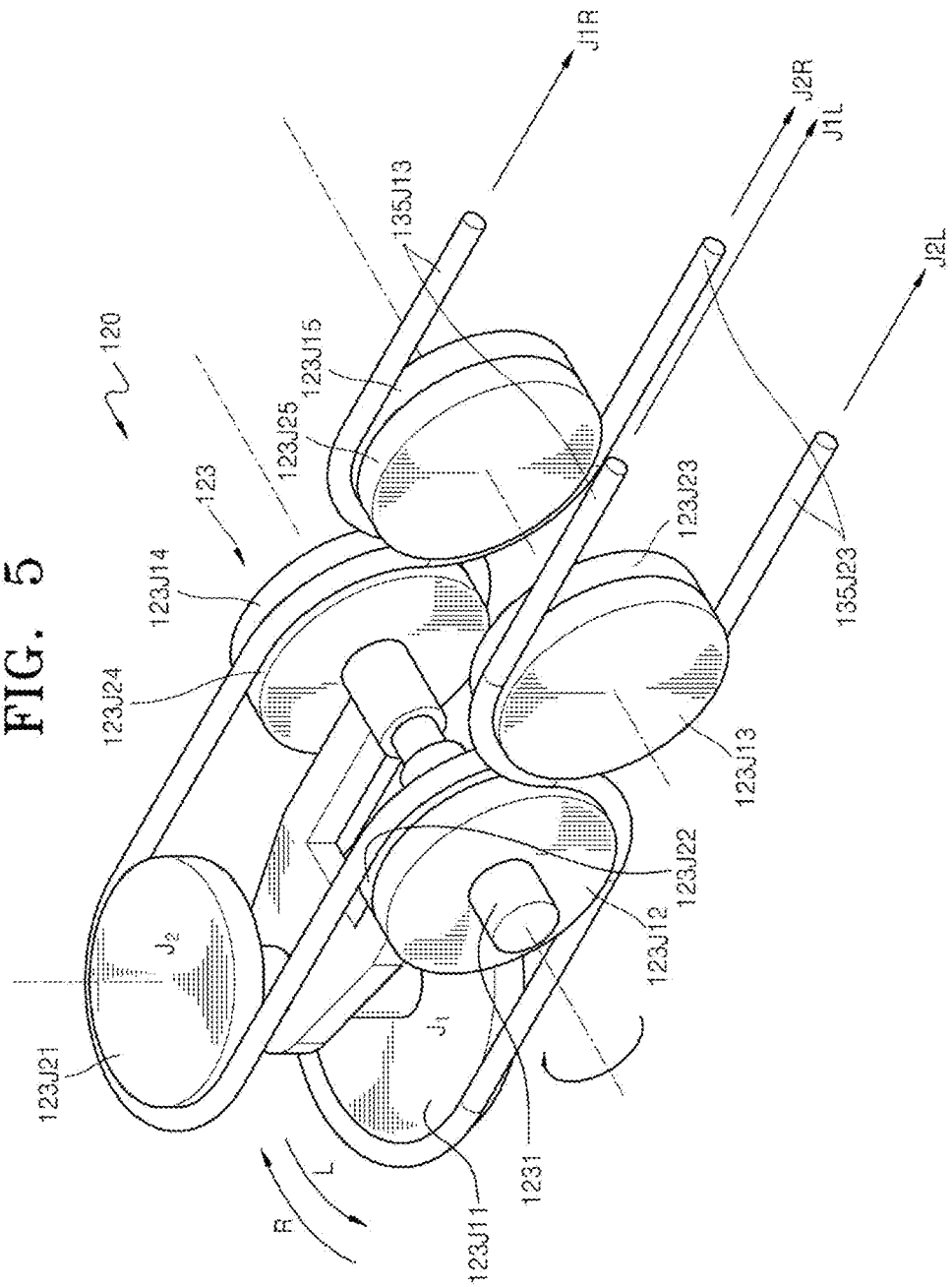
FIG. 5 is a detailed view of an end tool of the surgical instrument of FIG. 2.

FIG. 5 is a schematic view of the end tool 120 of the surgical instrument 100 of FIG. 2. Referring to FIGS. 1, 2, and 5, the end tool 120 of the surgical instrument 100 according to the first embodiment of the present invention includes the end tool control member 123. The end tool control member 123 includes a J11 pulley 123J11, a J12 pulley 123J12, a J13 pulley 123J13, a J14 pulley 123J14, and a J15 pulley 123J15 that are related to the rotation motion of the first jaw 121, and a J21 pulley 123J21, a J22 pulley 123J22, a J23 pulley 123J23, a J24 pulley 123J24, and a J25 pulley 123J25 that are related to the rotation motion of the second jaw 122. Herein, the J12 pulley 123J12, the J14 pulley 123J14, the J22 pulley 123J22, and the J24 pulley 123J24 may be formed to rotate around an end tool pitch operating axis 1231. Although it is illustrated that pulleys facing each other are formed to be parallel to each other and to have the same size, the present invention is not limited thereto. For example, the pulleys may be formed to have various positions and sizes suitable for the configuration of the end tool 120.

Herein, the end tool 120 of the surgical instrument 100 according to the first embodiment of the present invention includes the end tool control member 123 and only two wires, namely, a first jaw operating wire 135J13 and a second jaw operating wire 135J23, thereby making it possible to conveniently perform a pitch operation, a yaw operation, and an actuation operation of the end tool 120. This will be described below in more detail.

The J11 pulley 123J11 and the J21 pulley 123J21 are formed to face each other and rotate independently around the Z-axis direction. Although not illustrated in FIG. 5, the first jaw 121 may be coupled to the J11 pulley 123J11 to rotate along with the J11 pulley 123J11, and the second jaw 122 may be coupled to the J21 pulley 123J21 to rotate along with the J21 pulley 123J21. A yaw operation and an actuation operation of the end tool 120 are performed according to the rotations of the J11 pulley 123J11 and the J21 pulley 123J21. That is, the yaw operation is performed when the J11 pulley 123J11 and the J21 pulley 123J21 rotate in the same direction, and the actuation operation is performed when the J11 pulley 123J11 and the J21 pulley 123J21 rotate in opposite directions.

The elements related to the rotation of the J11 pulley 123J11 will be described below.

On one side of the J11 pulley 123J11, the J12 pulley 123J12 and the J14 pulley 123J14 are disposed to be spaced apart from each other by a predetermined distance and face each other. Herein, the J12 pulley 123J12 and the J14 pulley 123J14 are formed to rotate independently around the Y-axis direction. Also, on one side of the J12 pulley 123J12 and the J14 pulley 123J14, the J13 pulley 123J13 and the J15 pulley 123J15 are disposed to be spaced apart from each other by a predetermined distance and face each other. Herein, the J13 pulley 123J13 and the J15 pulley 123J15 are formed to rotate independently around the Y-axis direction. Although it is illustrated that all of the J12 pulley 123J12, the J13 pulley 123J13, the J14 pulley 123J14, and the J15 pulley 123J15 are formed to rotate around the Y-axis direction, the present invention is not limited thereto, and the rotating axes of the respective pulleys may be formed in various directions according to their configurations.

At least a portion of the first jaw operating wire 135J13 contacts the J13 pulley 123J13, the J12 pulley 123J12, the J11 pulley 123J11, the J14 pulley 123J14, and the J15 pulley 123J15, so that the first jaw operating wire 135J13 may move along the pulleys while rotating the pulleys.

Thus, when the first jaw operating wire 135J13 is pulled in the direction of an arrow J1R of FIG. 5, the first jaw operating wire 135J13 sequentially rotates the J15 pulley 123J15, the J14 pulley 123J14, the J11 pulley 123J11, the J12 pulley 123J12, and the J13 pulley 123J13. In this case, the J11 pulley 123J11 rotates in the direction of an arrow R of FIG. 5 to rotate the first jaw 121 together.

On the other hand, when the first jaw operating wire 135J13 is pulled in the direction of an arrow J1L of FIG. 5, the first jaw operating wire 135J13 sequentially rotates the J13 pulley 123J13, the J12 pulley 123J12, the J11 pulley 123J11, the J14 pulley 123J14, and the J15 pulley 123J15. In this case, the J11 pulley 123J11 rotates in the direction of an arrow L of FIG. 5 to rotate the first jaw 121 together therewith.

The elements related to the rotation of the J21 pulley 123J21 will be described below.

On one side of the J21 pulley 123J21, the J22 pulley 123J22 and the J24 pulley 123J24 are disposed to be spaced apart from each other by a predetermined distance and face each other. Herein, the J22 pulley 123J22 and the J24 pulley 123J24 are formed to rotate independently around the Y-axis direction. Also, on one side of the J22 pulley 123J22 and the J24 pulley 123J24, the J23 pulley 123J23 and the J25 pulley 123J25 are disposed to be spaced apart from each other by a predetermined distance and face each other. Herein, the J23 pulley 123J23 and the J25 pulley 123J25 are formed to rotate independently around the Y-axis direction. Although it is illustrated that all of the J22 pulley 123J22, the J23 pulley 123J23, the J24 pulley 123J24, and the J25 pulley 123J25 are formed to rotate around the Y-axis direction, the present invention is not limited thereto, and the rotating axes of the respective pulleys may be formed in various directions according to their configurations.

At least a portion of the second jaw operating wire 135J23 contacts the J23 pulley 123J23, the J22 pulley 123J22, the J21 pulley 123J21, the J24 pulley 123J24, and the J25 pulley 123J25, so that the second jaw operating wire 135J23 may move along the pulleys while rotating the pulleys.

Thus, when the second jaw operating wire 135J23 is pulled in the direction of an arrow J2R of FIG. 5, the second jaw operating wire 135J23 sequentially rotates the J25 pulley 123J25, the J24 pulley 123J24, the J21 pulley 123J21, the J22 pulley 123J22, and the J23 pulley 123J23. In this case, the J21 pulley 123J21 rotates in the direction of the arrow R of FIG. 5 to rotate the second jaw 122 together therewith.

On the other hand, when the second jaw operating wire 135J23 is pulled in the direction of an arrow J2L of FIG. 5, the second jaw operating wire 135J23 sequentially rotates the J23 pulley 123J23, the J22 pulley 123J22, the J21 pulley 123J21, the J24 pulley 123J24, and the J25 pulley 123J25. In this case, the J21 pulley 123J21 rotates in the direction of the arrow L of FIG. 5 to rotate the second jaw 122 together therewith.

When one end portion of the first jaw operating wire 135J13 is pulled in the direction of the arrow J1R of FIG. 5 and the other end portion of the first jaw operating wire 135J13 is pulled in the direction of the arrow J1L of FIG. 5, the end tool control member 123 rotates around the end tool pitch operating axis 1231 in the counterclockwise direction, so that the end tool 120 rotates downward to perform a pitch motion.

On the other hand, when one end portion of the second jaw operating wire 135J23 is pulled in the direction of the arrow J2R of FIG. 5 and the other end portion of the second jaw operating wire 135J23 is pulled in the direction of the arrow J2L of FIG. 5, the end tool control member 123 rotates around the end tool pitch operating axis 1231 in the clockwise direction, so that the end tool 120 rotates upward to perform a pitch motion.

That is, since the end tool 120 includes the end tool control member 123 and only two wires, namely, the first jaw operating wire 135J13 and the second jaw operating wire 135J23, a pitch operation, a yaw operation, and an actuation operation of the end tool 120 may be conveniently performed. This will be described later in detail.

In the end tool control member 123 of the end tool 120 according to an embodiment of the present invention, the end tool pitch operating axis 1231 is disposed adjacent to the first and second jaws 121 and 122 (that is, the end tool pitch operating axis 1231 is disposed adjacent to the J12 pulley 123J12 and the J14 pulley 123J14, not to the J13 pulley 123J13 and the J15 pulley 123J15), thereby reducing a pitch rotation radius of the first and second jaws 121 and 122. Accordingly, a space necessary for a pitch operation of the first and second jaws 121 and 122 may be reduced.

Figure 5A:
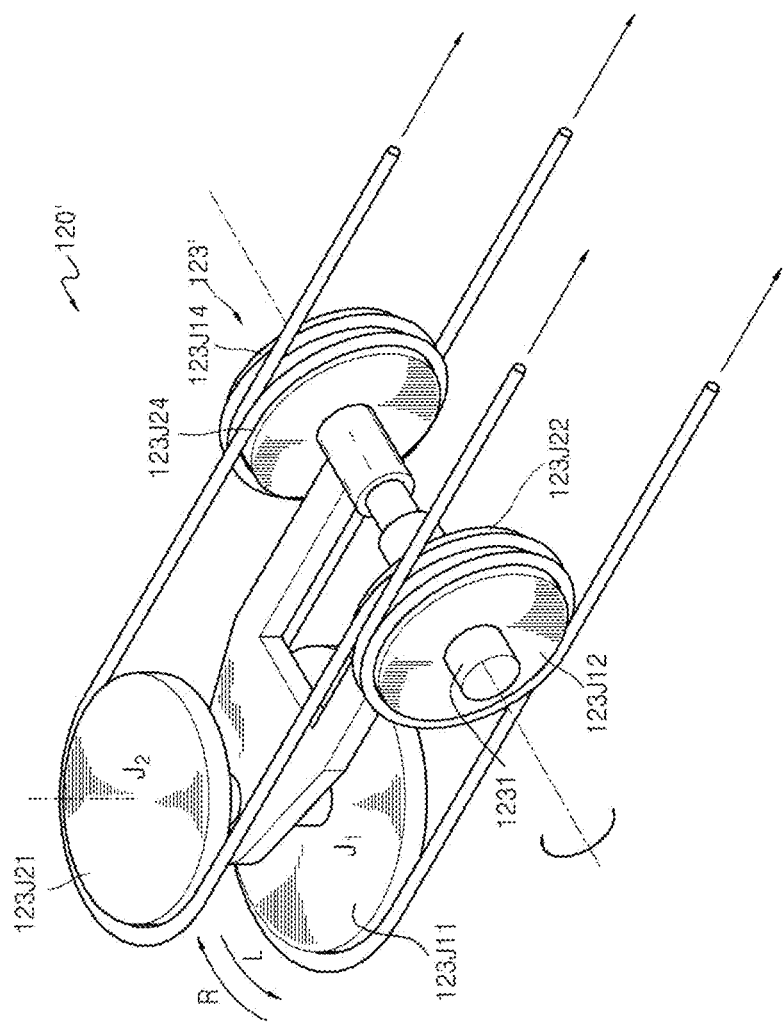
FIG. 5A illustrates a modification of the end tool of FIG. 5.

FIG. 5A illustrates a modification of the end tool 120 of FIG. 5.

Referring to FIG. 5A, an end tool 120' includes an end tool control member 123', and the end tool control member 123' includes a J11 pulley 123J11, a J12 pulley 123J12, a J14 pulley 123J14 related to the rotation motion of a first jaw, and a J21 pulley 123J21, a J22 pulley 123J22, a J24 pulley 123J24 related to the rotation motion of a second jaw. Herein, the J12 pulley 123J12, the J14 pulley 123J14, the J22 pulley 123J22, and the J24 pulley 123J24 may be formed to rotate around an end tool pitch operating axis 1231. Although it is illustrated that pulleys facing each other are formed to be parallel to each other and have the same size, the present invention is not limited thereto, and the pulleys may be formed to have various positions and sizes suitable for the configuration of the end tool 120.

In this modification, not two pairs of pulleys facing each other, but only a pair of pulleys (i.e., the J12 pulley 123J12 and the J14 pulley 123J14) are disposed on one side of the J11 pulley 123J11 coupled with the first jaw, wherein the first jaw operating wire 135J13 is wound one or more times around the pair of pulleys while contacting the pair of pulleys.

In detail, the J11 pulley 123J11 and the J21 pulley 123J21 are formed to face each other and rotate independently around the Z-axis direction.

On one side of the J11 pulley 123J11, the J12 pulley 123J12 and the J14 pulley 123J14 are disposed to be spaced apart from each other by a predetermined distance and face each other. Herein, the J12 pulley 123J12 and the J14 pulley 123J14 are formed to rotate independently around the Y-axis direction. At least a portion of the first jaw operating wire 135J13 contacts the J12 pulley 123J12, the J11 pulley 123J11, and the J14 pulley 123J14, so that the first jaw operating wire 135J13 may move along the pulleys while rotating the pulleys. Herein, the first jaw operating wire 135J13 may be wound one or more times around the J12 pulley 123J12 and then wound one or more times around the J14 pulley 123J14 through the J11 pulley 123J11.

Likewise, on one side of the J21 pulley 123J21, the J22 pulley 123J22 and the J24 pulley 123J24 are disposed to be spaced apart from each other by a predetermined distance and face each other. Herein, the J22 pulley 123J22 and the J24 pulley 123J24 are formed to rotate independently around the Y-axis direction. At least a portion of the second jaw operating wire 135J23 contacts the J22 pulley 123J22, the J21 pulley 123J21, and the J24 pulley 123J24, so that the second jaw operating wire 135J23 may move along the pulleys while rotating the pulleys. Herein, the second jaw operating wire 135J23 may be wound one or more times around the J22 pulley 123J22 and then wound one or more times around the J24 pulley 123J24 through the J21 pulley 123J21.

By the above configuration, the number of pulleys may be reduced, and thus the size of a surgical instrument may be further reduced.

(Pitch Operation Control and Wire Mirroring)

Figure 6:
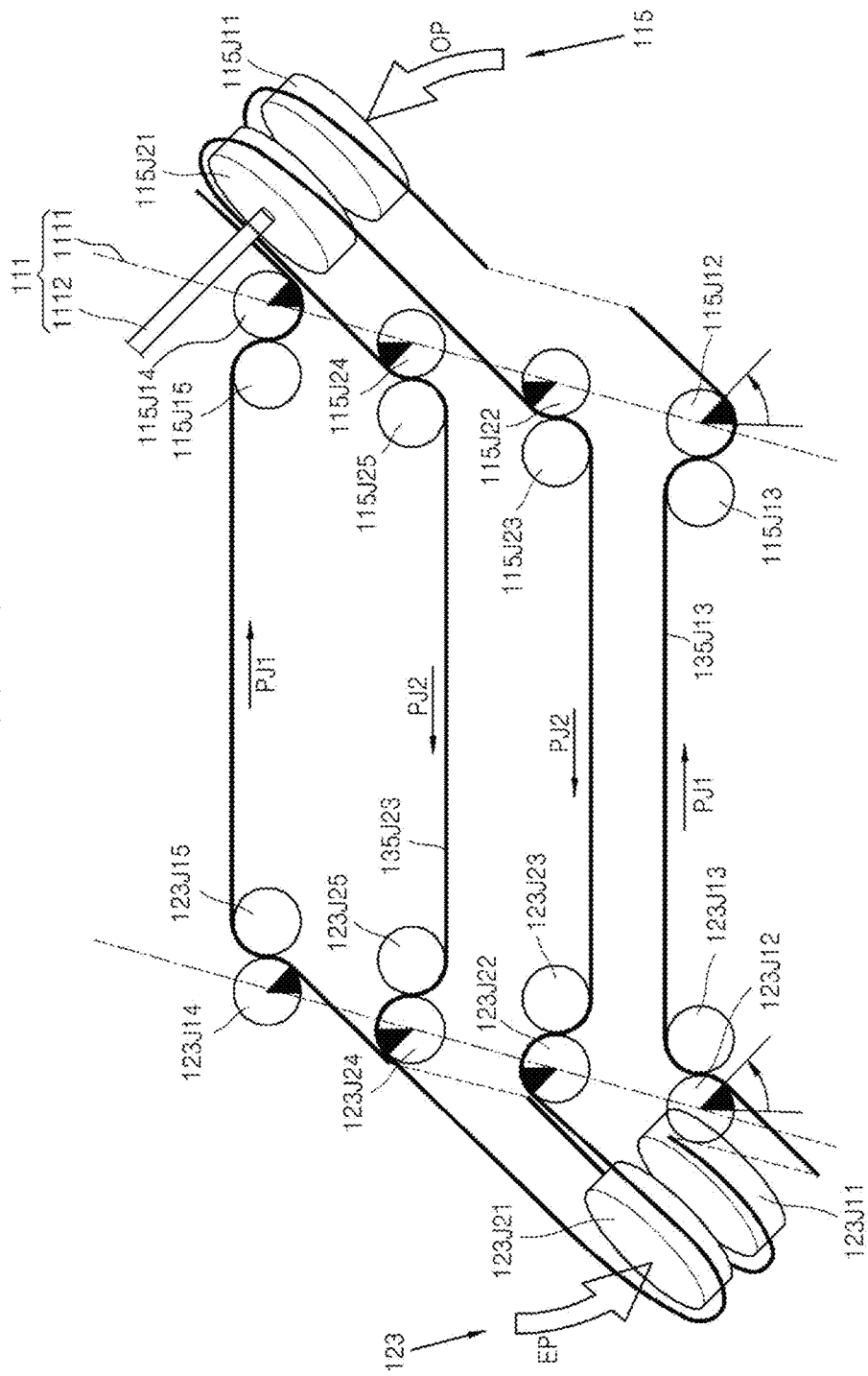
FIG. 6 is a schematic view illustrating a pitch operation of the surgical instrument of FIG. 2.

FIG. 6 is a schematic view illustrating a pitch operation of the surgical instrument 100 of FIG. 2.

As described above, the operator 110 of the surgical instrument 100 according to the first embodiment of the present invention further includes the operator control member 115 engaged with the pitch operating axis 1111 of the pitch operator 111. The operator control member 115 has substantially the same configuration of the end tool control member 123, and the end tool control member 123 and the operator control member 115 are disposed symmetrical to each other about the YZ plane of FIG. 1. In other words, it may be said that the end tool control member 123 and the operator control member 115 are mirrored with respect to the YZ plane of FIG. 1.

In detail, the operator control member 115 includes a J11 pulley 115J11, a J12 pulley 115J12, a J13 pulley 115J13, a J14 pulley 115J14, and a J15 pulley 115J15 that are related to the rotation motion of the first jaw 121, and a J21 pulley 115J21, a J22 pulley 115J22, a J23 pulley 115J23, a J24 pulley 115J24, and a J25 pulley 115J25 that are related to the rotation motion of the second jaw 122.

At least a portion of the first jaw operating wire 135J13 contacts the J13 pulley 115J13, the J12 pulley 115J12, the J11 pulley 115J11, the J14 pulley 115J14, and the J15 pulley 115J15, so that the first jaw operating wire 135J13 may move along the pulleys while rotating the pulleys.

At least a portion of the second jaw operating wire 135J23 contacts the J23 pulley 115J23, the J22 pulley 115J22, the J21 pulley 115J21, the J24 pulley 115J24, and the J25 pulley 115J25, so that the second jaw operating wire 135J23 may move along the pulleys while rotating the pulleys.

Herein, the rotating axis of the J12 pulley 115J12, the J14 pulley 115J14, the J22 pulley 115J22, and the J24 pulley 115J24 may be identical to the pitch operating axis 1111 of the pitch operator 111. Also, a bar extending from the rotating axis of the J11 pulley 115J11 and the J21 pulley 115J21 may be identical to the pitch operating bar 1112 of the pitch operator 111.

The pitch operation in the first embodiment of the present invention is performed as follows:

When the user grips the pitch operating bar 1112 of the pitch operator 111 of the operator 110 and rotates the pitch operating bar 1112 around the pitch operating axis 1111 in the direction of an arrow OP (Operator Pitch) of FIG. 6, the first jaw operating wire 135J13 is pulled toward the operator 110 and moves in the direction of an arrow PJ1 of FIG. 6. At the same time, the second jaw operating wire 135J23 is unwound from the operator 110, moves toward the end tool 120, and moves in the direction of an arrow PJ2 of FIG. 6. Then, as the first jaw operating wire 135J13 is pulled toward the operator 110, the J12 pulley 123J12 and the J14 pulley 123J14 rotate around the rotating axis (see FIG. 5) in the counterclockwise direction. At the same time, as the second jaw operating wire 135J23 is pulled toward the end tool 120, the J22 pulley 123J22 and the J24 pulley 123J24 rotate around the rotating axis (see FIG. 5) in the counterclockwise direction. Consequently, the end tool 120 rotates downward to perform a pitch motion.

In this manner, since the end tool control member 123 and the operator control member 115 are disposed symmetrical to each other (i.e., mirrored) about the YZ plane of FIG. 1, the pitch operation may be conveniently performed. That is, the pitch operation may be performed regardless of the yaw operation and the actuation operation. Herein, the yaw operation refers to a rotating operation of the first and second jaws 121 and 122 according to the rotations of the J11 pulley 123J11 and the J21 pulley 123J21 of the end tool control member 123 and the J11 pulley 115J11 and the J21 pulley 115J21 of the operator control member 115.

Overall Operation of First Embodiment

Hereinafter, an overall configuration for the pitch operation, the yaw operation, and the actuation operation of the surgical instrument 100 according to the first embodiment of the present invention will be summarized with reference to the above descriptions.

For the configuration of the end tool 120 of the present embodiment, the operating force transmitter 130 capable of dividing the operation input of the operator 110 into a pitch operation, a yaw operation, and an actuation operation is necessary to perform the pitch, yaw, and actuation operations of the end tool 120. As described above, through the structure in which the end tool control member 123 and the operator control member 115 are disposed symmetrical to each other, the rotation operation of the pitch operator 111 enables the pitch operation of the end tool 120 regardless of the operations of the yaw operator 112 and the actuation operator 113. However, in order for the operations of the yaw operator 112 and the actuation operator 113 to lead to the yaw operation and the actuation operation of the end tool 120, the operations of the yaw operator 112 and the actuation operator 113 have to be converted into the operations of two jaws of the end tool 120. The rotation of the yaw operator 112 causes the two jaws to rotate in the same direction, and the rotation of the actuation operator 113 causes the two jaws to rotate in different directions. That is, the first jaw 121 rotates as much as the sum of the operation inputs of the yaw operator 112 and the actuation operator 113, and the second jaw 122 rotates as much as the difference between the operation inputs of the yaw operator 112 and the actuation operator 113. This may be expressed as the following equation:

$J1 = Y + A$ (the first jaw rotates in the same direction in both the yaw operation and the actuation operation.)

$J2 = Y - A$ (the second jaw rotates in the same direction in the yaw operation and rotates in an opposite direction in the actuation operation.)

(where Y denotes the rotation of the yaw operating pulley, and A denotes the rotation of the actuation operating pulley.)

To this end, the operating force transmitter includes a differential pulley that receives Y and A and outputs the sum (J1) of Y and A, and a differential pulley that receives Y and A and outputs the difference (J2) between Y and A, and the rotation of the output unit of each differential pulley is transmitted to each jaw of the end tool.

This will be described below in more detail.

First, the pitch operation will be described below.

As described above, when the user grips the pitch operating bar 1112 of the pitch operator 111 of the operator 110 and rotates the pitch operating bar 1112 around the pitch operating axis 1111 in the direction of the arrow OP of FIG. 6, the operator control member 115 also rotates around the pitch operating axis 1111. Then, the first jaw operating wire 135J13 wound around the operation control member 115 is pulled toward the operator 110 and moves in the direction of the arrow PJ1 of FIG. 6. At the same time, the second jaw operating wire 135J23 wound around the operation control member 115 is unwound from the operator control member 115 and moves in the direction of the arrow PJ2 of FIG. 6. Then, the end tool control member 123 connected with the first jaw operating wire 135J13 and the second jaw operating wire 135J23 rotates around the end tool pitch operating axis 1231 in the direction of an arrow EP of FIG. 6 to perform a pitch motion.

The yaw operation will be described below.

When the yaw operator 112 rotates in the direction of the arrow Y of FIG. 2, the first pulley 1121a of the yaw operator 112, the YC1 wire 135YC1 wound around the first pulley 1121a, and the first input unit 1311 of the first differential pulley 131, around which the YC1 wire 135YC1 is wound, rotate together. In this manner, when the first input unit 1311 of the first differential pulley 131 rotates, the rotating force of the differential control wire 135J11 connecting the first input unit 1311 and the output unit 1313 rotates the output unit 1313 in the direction of the arrow R1 of FIG. 4A. Then, the rotation of the output unit 1313 is transmitted to the operator control member 115 through the J12 wire 135J12 wound around the output unit 1313, to rotate the J11 pulley 115J11 (see FIG. 6) of the operator control member 115. Then, when the J11 pulley 115J11 of the operator control member 115 rotates, the first jaw operating wire 135J13 connected therewith is moved, and the first jaw 121 of the end tool 120 connected with the first jaw operating wire 135J13 rotates in the direction of the arrow YJ of FIG. 2.

Also, when the yaw operator 112 rotates in the direction of the arrow Y of FIG. 2, the second pulley 1121b of the yaw operator 112, the YC2 wire 135YC2 wound around the second pulley 1121b, and the first input unit 1321 of the second differential pulley 132, around which the YC2 wire 135YC2 is wound, rotate together therewith. In this manner, when the first input unit 1321 of the second differential pulley 132 rotates, the rotating force of the differential control wire 135J21 connecting the first input unit 1321 and the output unit 1323 rotates the output unit 1323 in the direction of the arrow R3 of FIG. 4B. Then, the rotation of the output unit 1323 is transmitted to the operator control member 115 through the J22 wire 135J22 wound around the output unit 1323, to rotate the J21 pulley 115J21 (see FIG. 6) of the operator control member 115. Then, when the J21 pulley 115J21 of the operator control member 115 rotates, the second jaw operating wire 135J23 connected therewith is moved, and the second jaw 122 of the end tool 120 connected with the second jaw operating wire 135J23 rotates in the direction of the arrow YJ of FIG. 2.

In this manner, when the yaw operator 112 is rotated in one direction, the first and second jaws 121 and 122 rotate in the same direction to perform a yaw operation. Herein, the surgical instrument 100 according to an embodiment of the present invention includes one or more differential pulleys, so that the operation of the yaw operator 112 is not accompanied by the operation of the actuation operator 113.

The actuation operation will be described below.

When the actuation operator 113 rotates in the direction of the arrow A of FIG. 2, the first pulley 1131a of the actuation operator 113, the AC1 wire 135AC1 wound around the first pulley 1131a, and the second input unit 1312 of the first differential pulley 131, around which the AC1 wire 135AC1 is wound, rotate together. Herein, since the AC1 wire 135AC1 is twisted one time, the rotating force of the actuation operator 113 is reversed and transmitted to the first differential pulley 131. In this manner, when the second input unit 1312 of the first differential pulley 131 rotates, the rotating force of the differential control wire 135J11 connecting the second input unit 1312 and the output unit 1313 rotates the output unit 1313 in a direction opposite to the direction of the arrow R2 of FIG. 4A. Then, the rotation of the output unit 1313 is transmitted to the operator control member 115 through the J12 wire 135J12 wound around the output unit 1313, to rotate the J11 pulley 115J11 (see FIG. 6) of the operator control member 115. Then, when the J11 pulley 115J11 of the operator control member 115 rotates, the first jaw operating wire 135J13 connected therewith is rotated, and the first jaw 121 of the end tool 120 that is connected with the first jaw operating wire 135J13 rotates in the direction of the arrow YJ of FIG. 2.

Also, when the actuation operator 113 rotates in the direction of the arrow A of FIG. 2, the second pulley 1131b of the actuation operator 113, the AC2 wire 135AC2 wound around the second pulley 1131b, and the second input unit 1322 of the second differential pulley 132, around which the AC2 wire 135AC2 is wound, rotate together. In this manner, when the second input unit 1322 of the second differential pulley 132 rotates, the rotating force of the differential control wire 135J21 connecting the second input unit 1322 and the output unit 1323 rotates the output unit 1323 in the direction of the arrow R4 of FIG. 4A. Then, the rotation of the output unit 1323 is transmitted to the operator control member 115 through the J22 wire 135J22 wound around the output unit 1323, to rotate the J21 pulley 115J21 (see FIG. 6) of the operator control member 115. Then, when the J21 pulley 115J21 of the operator control member 115 rotates, the second jaw operating wire 135J23 connected therewith is rotated, and the second jaw 122 of the end tool 120 that is connected with the second jaw operating wire 135J23 rotates in a direction opposite to the direction of the arrow YJ of FIG. 2.

In this manner, when the actuation operator 113 is rotated in one direction, the first and second jaws 121 and 122 rotate in opposite directions to perform an actuation operation. Herein, the surgical instrument 100 according to an embodiment of the present invention includes one or more differential pulleys, so that the operation of the actuation operator 113 is not accompanied by the operation of the yaw operator 112.

Thus, according to the present invention, a surgical instrument performing an output operation of an end tool by the independent inputs of a pitch operator, a yaw operator, and an actuation operator may be implemented solely by a mechanical configuration without using motors, electronic control, or software. That is, since the pitch operation, the yaw operation, and the actuation operation, which affect each other, are separated from each other solely by a mechanism, the configuration of the surgical instrument may be significantly simplified.

Also, the rotating force of the operator 110 may be transmitted to the end tool 120 solely by a minimum wire and pulley structure. In particular, according to the present invention, since the operation direction of the operator 110 is intuitively identical to the operation direction of the end tool 120, the convenience of a surgical operator may be improved and the accuracy of a surgical operation may be improved. In addition, since the end tool 120 includes only two wires, namely, the first jaw operating wire 135J13 and the second jaw operating wire 135J23, the pitch operation, the yaw operation, and the actuation operation of the end tool 120 may be conveniently performed. Furthermore, since the end tool control member 123 and the operator control member 115 are disposed symmetrical to each other (i.e., mirrored) about the YZ plane of FIG. 1, the pitch operation may be conveniently performed. That is, the pitch operation may be performed regardless of the yaw operation and the actuation operation.

Modification of End Tool and Operator Control Member of First Embodiment

Figure 7:
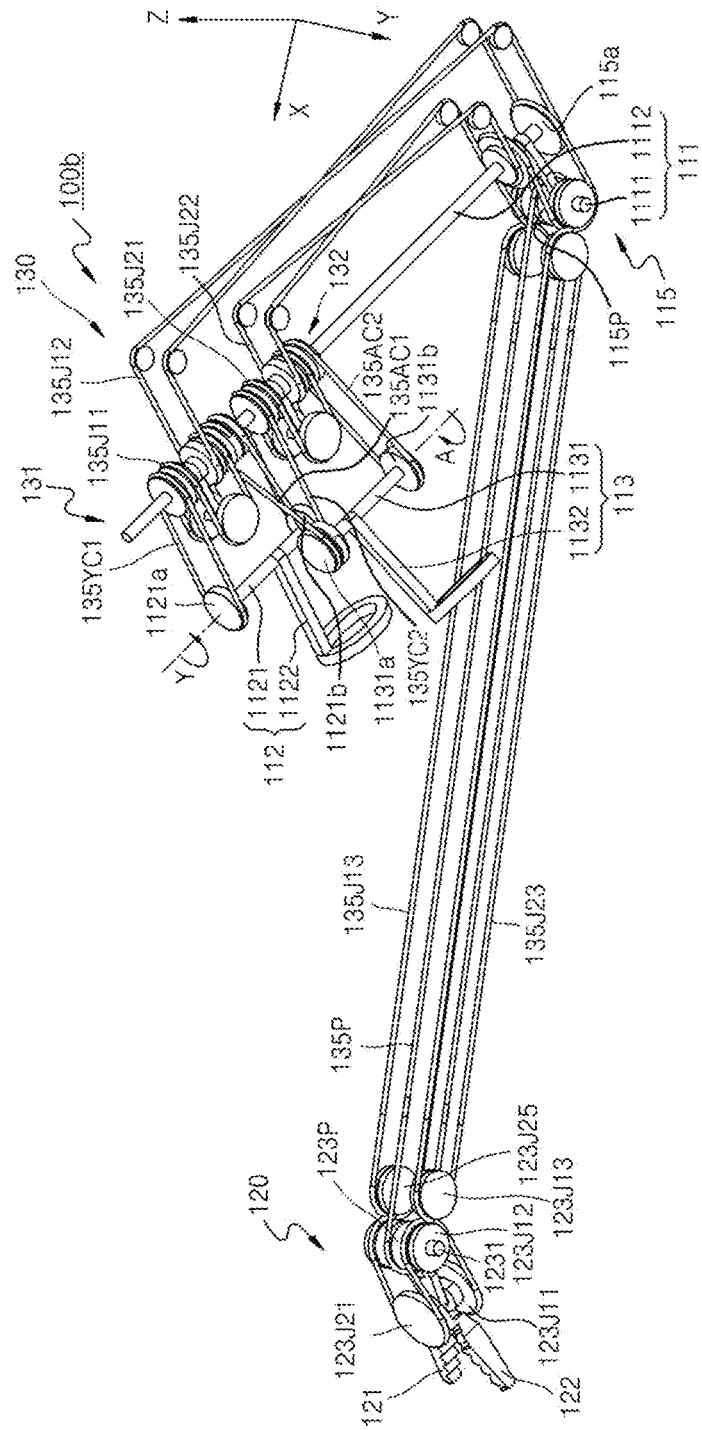
FIG. 7 is a view illustrating a surgical instrument according to a modification of the end tool of the first embodiment illustrated in FIG. 1.
Figure 8:
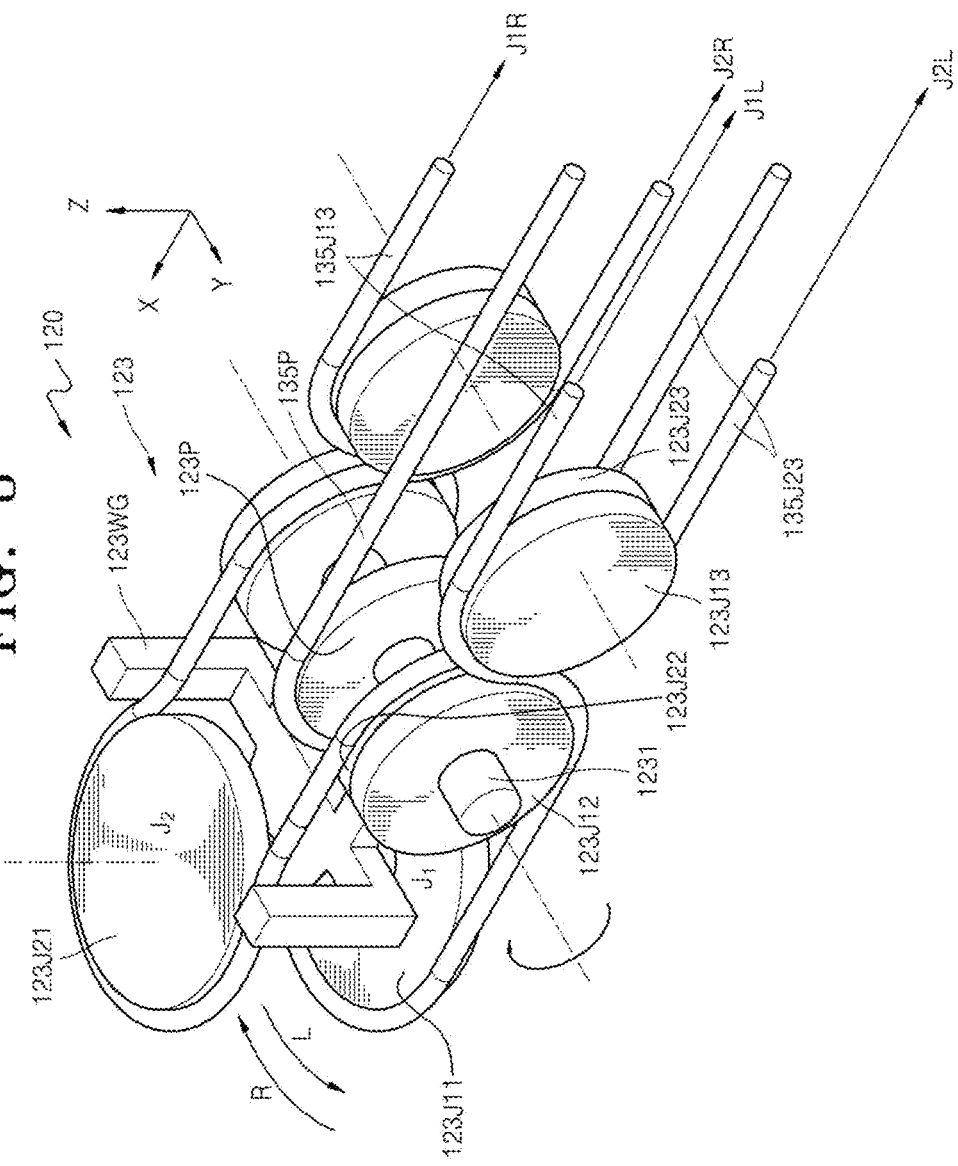
FIG. 8 is a detailed view of an end tool of the surgical instrument of FIG. 7.

FIG. 7 is a view illustrating a surgical instrument 100b according to a modification of the end tool 120 and the operator control member 115 of the first embodiment illustrated in FIG. 1, and FIG. 8 is a detailed view of the end tool 120 of the surgical instrument 100b of FIG. 7. Since the surgical instrument 100b according to a modification of the end tool 120 of the first embodiment of the present invention is similar to the surgical instrument 100 according to the first embodiment of the present invention and is different from the surgical instrument 100 in terms of the configuration of the end tool 120, the configuration of the end tool 120 will be mainly described below.

Referring to FIGS. 7 and 8, the surgical instrument 100b according to a modification of the end tool 120 of the first embodiment of the present invention includes an operator 110, an end tool 120, an operating force transmitter 130, and a connector (not illustrated).

The end tool 120 includes an end tool control member 123, and the end tool control member 123 includes a J11 pulley 123J11, a J12 pulley 123J12, a J13 pulley 123J13, a J14 pulley 123J14, and a J15 pulley 123J15 that are related to the rotation motion of the first jaw 121, and a J21 pulley 123J21, a J22 pulley 123J22, a J23 pulley 123J23, a J24 pulley 123J24, and a J25 pulley 123J25 that are related to the rotation motion of the second jaw 122. Herein, the first jaw 121, the J11 pulley 123J11, the J12 pulley 123J12, the J14 pulley 123J14, the second jaw 122, the J21 pulley 123J21, the J22 pulley 123J22, and the J24 pulley 123J24 may be formed to rotate around the end tool pitch operating axis 1231.

The surgical instrument 100b is different from the surgical instrument 100 of the first embodiment in that the end tool 120 further includes a pitch pulley 123P, the operator 110 further includes a pitch pulley 115P, and the operating force transmitter 130 further includes a pitch wire 135P. In detail, the pitch pulley 123P of the end tool 120 may be integrated with the end tool pitch operating axis 1231 to rotate along with the end tool pitch operating axis 1231. The pitch pulley 115P of the operator 110 may be integrated with the pitch operating axis 1111 to rotate along with the pitch operating axis 1111. Also, the pitch wire 135P may connect the pitch pulley 123P of the end tool 120 and the pitch pulley 115P of the operator 110.

Thus, when the user grips the pitch operating bar 1112 of the pitch operator 111 and rotates the pitch operating bar 1112 around the pitch operating axis 1111, the pitch operating axis 1111 connected with the pitch operating bar 1112 and the pitch pulley 115P connected therewith rotate, the rotation of the pitch pulley 115P is transmitted to the pitch pulley 123P of the end tool 120 through the pitch wire 135P, and the pitch pulley 123P also rotates together therewith. Consequently, the end tool 120 rotates to perform a pitch motion.

In the surgical instrument 100 of the first embodiment, since the pitch operation of the surgical instrument 100 is performed solely by the first jaw operating wire 135J13 and the second jaw operating wire 135J23, when the first jaw operating wire 135J13 and the second jaw operating wire 135J23 are extended due to long-term use, the pitch operation may not be performed properly. In addition, the operating force of the pitch operator 111 may not be properly transmitted to the end tool 120. In order to solve such problems, the surgical instrument 100b according to a modification of the end tool 120 of the first embodiment of the present invention further includes the pitch pulley 123P of the end tool 120, the pitch pulley 115P of the operator 110, and the pitch wire 135P of the operating force transmitter 130 to more perfectly transmit the operating force of the pitch operation of the pitch operator 111 to the end tool 120, thereby improving operational reliability.

The end tool 120 of the surgical instrument 100b may further include a wire guide 123WG. In detail, the wire guide 123WG may be formed to protrude in the Z-axis direction in the end tool control member 123. The wire guide 123WG may be formed to contact the first jaw operating wire 135J13 and guide a rotating path of the first jaw operating wire 135J13, thereby making it possible to prevent the first jaw operating wire 135J13 from being removed from the J12 pulley 115J12 and the J14 pulley 115J14.

In this manner, in order to increase the reliability of the pitch operation, the first embodiment may be modified such that pulleys are added in the end tool and operator and wires are added, and may be modified such that a wire guide is also added in the end tool.

Also, the above modification of the end tool of the first embodiment of the present invention may also be applied to various other modifications and embodiments that will be described later.

Although FIG. 7 illustrates that the pitch operation is performed by the wires and pulleys, the present invention is not limited thereto. That is, various structures, in which the end tool control member 123 and the operator control member 115 may be connected symmetrically, may be applied to the present invention. For example, a four-bar link may be used to connect the end tool control member 123 and the operator control member 115. That is, when a long side of the four-bar link functions as the jaw operating wires 135J13 and 135J23 and the end tool control member 123 and the operator control member 115 are connected to a central portion of a short side of the four-bar link, the end tool control member 123 and the operator control member 115 may be disposed symmetrical to each other (i.e., mirrored) about the YZ plane of FIG. 1.

Modification of Operator of First Embodiment

Figure 9:
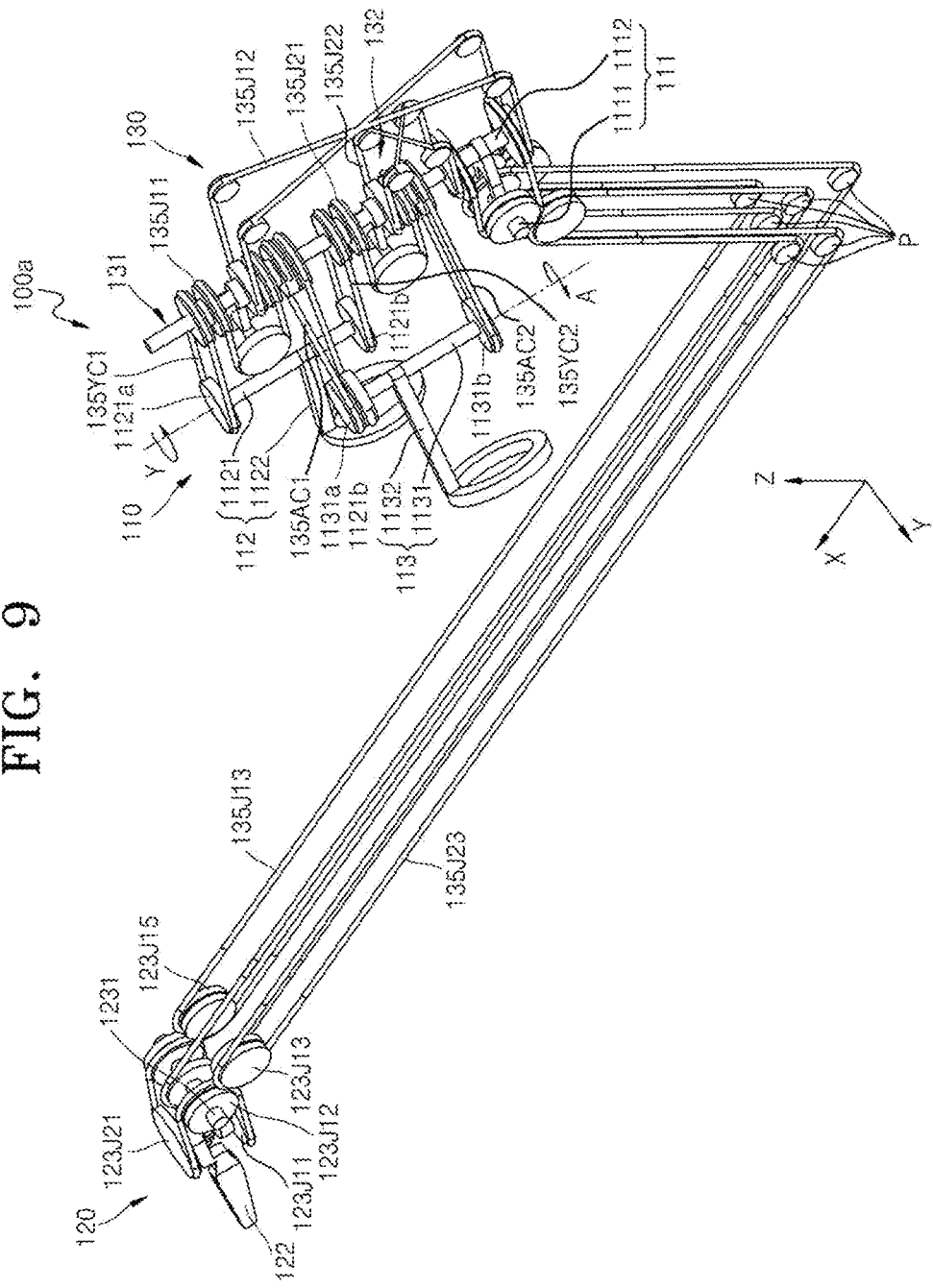
FIG. 9 is a view illustrating a surgical instrument according to a modification of the operator of the first embodiment illustrated in FIG. 1.

FIG. 9 is a view illustrating a surgical instrument 100a according to a modification of the operator 110 of the first embodiment illustrated in FIG. 1. Since the surgical instrument 100a according to a modification of the operator 110 of the first embodiment of the present invention is similar to the surgical instrument 100 according to the first embodiment of the present invention and is different from the surgical instrument 100 in terms of the position of the operator 110, the configuration of the operator 110 will be mainly described below.

Referring to FIG. 9, the surgical instrument 100a according to a modification of the operator 110 of the first embodiment of the present invention includes an operator 110, an end tool 120, an operating force transmitter 130, and a connector (not illustrated).

In the surgical instrument 100a, the pitch operator 111 and the end tool 120 are not formed on the same axis (X axis), but are formed on different axes. That is, additional direction-changing pulleys P are further provided between the first jaw operating wire 135J13 and the second jaw operating wire 135J23, and the first jaw operating wire 135J13 and the second jaw operating wire 135J23 are bent one time. Accordingly, the pitch operator 111 and the end tool 120 are not formed on the same axis (X axis), and the pitch operator 111 may be formed adjacent to the yaw operator 112 and the actuation operator 113.

In the surgical instrument 100a, the pitch operator 111 may be formed adjacent to the yaw operator 112 and the actuation operator 113. In this manner, the relative positions of the pitch operator 111, the yaw operator 112, and the actuation operator 113 may be modified within the scope of improving user convenience.

Also, by forming the connector to be nonlinear, the relative positions of the end tool, the pitch operator, the yaw operator, and the actuation operator may be modified variously.

Also, the above modification of the operator of the first embodiment of the present invention may also be applied to various other modifications and embodiments.

Modification of Operator Control Member of First Embodiment

Figure 10:
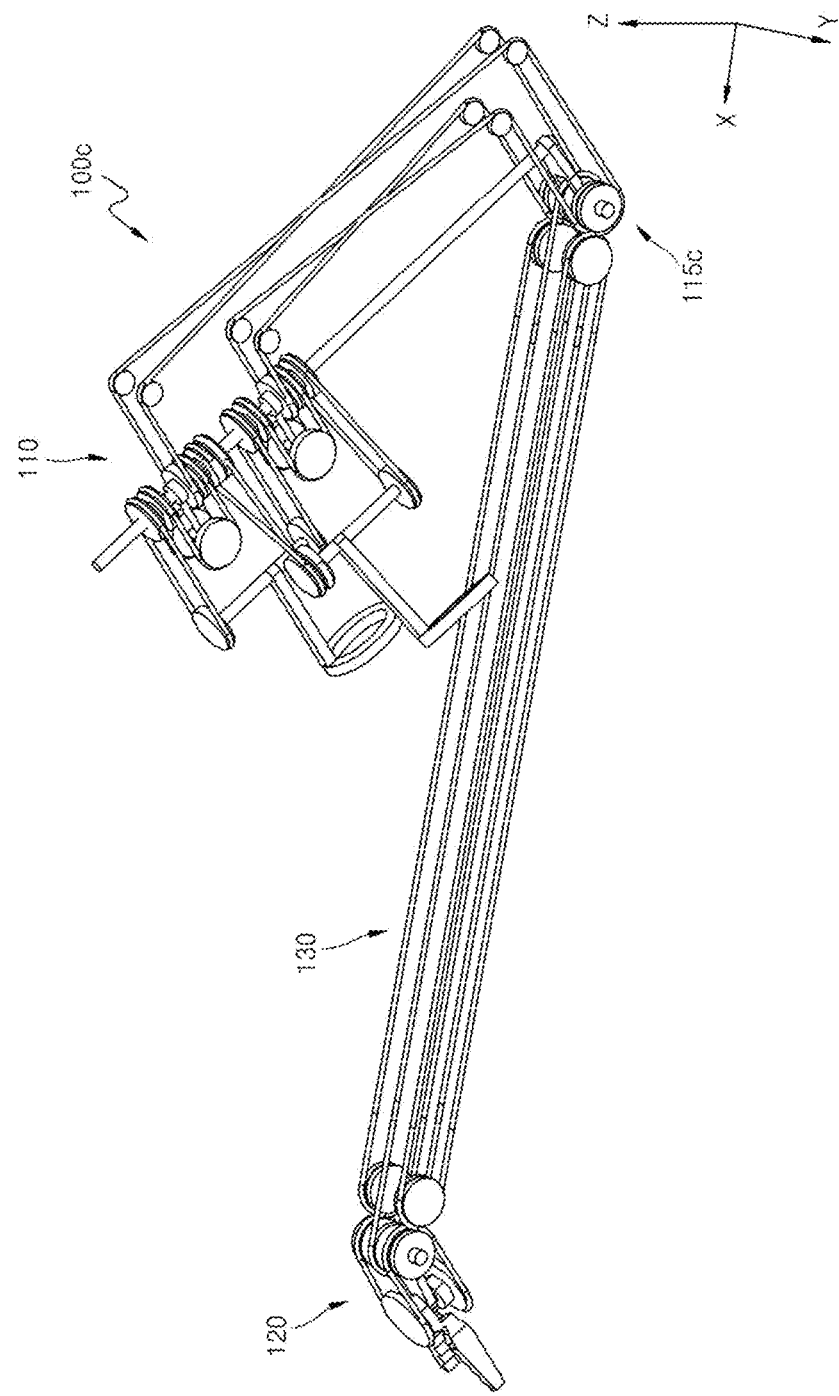
FIG. 10 is a view illustrating a surgical instrument according to a modification of an operator control member of the first embodiment illustrated in FIG. 1.

FIG. 10 is a view illustrating a surgical instrument 100c according to a modification of the operator control member 115 of the first embodiment illustrated in FIG. 1. Since the surgical instrument 100c according to a modification of the operator control member 115 of the first embodiment of the present invention is similar to the surgical instrument 100 according to the first embodiment of the present invention and is different from the surgical instrument 100 in terms of the configuration of the operator control member, the configuration of the operator control member will be mainly described below.

Referring to FIG. 10, the surgical instrument 100c according to a modification of the operator control member 115 of the first embodiment of the present invention includes an operator 110, an end tool 120, an operating force transmitter 130, and a connector (not illustrated). Also, the operator 110 includes an operator control member 115c, and the operator control member 115c does not include the relay pulley 115a (see FIG. 2), unlike in the surgical instrument 100 of the first embodiment of the present invention illustrated in FIG. 2. Since a relay pulley is removed from the operator control member 115c, the configuration of the operator control member 115c may be simplified.

In this manner, a relay pulley may be removed from the operator 110.

Also, the above modification of the operator control member 115 of the first embodiment of the present invention may also be applied to various other modifications and embodiments.

Figure 11:
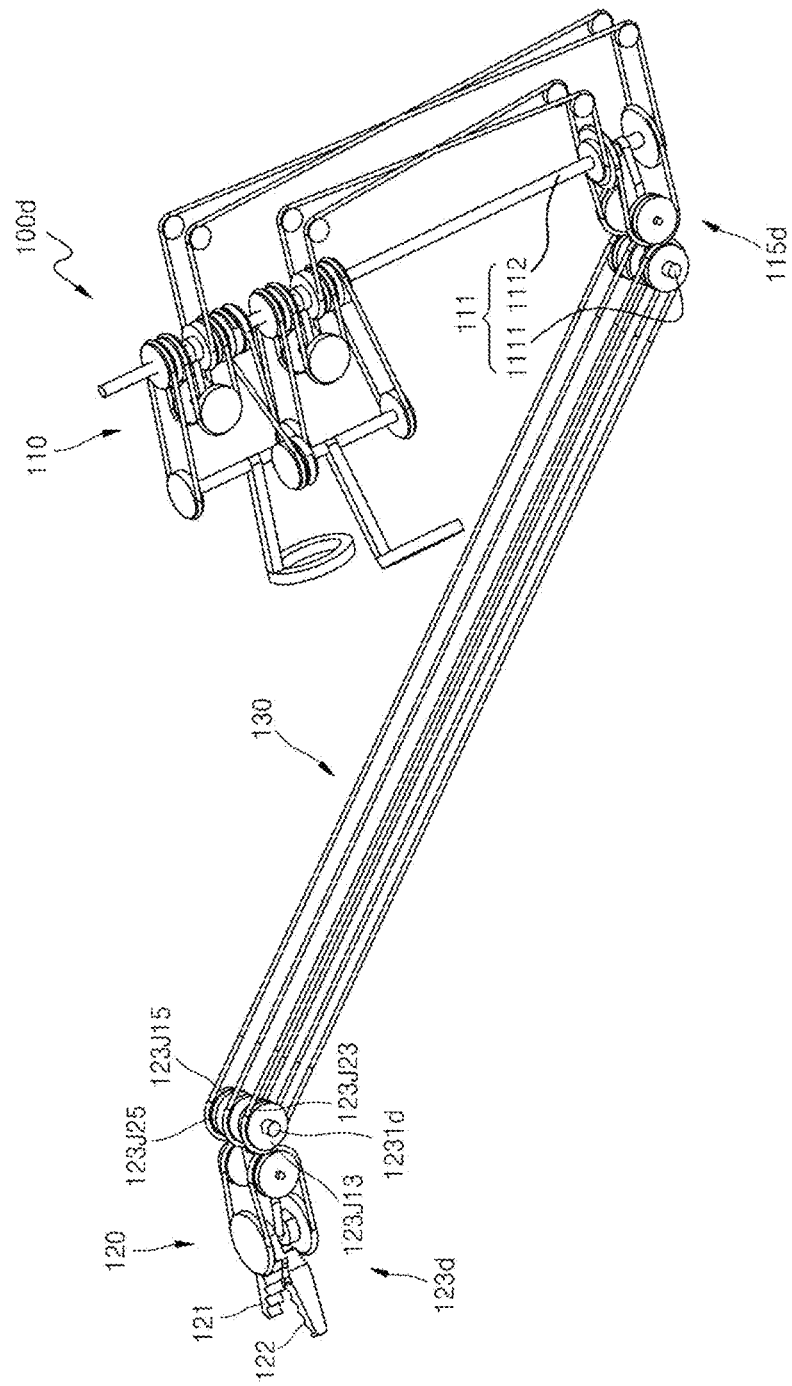
FIG. 11 is a view illustrating a surgical instrument according to a modification of an end tool control member of the first embodiment illustrated in FIG. 1.

<Modification of End Tool Control Member and Operator Control Member of First Embodiment FIG. 11 is a view illustrating a surgical instrument 100d according to a modification of the end tool control member 123 and the operator control member 115 of the first embodiment illustrated in FIG. 1. Since the surgical instrument 100d according to a modification of the end tool control member 123 and the operator control member 115 of the first embodiment of the present invention is similar to the surgical instrument 100 according to the first embodiment of the present invention and is different from the surgical instrument 100 in terms of the configuration of the end tool control member and the operator control member, the configurations of the end tool control member and the operator control member will be mainly described below.

Referring to FIG. 11, the surgical instrument 100d according to a modification of the end tool control member 123 and the operator control member 115 of the first embodiment of the present invention includes an operator 110, an end tool 120, an operating force transmitter 130, and a connector (not illustrated). Herein, the operator 110 includes an operator control member 115d, and the end tool 120 includes an end tool control member 123d.

This will be described below in more detail.

In the surgical instrument 100 according to the first embodiment of the present invention illustrated in FIGS. 2 and 5, the end tool pitch operating axis 1231 is formed adjacent to the first jaw 121 and the second jaw 122. That is, the end tool pitch operating axis 1231 functions as the rotating axis of the J12 pulley 123J12, the J14 pulley 123J14, the J22 pulley 123J22, and the J24 pulley 123J24, and the first jaw 121 and the second jaw 122 rotate around the end tool pitch operating axis 1231.

However, as illustrated in FIG. 11, in the surgical instrument 100d according to a modification of the end tool control member 123 of the first embodiment of the present invention, an end tool pitch operating axis 1231d is formed distant from the first jaw 121 and the second jaw 122. That is, the end tool pitch operating axis 1231d functions as the rotating axis of the J13 pulley 123J13, the J15 pulley 123J15, the J23 pulley 123J23, and the J25 pulley 123J25, so that the J11 pulley 123J11, the J12 pulley 123J12, the J13 pulley 123J13, the J14 pulley 123J14, and the J15 pulley 123J15 related to the rotation motion of the first jaw 121 and the J21 pulley 123J21, the J22 pulley 123J22, the J23 pulley 123J23, the J24 pulley 123J24, and the J25 pulley 123J25 related to the rotation motion of the second jaw 122 rotate around the end tool pitch operating axis 1231d. In this manner, by moving the position of the end tool pitch operating axis 1231d, the rotation radius of the end tool 120 and rotating elements may be modified. Likewise, the operating axis of the operator control member 115d may also be formed distant from the relay pulley 115a (see FIG. 2).

Also, the above modification of the end tool control member 123 and the operator control member 115 of the first embodiment of the present invention may also be applied to various other modifications and embodiments.

Figure 12:
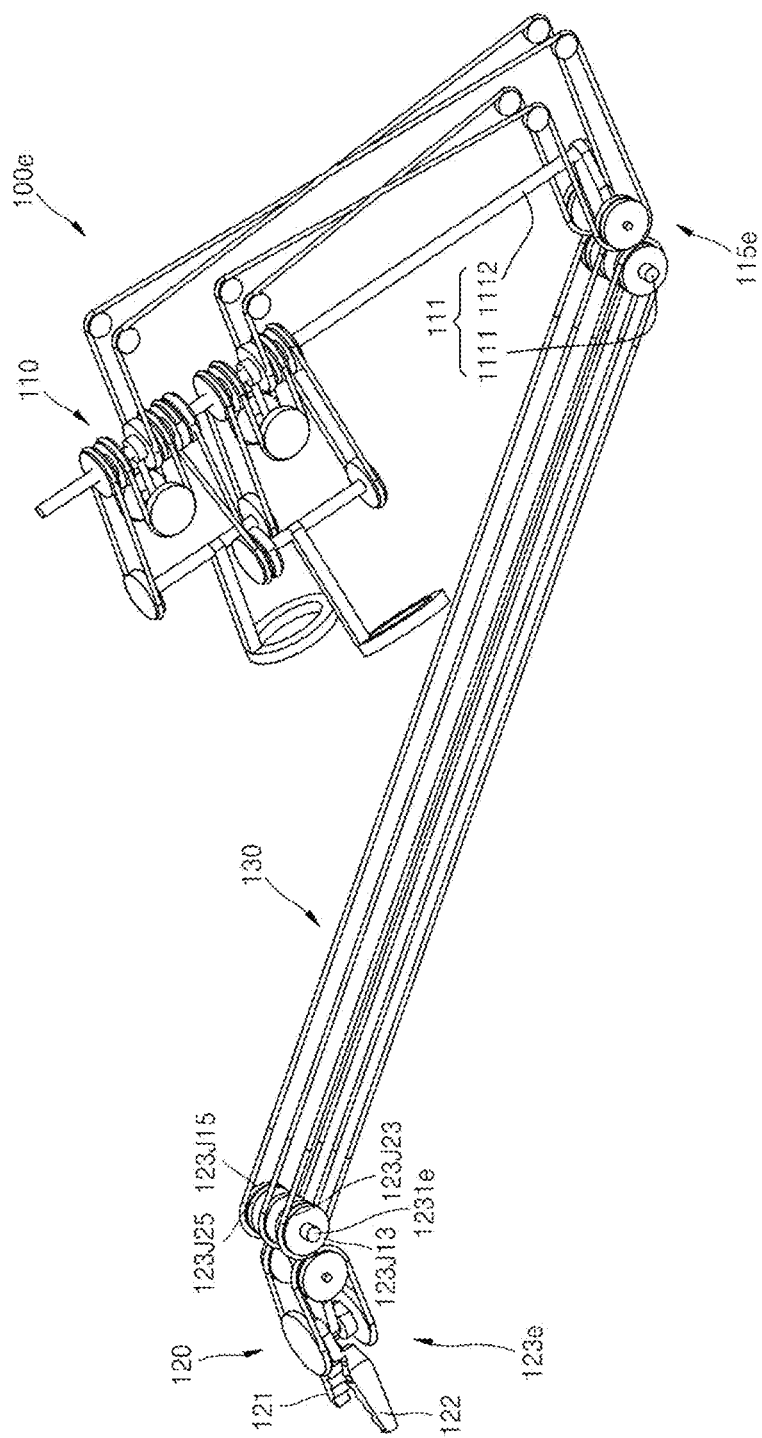
FIG. 12 is a view illustrating a surgical instrument according to a modification of the end tool control member and the operator control member of the first embodiment illustrated in FIG. 1.

Modification of End Tool Control Member and Operator Control Member of First Embodiment FIG. 12 is a view illustrating a surgical instrument 100e according to a modification of the end tool control member 123 and the operator control member 115 of the first embodiment illustrated in FIG. 1. Since the surgical instrument 100e according to a modification of the end tool control member 123 and the operator control member 115 of the first embodiment of the present invention is similar to the surgical instrument 100 according to the first embodiment of the present invention and is different from the surgical instrument 100 in terms of the configuration of the end tool control member 123 and the operator control member 115, the configurations of the end tool control member and the operator control member will be mainly described below.

Referring to FIG. 12, the surgical instrument 100e according to a modification of the end tool control member 123 and the operator control member 115 of the first embodiment of the present invention includes an operator 110, an end tool 120, an operating force transmitter 130, and a connector (not illustrated). Herein, the operator 110 includes an operator control member 115e, and the end tool 120 includes an end tool control member 123c.

As illustrated in FIG. 12, the surgical instrument 100e according to a modification of the end tool control member 123 of the first embodiment of the present invention is an example of the combination of the structure of FIG. 10 in which a relay pulley is not provided and the structure of FIG. 11 in which an axis is disposed therebehind, and corresponds to the structure in which the relay pulley 115a (see FIG. 2) is removed from the surgical instrument 100d illustrated in FIG. 11. Since a relay pulley is removed from the operator control member 115e, the configuration of the operator control member 115e may be simplified.

Also, the above modification of the end tool control member 123 and the operator control member 115 of the first embodiment of the present invention may also be applied to various other modifications and embodiments.

Figure 13:
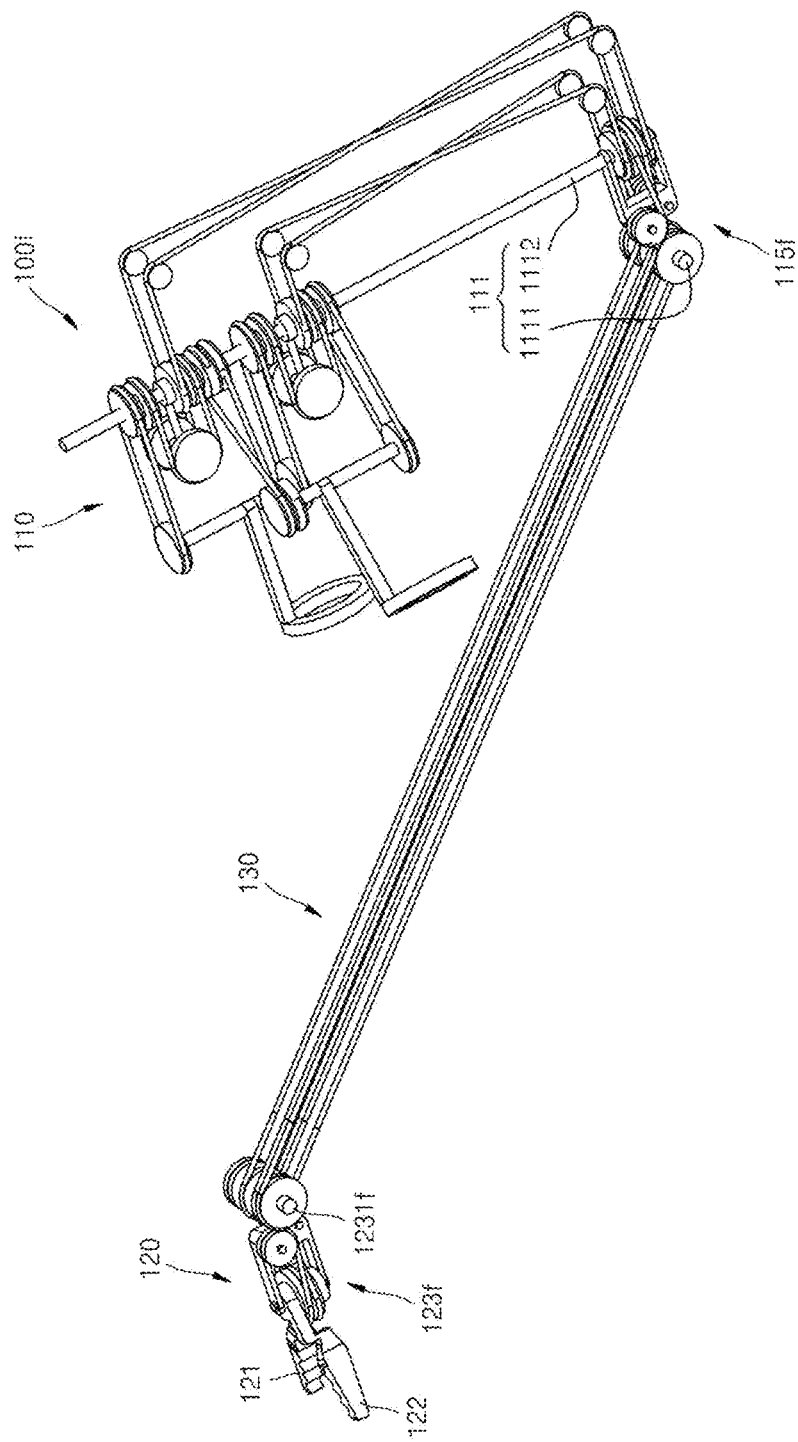
FIG. 13 is a view illustrating a surgical instrument according to another modification of the end tool control member of the first embodiment illustrated in FIG. 1.
Figure 14:
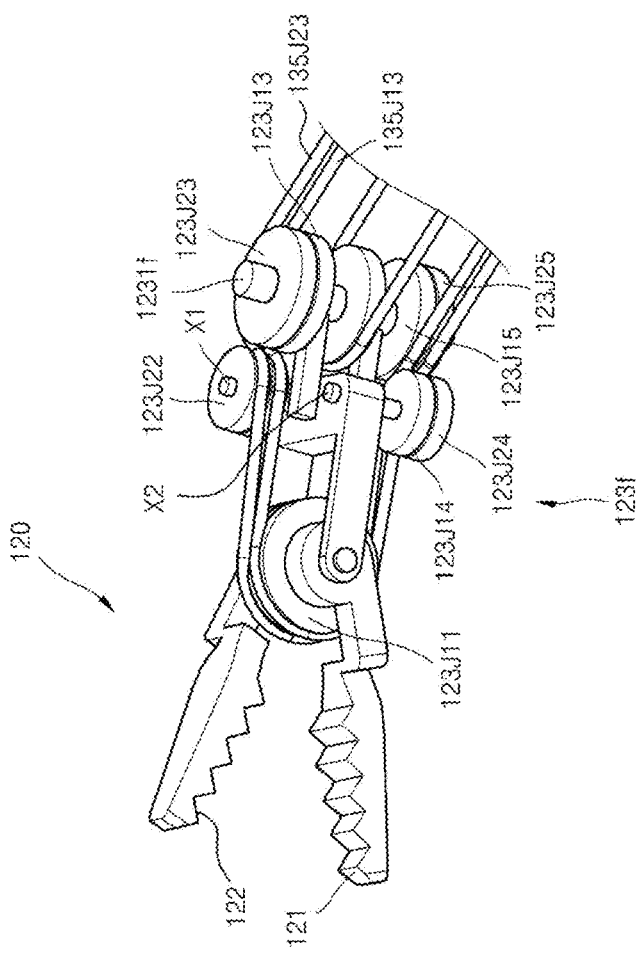
FIG. 14 is a bottom perspective view of the end tool control member of FIG. 13.

Another Modification of End Tool Control Member and Operator Control Member of First Embodiment FIG. 13 is a view illustrating a surgical instrument 100f according to another modification of the end tool control member 123 and the operator control member 115 of the first embodiment illustrated in FIG. 1, and FIG. 14 is a bottom perspective view of an end tool control member 123f of FIG. 13. Since the surgical instrument 100f according to a modification of the end tool control member 123 and the operator control member 115 of the first embodiment of the present invention is similar to the surgical instrument 100 according to the first embodiment of the present invention and is different from the surgical instrument 100 in terms of the configuration of the end tool control member and the operator control member, the configurations of the end tool control member and the operator control member will be mainly described below. That is, an end tool control member that is different in form from the end tool control member 123 illustrated in FIGS. 5 and 8 is used in this modification.

Referring to FIGS. 13 and 14, the surgical instrument 100f according to a modification of the end tool control member 123 and the operator control member 115 of the first embodiment of the present invention includes an operator 110, an end tool 120, an operating force transmitter 130, and a connector (not illustrated). Herein, the end tool 120 includes the end tool control member 123f. The end tool control member 123f includes a J11 pulley 123J11, a J12 pulley 123J12, a J13 pulley 123J13, a J14 pulley 123J14, and a J15 pulley 123J15 that are related to the rotation motion of the first jaw 121, and a J21 pulley 123J21, a J22 pulley 123J22, a J23 pulley 123J23, a J24 pulley 123J24, and a J25 pulley 123J25 that are related to the rotation motion of the second jaw 122. Herein, the J13 pulley 123J13, the J15 pulley 123J15, the J23 pulley 123J23, and the J25 pulley 123J25 may be formed to rotate around an end tool pitch operating axis 1231f.

Herein, the surgical instrument 100f of this modification is different from the surgical instrument 100 illustrated in FIG. 5 or 8 in terms of the winding mode of arranged pulleys. That is, at least a portion of the first jaw operating wire 135J13 contacts the J13 pulley 123J13, the J12 pulley 123J12, the J11 pulley 123J11, the J14 pulley 123J14, and the J15 pulley 123J15, so that the first jaw operating wire 135J13 may move along the pulleys while rotating the pulleys. In this case, in the surgical instrument 100 illustrated in FIG. 5, the first jaw operating wire 135J13 entering at the upper portion of the J13 pulley 123J13 exits through the upper portion of the J15 pulley 123J15. However, in the surgical instrument 100f of this modification, the first jaw operating wire 135J13 entering at the upper portion of the J13 pulley 123J13 exits through the lower portion of the J15 pulley 123J15.

Likewise, at least a portion of the second jaw operating wire 135J23 contacts the J23 pulley 123J23, the J22 pulley 123J22, the J21 pulley 123J21, the J24 pulley 123J24, and the J25 pulley 123J25, so that the second jaw operating wire 135J23 may move along the pulleys while rotating the pulleys. In the surgical instrument 100f of this modification, the second jaw operating wire 135J23 entering at the upper portion of the J23 pulley 123J23 exits through the lower portion of the J25 pulley 123J25.

To this end, the arrangement of pulleys may also be modified. That is, the rotating axis (X1) of the J12 pulley 123J12 and the J22 pulley 123J22 and the rotating axis (X2) of the J14 pulley 123J14 and the J24 pulley 123J24 may not be located on the same line so that the first jaw operating wire 135J13 entering at the upper portion of the J13 pulley 123J13 exits through the lower portion of the J15 pulley 123J15, as illustrated in FIGS. 13 and 14. That is, the rotating axis (X1) of the J12 pulley 123J12 and the J22 pulley 123J22 may be formed over the end tool pitch operating axis 1231f, while the rotating axis (X2) of the J14 pulley 123J14 and the J24 pulley 123J24 may be formed under the end tool pitch operating axis 1231f.

In addition, due to a difference in the wire winding mode, there may be a difference in the pitch operating mode. In the surgical instrument 100 illustrated in FIG. 5, all of the pitch operation, the yaw operation, and the actuation operation may be performed by two wires, namely, the first jaw operating wire 134J13 and the second jaw operating wire 134J23. However, in the surgical instrument 100f of this modification, a wire for performing the pitch operation is additionally provided, in addition to the first jaw operating wire 134J13 and the second jaw operating wire 134J23 for performing the yaw operation and the actuation operation.

Also, the above modification of the end tool control member 123 and the operator control member 115 of the first embodiment of the present invention may also be applied to various other modifications and embodiments.

<First Modification of Differential Pulley> (D1)

Figure 15:
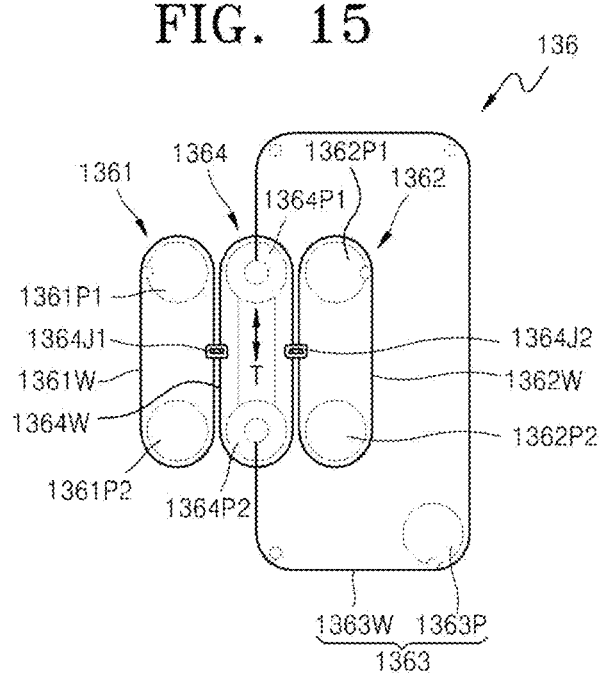
FIG. 15 is a view illustrating a first modification of a differential pulley of the surgical instrument illustrated in FIG. 2.
Figure 16:
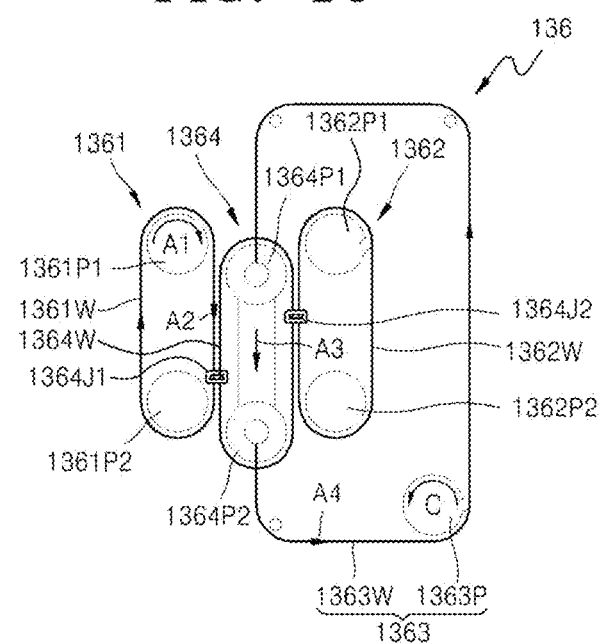
FIGS. 16 and 17 are views illustrating an operation of the first modification of the differential pulley illustrated in FIG. 15.
Figure 17:
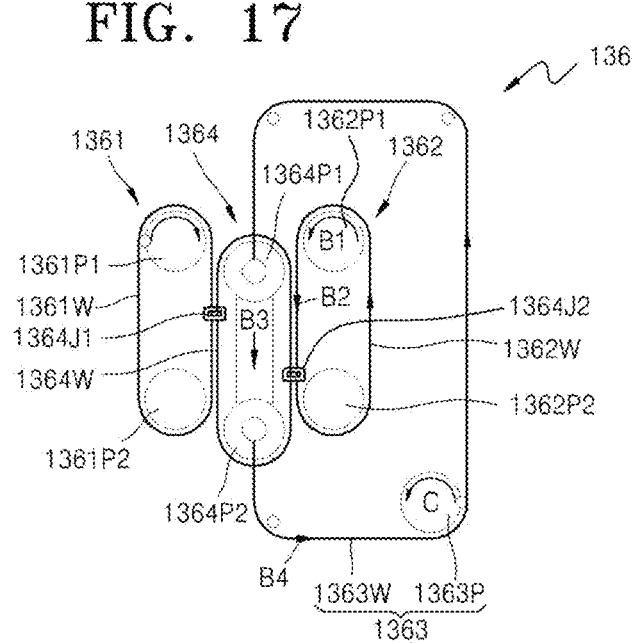

FIG. 15 is a view illustrating a first modification of the differential pulley of the surgical instrument 100 illustrated in FIG. 2, and FIGS. 16 and 17 are views illustrating an operation of the first modification of a differential pulley illustrated in FIG. 15.

As described above, the differential pulley according to the present invention includes two or more input units and one output unit, receives an input of rotating forces from the two or more input units, extracts a desired rotating force from the sum of (or the difference between) the input rotating forces, and outputs the desired rotating force through the output unit.

Referring to FIG. 15, the first modification of the differential pulley of the surgical instrument includes a first input unit 1361, a second input unit 1362, an output unit 1363, and a differential control member 1364.

The first input unit 1361 includes a first pulley 1361P1, a second pulley 1361P2, and a first input wire 1361W. The first pulley 1361P1 and the second pulley 1361P2 are connected by the first input wire 1361W to rotate together.

The second input unit 1362 includes a first pulley 1362P1, a second pulley 1362P2, and a second input wire 1362W. The first pulley 1362P1 and the second pulley 1362P2 are connected by the second input wire 1362W to rotate together.

The output unit 1363 includes an output pulley 1363P and an output wire 1363W. The output pulley 1363P and the differential control member 1364 are connected by the output wire 1363W. When the differential control member 1364 translates, the output pulley 1363P connected with the differential control member 1364 by the output wire 1363W rotates.

The differential control member 1364 includes a first pulley 1364P1, a second pulley 1364P2, and a differential control wire 1364W. In addition, the differential control member 1364 includes a first differential joint 1364J1 and a second differential joint 1364J2. The first pulley 1364P1 and the second pulley 1364P2 are connected by the differential control wire 1364W to rotate together. The differential control member 1364 may translate in the direction of an arrow T of FIG. 15. For example, the differential control member 1364 may be installed on a guide rail (not illustrated), and may translate along the guide rail in the direction of the arrow T of FIG. 15.

The first differential joint 1364J1 may be coupled to the first input wire 1361W and the differential control wire 1364W to transmit a rotation of the first input wire 1361W to the differential control wire 1364W. The second differential joint 1364J2 may be coupled to the second input wire 1362W and the differential control wire 1364W to transmit a rotation of the second input wire 1362W to the differential control wire 1364W.

An operation of the first modification of the differential pulley will be described below.

First, a case where the first input unit 1361 rotates will be described below.

Referring to FIGS. 15 and 16, when the first pulley 1361P1 of the first input unit 1361 rotates in the direction of an arrow A1 of FIG. 16, the first input wire 1361W connected therewith moves along the first pulley 1361P1 in the direction of an arrow A2 of FIG. 16. Also, since the first input wire 1361W and the differential control wire 1364W are coupled to the first differential joint 1364J1, when the first input wire 1361W moves in the direction of the arrow A2 of FIG. 16, the first differential joint 1364J1 connected therewith also moves in the direction of the arrow A2. In this case, when the second input unit 1362 is fixed due to no rotation input, the second differential joint 1364J2 is also fixed. Thus, the differential control member 1364 translates in the direction of an arrow A3 as much as the movement of the first differential joint 1364J1, the first pulley 1364P1, the second pulley 1364P2, and the differential control wire 1364W also move together as much, and the first pulley 1364P1 and the second pulley 1364P2 rotate in the counterclockwise direction. When the differential control member 1364 moves in the direction of the arrow A3, the output wire 1363W connected therewith moves in the direction of an arrow A4 and thus the output pulley 1363P connected with the output wire 1363W rotates in the direction of an arrow C.

According to this configuration of the present invention, the rotation of the first input unit 1361 does not affect the second input unit 1362 and may be transmitted only to the output unit 1363 to rotate the output pulley 1363P.

A case where the second input unit 1362 rotates will be described below.

Referring to FIGS. 15 and 17, when the first pulley 1362P1 of the second input unit 1362 rotates in the direction of an arrow B1 of FIG. 17, the second input wire 1362W connected therewith moves along the first pulley 1362P1 in the direction of an arrow B2 of FIG. 17. Also, since the second input wire 1362W and the differential control wire 1364W are coupled to the second differential joint 1364J2, when the second input wire 1362W moves in the direction of the arrow B2 of FIG. 17, the second differential joint 1364J2 connected therewith also moves in the direction of the arrow B2. In this case, when the first input unit 1361 is fixed due to no rotation input, the first differential joint 1364J1 is also fixed. Thus, the differential control member 1364 translates in the direction of an arrow B3 as much as the movement of the second differential joint 1364J2, the first pulley 1364P1, the second pulley 1364P2, and the differential control wire 1364W also move together as much, and the first pulley 1364P1 and the second pulley 1364P2 rotate in the clockwise direction. When the differential control member 1364 moves in the direction of the arrow B3, the output wire 1363W connected therewith moves in the direction of an arrow B4 and thus the output pulley 1363P connected with the output wire 1363W rotates in the direction of the arrow C.

According to this configuration of the present invention, the rotation of the second input unit 1362 does not affect the first input unit 1361 and may be transmitted only to the output unit 1363 to rotate the output pulley 1363P.

A case where the first input unit 1361 and the second input unit 1362 rotate together will be described below.

When the first pulley 1361P1 of the first input unit 1361 rotates in the clockwise direction, the output pulley 1363P of the output unit 1363 rotates in the counterclockwise direction; and when the first pulley 1362P1 of the second input unit 1362 rotates in the counterclockwise direction, the output pulley 1363P of the output unit 1363 rotates in the counterclockwise direction. Thus, when the first pulley 1361P1 of the first input unit 1361 and the second pulley 1362P1 of the second input unit 1362 rotate in opposite directions, the output pulley 1363P of the output unit 1363 rotates as much as the sum of the two rotating forces. On the other hand, when the first pulley 1361P1 of the first input unit 1361 and the second pulley 1362P1 of the second input unit 1362 rotate in the same direction, the output pulley 1363P of the output unit 1363 rotates as much as the difference between the two rotating forces.

Thus, according to the present invention, when only one of the two or more input units rotates, only the output unit may be rotated without other input units rotating. Also, when the two or more input units rotate together, a single rotating force equal to the sum of (or the difference between) the rotating forces of the two input units may be output through the output unit.

The differential pulley of the first modification is a modification of the differential pulley illustrated in FIGS. 4A and 4B, and an example of applying the differential pulley of the first modification to the surgical instrument will not be described herein.

<Second Modification of Differential Pulley> (D2)

Figure 18:
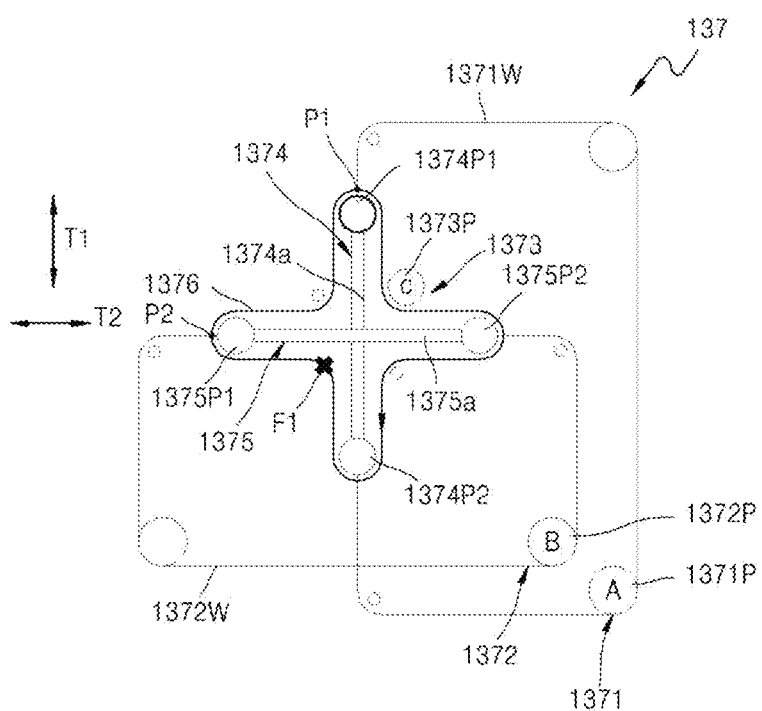
FIG. 18 is a view illustrating a second modification of the differential pulley of the surgical instrument illustrated in FIG. 2.
Figure 19:
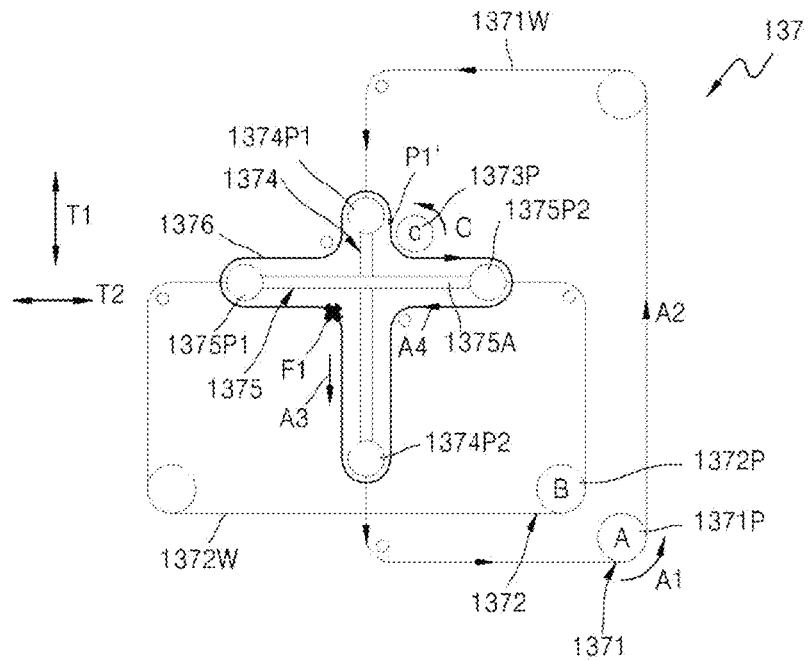
FIGS. 19 and 20 are views illustrating an operation of the second modification of the differential pulley illustrated in FIG. 18.
Figure 20:
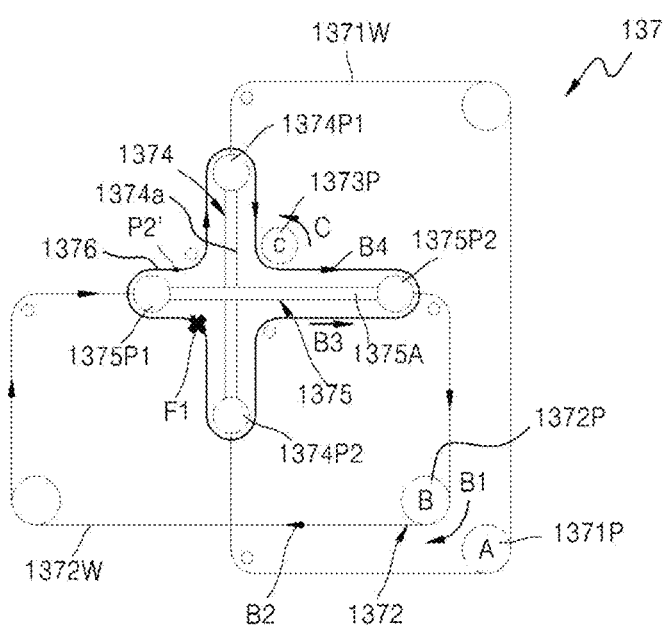

FIG. 18 is a view illustrating a second modification of the differential pulley of the surgical instrument 100 illustrated in FIG. 2, and FIGS. 19 and 20 are views illustrating an operation of the second modification of the differential pulley illustrated in FIG. 18.

As described above, the differential pulley according to the present invention includes two or more input units and one input unit, and outputs rotating forces, which are input from the two or more input units, as a desired rotating force, while each of the two or more input units does not affect other input units.

Referring to FIG. 18, the second modification of the differential pulley of the surgical instrument includes a first input unit 1371, a second input unit 1372, an output unit 1373, a first differential control member 1374, a second differential control member 1375, and a differential control wire 1376.

The first input unit 1371 includes a first input pulley 1371P and a first input wire 1371W. The first input pulley 1371P is connected with the first input wire 1371W to rotate along with the first input wire 1371W.

The second input unit 1372 includes a second input pulley 1372P and a second input wire 1372W. The second input pulley 1372P is connected with the second input wire 1372W to rotate along with the second input wire 1372W.

The output unit 1373 includes an output pulley 1373P. The output pulley 1373P is connected with the differential control wire 1376 to rotate along with the differential control wire 1376.

The first differential control member 1374 includes a first pulley 1374P1, a second pulley 1374P2, and a first differential control bar 1374a. The first pulley 1374P1 and the second pulley 1374P2 are respectively formed at both end portions of the first differential control bar 1374a, and may rotate independently. Also, both end portions of the first input wire 1371W are coupled to both end portions of the first differential control member 1374. The first differential control member 1374 may translate in the direction of an arrow T1 of FIG. 18. For example, the first differential control member 1374 may be installed on a guide rail (not illustrated), and may translate along the guide rail in the direction of the arrow T1 of FIG. 18. Thus, when the first input pulley 1371P rotates, the first input wire 1371W connected therewith rotates, and when the first input wire 1371W rotates, the first differential control member 1374 coupled to both end portions thereof translates in the direction of the arrow T1 of FIG. 18.

The second differential control member 1375 includes a first pulley 1375P1, a second pulley 1375P2, and a second differential control bar 1375a. The first pulley 1375P1 and the second pulley 1375P2 are respectively formed at both end portions of the second differential control bar 1375a, and may rotate independently. Also, both end portions of the second input wire 1372W are coupled to both end portions of the second differential control member 1375, respectively. The second differential control member 1375 may translate in the direction of an arrow T2 of FIG. 18. For example, the second differential control member 1375 may be installed on a guide rail (not illustrated), and may translate along the guide rail in the direction of the arrow T2 of FIG. 18. Thus, when the second input pulley 1372P rotates, the second input wire 1372W connected therewith rotates, and when the second input wire 1372W rotates, the second differential control member 1375 coupled to both end portions thereof translates in the direction of the arrow T2 of FIG. 18.

The differential control wire 1376 is connected along the first pulley 1374P1 of the first differential control member 1374, the first pulley 1375P1 of the second differential control member 1375, the second pulley 1374P2 of the first differential control member 1374, and the second pulley 1375P2 of the second differential control member 1375. The differential control wire 1376 is wound along the four pulleys, and is formed to move according to the translation motions of the first differential control member 1374 and the second differential control member 1375. Herein, a fixed point F1 may be formed at the differential control wire 1376, as a reference point for the movement of the differential control wire 1376.

An operation of the second modification of the differential pulley will be described below.

First, a case where the first input unit 1371 rotates will be described below.

Referring to FIGS. 18 and 19, when the first input pulley 1371P1 of the first input unit 1371 rotates in the direction of an arrow A1 of FIG. 19, the first input wire 1371W connected therewith moves along the first input pulley 1371P1 in the direction of an arrow A2 of FIG. 19. Since the first input wire 1371W is connected with the first differential control member 1374, when the first input wire 1371W moves in the direction of the arrow A2 of FIG. 19, the first differential control member 1374 translates in the direction of an arrow A3. When the first differential control member 1374 translates in the direction of the arrow A3, a point P1 of the differential control wire 1376 of FIG. 18 moves to a point P1' of the differential control wire 1376 of FIG. 19, and thus the differential control wire 1376 moves in the direction of an arrow A4 of FIG. 19. Thus, the output pulley 1373P connected with the differential control wire 1376 rotates in the direction of an arrow C. In this case, the first pulley 1374P1 and the second pulley 1374P2 of the first differential control member 1374 and the second pulley 1375P2 of the second differential control member 1375 rotate in the clockwise direction.

According to this configuration of the present invention, the rotation of the first input unit 1371 does not affect the second input unit 1372 and may be transmitted only to the output unit 1373 to rotate the output pulley 1373P.

A case where the second input unit 1372 rotates will be described below.

Referring to FIGS. 18 and 20, when the second input pulley 1372P of the second input unit 1372 rotates in the direction of an arrow B1 of FIG. 20, the second input wire 1372W connected therewith moves along the second input pulley 1372P in the direction of an arrow B2 of FIG. 20. Since the second input wire 1372W is connected with the second differential control member 1375, when the second input wire 1372W moves in the direction of the arrow B2 of FIG. 20, the second differential control member 1375 translates in the direction of an arrow B3. When the second differential control member 1375 translates in the direction of the arrow B3, a point P2 of the differential control wire 1376 of FIG. 18 moves to a point P2' of the differential control wire 1376 of FIG. 20, and thus the differential control wire 1376 moves in the direction of an arrow B4 of FIG. 20. Thus, the output pulley 1373P connected with the differential control wire 1376 rotates in the direction of an arrow C. In this case, the first pulley 1375P1 and the second pulley 1375P2 of the second differential control member 1375 and the first pulley 1374P1 of the first differential control member 1374 rotate in the clockwise direction.

According to this configuration of the present invention, the rotation of the second input unit 1372 does not affect the first input unit 1371 and may be transmitted only to the output unit 1373 to rotate the output pulley 1373P.

A case where the first input unit 1371 and the second input unit 1372 rotates together will be described below.

When the first input pulley 1371P of the first input unit 1371 rotates in the counterclockwise direction, the output pulley 1373P of the output unit 1373 rotates in the counterclockwise direction; and when the second input pulley 1372P of the second input unit 1372 rotates in the clockwise direction, the output pulley 1373P of the output unit 1373 rotates in the counterclockwise direction. Thus, when the first input pulley 1371P of the first input unit 1371 and the second input pulley 1372P of the second input unit 1372 rotate in opposite directions, the output pulley 1373P of the output unit 1373 rotates as much as the sum of the two rotating forces. On the other hand, when the first input pulley 1371P of the first input unit 1371 and the second input pulley 1372P of the second input unit 1372 rotate in the same direction, the output pulley 1373P of the output unit 1373 rotates as much as the difference between the two rotating forces.

Thus, according to the present invention, when only one of the two or more input units rotates, only the output unit may be rotated without other input units rotating. Also, when the two or more input units rotate together, a single rotating force equal to the sum of (or the difference between) the rotating forces of the two input units may be output through the output unit.

Other examples of the second modification of the differential pulley of the surgical instrument will be described below. FIGS. 21A to 21E are views illustrating other examples of the second modification of the differential pulley illustrated in FIG. 18. In FIGS. 21A to 21E, the first input and the second input are omitted, and first differential control members 1374a to 1374c, second differential control members 1375a to 1375e, output units 1373a to 1373e, and differential control wires 1376a to 1376e connecting them are illustrated. Although their external shapes are slightly different from each other, the respective examples are substantially identical to the second modification of the differential pulley of FIGS. 18 to 20 in that when the first input unit (not illustrated) rotates, the first differential control members 1374a to 1374c translate vertically to rotate the differential control wires 1376a to 1376e to rotate the output units 1373a to 1373e, and when the second input unit (not illustrated) rotates, the second differential control members 1375a to 1375e translate vertically to rotate the differential control wires 1376a to 1376e to rotate the output units 1373a to 1373c.

The differential pulley of the second modification is a modification of the differential pulley illustrated in FIGS. 4A and 4B, and an example of applying the differential pulley of the second modification to the surgical instrument will not be described herein.

<Third Modification of Differential Pulley> (D4)

Figure 22:
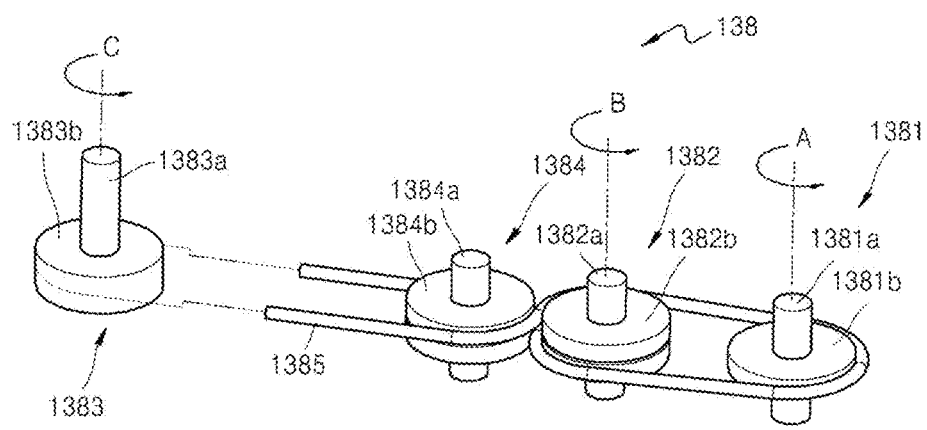
FIGS. 22 and 23 are views illustrating a third modification of the differential pulley of the surgical instrument illustrated in FIG. 2.
Figure 23:
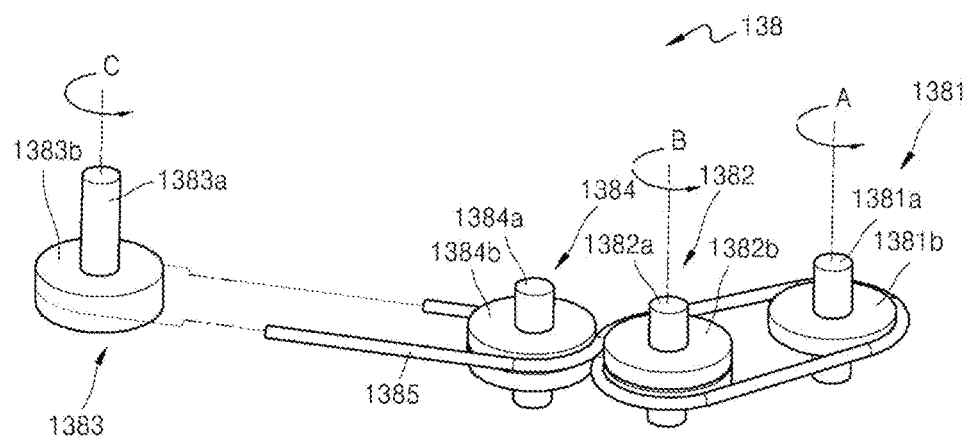

FIGS. 22 and 23 are views illustrating a third modification of the differential pulley of the surgical instrument 100 illustrated in FIG. 2.

As described above, the differential pulley according to the present invention includes two or more input units and one input unit, and outputs rotating forces, which are input from the two or more input units, as a desired rotating force, while each of the two or more input units does not affect other input units.

Referring to FIGS. 22 and 23, the third modification of the differential pulley of the surgical instrument includes a first input unit 1381, a second input unit 1382, an output unit 1383, and a connector 1384.

The first input unit 1381 includes a first rotating axis 1381a and a first input pulley 1381b, and the first input pulley 1381b is coupled with the first rotating axis 1381a to rotate around the first rotating axis 1381a.

The second input unit 1382 includes a second rotating axis 1382a and two second input pulleys 1382b facing each other, and the two second input pulleys 1382b are not coupled with the second rotating axis 1382a and rotate around the second rotating axis 1382a. The first input unit 1381 is formed to extend from the second input pulley 1382b. That is, since the first input pulley 1381b is connected to the second input pulley 1382b by a connecting member (not illustrated), when the second input pulley 1382b rotates, the first input unit 1381, including the first input pulley 1381b connected therewith, rotates.

The output unit 1383 includes a third rotating axis 1383a and an output pulley 1383b, and the output pulley 1383b is coupled with the third rotating axis 1383a to rotate around the third rotating axis 1383a.

The connector 1384 includes a fourth rotating axis 1384a and two connecting pulleys 1384b facing each other, and the two connecting pulleys 1384b are not coupled with the fourth rotating axis 1384a and rotate around the fourth rotating axis 1384a.

A differential control wire 1385 is formed to sequentially contact the output unit 1383, one of the two connecting pulleys 1384b, one of the two input pulleys 1382b, the first input pulley 1381b, the other of the two second input pulleys 1382b, the other of the two connecting pulleys 1384b, and the output unit 1383 and rotate along the output unit 1383, the connector 1384, the second input unit 1382, and the first input unit 1381.

Although not illustrated, a coupling member (not illustrated) connecting the first input unit 1381 and the second input unit 1382 may be further provided. The first rotating axis 1381a of the first input unit 1381 and the second rotating axis 1382a of the second input unit 1382 may be connected to the coupling member. Since the coupling member and the second rotating axis 1382a are fixedly coupled, when the second rotating axis 1382a rotates, the coupling member and the first input unit 1381 connected therewith rotate together therewith. On the other hand, since the coupling member and the first rotating axis 1381a are not fixedly coupled, even when the first rotating axis 1381a rotates, the coupling member may not rotate.

An operation of the third modification of the differential pulley will be described below.

First, a case where the first input unit 1381 rotates will be described below. When the first input pulley 1381b of the first input unit 1381 rotates around the first rotating axis 1381a, the differential control wire 1385 and the first input pulley 1381b rotate together by a frictional force or a fixed point and thus the differential control wire 1385 wound around the two second input pulleys 1382b and the connecting pulley 1384b also move. Consequently, the output pulley 1383b of the output unit 1383 connected to the opposite side of the differential control wire 1385 also rotate around the third rotating axis 1383a. In this case, the two second input pulleys 1382a and the two connecting pulleys 1384b, around which the moving differential control wire 1385 is wound, also rotate together.

A case where the second input unit 1382 rotates will be described below. When the second input pulley 1382b of the second input unit 1382 rotates around the second rotating axis 1382a in the counterclockwise direction in the state of FIG. 22, the first input unit 1381 rotates around the second rotating axis 1382a in the counterclockwise direction as illustrated in FIG. 23. In this case, when there is no rotation input to the first input unit 1381 and thus the rotation of the differential control wire 1385 wound around the first input pulley 1381b is relatively small on the first rotating axis 1381a, the differential control wire 1385 wound around the first rotating axis 1381a rotates around the second rotating axis 1382a. Accordingly, the differential control wire 1385 wound around the two second input pulleys 1382b is pulled and extended to rotate the two second input pulleys 1382b. The movement of the differential control wire 1385 on the two second input pulleys 1382b causes the two connecting pulleys 1384b and the output pulley 1383b to rotate.

Thus, according to the present invention, the rotation of one of the two or more input units may lead to the rotation of the output unit without other input units rotating. Also, when the two or more input units rotate together, a single rotating force equal to the sum of (or the difference between) the rotating forces of the two input units may be output through the output unit.

The third modification of the differential pulley is different from the first and second modifications of the differential pulley in that one input unit is provided on the rotating axis of another input unit and the position of the input unit rotates according to another rotation input. That is, while the input units are disposed independently of each other in the first and second modifications of the differential pulley, one input unit is disposed on a coordinate system of another input unit in the third modification of the differential pulley. As an example of this, in a second embodiment (which will be described later with reference to FIG. 28), one operation input unit is provided on another operation input unit, and the operation input unit also rotates or moves together when the other operation input unit rotates or moves.

Although it is illustrated that the output unit 1383, the connector 1384, the second input unit 1382, and the first input unit 1381 are sequentially arranged in the order stated, the present invention is not limited thereto. For example, the positions of the connector 1384 and the second input unit 1382 may be interchanged with each other. Also in this case, the first input pulley may be connected to the second input pulley by a connecting member (not illustrated), and when the second input pulley rotates, the first input pulley of the first input unit and the connecting pulley of the connector connected thereto may rotate together therewith.

The differential pulley of the third modification is a modification of the differential pulley illustrated in FIGS. 4A and 4B, and an example of applying the differential pulley of the third modification to the surgical instrument will not be described herein.

<Differential Gear>

Figure 24:
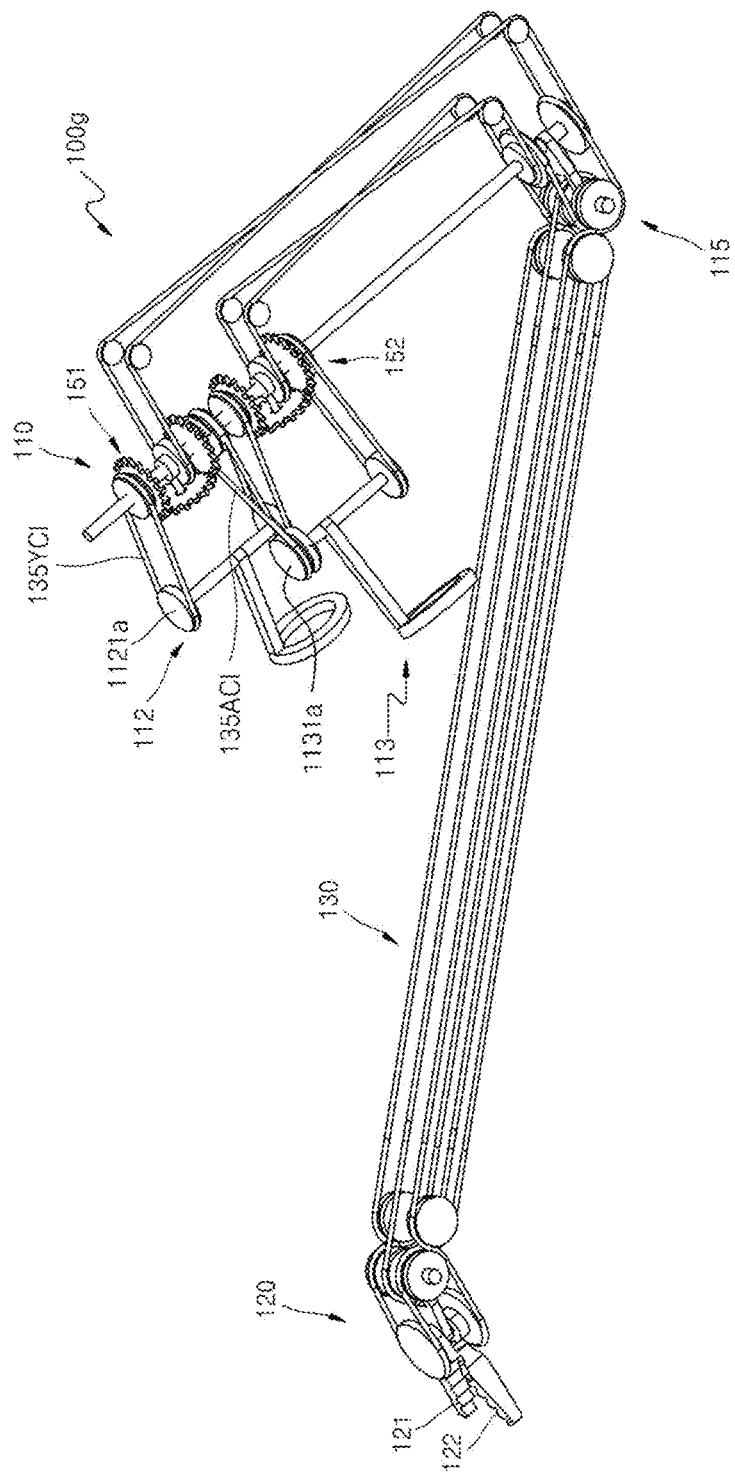
FIG. 24 is a view illustrating a surgical instrument according to a modification of an operating force transmitter of the surgical instrument illustrated in FIG. 2.
Figure 25:
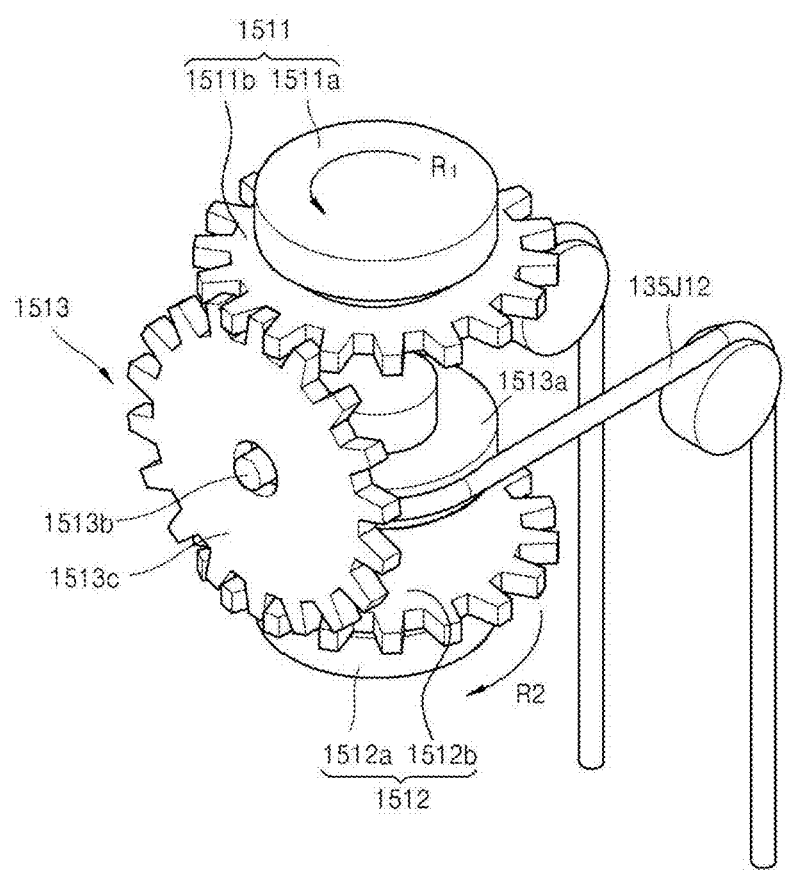
FIG. 25 is a detailed view of a differential gear of FIG. 24.

FIG. 24 is a view illustrating a surgical instrument 100g according to a modification of the operating force transmitter of the surgical instrument 100 illustrated in FIG. 2, and FIG. 25 is a detailed view of a differential gear of FIG. 24. Since the surgical instrument 100g according to a modification of the operating force transmitter 130 of the first embodiment of the present invention is similar to the surgical instrument 100 according to the first embodiment of the present invention and is different from the surgical instrument 100 in terms of the configuration of the operating force transmitter, the configuration of the operating force transmitter will be mainly described below.

In this modification, a differential gear is used instead of the differential pulleys of FIGS. 2 and 4A. That is, the differential gear of the surgical instrument 100g illustrated in FIGS. 24 and 25 may be considered as a structure in which the pulley and wire of the differential pulley of the surgical instrument 100 illustrated in FIG. 4A are replaced with a gear.

Referring to FIGS. 24 and 25, the surgical instrument 100g according to a modification of the operating force transmitter 130 of the first embodiment of the present invention includes an operator 110, an end tool 120, an operating force transmitter 130, and a connector (not illustrated). The operating force transmitter 130 includes a first differential gear 151 and a second differential gear 152.

In detail, the first differential gear 151 includes a first input unit 1511, a second input unit 1512, and an output unit 1513.

The first input unit 1511 includes a first pulley 1511a and a first gear 1511b. The first pulley 1511a and the first gear 1511b rotate together around the same rotating axis. Herein, the first pulley 1511a of the first input unit 1511 is connected with the first pulley 1121a of the yaw operator 112 by the YC1 wire 135YC1 to transmit a rotation of the yaw operator 112 to the first input unit 1511. Also, the first gear 1511b of the first input unit 1511 is connected with the output unit 1513 to transmit a rotation of the first input unit 1511 to the output unit 1513.

The second input unit 1512 includes a second pulley 1512a and a second gear 1512b. The second pulley 1512a and the second gear 1512b rotate together around the same rotating axis. Herein, the second pulley 1512a of the second input unit 1512 is connected with the first pulley 1131a of the actuation operator 113 by the AC1 wire 135AC1 to transmit a rotation of the actuation operator 113 to the second input unit 1512. Also, the second gear 1512b of the second input unit 1512 is connected with the output unit 1513 to transmit a rotation of the second input unit 1512 to the output unit 1513.

The output unit 1513 includes an output pulley 1513a, an extension portion 1513b, and a differential control gear 1513c. Herein, the output pulley 1513a of the output unit 1513 is connected with the operator control member 115 by the J12 wire 135J12 to transmit a rotation of the output unit 1513 to the first jaw 121 of the end tool 120 through the operator control member 115. The extension portion 1513b extends in one direction from a rotating axis of the output pulley 1513a to rotate around the rotating axis of the output pulley 1513a along with the output pulley 1513a. The extension portion 1513b is inserted through the differential control gear 1513c such that the differential control gear 1513c rotates around the extension portion 1513b.

Herein, the first input unit 1511, the second input unit 1512, and the output unit 1513 rotate independently around independent axes.

Herein, the first differential gear 151 includes the first input unit 1511, the second input unit 1512, and the output unit 1513, receives an input of rotating forces from the first input unit 1511 and the second input unit 1512, and outputs the sum of (or the difference between) the rotating forces through the output unit 1513. That is, when only the first input unit 1511 rotates, the rotation of the first input unit 1511 is output through the output unit 1513; when only the second input unit 1512 rotates, the rotation of the second input unit 1512 is output through the output unit 1513; when the first input unit 1511 and the second input unit 1512 rotate in the same direction, the sum of the rotations of the first input unit 1511 and the second input unit 1512 is output through the output unit 1513; and when the first input unit 1511 and the second input unit 1512 rotate in opposite directions, the difference between the rotations of the first input unit 1511 and the second input unit 1512 is output through the output unit 1513. This may be expressed as the following equation:

$$C = A + B$$

(where C denotes a rotation of the output unit, A denotes a rotation of the first input unit, and B denotes a rotation of the second input unit.)

By the first differential gear 151 and the second differential gear 152, even when the yaw operator 112 and the actuation operator 113 rotate freely, the output unit of each differential gear rotates independently of the rotations of the yaw operator 112 and the actuation operator 113. Consequently, the output unit of each differential gear moves as much as the sum of (or the difference between) the rotations of the yaw operator 112 and the actuation operator 113 to extract a desired rotating force.

First Modification of Differential Gear

Figure 26:
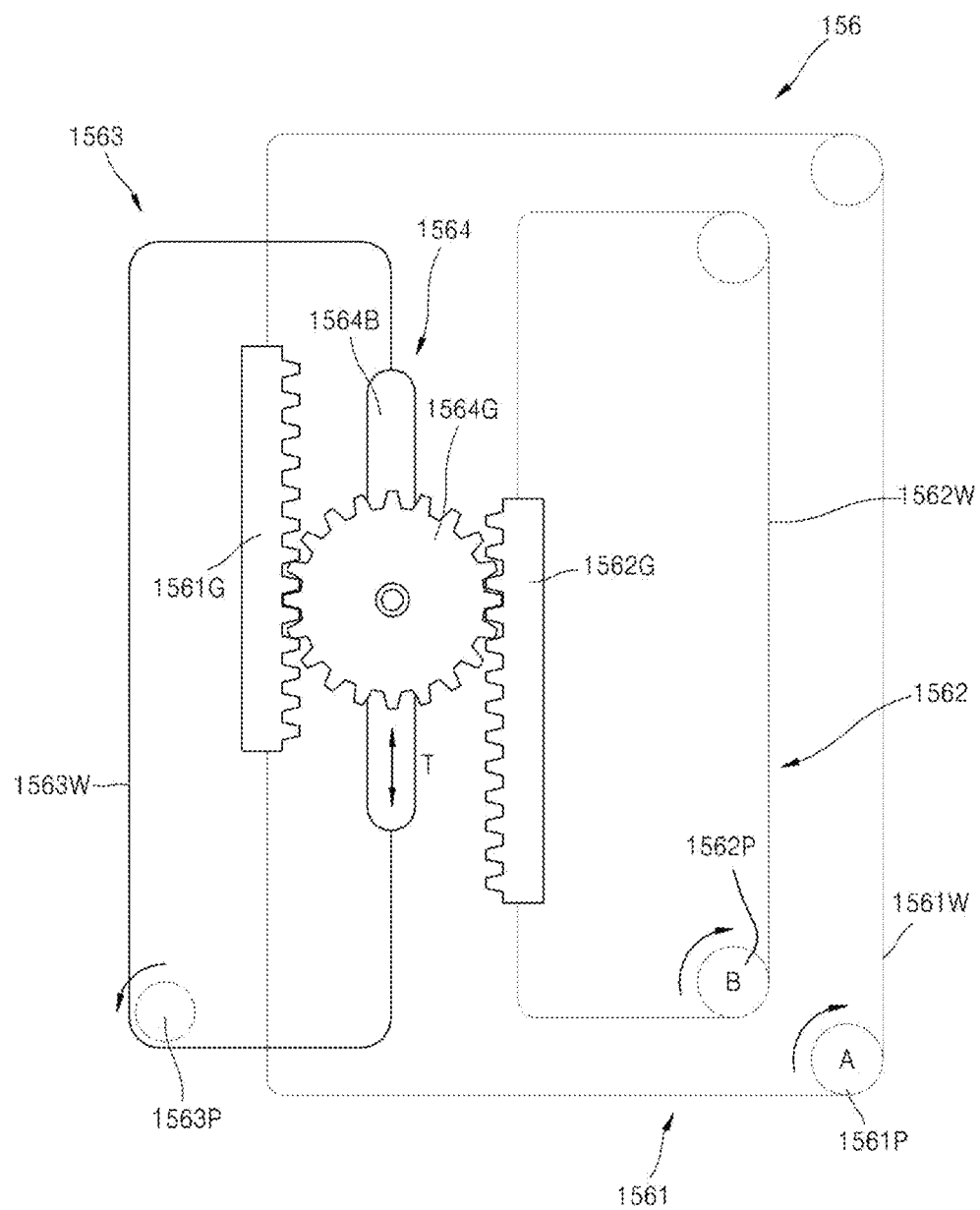
FIG. 26 is a view illustrating a first modification of the differential gear of FIG. 24.

FIG. 26 is a view illustrating a first modification of the differential gear of FIG. 24.

As described above, the differential gear according to the present invention includes two or more input units and one input unit, receives an input of rotating forces from the two or more input units, extracts a desired rotating force from the sum of (or the difference between) the input rotating forces, and outputs the desired rotating force through the output unit.

Referring to FIG. 26, the first modification of the differential gear of the surgical instrument includes a first input unit 1561, a second input unit 1562, an output unit 1563, and a differential control member 1564. The first modification of the differential gear of the surgical instrument illustrated in FIG. 26 may be considered as a structure in which the pulley and wire in the first modification of the differential pulley of the surgical instrument illustrated in FIG. 15 are replaced with a gear.

The first input unit 1561 includes a first pulley 1561P, a first gear 1561G, and a first input wire 1561W. The first pulley 1561P and the first gear 1561G are connected by the first input wire 1561W, so that the first gear 1561G moves vertically when the first pulley 1561P rotates.

The second input unit 1562 includes a second pulley 1562P, a second gear 1562G, and a second input wire 1562W. The second pulley 1562P and the second gear 1562G are connected by the second input wire 1562W, so that the second gear 1562G moves vertically when the second pulley 1562P rotates.

The output unit 1563 includes an output pulley 1563P and an output wire 1563W. The output pulley 1563P and the differential control member 1564 are connected by the output wire 1563W. Thus, when the differential control member 1564 translates, the output pulley 1563P connected with the differential control member 1564 by the output wire 1563W rotates.

The differential control member 1564 includes a differential control gear 1564G and a differential control base 1564B. The differential control gear 1564G is formed to engage with the first gear 1561G and the second gear 1562G. Thus, when the first gear 1561G and the second gear 1562G move vertically, the differential control gear 1564G rotates and translates vertically. That is, the first gear 1561G and the second gear 1562G function as a rack, and the differential control gear 1564G functions as a pinion. Thus, the differential control member 1564 may translate in the direction of an arrow T of FIG. 26. For example, the differential control base 1564B of the differential control member 1564 may be installed on a guide rail (not illustrated), so that the differential control member 1564 may translate along the guide rail in the direction of the arrow T of FIG. 26.

Thus, according to the present invention, when only one of the two or more input units rotates, only the output unit may be rotated without other input units rotating. Also, when the two or more input units rotate together, a single rotating force equal to the sum of (or the difference between) the rotating forces of the two input units may be output through the output unit.

Second Modification of Differential Gear

Figure 27:
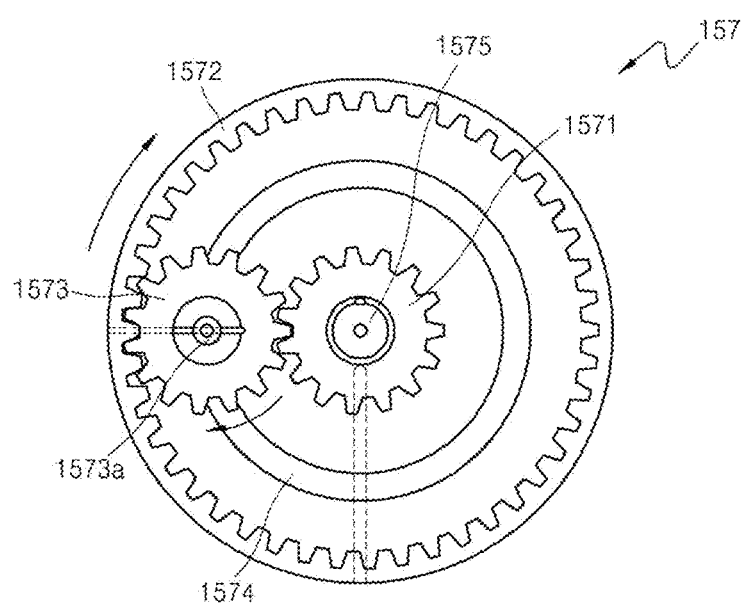
FIG. 27 is a view illustrating a second modification of the differential gear of FIG. 24.

FIG. 27 is a view illustrating a second modification of the differential gear of FIG. 24.

As described above, the differential gear according to the present invention includes two or more input units and one input unit, receives an input of rotating forces from the two or more input units, extracts a desired rotating force from the sum of (or the difference between) the input rotating forces, and outputs the desired rotating force through the output unit.

Referring to FIG. 27, the second modification of the differential gear of the surgical instrument includes a first input unit 1571, a second input unit 1572, an output unit 1574, and a differential control member 1573.

In detail, the first input unit 1571 and the second input unit 1572 may be provided in the form of a gear that may rotate around a central rotating axis 1575. In particular, the second input unit 1572 is provided in the form of a gear that has sawteeth inside a pitch cylinder, and the differential control member 1573 is provided to engage with the gears of the first input unit 1571 and the second input unit 1572. The differential control member 1573 may rotate around a differential control member gear axis 1573a that is connected to the output unit 1574. The output unit 1574 may rotate around the central rotating axis 1575.

When only the first input unit 1571 rotates, the differential control member 1573 engaged with the gear teeth rotates around the differential control member gear axis 1573a and simultaneously rotates around the central rotating axis 1575 of the output unit 1574 connected to the differential control member gear axis 1573a. Also, when only the second input unit 1572 rotates, the differential control member 1573 engaged with the gear teeth rotates around the differential control member gear axis 1573a and simultaneously rotates around the central rotating axis 1575 of the output unit 1574 connected to the differential control member gear axis 1573a. When the first input unit 1571 and the second input unit 1572 rotate in the same direction, the differential control member 1573 and the output unit 1574 rotate around the central rotating axis 1575 in the same direction. In this case, the differential control member 1573 may not rotate around the differential control member gear axis 1573a.

On the other hand, when the first input unit 1571 and the second input unit 1572 rotate in opposite directions, the differential control member 1573 and the output unit 1574 may not rotate around the central rotating axis 1575. In this case, the differential control member 1573 may rotate around the differential control member gear axis 1573a.

Thus, according to the present invention, a single rotating force equal to the sum of (or the difference between) the rotation inputs of two or more input units may be output through the output unit.

MODE OF THE INVENTION

<Second Embodiment of Surgical Instrument>
(E3+H2+D3)

Hereinafter, a surgical instrument 200 according to a second embodiment of the present invention will be described. The surgical instrument 200 according to the second embodiment of the present invention is different from the surgical instrument 100 according to the first embodiment of the present invention in terms of the configuration of an operator. That is, in the surgical instrument 100 according to the first embodiment of the present invention, the yaw operator and the actuation operator are formed independently of each other and the rotation of the yaw operating axis and the rotation of the actuation operating axis are performed independently of each other, while in the surgical instrument 200 according to the second embodiment of the present invention, the actuation operator is formed on the yaw operator and the actuation operator rotates along with the yaw operator when the yaw operator rotates. This difference in the configuration of the operator from the first embodiment will be described later in detail.

Figure 28:
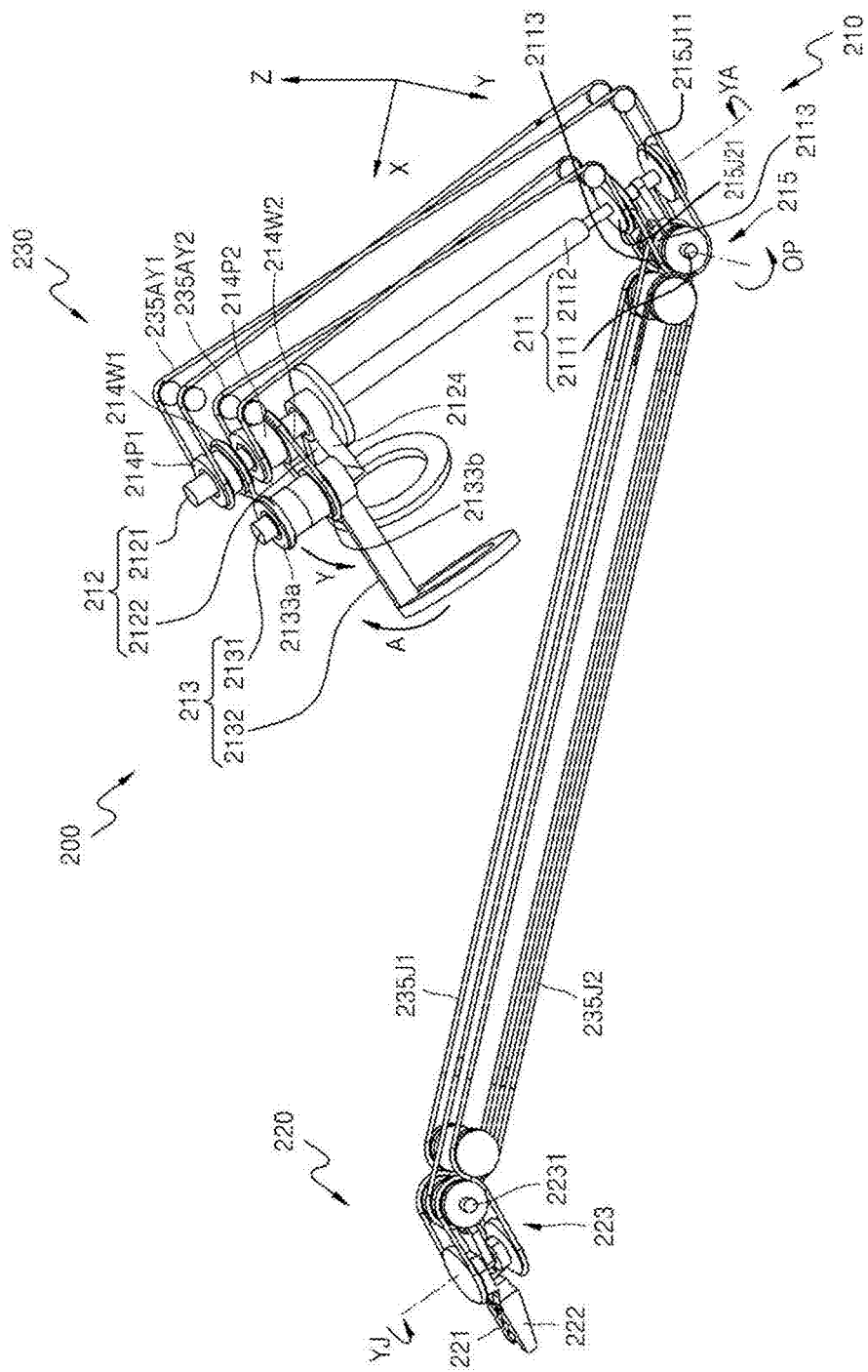
FIG. 28 is a view illustrating a surgical instrument according to a second embodiment of the present invention.

FIG. 28 is a view illustrating a surgical instrument 200 according to a second embodiment of the present invention. Referring to FIG. 28, the surgical instrument 200 according to the second embodiment of the present invention includes an operator 210, an end tool 220, an operating force transmitter 230, and a connector (not illustrated).

The end tool 220 includes a first jaw 221, a second jaw 222, and an end tool control member 223, and the operating force transmitter 230 includes a first jaw operating wire 235J1 and a second jaw operating wire 235J2, so that a pitch operation, a yaw operation, and an actuation operation of the end tool 220 may be conveniently performed. Since the end tool 220 is substantially identical to the end tool 120 of the first embodiment, a detailed description thereof will be omitted herein.

The operating force transmitter 230 includes a plurality of pulleys and a plurality of wires 235AY1, 235AY2, 235J1, and 235J2. Since the operating force transmitter 230 is substantially identical to the operating force transmitter 130 of the first embodiment, a detailed description thereof will be omitted herein.

Hereinafter, the operator 210 of the surgical instrument 200 according to the second embodiment of the present invention will be described in more detail.

Referring to FIG. 28, the operator 210 of the surgical instrument 200 according to the second embodiment of the present invention includes a pitch operator 211 controlling a pitch motion of the end tool 220, a yaw operator 212 controlling a yaw motion of the end tool 220, and an actuation operator 213 controlling an actuation motion of the end tool 220.

The pitch operator 211 includes a pitch operating axis 2111 and a pitch operating bar 2112. Herein, the pitch operating axis 2111 may be formed in a direction parallel to the Y axis, and the pitch operating bar 2112 may be connected with the pitch operating axis 2111 to rotate along with the pitch operating axis 2111. For example, when the user grips and rotates the pitch operating bar 2112, the pitch operating axis 2111 connected with the pitch operating bar 2112 and a pitch operating pulley 2113 connected therewith rotate together therewith. Then, the resulting rotating force is transmitted to the end tool 220 through the operating force transmitter 230, so that the end tool 220 rotates in the same direction as the rotation direction of the pitch operating axis 2111. That is, when the pitch operator 211 rotates in the clockwise direction around the pitch operating axis 2111, the end tool 230 also rotates in the clockwise direction around an end tool pitch operating axis 2231, and when the pitch operator 211 rotates in the counterclockwise direction around the end tool pitch operating axis 2231, the end tool 230 also rotates in the counterclockwise direction around the end tool pitch operating axis 2231. The pitch operating pulley 2113 is integrated with the pitch operating axis 2111 to rotate along with the pitch operating axis 2111.

The yaw operator 212 includes a yaw operating axis 2121 and a yaw operating bar 2122. Although it is illustrated that the yaw operating axis 2121 is formed to extend from the pitch operating bar 2112, the present invention is not limited thereto. For example, the pitch operating bar 2112 and the yaw operating axis 2121 may be formed as separate members on different axes. In this case, the yaw operating axis 2121 may be formed in various directions by ergonomic design according to the structure of the hand of the user gripping the operator 210.

When the pitch operator 211 rotates as described above, a coordinate system of the yaw operator 212 may change accordingly. In this case, the yaw operating bar 2122 is formed to rotate around the yaw operating axis 2121. For example, when the user holds and rotates the yaw operating bar 2122 with the index finger, the yaw operating bar 2122 rotates around the yaw operating axis 2121. Then, the resulting rotating force is transmitted to the end tool 220 through a first yaw-actuation operating wire 235AY1 and a second yaw-actuation operating wire 235AY2, so that the first and second jaws 221 and 222 of the end tool 220 horizontally rotate in the same direction as the rotation direction of the yaw operator 212.

The actuation operator 213 includes an actuation operating axis 2131, an actuation operating bar 2132, a first actuation operating pulley 2133a, and a second actuation operating pulley 2133b. Herein, the actuation operating bar 2132, the first actuation operating pulley 2133a, and the second actuation operating pulley 2133b are formed to rotate around the actuation operating axis 2131. For example, when the user holds and rotates the actuation operating bar 2132 with the thumb finger, the first actuation operating pulley 2133a and the second actuation operating pulley 2133b connected with the actuation operating bar 2132 rotate around the actuation operating axis 2131. Then, the resulting rotating force is transmitted to the end tool 220 through the operating force transmitter 230, so that the first and second jaws 221 and 222 of the end tool 220 perform an actuation operation. Although it is illustrated that the operating axis of the actuation operator is parallel to the operating axis of the yaw operator, the present invention is not limited thereto, and they may be formed in various shapes by ergonomic design.

The actuation operator 213 is formed on a yaw-actuation connector 2124 extending from the yaw operator 212. Thus, when the yaw operator 212 rotates, the actuation operator 213 also rotates along with the yaw operator 212. A first yaw-actuation operating pulley 214P1 and a second yaw-actuation operating pulley 214P2 are formed to rotate around the yaw operating axis 2121. The first actuation operating pulley 2133a and the first yaw-actuation operating pulley 214P1 are connected by a first yaw-actuation connecting wire 214W1, and the first yaw-actuation operating wire 235AY1 is connected to the first yaw-actuation operating pulley 214P1. Likewise, the second actuation operating pulley 2133b and the second yaw-actuation operating pulley 214P2 are connected by a second yaw-actuation connecting wire 214W2, and the second yaw-actuation operating wire 235AY2 is connected to the second yaw-actuation operating pulley 214P2.

Consequently, the first yaw-actuation operating pulley 214P1 and the second yaw-actuation operating pulley 214P2 are formed to rotate when the yaw operator 212 rotates and also rotate when the actuation operator 213 rotates.

However, the first yaw-actuation connecting wire 214W1 is twisted one time and connected to the first yaw-actuation operating pulley 214P1 to reversely transmit an operation input of the actuation operator 213, while the second yaw-actuation connecting wire 214W2 is straightly connected to the second yaw-actuation operating pulley 214P2 to straightly transmit an operation input of the actuation operator 213.

The operator 210 of the surgical instrument 200 according to the second embodiment of the present invention further includes an operator control member 215 engaged with the pitch operating axis 2111 of the pitch operator 211. Since the operator control member 215 is substantially identical to the operator control member 115 described with reference to FIG. 5, a detailed description thereof will be omitted herein.

Overall Operation of Second Embodiment

Hereinafter, an overall configuration for the pitch operation, the yaw operation, and the actuation operation of the surgical instrument 200 according to the second embodiment of the present invention will be summarized with reference to the above descriptions.

For the configuration of the end tool 220 of the present embodiment, the operating force transmitter 230 capable of dividing the operation input of the operator 210 into a pitch operation, a yaw operation, and an actuation operation is necessary to perform the pitch, yaw, and actuation operations of the end tool 220. As described above, through the structure in which the end tool control member 223 and the operator control member 215 are disposed symmetrical to each other, the rotation operation of the pitch operator 211 enables the pitch operation of the end tool 220 regardless of the operations of the yaw operator 212 and the actuation operator 213. However, in order for the operations of the yaw operator 212 and the actuation operator 213 to lead to the yaw operation and the actuation operation of the end tool 220, the operations of the yaw operator 212 and the actuation operator 213 have to be converted into the operations of two jaws of the end tool 220. The rotation of the yaw operator 212 causes the two jaws to rotate in the same direction, and the rotation of the actuation operator 213 causes the two jaws to rotate in different directions. That is, the first jaw 221 rotates as much as the sum of the operation inputs of the yaw operator 212 and the actuation operator 213, and the second jaw 222 rotates as much as the difference between the operation inputs of the yaw operator 212 and the actuation operator 213. This may be expressed as the following equation:

J1=Y+A (the first jaw rotates in the same direction in both the yaw operation and the actuation operation.)

J2=Y−A (the second jaw rotates in the same direction in the yaw operation and rotates in an opposite direction in the actuation operation.)

However, since the actuation operator 213 is disposed on the yaw operator 212, the sum of the operation input of the actuation operator 213 and the operation input of the yaw operator 212 is transmitted to the operating force transmitter 230. This may be expressed as the following equation:

$$Y_A = Y + A$$

This is equal to the above J1 component and may be transmitted to the first jaw 221.

However, in order to extract the J2 component of the second jaw 222, the difference between the operation input of the yaw operator 212 and the operation input of the actuation operator 213 has to be obtained as described above. To this end, as described above, the first yaw-actuation connecting wire 214W1 is twisted one time and connected to the first yaw-actuation operating pulley 214P1 to reversely transmit the operation input of the actuation operator 213. This may be expressed as the following equation:

$$Y_{A2} = Y - A$$

This is equal to the above J2 component and may be transmitted to the second jaw 222.

(where Y denotes the rotation of the yaw operating pulley, and A denotes the rotation of the actuation operating pulley.)

By this configuration, in the operator 210 having the actuation operator 213 disposed on the yaw operator 212, the operation inputs of the yaw operator 212 and the actuation operator 213 may be converted into the operation components of the two jaws. This will be described below in more detail.

First, the pitch operation will be described below.

As described above, when the user grips the pitch operating bar 2112 of the pitch operator 211 of the operator 210 and rotates the pitch operating bar 2112 around the pitch operating axis 2111 in the direction of an arrow OP of FIG. 28, the operator control member 215 also rotates around the pitch operating axis 2111. Then, the first jaw operating wire 235J1 wound around the operation control member 215 is pulled toward the operator 210. At the same time, the second jaw operating wire 235J2 wound around the operation control member 215 is unwound from the operation control member 215. Then, the end tool control member 223 connected with the first jaw operating wire 235J1 and the second jaw operating wire 235J2 rotates around the end tool pitch operating axis 2231 to perform a pitch motion.

The yaw operation will be described below.

When the user holds and rotates the yaw operating bar 2122 with the index finger in the direction of an arrow Y of FIG. 28, the yaw operator 212 and the actuation operator 213 connected therewith rotate around the yaw operating axis 2121. Then, the resulting rotating force is transmitted to the operation control member 215 through the first yaw-actuation connecting wire 214W1, the first yaw-actuation operating pulley 214P1, and the first yaw-actuation operating wire 235AY1 to rotate a J11 pulley 215J11 of the operator control member 215 in the direction of an arrow YA of FIG. 8. When the J11 pulley 215J11 of the operator control member 215 rotates, the first jaw operating wire 235J1 connected therewith is rotated, and the first jaw 221 of the end tool 220 that is connected with the first jaw operating wire 235J1 rotates in the direction of an arrow YJ of FIG. 28.

At the same time, when the user rotates the yaw operating bar 2122 in the direction of the arrow Y of FIG. 28, the yaw operator 212 and the actuation operator 213 connected therewith rotate around the yaw operating axis 2121. Then, the resulting rotating force is transmitted to the operation control member 215 through the second yaw-actuation connecting wire 214W2, the second yaw-actuation operating pulley 214P2, and the second yaw-actuation operating wire 235AY2 to rotate a J21 pulley 215J21 of the operator control member 215 in the direction of the arrow YA of FIG. 28 When the J21 pulley 215J21 of the operator control member 215 rotates, the second jaw operating wire 235J2 connected therewith is rotated, and the second jaw 222 of the end tool 220 that is connected with the second jaw operating wire 235J2 rotates in the direction of the arrow YJ of FIG. 28.

In this manner, when the yaw operator 212 is rotated in one direction, the first and second jaws 221 and 222 rotate in the same direction to perform a yaw operation.

The actuation operation will be described below.

When the user holds and rotates the actuation operating bar 2132 with the thumb finger in the direction of an arrow A of FIG. 28, the actuation operator 213 rotates around the actuation operating axis 2131. Then, the resulting rotating force is transmitted to the operation control member 215 through the first yaw-actuation connecting wire 214W1, the first yaw-actuation operating pulley 214P1, and the first yaw-actuation operating wire 235AY1 to rotate the J11 pulley 215J11 of the operator control member 215 in the direction of the arrow YA of FIG. 28 When the J11 pulley 215J11 of the operator control member 215 rotates, the first jaw operating wire 235J1 connected therewith is rotated, and the first jaw 221 of the end tool 220 that is connected with the first jaw operating wire 235J1 rotates in the direction of the arrow YJ of FIG. 28.

At the same time, when the user rotates the actuation operating bar 2132 in the direction of the arrow A of FIG. 28, the actuation operator 213 rotates around the actuation operating axis 2131. Then, the resulting rotating force is transmitted to the operation control member 215 through the second yaw-actuation connecting wire 214W2, the second yaw-actuation operating pulley 214P2, and the second yaw-actuation operating wire 235AY2 to rotate the J21 pulley 215J21 of the operator control member 215 in a direction opposite to the direction of the arrow YA of FIG. 28. When the J21 pulley 215J21 of the operator control member 215 rotates, the second jaw operating wire 235J2 connected therewith is rotated, and the second jaw 222 of the end tool 220 that is connected with the second jaw operating wire 235J2 rotates in a direction opposite to the direction of the arrow YJ of FIG. 28.

In this manner, when the actuation operator 213 is rotated in one direction, the first and second jaws 221 and 222 rotate in opposite directions to perform an actuation operation.

Any combination of various configurations of the operator described with reference to FIG. 3A, various configurations of the operating force transmitter described with reference to FIGS. 4A and 15 to 27, and various modifications described with reference to FIGS. 7 to 14 may be applied to the surgical instrument 200 according to the second embodiment of the present invention.

<Modification of Operating Force Transmitter of Second Embodiment of Surgical Instrument>
(E3+H2+D4)

Figure 29:
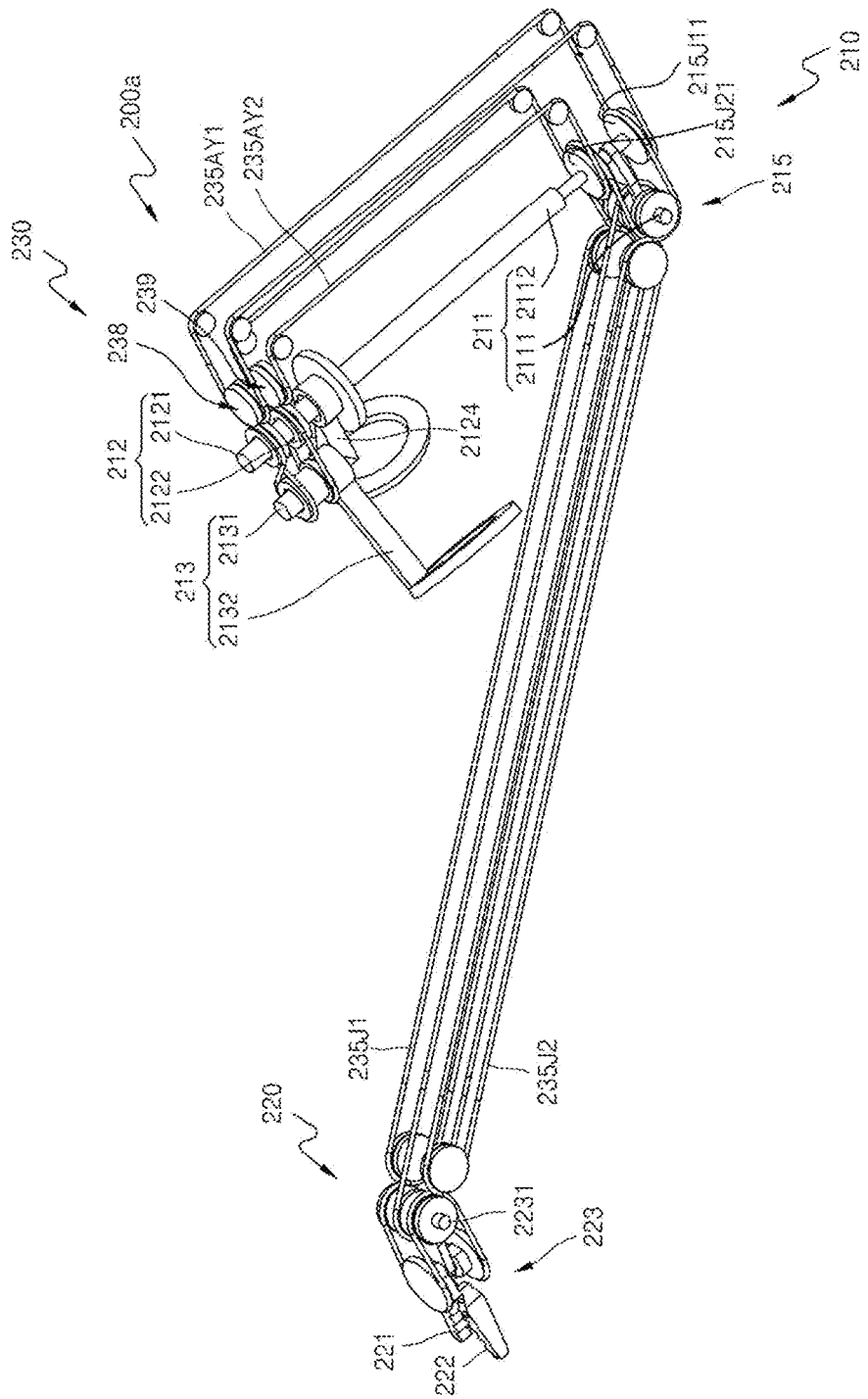
FIG. 29 is a view illustrating a surgical instrument according to a modification of a differential pulley of the second embodiment illustrated in FIG. 28.

FIG. 29 is a view illustrating a surgical instrument 200a according to a modification of the operating force transmitter 230 of the second embodiment illustrated in FIG. 28. Since the surgical instrument 200a according to a modification of the operating force transmitter 230 of the second embodiment of the present invention is similar to the surgical instrument 200 (see FIG. 28) according to the second embodiment of the present invention and is different from the surgical instrument 200 in terms of the configuration of the operating force transmitter, the configuration of the operating force transmitter will be mainly described below.

Referring to FIG. 29, the surgical instrument 200a according to a modification of the operating force transmitter 230 of the second embodiment of the present invention includes an operator 210, an end tool 220, an operating force transmitter 230, and a connector (not illustrated).

The end tool 220 includes a first jaw 221, a second jaw 222, and an end tool control member 223, and the operating force transmitter 230 includes a first jaw operating wire 235J1 and a second jaw operating wire 235J2, so that a pitch operation, a yaw operation, and an actuation operation of the end tool 220 may be conveniently performed. Since the end tool 220 is substantially identical to the end tool 220 of the second embodiment described with reference to FIG. 28, a detailed description thereof will be omitted herein.

The operating force transmitter 230 includes a plurality of pulleys and a plurality of wires 235AY1, 235AY2, 235J1, and 235J2. The operating force transmitter 230 of the surgical instrument 200a according to this modification uses the third modification of the differential pulley illustrated in FIGS. 22 and 23.

In detail, the yaw and actuation operations of the end tool 220 of this modification are performed by the rotation of two jaws, and the operation of the operator 210 is converted into a rotation component of each jaw of the end tool 220. Thus, the rotation component of each jaw may correspond to the sum of or difference between a yaw operation input and an actuation operation input as follows:

$$J1 = Y + A$$

$$J2 = Y - A$$

According to the configuration of the operator of this embodiment, since the actuation operator 213 is formed to extend from the yaw operator 212, the actuation operator 213 moves along with the rotation of the yaw operator 212. In this case, since the rotation input of actuation is a relative rotation of an actuation pulley with respect to an actuation axis, it is not affected by the rotation of the yaw operator. This configuration may be implemented by using the third modification of the differential pulley (see FIGS. 22 and 23) in which one input unit is formed on another input unit. Thus, a differential pulley is configured to include a first input unit corresponding to a reference numeral 2132 of FIG. 29 and a second input unit corresponding to a reference numeral 2122 of FIG. 29, each of two differential pulleys is connected to one jaw of the end tool 220. One differential pulley according to the above equation may be configured to transmit the sum of the two inputs, namely, the yaw input and the actuation input to a relevant jaw, and another differential pulley may be configured to transmit the difference between the two inputs, namely, the yaw input and the actuation input to a relevant jaw.

That is, the operating force transmitter 230 of the surgical instrument 200a according to this modification includes a first differential pulley 238 and a second differential pulley 239, and each of the differential pulleys 238 and 239 includes a first input unit 1381 (see FIG. 22), a second input unit 1382 (see FIG. 22), an output unit 1383 (see FIG. 22), and a connector 1384 (see FIG. 22). In this case, when only one of two or more input units rotates, only the output unit is rotated without other input units rotating, and when two or more input units rotate simultaneously, a single rotating force equal to the sum of (or the difference between) the rotating forces of two input units is output through the output unit.

Any combination of various configurations of the operator described with reference to FIG. 3A, various configurations of the operating force transmitter described with reference to FIGS. 4A and 15 to 27, and various modifications described with reference to FIGS. 7 to 14 may be applied to the surgical instrument 200 according to the second embodiment of the present invention.

<Third Embodiment of Surgical Instrument>
(E3+H3+D3)

Hereinafter, a surgical instrument 300 according to a third embodiment of the present invention will be described. The surgical instrument 300 according to the third embodiment of the present invention is different from the surgical instrument 100 according to the first embodiment of the present invention in terms of the configuration of an operator. That is, the surgical instrument 100 according to the first embodiment of the present invention includes the yaw operator and the actuation operator are formed independently of each other such that the rotation of the yaw operating axis and the rotation of the actuation operating axis are performed independently of each other, while the surgical instrument 300 according to the third embodiment of the present invention includes a first jaw operator and a second jaw operator that operate a first jaw and a second jaw independently instead of the yaw operator and the actuation operator. This difference in the configuration of the operator from the first embodiment will be described later in detail.

Figure 30:
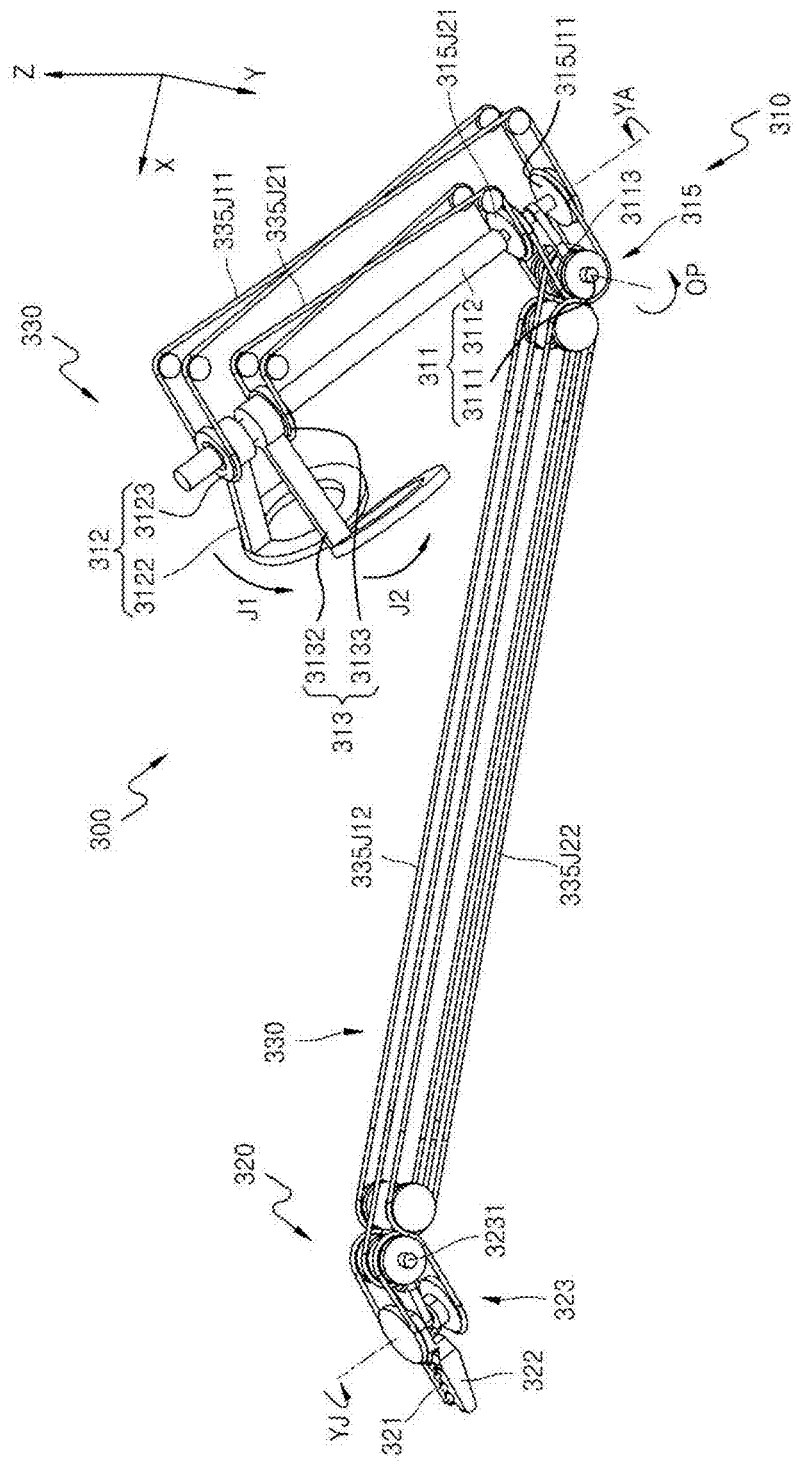
FIG. 30 is a view illustrating a surgical instrument according to a third embodiment of the present invention.

FIG. 30 is a view illustrating the surgical instrument 300 according to the third embodiment of the present invention. Referring to FIG. 30, the surgical instrument 300 according to the third embodiment of the present invention includes an operator 310, an end tool 320, an operating force transmitter 330, and a connector (not illustrated).

The end tool 320 includes a first jaw 321, a second jaw 322, and an end tool control member 323, and the operating force transmitter 330 includes a first jaw operating wire 335J12 and a second jaw operating wire 335J22, so that a pitch operation, a yaw operation, and an actuation operation of the end tool 320 may be conveniently performed. Since the end tool 320 is substantially identical to the end tool 120 described with reference to FIG. 5, a detailed description thereof will be omitted herein.

The operating force transmitter 330 includes a plurality of pulleys and a plurality of wires 335J11, 335J12, 335J21, and 335J22. Since the operating force transmitter 330 is substantially identical to the operating force transmitter 130 of the first embodiment, a detailed description thereof will be omitted herein.

Hereinafter, the operator 310 of the surgical instrument 300 according to the third embodiment of the present invention will be described in more detail.

Referring to FIG. 30, the operator 310 of the surgical instrument 300 according to the third embodiment of the present invention includes a pitch operator 311 controlling a pitch motion of the end tool 320, a first jaw operator 312 controlling a motion of the first jaw 321 of the end tool 320, and a second jaw operator 313 controlling a motion of the second jaw 322 of the end tool 320.

The pitch operator 311 includes a pitch operating axis 3111 and a pitch operating bar 3112. Herein, the pitch operating axis 3111 may be formed in a direction parallel to the Y axis, and the pitch operating bar 3112 may be connected with the pitch operating axis 3111 to rotate along with the pitch operating axis 3111. For example, when the user grips and rotates the pitch operating bar 3112, the pitch operating axis 3111 connected with the pitch operating bar 3112 and a pitch operating pulley 3113 connected therewith rotate together. Then, the resulting rotating force is transmitted to the end tool 320 through the operating force transmitter 330, so that the end tool 320 rotates in the same direction as the rotation direction of the pitch operating axis 3111. That is, when the pitch operator 311 rotates in the clockwise direction around the pitch operating axis 3111, the end tool 320 also rotates in the clockwise direction around the pitch operating axis 3111, and when the pitch operator 311 rotates in the counterclockwise direction around the pitch operating axis 3111, the end tool 320 also rotates in the counterclockwise direction around the pitch operating axis 3111. The pitch operating pulley 3113 is integrated with the pitch operating axis 3111 to rotate along with the pitch operating axis 3111.

The first jaw operator 312 includes a first jaw operating axis, a first jaw operating bar 3122, and a first jaw operating pulley 3123. Although it is illustrated that the first jaw operating axis is formed to extend from the pitch operating bar 3112 and the pitch operating bar 3112 is inserted into the first jaw operating pulley 3123, the present invention is not limited thereto. For example, the pitch operating bar 3112 and the first jaw operating axis may be formed as separate members on different axes. In this case, the first jaw operating axis may be formed in various directions by ergonomic design according to the structure of the hand of the user gripping the operator 310. The first jaw operating wire 335J12 may be connected to the first jaw operating pulley 3123. The first jaw operating bar 3122 and the first jaw operating pulley 3123 are formed to rotate around the first jaw operating axis. For example, when the user holds and rotates the first jaw operating bar 3122 with the index finger, the first jaw operating pulley 3123 connected with the first jaw operating bar 3122 rotates around the first jaw operating axis. Then, the resulting rotating force is transmitted to the end tool 320 through the operating force transmitter 330, so that the first jaw 321 of the end tool 120 horizontally rotates in the same direction as the rotation direction of the first jaw operating pulley 3123.

The second jaw operator 313 includes a second jaw operating axis, a second jaw operating bar 3132, and a second jaw operating pulley 3133. Although it is illustrated that the second jaw operating axis is formed to extend from the pitch operating bar 3112 and the pitch operating bar 3112 is inserted into the second jaw operating pulley 3133, the present invention is not limited thereto. For example, the pitch operating bar 3112 and the second jaw operating axis may be formed as separate members on different axes. In this case, the second jaw operating axis may be formed in various directions by ergonomic design according to the structure of the hand of the user gripping the operator 310. The second jaw operating wire 335J22 may be connected to the second jaw operating pulley 3133. The second jaw operating bar 3132 and the second jaw operating pulley 3133 are formed to rotate around the second jaw operating axis. For example, when the user holds and rotates the second jaw operating bar 3132 with the thumb finger, the second jaw operating pulley 3133 connected with the second jaw operating bar 3132 rotates around the second jaw operating axis. Then, the resulting rotating force is transmitted to the end tool 320 through the operating force transmitter 330, so that the second jaw 322 of the end tool 320 horizontally rotates in the same direction as the rotation direction of the second jaw operating pulley 3133.

The operator 310 of the surgical instrument 300 according to the third embodiment of the present invention further includes an operator control member 315 engaged with the pitch operating axis 3111 of the pitch operator 311. Since the operator control member 315 is substantially identical to the operator control member with reference to FIG. 5, a detailed description thereof will be omitted herein.

Overall Operation of Third Embodiment

Hereinafter, an overall configuration for the pitch operation, the yaw operation, and the actuation operation of the surgical instrument 300 according to the third embodiment of the present invention will be summarized with reference to the above descriptions.

For the configuration of the end tool 320 of the present embodiment, the operating force transmitter 330 capable of dividing the operation input of the operator 310 into a pitch operation, a yaw operation, and an actuation operation is necessary to perform the pitch, yaw, and actuation operations of the end tool 320. As described above, through the structure in which the end tool control member 323 and the operator control member 315 are disposed symmetrical to each other, the rotation operation of the pitch operator 311 enables the pitch operation of the end tool 320 regardless of the operations of the first jaw operator 312 and the second jaw operator 313.

The operator 310 includes the first jaw operator 312 and the second jaw operator 313. Thus, without the need to provide an additional configuration for conversion into the operations of two jaws of the end tool 320, the operation input of the first jaw operator 312 is directly transmitted to the first jaw 321, and the operation input of the second jaw operator 313 is directly transmitted to the second jaw 322.

Through this configuration, a pitch operation, a yaw operation (two jaws moves in the same direction), an actuation operation (two jaws moves in opposite directions) may be implemented. This will be described below in more detail.

First, the pitch operation will be described below.

As described above, when the user grips the pitch operating bar 3112 of the pitch operator 311 of the operator 310 and rotates the pitch operating bar 3112 around the pitch operating axis 3111 in the direction of an arrow OP of FIG. 30, the operator control member 315 also rotates around the pitch operating axis 3111. Then, the first jaw operating wire 335J12 wound around the operation control member 315 is pulled toward the operator 310. At the same time, the second jaw operating wire 335J22 wound around the operation control member 315 is unwound from the operation control member 315. Then, the end tool control member 323 connected with the first jaw operating wire 335J12 and the second jaw operating wire 335J22 rotates around the end tool pitch operating axis 3231 to perform a pitch motion.

The yaw operation will be described below.

For a yaw operation, the user holds and rotates the first jaw operating bar 3122 with the index finger in the direction of an arrow J1 of FIG. 30, and holds and rotates the second jaw operating bar 3132 with the thumb finger in the direction of an arrow J2 of FIG. 30 (that is, rotates the first jaw operating bar 3122 and the second jaw operating bar 3132 in the same direction).

Then, the first jaw operating pulley 3123 connected with the first jaw operating bar 3122 rotates around the first jaw operating axis, and the resulting rotating force is transmitted to the operator control member 315 through the first jaw operating wire 335J11 to rotate a J11 pulley 315J11 of the operator control member 315 in the direction of an arrow YA of FIG. 30. When the J11 pulley 315J11 of the operator control member 315 rotates, the first jaw operating wire 335J12 connected therewith is rotated, and the first jaw 321 of the end tool 320 that is connected with the first jaw operating wire 335J12 rotates in the direction of an arrow YJ of FIG. 30.

At the same time, the second jaw operating pulley 3133 connected with the second jaw operating bar 3132 rotates around the second jaw operating axis, and the resulting rotating force is transmitted to the operator control member 315 through the second jaw operating wire 335J21 to rotate a J21 pulley 315J21 of the operator control member 315 in the direction of the arrow YA of FIG. 30. When the J21 pulley 315J21 of the operator control member 315 rotates, the second jaw operating wire 335J2 connected therewith is rotated, and the second jaw 322 of the end tool 320 that is connected with the second jaw operating wire 335J22 rotates in the direction of the arrow YJ of FIG. 30.

In this manner, when the first jaw operator 312 and the second jaw operator 313 are rotated in the same direction, the first and second jaws 321 and 322 rotate in the same direction to perform a yaw operation.

The actuation operation will be described below.

For an actuation operation, the user holds and rotates the first jaw operating bar 3122 with the index finger in the direction of the arrow J1 of FIG. 30, and holds and rotates the second jaw operating bar 3132 with the thumb finger in a direction opposite to the direction of the arrow J2 of FIG. 30 (that is, rotates the first jaw operating bar 3122 and the second jaw operating bar 3132 in opposite directions).

Then, the first jaw operating pulley 3123 connected with the first jaw operating bar 3122 rotates around the first jaw operating axis, and the resulting rotating force is transmitted to the operator control member 315 through the first jaw operating wire 335J11 to rotate the J11 pulley 315J11 of the operator control member 315 in the direction of the arrow YA of FIG. 30. When the J11 pulley 315J11 of the operator control member 315 rotates, the first jaw operating wire 335J1 connected therewith is rotated, and the first jaw 321 of the end tool 320 that is connected with the first jaw operating wire 335J12 rotates in the direction of the arrow YJ of FIG. 30.

At the same time, the second jaw operating pulley 3133 connected with the second jaw operating bar 3132 rotates around the second jaw operating axis, and the resulting rotating force is transmitted to the operator control member 315 through the second jaw operating wire 335J22 to rotate the J21 pulley 315J21 of the operator control member 315 in a direction opposite to the direction of the arrow YA of FIG. 30. When the J21 pulley 315J21 of the operator control member 315 rotates, the second jaw operating wire 335J22 connected therewith is rotated, and the second jaw 322 of the end tool 320 that is connected with the second jaw operating wire 335J22 rotates in a direction opposite to the direction of the arrow YJ of FIG. 30.

In this manner, when the first jaw operator 312 and the second jaw operator 313 are rotated in opposite directions, the first and second jaws 321 and 322 rotate in opposite directions to perform an actuation operation.

Any combination of various configurations of the operator described with reference to FIG. 3A, various configurations of the operating force transmitter described with reference to FIGS. 4A and 15 to 27, and various modifications described with reference to FIGS. 7 to 14 may be applied to the surgical instrument 300 according to the third embodiment of the present invention.

<Modification of Third Embodiment of Surgical Instrument> (One-Armed Cautery)

Figure 31:
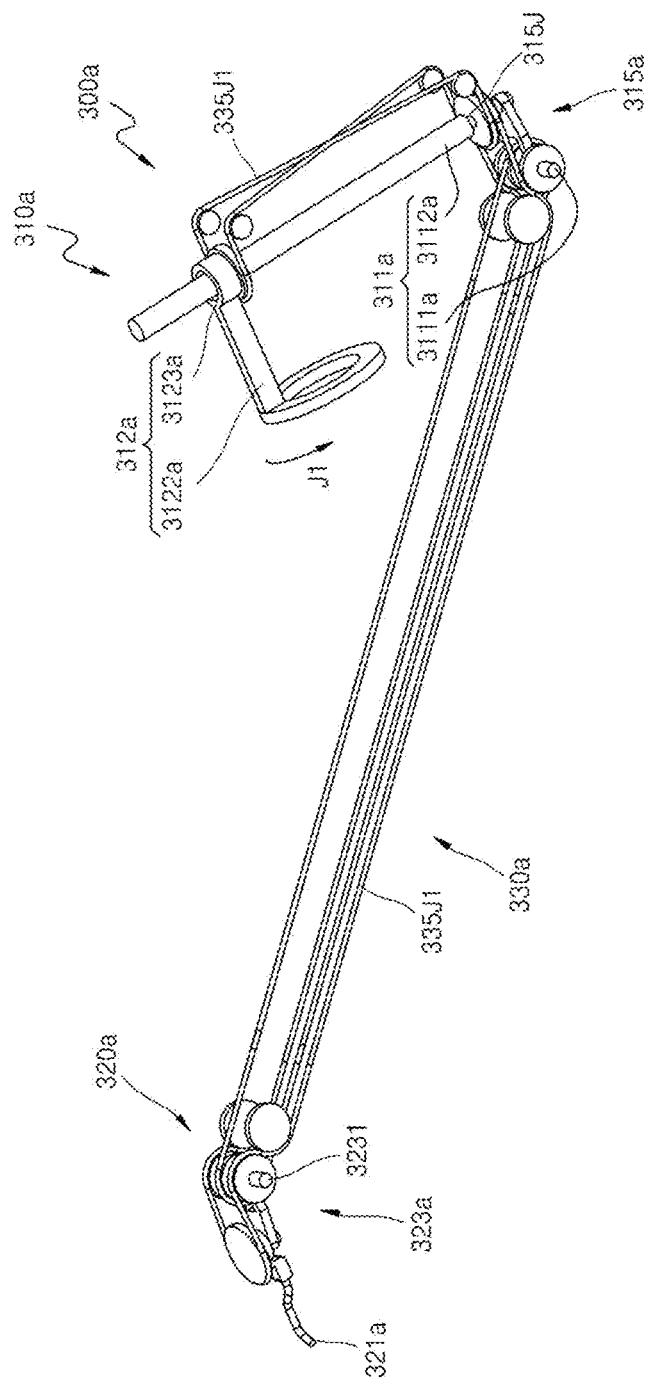
FIG. 31 is a view illustrating a surgical instrument according to a modification of the third embodiment illustrated in FIG. 30.

FIG. 31 is a view illustrating a surgical instrument 300*a* according to a modification of the third embodiment illustrated in FIG. 30. Since the surgical instrument 300*a* according to a modification of the third embodiment of the present invention is similar to the surgical instrument 300 (see FIG. 30) according to the third embodiment of the present invention and is different from the surgical instrument 300 in that only one jaw is provided, the configuration of one jaw will be mainly described below.

Referring to FIG. 31, the surgical instrument 300*a* according to a modification of the third embodiment of the present invention includes an operator 310*a*, an end tool 320*a*, an operating force transmitter 330*a*, and a connector (not illustrated).

The end tool 320*a* includes a jaw 321*a* and an end tool control member 323*a*, and the operating force transmitter 330*a* includes only a jaw operating wire 335J1, so that a pitch operation and a yaw operation of the end tool 320*a* may be conveniently performed. Since the end tool 320*a* is substantially identical to the end tool 120 described with reference to FIG. 5, a detailed description thereof will be omitted herein.

The operating force transmitter 330*a* includes one or more pulleys and wires 335J1. Since the operating force transmitter 330*a* is substantially identical to the operating force transmitter 130 of the first embodiment, a detailed description thereof will be omitted herein.

The operator 310*a* includes a pitch operator 311*a* controlling a pitch motion of the end tool 320*a* and a jaw operator 312*a* controlling a jaw motion of the end tool 320*a*.

The pitch operator 311*a* includes a pitch operating axis 3111*a* and a pitch operating bar 3112*a*.

The jaw operator 312*a* includes a jaw operating axis, a jaw operating bar 3122*a*, and a jaw operating pulley 3123*a*. Although it is illustrated that the jaw operating axis is formed to extend from the pitch operating bar 3112*a* and the pitch operating bar 3112*a* is inserted into the jaw operating pulley 3123*a*, the present invention is not limited thereto. For example, the pitch operating bar 3112*a* and the jaw operating axis may be formed as separate members on different axes. In this case, the jaw operating axis may be formed in various directions by ergonomic design according to the structure of the hand of the user gripping the operator 310*a*. The jaw operating wire 335J1 may be connected to the jaw operating pulley 3123*a*. The jaw operating bar 3122*a* and the jaw operating pulley 3123*a* are formed to rotate around the jaw operating axis. For example, when the user holds and rotates the jaw operating bar 3122*a* with the index finger, the jaw operating pulley 3123*a* connected with the jaw operating bar 3122*a* rotates around the jaw operating axis. Then, the resulting rotating force is transmitted to the end tool 320*a* through the operating force transmitter 330*a*, so that the first jaw 321*a* of the end tool 320*a* horizontally rotate in the same direction as the rotation direction of the jaw operating pulley 3123*a*.

<End Tools of Fourth to Sixth Embodiments of Surgical Instrument> (E1)

Hereinafter, surgical instruments 400, 500, and 600 according to fourth, fifth, and sixth embodiment of the present invention will be described. The surgical instruments 400, 500, and 600 according to the fourth, fifth, and sixth embodiment of the present invention are substantially identical to the surgical instruments 100, 200, and 300 according to the first, second, and third embodiments of the present invention and are different in terms of the configuration of the end tool from the surgical instruments 100, 200, and 300 according to the first, second, and third embodiments of the present invention. Thus, the configuration of the end tool applied in common to the fourth, fifth, and sixth embodiment will be described first.

Figure 32:
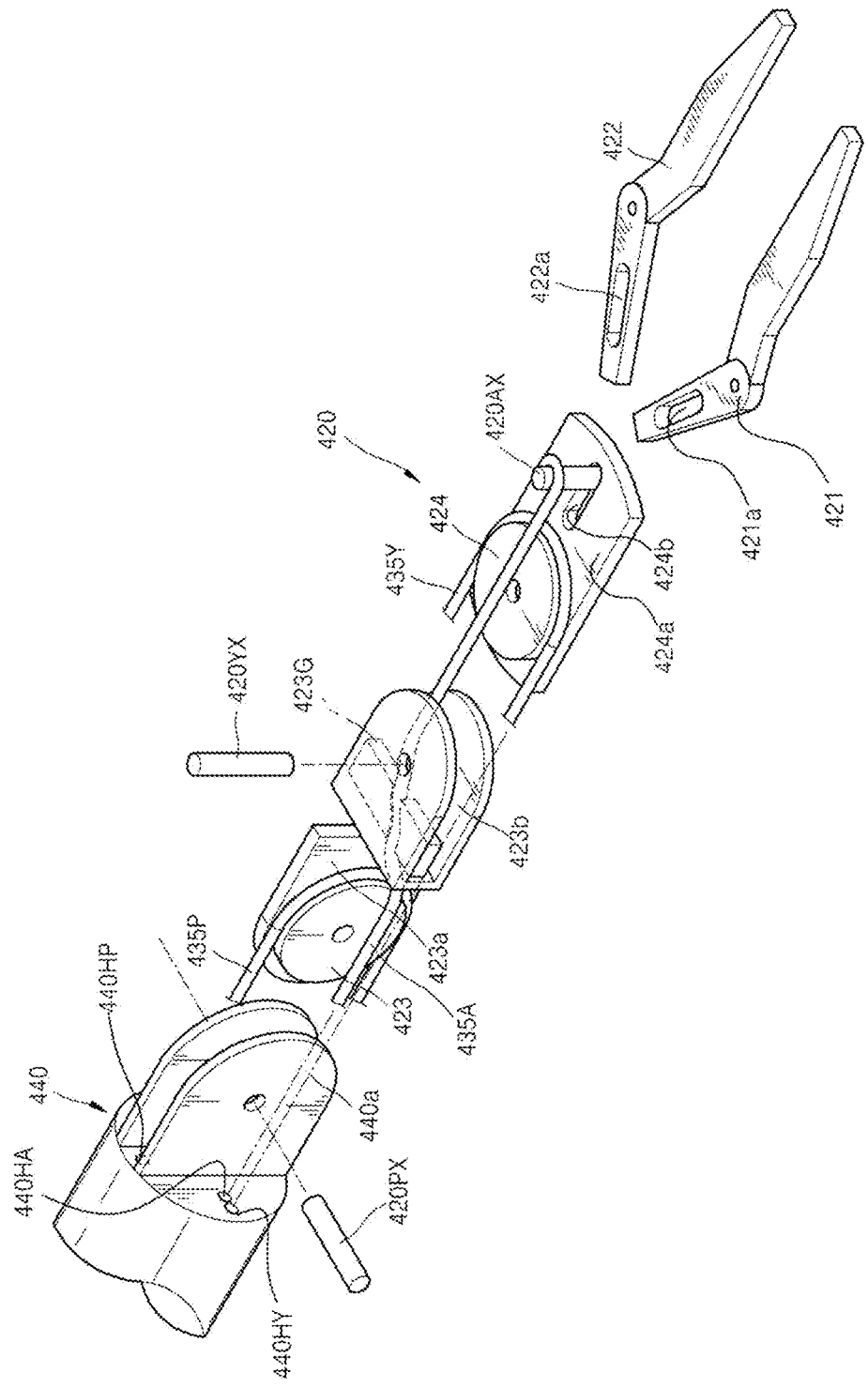
FIG. 32 is an exploded perspective view of an end tool included in a surgical instrument 400 according to a fourth embodiment of the present invention.
Figure 33:
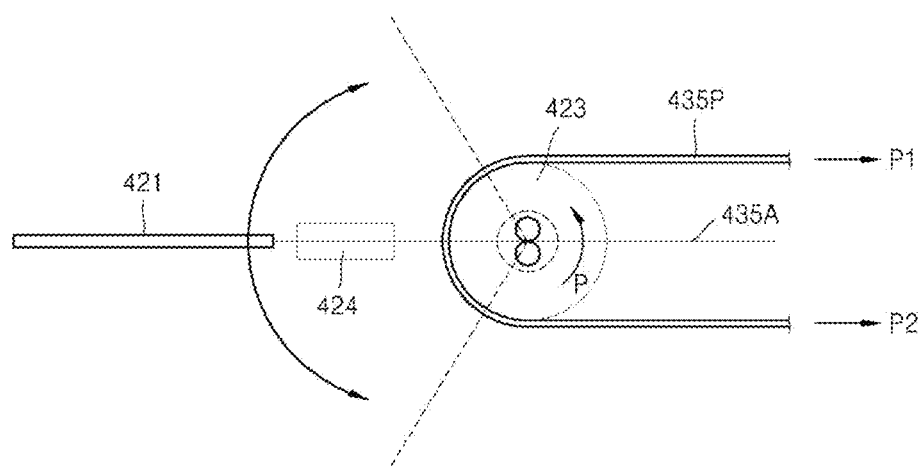
FIG. 33 is an XZ-plane side view of the end tool.
Figure 34:
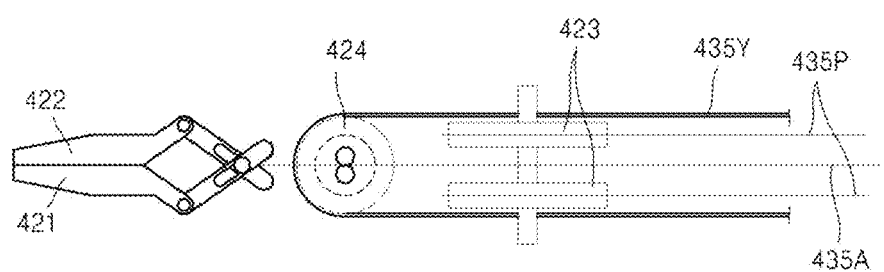
FIG. 34 is an XY-plane plan view of the end tool.
Figure 35:
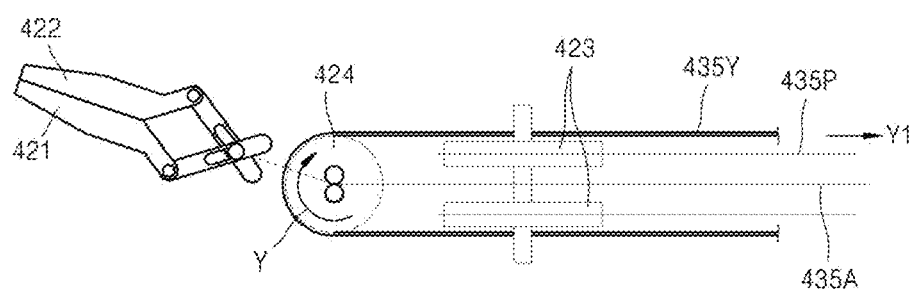
FIG. 35 is a plan view illustrating a yaw motion of the end tool of FIG. 34.
Figure 36:
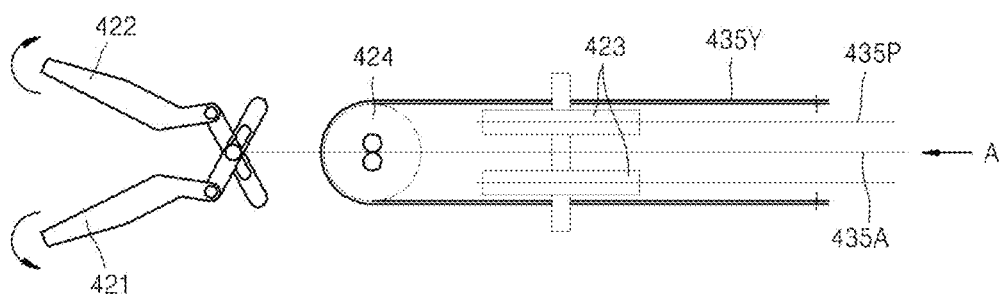
FIG. 36 is a plan view illustrating an actuation motion of the end tool of FIG. 34.

FIGS. 32 to 36 are schematic views illustrating an end tool 420 included in a surgical instrument 400 according to a fourth embodiment of the present invention. FIG. 32 is an exploded perspective view of the end tool 420, FIG. 33 is an XZ-plane side view of the end tool 420, FIG. 34 is an XY-plane plan view of the end tool 420, FIG. 35 is a plan view illustrating a yaw motion of the end tool 420 of FIG. 34, and FIG. 36 is a plan view illustrating an actuation motion of the end tool 420 of FIG. 34.

Referring to FIGS. 32 to 36, the end tool 420 included in the surgical instrument 400 according to the fourth embodiment of the present invention includes a first jaw 421, a second jaw 422, one or more pitch pulleys 423, and one or more yaw pulleys 424. An operating force transmitter included in the surgical instrument 400 according to the fourth embodiment of the present invention includes one or more pitch wires 435P, one or more yaw wires 435Y, and an actuation wire 435A.

In the present embodiments, a pitch operation is performed by the rotation of the pitch wire wound around the pitch pulley, the yaw wire is formed to intersect the pitch pulley and extend toward the end tool, and the yaw wire is wound around the yaw pulley to perform a yaw operation. When a yaw operation is performed by the rotation of the yaw wire, since the yaw wire is formed to intersect the pitch pulley, the yaw wire is minimally affected by the rotation of the pitch pulley during a pitch operation. Likewise, the actuation wire is formed to intersect the pitch pulley and the yaw pulley and extend toward the end tool, and is connected to an opening (421*a* and 422*a*) formed in each of the two jaws. The actuation wire is pulled and pushed to perform an actuation operation for opening and closing the two jaws. Since the actuation wire is formed to intersect the pitch pulley and the yaw pulley, the actuation wire is minimally affected by the rotations of the pitch pulley and the yaw pulley during a pitch operation and a yaw operation.

In detail, a pitch pulley coupler 440*a* is formed to protrude from one end portion of a connector 440, and the pitch pulley 423 is coupled with the pitch pulley coupler 440*a* to rotate around a pitch rotating axis 420PX with respect to the pitch pulley coupler 440*a*. Also, the pitch pulley 423 is integrated with a pitch pulley base 423*a*, and a yaw pulley coupler 423*b* is formed on one side of the pitch pulley base 423*a*. Thus, the pitch pulley 423 is formed to rotate around the pitch rotating axis 420PX, and the yaw pulley coupler 423*b* and the pitch pulley base 423*a* coupled therewith rotate along with the pitch pulley 423. Herein, a pitch wire pass hole 440HP is formed at the one end portion of the connector 440, and the pitch wire 435P extends through the pitch wire pass hole 440HP toward the end tool 420.

The yaw pulley 424 is coupled with the yaw pulley coupler 423b to rotate around a yaw rotating axis 420YX with respect to the yaw pulley coupler 423b. Also, the yaw pulley 424 is integrated with a yaw pulley base 424a. A guide hole 424b is formed in the yaw pulley base 424a. The yaw pulley 424 is formed to rotate around the yaw rotating axis 420YX, and the yaw pulley base 424a coupled therewith rotates along with the yaw pulley 424. Herein, a yaw wire pass hole 440HY is formed at one end portion of the connector 440, and the yaw wire 435Y passes through the yaw wire pass hole 440HY toward the end tool 420.

An actuation wire pass hole 440HA is formed at one end portion of the connector 440, and the actuation wire 435A passes through the actuation wire pass hole 440HA toward the end tool 420. The actuation wire 435A passing through the actuation wire pass hole 440HA is connected to an actuation axis 420AX along an actuation wire guide 423G formed at the yaw pulley coupler 423b.

Guide holes 421a and 422a are formed respectively at the first jaw 421 and the second jaw 422, and the actuation axis 420AX is inserted through the guide hole 421a of the first jaw 421, the guide hole 422a of the second jaw 422, and the guide hole 424b of the yaw pulley base 424a. The actuation wire 435A is coupled to the actuation axis 420AX. When the actuation wire 435A translates, the actuation axis 420AX connected therewith translates along the guide hole 424b to perform an actuation operation of the first jaw 421 and the second jaw 422.

In the end tool 420 of the surgical instrument 400 according to the fourth embodiment of the present invention, the pulley/wire for a pitch operation, the pulley/wire for a yaw operation, and the pulley/wire for an actuation operation are separately formed such that one operation does not affect other operations. This will be described below in more detail.

First, the pitch operation of the present embodiment will be described below.

The pitch wire 435P of the operating force transmitter 430 for a pitch operation of the end tool 420 connects a pitch operator (not illustrated) of an operator (not illustrated) and the pitch pulley 423 of the end tool 420. Thus, when the pitch operator rotates around a pitch operating axis (not illustrated) in the counterclockwise direction in FIG. 33, the pitch wire 435P connected therewith moves in the direction of an arrow P2 of FIG. 33. Accordingly, the pitch pulley 423 connected with the pitch wire 435P, the yaw pulley 424 connected therewith, the first jaw 421, and the second jaw 422 rotate around the pitch rotating axis 420PX in the direction of an arrow P of FIG. 33 to perform a pitch operation. On the other hand, when the pitch operator rotates around the pitch operating axis in the clockwise direction in FIG. 33, the pitch wire 435P connected therewith moves in the direction of an arrow P1 of FIG. 33. Accordingly, the pitch pulley 423 connected with the pitch wire 435P, the yaw pulley 424 connected therewith, the first jaw 421, and the second jaw 422 rotate around the pitch rotating axis 420PX in the direction of the arrow P of FIG. 33 to perform a pitch operation.

The yaw operation of the present embodiment will be described below.

The yaw wire 435Y of the operating force transmitter 430 for a yaw operation of the end tool 420 connects a yaw operator (not illustrated) of an operator (not illustrated) and the yaw pulley 424 of the end tool 420. Thus, when the yaw operator rotates around a yaw operating axis (not illustrated) in the clockwise direction, the yaw wire 435Y connected therewith moves in the direction of an arrow Y1 of FIG. 35. Accordingly, the yaw pulley 424 connected with the yaw wire 435Y, and the first jaw 421 and the second jaw 422 connected therewith rotate around the yaw rotating axis 420YX in the direction of an arrow Y of FIG. 35 to perform a yaw operation.

The actuation operation of the present embodiment will be described below.

The actuation wire 435A of the operating force transmitter 430 for an actuation operation of the end tool 420 connects an actuation operator (not illustrated) of an operator (not illustrated) and the actuation axis 420AX of the end tool 420. Thus, when the actuation operator rotates around an actuation operating axis (not illustrated), the actuation wire 435A moves linearly in the direction of an arrow A of FIG. 35. Accordingly, the actuation axis 420AX connected with the actuation wire 435A translates along the guide hole 424b to perform an actuation operation of the first jaw 421 and the second jaw 422.

<Fourth Embodiment of Surgical Instrument>
(E1+H1+D)

Hereinafter, the surgical instrument 400 according to the fourth embodiment of the present invention will be described. In the surgical instrument 400 according to the fourth embodiment of the present invention, the end tool 420 has the configuration described with reference to FIGS. 32 to 36, and an operator 410 has a yaw operator and an actuation operator formed independently of each other as in the surgical instrument 100 according to the first embodiment of the present invention (illustrated in FIG. 2), so that a rotation of a yaw operating axis and a rotation of an actuation operating axis are performed independently of each other.

Figure 37:
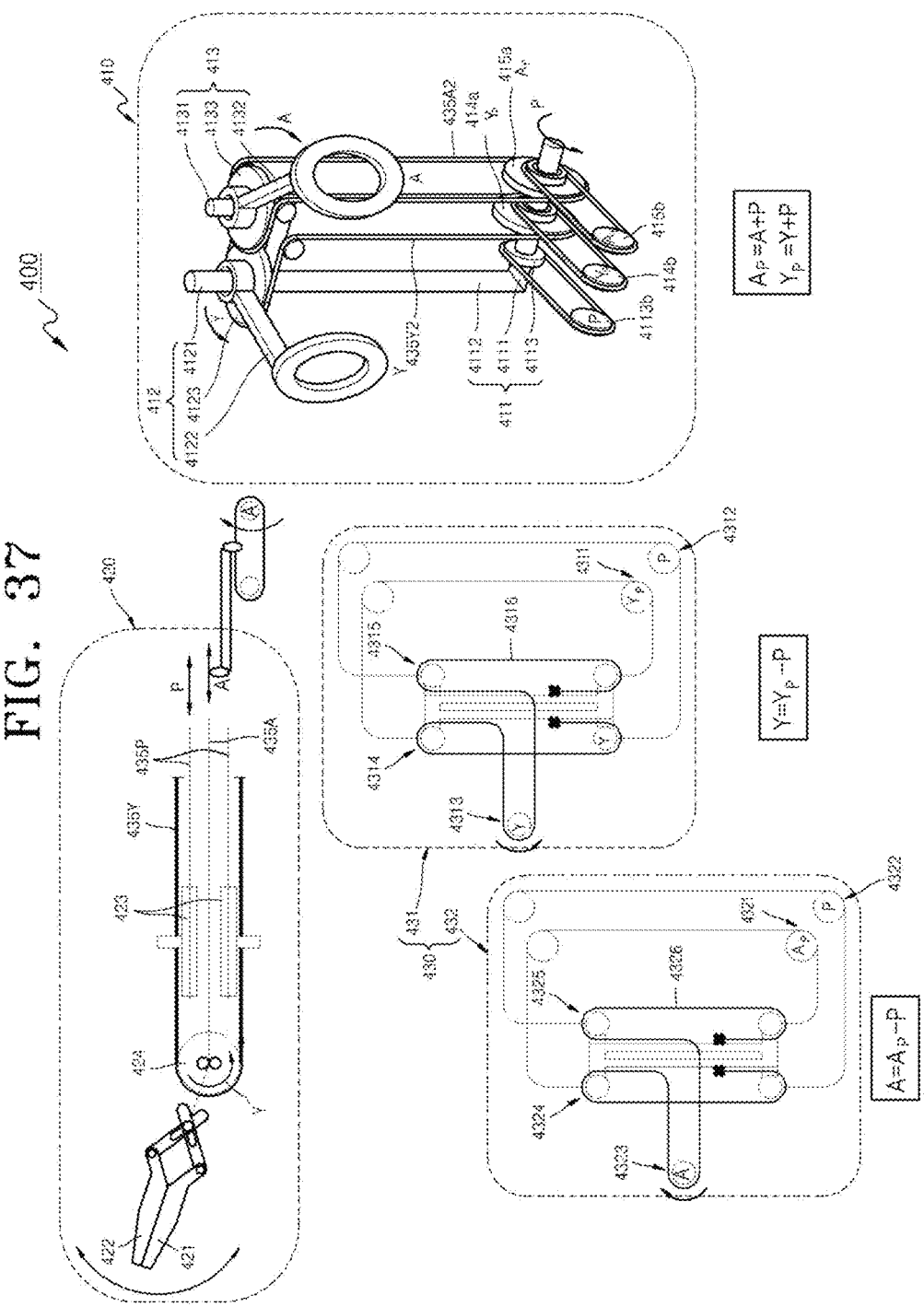
FIG. 37 is a view illustrating a surgical instrument according to a fourth embodiment of the present invention.

FIG. 37 is a view illustrating the surgical instrument 400 according to the fourth embodiment of the present invention. Referring to FIG. 37, the surgical instrument 400 according to the fourth embodiment of the present invention includes an operator 410, the end tool 420, the operating force transmitter 430, and a connector (not illustrated).

The end tool 420 includes the first jaw 421, the second jaw 422, one or more pitch pulleys 423, and one or more yaw pulleys 424, and the operating force transmitter 430 includes one or more pitch wires 435P, one or more yaw wires 435Y, and one or more actuation wires 435A. In the end tool 420, the pulley/wire for a pitch operation, the pulley/wire for a yaw operation, and the pulley/wire for an actuation operation are separately formed such that one operation does not affect other operations. Since the end tool 420 is substantially identical to the end tool described with reference to FIGS. 32 to 36, a detailed description thereof will be omitted herein.

Figure 21A:
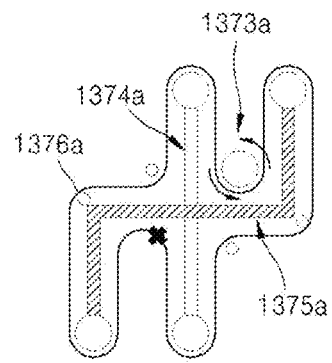
FIGS. 21A to 21E are views illustrating other examples of the second modification of the differential pulley illustrated in FIG. 18.
Figure 21B:
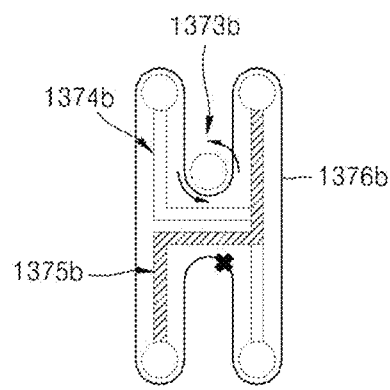
Figure 21C:
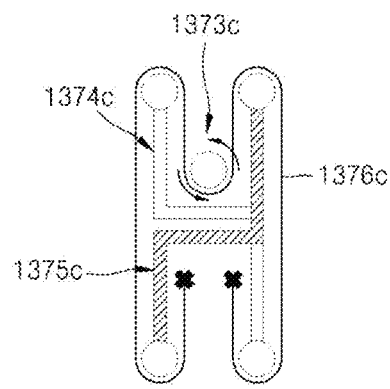
Figure 21D:
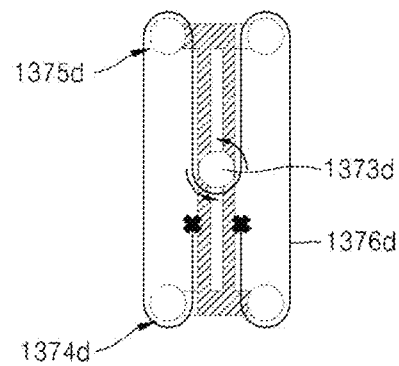
Figure 21E:
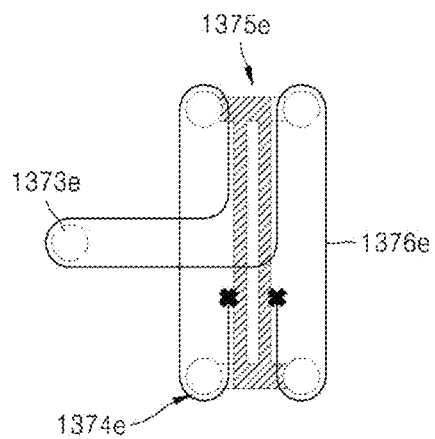

The operating force transmitter 430 includes a first differential member 431 and a second differential member 432. The first differential member 431 and the second differential member 432 each include two or more input units and one input unit, receives an input of rotating forces from the two or more input units, extract a desired rotating force from the sum of (or the difference between) the input rotating forces, and output the desired rotating force through the output unit. The first and second differential members 431 and 432 may include various differential pulleys and differential gears, such as, the differential pulley of the surgical instrument 100 according to the first embodiment illustrated in FIGS. 4A and 4B, the first modification of the differential pulley illustrated in FIG. 15, the second modification of the differential pulley illustrated in FIG. 18, and the third modification of the differential pulley illustrated in FIG. 22. That is, although the differential pulley of FIG. 21E is illustrated as the first and second differential members 431 and 432 of the surgical instrument 400 according to the fourth embodiment in FIG. 37, the present invention is not limited thereto, and various differential pulleys and differential gears may be used in the present embodiment.

Hereinafter, the operator 410 of the surgical instrument 400 according to the fourth embodiment of the present invention will be described in more detail.

Referring to FIG. 37, the operator 410 of the surgical instrument 400 according to the fourth embodiment of the present invention includes a pitch operator 411 controlling a pitch motion of the end tool 420, a yaw operator 412 controlling a yaw motion of the end tool 420, and an actuation operator 413 controlling an actuation motion of the end tool 420.

The pitch operator 411 includes a pitch operating axis 4111, a pitch operating bar 4112, and a pitch operating pulley 4113. Herein, the pitch operating axis 4111 may be formed in a direction parallel to the Y axis, and the pitch operating bar 4112 may be connected with the pitch operating axis 4111 to rotate along with the pitch operating axis 4111. For example, when the user grips and rotates the pitch operating bar 4112, the pitch operating axis 4111 connected with the pitch operating bar 4112 and the pitch operating pulley 4113 connected therewith rotate together therewith. Then, the resulting rotating force is transmitted to the end tool 420 through the operating force transmitter 430, so that the end tool 420 rotates in the same direction as the rotation direction of the pitch operating axis 4111. That is, when the pitch operator 411 rotates in the clockwise direction around the pitch operating axis 4111, the end tool 420 also rotates in the clockwise direction around a pitch pulley operating axis (not illustrated), and when the pitch operator 411 rotates in the counterclockwise direction around the pitch operating axis 4111, the end tool 420 also rotates in the counterclockwise direction around the pitch pulley operating axis. The pitch operating pulley 4113 is integrated with the pitch operating axis 4111 to rotate along with the pitch operating axis 4111.

The yaw operator 412 includes a yaw operating axis 4121, a yaw operating bar 4122, and a yaw operating pulley 4123. A yaw operating wire 435Y2 may be connected to the yaw operating pulley 4123. Although it is illustrated that the yaw operating axis 4121 is formed to extend from the pitch operating bar 4112, the present invention is not limited thereto. For example, the pitch operating bar 4112 and the yaw operating axis 4121 may be formed as separate members on different axes. In this case, the yaw operating axis 4121 may be formed in various directions by ergonomic design according to the structure of the hand of the user gripping the operator 410.

As described above, when the pitch operator 411 rotates, a coordinate system of the yaw operator 412 may change relatively. The yaw operating bar 4122 and the yaw operating pulley 4123 are formed to rotate around the yaw operating axis 4121. For example, when the user holds and rotates the yaw operating bar 4122 with the index finger, the yaw operating pulley 4123 connected with the yaw operating bar 4122 rotates around the yaw operating axis 4121. Then, the resulting rotating force is transmitted to the end tool 420 through the operating force transmitter 430, so that the first and second jaws 420 and 421 of the end tool 420 horizontally rotate in the same direction as the rotation direction of the yaw operating pulley 4123.

The actuation operator 413 includes an actuation operating axis 4131, an actuation operating bar 4132, and an actuation operating pulley 4133. An actuation operating wire 435A2 may be connected to the actuation operating pulley 4133. The actuation operating axis 4131 is formed to extend from the pitch operating bar 4112 and may be formed in the direction parallel to the Z axis or in various directions by ergonomic design according to the structure of the hand of the user gripping the operator 410. As described above, when the pitch operator 411 rotates, a coordinate system of the actuation operator 413 may change relatively. The actuation operating bar 4132 and the actuation operating pulley 4133 are formed to rotate around the actuation operating axis 4131. For example, when the user holds and rotates the actuation operating bar 4132 with the thumb finger, the actuation operating pulley 4133 connected with the actuation operating bar 4132 rotates around the actuation operating axis 4131. Then, the resulting rotating force is transmitted to the end tool 420 through the operating force transmitter 430, so that the first and second jaws 420 and 421 of the end tool 120 perform an actuation operation.

The pitch operating axis 4111 is inserted into a first yaw-pitch (YP) pulley 414a and a first actuation-pitch (AP) pulley 415a such that the first YP pulley 414a and the first AP pulley 415a rotate around the pitch operating axis 4111.

When the yaw operating bar 4122 rotates, the first YP pulley 414a and a second YP pulley 414b connected therewith rotate along with the yaw operating pulley 4123; and when the pitch operating bar 4112 and the yaw operator 412 and the actuation operator 413 connected therewith rotate together around the pitch operating axis 4111, the first YP pulley 414a and the second YP pulley 414b connected therewith rotate along with the pitch operating pulley 4113. That is, the first YP pulley 414a and the second YP pulley 414b may be considered as pulleys that reflect the rotations of the yaw operating bar 4122 and the rotation of the pitch operating bar 4112 together.

In detail, when the yaw operating bar 4122 rotates, the yaw operating pulley 4123 connected with the yaw operating bar 4122 rotates along with the yaw operating bar 4122, and thus the yaw operating wire 435Y2 moves to rotate the first YP pulley 414a and the second YP pulley 414b connected therewith. When the pitch operating axis 4111 and the pitch operating bar 4112 rotate in the direction of an arrow P of FIG. 37, the yaw operating axis 4121 and the yaw operating pulley 4123 also rotate around the pitch operating axis 4111. Then, the yaw operating wire 435Y2 rotates around the pitch operating axis 4111 in the direction of the arrow P of FIG. 37 according to the rotation of the operator 410, and the first YP pulley 414a connected therewith also rotates accordingly. Consequently, the first YP pulley 414a and the second YP pulley 414b rotate when the yaw operating pulley 4123 rotates, and also rotate when the pitch operating pulley 4113 rotates. This means that a yaw operation input and a pitch operation input are added together by the first YP pulley 414a and the second YP pulley 414b of the operator 410 to output the sum of the yaw operation input and the pitch operation input.

When the actuation operating bar 4132 rotates, the first AP pulley 415a and a second AP pulley 415b connected therewith rotate along with the actuation operating pulley 4133; and when the actuation operating bar 4112 and the yaw operator 412 and the actuation operator 413 connected therewith rotate together around the pitch operating axis 4111, the first AP pulley 415a and the second AP pulley 415b connected therewith rotate along with the pitch operating pulley 4113. That is, the first AP pulley 415a and the second AP pulley 415b may be considered as pulleys that reflect the rotations of the actuation operating bar 4132 and the rotation of the pitch operating bar 4112 together.

In detail, when the actuation operating bar 4132 rotates, the actuation operating pulley 4133 connected with the actuation operating bar 4132 rotates along with the actuation operating bar 4132, and thus the actuation operating wire 435A2 connected therewith moves to rotate the first AP pulley 415a and the second AP pulley 415b connected therewith. When the pitch operating axis 4111 and the pitch operating bar 4112 rotate in the direction of the arrow P of FIG. 37, the actuation operating axis 4131 and the actuation operating pulley 4133 also rotate around the pitch operating axis 4111. Then, the actuation operating wire 435A2 rotates around the pitch operating axis 4111 in the direction of the arrow P of FIG. 37 according to the rotation of the operator 410, and the first AP pulley 415a connected therewith also rotates accordingly. Consequently, the first AP pulley 415a and the second AP pulley 415b rotate when the actuation operating pulley 4133 rotates, and also rotate when the pitch operating pulley 4113 rotates. This means that an actuation operation input and a pitch operation input are added together by the first AP pulley 415a and the second AP pulley 415b of the operator 410 to output the sum of the actuation operation input and the pitch operation input.

Although it is illustrated that the first YP pulley 414a is connected to the second YP pulley 414b, and the second YP pulley 414b is connected to a first input unit 4311 of the first differential member 431, this is merely for convenience of description, and the first YP pulley 414a may be directly connected to the first input unit 4311 of the first differential member 431, without using the second YP pulley 414b.

Likewise, although it is illustrated that the first AP pulley 415a is connected to the second AP pulley 415b, and the second AP pulley 415b is connected to a first input unit 4321 of the second differential member 432, this is merely for convenience of description, and the first AP pulley 415a may be directly connected to the first input unit 4321 of the second differential member 432, without using the second AP pulley 415b.

Likewise, although it is illustrated that the pitch operating pulley 4113 is connected to a second pitch operating pulley 4113b, and the second pitch operating pulley 4113b is connected to a second input unit 4312 of the first differential member 431 and a second input unit 4322 of the second differential member 432, this is merely for convenience of description, and the pitch operating pulley 4113 may be directly connected to the second input unit 4312 of the first differential member 431 and the second input unit 4322 of the second differential member 432, without using the second pitch operating pulley 4113b.

Overall Operation of Fourth Embodiment

Hereinafter, an overall configuration for the pitch operation, the yaw operation, and the actuation operation of the surgical instrument 400 according to the fourth embodiment of the present invention will be summarized with reference to the above descriptions.

In the surgical instrument 400 according to the fourth embodiment of the present invention, the first differential member 431 includes the first input unit 4311, the second input unit 4312, an output unit 4313, a first differential control member 4314, a second differential control member 4315, and a differential control wire 4316, and the second differential member 432 includes the first input unit 4321, the second input unit 4322, an output unit 4323, a first differential control member 4324, a second differential control member 4325, and a differential control wire 4326.

In detail, for the configuration of the end tool 420 of the present embodiment, the operating force transmitter 430 capable of dividing the operation input of the operator 410 into a pitch operation, a yaw operation, and an actuation operation is necessary to perform the pitch, yaw, and actuation operations of the end tool 420. The rotation operation of the pitch operating bar may be directly connected to the pitch operation of the end tool. However, since the yaw operator and the actuation operator are disposed on the pitch operator, the operation input of the yaw operator and the operation input of the actuation operator may be added to the pitch operation input prior to transmission thereof to the operating force transmitter, as described above. This may be expressed as the following equation:

$$Y_P = Y + P$$

$$A_P = A + P$$

(where $Y_P$ denotes a rotation of the $Y_P$ pulley, $A_P$ denotes a rotation of the $A_P$ pulley, Y denotes a rotation of the yaw operating pulley, and P denotes a rotation of the pitch operating pulley.)

Thus, in order to transmit the output of the operator 410 as only the Y and A components to the end tool 420, the operating force transmitter 430 extracts the following components:

$$Y = Y_P - P$$

$$A = A_P - P$$

To this end, the operating force transmitter 430 includes a differential pulley that receives an input of $Y_P$ and P and outputs only the difference (Y component) between $Y_P$ and P, and a differential pulley that receives an input of $A_P$ and P and outputs only the difference (A component) between $A_P$ and P.

Herein, the first input unit 4311 of the first differential member 431 is connected with the first YP pulley 414a (or the second YP pulley 414b connected therewith) to rotate when the yaw operating pulley 4123 rotates and also rotate when the pitch operating pulley 4113 rotates. Also, the second input unit 4312 of the first differential member 431 is connected with the pitch operating pulley 4113 to rotate when the pitch operating pulley 4113 rotates. Also, the output unit 4313 of the first differential member 431 is connected with the yaw wire 435Y to control the yaw operation of the end tool 420.

The first input unit 4321 of the second differential member 432 is connected with the first AP pulley 415a (or the second AP pulley 415b connected therewith) to rotate when the actuation operating pulley 4133 rotates and also rotate when the pitch operating pulley 4113 rotates. Also, the second input unit 4322 of the second differential member 432 is connected with the pitch operating pulley 4113 to rotate when the pitch operating pulley 4113 rotates. Also, the output unit 4323 of the second differential member 432 is connected with the actuation wire 435A to control the actuation operation of the end tool 420.

The pitch operating pulley 4113 is connected with the pitch wire 435P to control the pitch operation of the end tool 420.

First, the pitch operation will be described below.

As described above, when the user grips the pitch operating bar 4112 of the pitch operator 411 of the operator 410 and rotates the pitch operating bar 4112 around the pitch operating axis 4111 in the direction of an arrow P (pitch) of FIG. 37, the pitch operating pulley 4113 rotates along with the pitch operating axis 4111. Then, the pitch pulley 423 connected with the pitch operating pulley 4113 by the pitch wire 435P, the yaw pulley 424 connected therewith, the first jaw 421, and the second jaw 422 rotate around the pitch rotating axis 420PX (see FIG. 32) to perform a pitch operation.

In this case, the pitch operation does not affect the output units of the differential pulleys 431 and 432 of the operating force transmitter 430 which determine the yaw and actuation operations of the end tool 420. In more detail, when the first YP pulley 414a and the first AP pulley 415a rotate around the pitch operating axis 4111 according to the pitch operation, the first input unit 4311 of the first differential member 431 that is connected with the second YP pulley 414b and the second input unit 4312 of the first differential member 431 that is connected with the pitch operating pulley 4113 rotate; however, since the rotations are offset in the first differential member 431, the output unit 4313 of the first differential member 431 does not rotate. Likewise, the first input unit 4321 of the second differential member 432 that is connected with the second AP pulley 415b and the second input unit 4322 of the second differential member 432 that is connected with the pitch operating pulley 4113 rotate; however, since the rotations are offset in the second differential member 432, the output unit 4323 of the second differential member 432 does not rotate. Thus, the pitch operation may be performed independently of the yaw operation and the actuation operation.

The yaw operation of the present embodiment will be described below.

When the user holds and rotates the yaw operating bar 4122 with the index finger in the direction of an arrow Y of FIG. 37, the yaw operating pulley 4123 connected with the yaw operating bar 4122 rotates around the yaw operating axis 4121. Then, the resulting rotating force is transmitted through the yaw operating wire 435Y2 to the first YP pulley 414a and the second YP pulley 414b connected therewith, to rotate the second YP pulley 414b. When the second YP pulley 414b rotates, the first input unit 4311 of the first differential member 431 connected therewith and the output unit 4313 of the first differential member 431 connected therewith rotate. Consequently, when the output unit 4313 of the first differential member 431 rotates, the yaw wire 435Y connected with the output unit 4313, the yaw pulley 424 connected with the yaw wire 435Y, and the first and second jaws 421 and 422 connected with the yaw pulley 424 rotate around the yaw rotating axis 420YX (see FIG. 32) to perform a yaw operation.

The actuation operation of the present embodiment will be described below.

When the user holds and rotates the actuation operating bar 4132 with the thumb finger in the direction of an arrow A of FIG. 37, the actuation operating pulley 4133 connected with the actuation operating bar 4132 rotates around the actuation operating axis 4131. Then, the resulting rotating force is transmitted through the actuation operating wire 435A2 to the first AP pulley 415a and the second AP pulley 415b connected therewith, to rotate the second AP pulley 415b. When the second AP pulley 415b rotates, the first input unit 4321 of the second differential member 432 connected therewith and the output unit 4323 of the second differential member 432 connected therewith rotate. Consequently, when the output unit 4323 of the second differential member 432 rotates, the actuation wire 435A connected with the output unit 4323 moves linearly in the direction of the arrow A of FIG. 37. Accordingly, the actuation axis 420AX (see FIG. 32) connected with the actuation wire 435A translates to perform an actuation operation of the first jaw 421 and the second jaw 422.

A case where the yaw operating pulley 4123 and the pitch operating pulley 4113 rotate together will be described below.

As described above, the first YP pulley 414a and the second YP pulley 414b connected therewith rotate along with the yaw operating pulley 4123 when the yaw operating pulley 4123 rotates, and rotate along with the pitch operating pulley 4113 when the pitch operating pulley 4113 rotates. The yaw wire 435Y for performing the yaw operation of the end tool 420 is only affected by the operation of the yaw operator 412 but not by the operation of the pitch operator 411. Thus, the first input unit 4311 of the first differential member 431 is connected with the second YP pulley 414b, and the second input unit 4312 of the first differential member 431 is connected with the pitch operating pulley 4113, to extract only a pure yaw operation control component from the rotation of the pitch operating pulley 4113 and the rotation of the yaw operating pulley 4123.

According to the present invention, even when the yaw operator 412 rotates along with the pitch operating axis 4111, the yaw operation of the end tool 420 may depend only on the operation of the yaw operator 412 and not be affected by the pitch operating axis 4111.

A case where the actuation operating pulley 4133 and the pitch operating pulley 4113 rotate together will be described below.

As described above, the first AP pulley 415a and the second AP pulley 415b connected therewith rotate along with the actuation operating pulley 4133 when the actuation operating pulley 4133 rotates, and rotate along with the pitch operating pulley 4113 when the pitch operating axis 4111 rotates. The actuation wire 435A for performing the actuation operation of the end tool 420 is only affected by the operation of the actuation operator 413 but not by the operation of the pitch operator 411. Thus, the first input unit 4321 of the second differential member 432 is connected with the second AP pulley 415b, and the second input unit 4322 of the second differential member 432 is connected with the pitch operating pulley 4113, to extract only a pure actuation operation control component from the rotation of the pitch operating pulley 4113 and the rotation of the actuation operating pulley 4133.

According to the present invention, even when the actuation operator 413 rotates along with the pitch operating pulley 4113, the actuation operation of the end tool 420 may depend only on the operation of the actuation operator 413 and not be affected by the pitch operating pulley 4113.

Thus, as described above, the pitch, yaw, and actuation operations of the operator are independently divided into the pitch, yaw, and actuation operations of the end tool. Also, even when the pitch, yaw, and actuation operations of the operator occur simultaneously or not, the pitch, yaw, and actuation operations of the operator may be independently divided into the pitch, yaw, and actuation operations of the end tool.

Any combination of various configurations of the operator described with reference to FIG. 3A, various configurations of the operating force transmitter described with reference to FIGS. 4A and 15 to 27, and various modifications described with reference to FIGS. 7 to 14 may be applied to the surgical instrument 400 according to the fourth embodiment of the present invention.

<Fifth Embodiment of Surgical Instrument>
(E1+H2+D)

Hereinafter, the surgical instrument 500 according to the fifth embodiment of the present invention will be described. In the surgical instrument 500 according to the fifth embodiment of the present invention, an end tool 520 has the configuration described with reference to FIGS. 32 to 36, and an operator 510 has an actuation operator formed on a yaw operator as in the surgical instrument 200 according to the second embodiment of the present invention (illustrated in FIG. 8), so that the actuation operator rotates along with the yaw operator when the yaw operator rotates.

Figure 38:
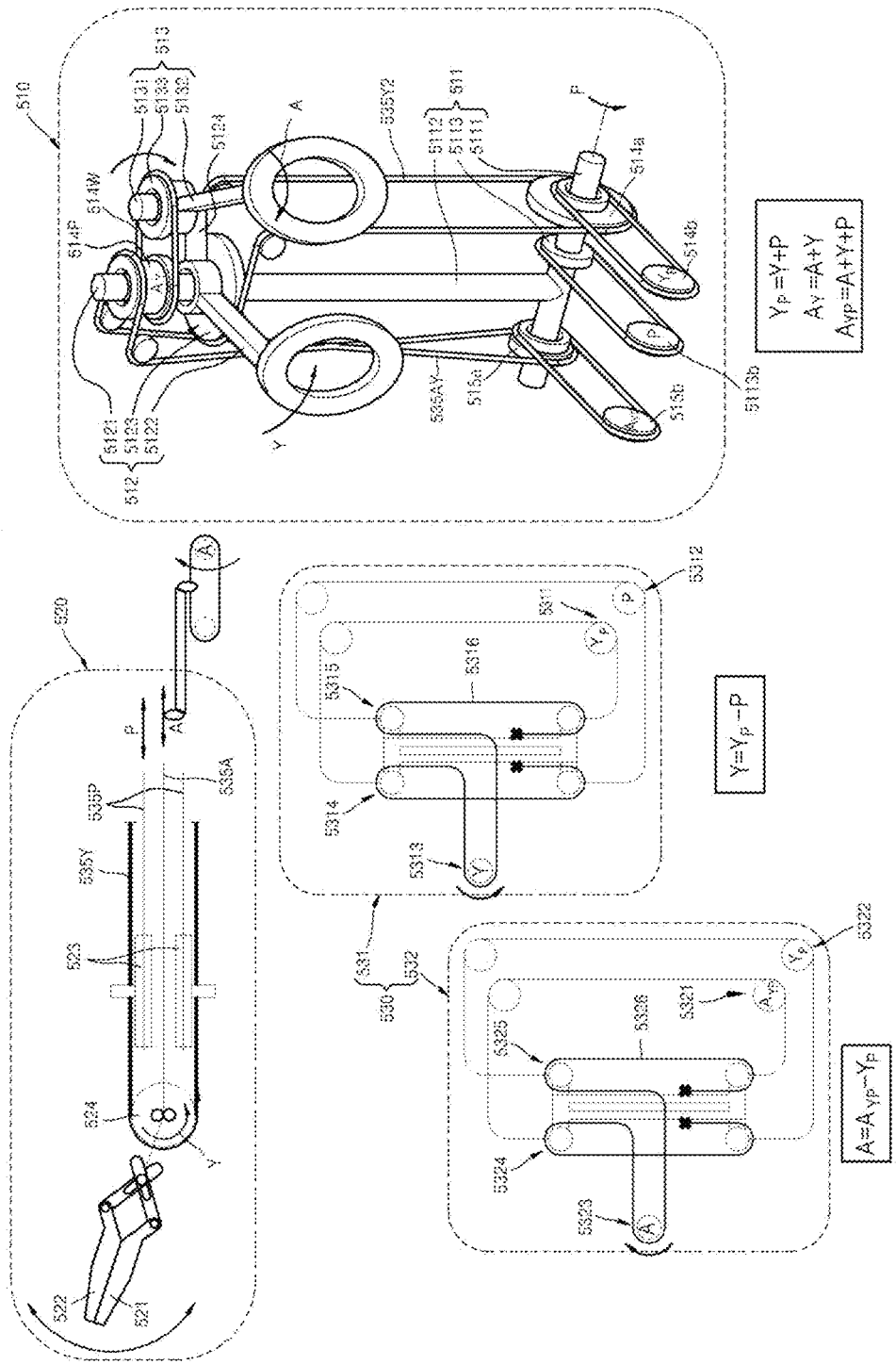
FIG. 38 is a view illustrating a surgical instrument according to a fifth embodiment of the present invention.

FIG. 38 is a view illustrating a surgical instrument 500 according to a fifth embodiment of the present invention. Referring to FIG. 38, the surgical instrument 500 according to the fifth embodiment of the present invention includes an operator 510, an end tool 520, an operating force transmitter 530, and a connector (not illustrated).

The end tool 520 includes a first jaw 521, a second jaw 522, one or more pitch pulleys 523, and one or more yaw pulleys 524, and the operating force transmitter 530 includes one or more pitch wires 535P, one or more yaw wires 535Y, and one or more actuation wires 535A. In the end tool 520, the pulley/wire for a pitch operation, the pulley/wire for a yaw operation, and the pulley/wire for an actuation operation are separately formed such that one operation does not affect other operations. Since the end tool 520 is substantially identical to the end tool 420 described with reference to FIGS. 32 to 36, a detailed description thereof will be omitted herein.

The operating force transmitter 530 includes a first differential member 531 and a second differential member 532. The first differential member 531 and the second differential member 532 includes two or more input units and one input unit, receives an input of rotating forces from the two or more input units, extracts a desired rotating force from the sum of (or the difference between) the input rotating forces, and outputs the desired rotating force through the output unit. The first and second differential members 531 and 532 may include various differential pulleys and differential gears, such as, the differential pulley of the surgical instrument 100 according to the first embodiment illustrated in FIGS. 4A and 4B, the first modification of the differential pulley illustrated in FIG. 15, the second modification of the differential pulley illustrated in FIG. 18, and the third modification of the differential pulley illustrated in FIG. 22. That is, although the differential pulley of FIG. 21E is illustrated as the first and second differential members 531 and 532 of the surgical instrument 500 according to the fifth embodiment in FIG. 38, the present invention is not limited thereto, and various differential pulleys and differential gears may be used in the present embodiment.

Hereinafter, the operator 510 of the surgical instrument 500 according to the fifth embodiment of the present invention will be described in more detail.

Referring to FIG. 38, the operator 510 of the surgical instrument 500 according to the fifth embodiment of the present invention includes a pitch operator 511 controlling a pitch motion of the end tool 520, a yaw operator 512 controlling a yaw motion of the end tool 520, and an actuation operator 513 controlling an actuation motion of the end tool 520.

The pitch operator 511 includes a pitch operating axis 5111, a pitch operating bar 5112, and a pitch operating pulley 5113. Herein, the pitch operating axis 5111 may be formed in a direction parallel to the Y axis, and the pitch operating bar 5112 may be connected with the pitch operating axis 5111 to rotate along with the pitch operating axis 5111. For example, when the user grips and rotates the pitch operating bar 5112, the pitch operating axis 5111 connected with the pitch operating bar 5112 and the pitch operating pulley 5113 connected therewith rotate together therewith. Then, the resulting rotating force is transmitted to the end tool 520 through the operating force transmitter 530, so that the end tool 520 rotates in the same direction as the rotation direction of the pitch operating axis 5111. That is, when the pitch operator 511 rotates in the clockwise direction around the pitch operating axis 5111, the end tool 520 also rotates in the clockwise direction around a pitch pulley operating axis (not illustrated), and when the pitch operator 511 rotates in the counterclockwise direction around the pitch operating axis 5111, the end tool 520 also rotates in the counterclockwise direction around the pitch pulley operating axis. The pitch operating pulley 5113 is integrated with the pitch operating axis 5111 to rotate along with the pitch operating axis 5111.

The yaw operator 512 includes a yaw operating axis 5121, a yaw operating bar 5122, and a yaw operating pulley 5123. Although it is illustrated that the yaw operating axis 5121 is formed to extend from the pitch operating bar 5112, the present invention is not limited thereto. For example, the pitch operating bar 5112 and the yaw operating axis 5121 may be formed as separate members on different axes. In this case, the yaw operating axis 5121 may be formed in various directions by ergonomic design according to the structure of the hand of the user gripping the operator 510. A yaw operating wire 535Y2 may be connected to the yaw operating pulley 5123.

As described above, when the pitch operator 511 rotates, a coordinate system of the yaw operator 512 may change relatively. The yaw operating bar 5122 and the yaw operating pulley 5123 are formed to rotate around the yaw operating axis 5121. For example, when the user holds and rotates the yaw operating bar 5122 with the index finger, the yaw operating pulley 5123 connected with the yaw operating bar 5122 rotates around the yaw operating axis 5121. Then, the resulting rotating force is transmitted to the end tool 520 through the yaw operating wire 535Y2, so that the first and second jaws 521 and 522 of the end tool 520 horizontally rotate in the same direction as the rotation direction of the yaw operating pulley 5123.

The actuation operator 513 includes an actuation operating axis 5131, an actuation operating bar 5132, and an actuation operating pulley 5133. The actuation operating bar 5132 and the actuation operating pulley 5133 are formed to rotate around the actuation operating axis 5131. For example, when the user holds and rotates the actuation operating bar 5132 with the thumb finger, the actuation operating pulley 5133 connected with the actuation operating bar 5132 rotates around the actuation operating axis 5131. Then, the resulting rotating force is transmitted to the end tool 520 through the operating force transmitter 530, so that the first and second jaws 521 and 522 of the end tool 520 perform an actuation operation. In this case, the actuation operator 513 may be formed in various directions by ergonomic design according to the structure of the hand of the user gripping the operator 510.

The actuation operator 513 is formed on a yaw-actuation connector 5124 extending from the yaw operator 512. Thus, when the yaw operating bar 5122 of the yaw operator 512 rotates, the actuation operator 513 rotates around the yaw operating axis 5121 along with the yaw operating bar 5122 and the yaw operating pulley 5123. A yaw-actuation operating pulley 514P may be formed to rotate around the yaw operating axis 5121. The actuation operating pulley 5133 and the yaw-actuation operating pulley 514P are connected by a yaw-actuation connecting wire 514W. A yaw-actuation operating wire 535AY is connected to the yaw-actuation operating pulley 514P.

Thus, when the yaw operating bar 5122 rotates, the yaw-actuation connector 5124 extending therefrom and the actuation operator 513 rotate around the yaw operating axis 5121, the yaw-actuation connecting wire 514W connected to the actuation operating pulley 5133 also rotates around the yaw operating axis 5121, and consequently, the yaw-actuation operating pulley 514P rotates around the yaw operating axis 5121.

Consequently, the yaw-actuation operating pulley 514P rotates when the yaw operating pulley 5123 rotates, and also rotates when the actuation operating pulley 5133 rotates.

The pitch operating axis 5111 is inserted into a first yaw-pitch (YP) pulley 514*a* and a first actuation-yaw-pitch (AYP) pulley 515*a* such that the first YP pulley 514*a* and the first AYP pulley 515*a* rotate around the pitch operating axis 5111.

When the yaw operating bar 5122 rotates, the first YP pulley 514*a* and a second YP pulley 514*b* connected therewith rotate along with the yaw operating pulley 5123; and when the pitch operating bar 5112 and the yaw operator 512 and the actuation operator 513 connected therewith rotate together around the pitch operating axis 5111, the first YP pulley 514*a* and the second YP pulley 514*b* connected therewith rotate along with the pitch operating pulley 5113. That is, the first YP pulley 514*a* and the second YP pulley 514*b* may be considered as pulleys that reflect the rotations of the yaw operating bar 5122 and the rotation of the pitch operating bar 5112 together.

In detail, when the yaw operating bar 5122 rotates, the yaw operating pulley 5123 connected with the yaw operating bar 5122 rotates along with the yaw operating bar 5122, and thus the yaw operating wire 535Y2 moves to rotate the first YP pulley 514*a* and the second YP pulley 514*b* connected therewith. When the pitch operating axis 5111 and the pitch operating bar 5112 rotate in the direction of an arrow P of FIG. 38, the yaw operating axis 5121 and the yaw operating pulley 5123 also rotate around the pitch operating axis 5111. Then, the yaw operating wire 535Y2 rotates around the pitch operating axis 5111 in the direction of the arrow P of FIG. 38 according to the rotation of the operator 510, and the first YP pulley 514*a* connected therewith also rotates accordingly. Consequently, the first YP pulley 514*a* and the second YP pulley 514*b* rotate when the yaw operating pulley 5123 rotates, and also rotate when the pitch operating pulley 5113 rotates. This means that a yaw operation input and a pitch operation input are added together by the first YP pulley 514*a* and the second YP pulley 514*b* of the operator 510 to output the sum of the yaw operation input and the pitch operation input.

The first AYP pulley 515*a* and a second AYP pulley 515*b* connected therewith rotate along with the actuation operating pulley 5133 when the actuation operating bar 5132 rotates, rotate along with the yaw operating pulley 5123 when the yaw operating bar 5122 rotates, and rotate along with the pitch operating pulley 5113 when the pitch operating bar 5112 rotates. That is, the first AYP pulley 515*a* and the second AYP pulley 515*b* may be considered as pulleys that reflect the rotations of the actuation operating bar 5132 and the rotation of the yaw operating bar 5122 together.

In detail, when the actuation operating bar 5132 rotates, the actuation operating pulley 5133 connected with the actuation operating bar 5132 rotates along with the actuation operating bar 5132, and thus the yaw-actuation connecting wire 514W moves to rotate the yaw-actuation operating pulley 514P. When the yaw-actuation operating pulley 514P rotates, the yaw-actuation operating wire 535AY connected therewith moves to rotate the first AYP pulley 515*a* and the second AYP pulley 515*b* connected therewith. When the yaw operating bar 5122 rotates, the actuation operator 513 connected with the yaw operating bar 5122 rotates along with the yaw operating bar 5122, and thus the yaw-actuation connecting wire 514W connected with the actuation operating pulley 5133 of the actuation operator 513 rotates around the yaw operating axis 5121 to rotate the yaw-actuation operating pulley 514P. When the yaw-actuation operating pulley 514P rotates, the yaw-actuation operating wire 535AY connected therewith moves to rotate the first AYP pulley 515*a* and the second AYP pulley 515*b* connected therewith. When the pitch operating axis 5111 and the pitch operating bar 5112 rotate in the direction of the arrow P of FIG. 38, the actuation operating axis 5131 and the actuation operating pulley 5133 also rotate around the pitch operating axis 5111. Then, the yaw-actuation operating wire 535AY rotates around the pitch operating axis 5111 in the direction of the arrow P of FIG. 38 according to the rotation of the operator 510, and the first AYP pulley 515*a* connected therewith also rotates accordingly. Consequently, the first AYP pulley 515*a* and the second AYP pulley 515*b* rotate when the actuation operating bar 5132 rotates, rotate when the yaw operating bar 5122 rotates, and rotate when the pitch operating bar 5112 rotates. This means that an actuation operation input, a yaw operation input, and a pitch operation input are added together by the first AYP pulley 515*a* and the second AYP pulley 515*b* of the operator 510 to output the sum of the actuation operation input, the yaw operation input, and the pitch operation input.

Although it is illustrated that the first YP pulley 514*a* is connected to the second YP pulley 514*b*, and the second YP pulley 514*b* is connected to a first input unit 5311 of the first differential member 531, this is merely for convenience of description, and the first YP pulley 514*a* may be directly connected to the first input unit 5311 of the first differential member 531, without using the second YP pulley 514*b*.

Likewise, although it is illustrated that the first AYP pulley 515*a* is connected to the second AYP pulley 515*b*, and the second AYP pulley 515*b* is connected to a first input unit 5321 of the second differential member 532, this is merely for convenience of description, and the first AYP pulley 515*a* may be directly connected to the first input unit 5321 of the second differential member 532, without using the second AYP pulley 515*b*.

Likewise, although it is illustrated that the pitch operating pulley 5113 is connected to a second pitch operating pulley 5113*b*, and the second pitch operating pulley 5113*b* is connected to a second input unit 5312 of the first differential member 531, this is merely for convenience of description, and the pitch operating pulley 5113 may be directly connected to the second input unit 5312 of the first differential member 531, without using the second pitch operating pulley 5113*b*.

Overall Operation of Fifth Embodiment

Hereinafter, an overall configuration for the pitch operation, the yaw operation, and the actuation operation of the surgical instrument 500 according to the fifth embodiment of the present invention will be summarized with reference to the above descriptions.

In the surgical instrument 500 according to the fifth embodiment of the present invention, the first differential member 531 includes the first input unit 5311, the second input unit 5312, an output unit 5313, a first differential control member 5314, a second differential control member 5315, and a differential control wire 5316, and the second differential member 532 includes a first input unit 5321, a second input unit 5322, an output unit 5323, a first differential control member 5324, a second differential control member 5325, and a differential control wire 5326.

For the configuration of the end tool 520 of the present embodiment, the operating force transmitter 530 capable of dividing the operation input of the operator 510 into a pitch operation, a yaw operation, and an actuation operation is necessary to perform the pitch, yaw, and actuation operations of the end tool 520. The rotation operation of the pitch operating bar may be directly connected to the pitch operation of the end tool. However, since the yaw operator and the actuation operator are disposed on the pitch operator and the actuation operator is disposed on the yaw operator, the yaw operation input is added to the pitch operation input and the actuation operation input is added to the yaw operation input and the pitch operation input, prior to transmission thereof to the operating force transmitter, as described above. This may be expressed as the following equation:

$$Y_P = Y + P$$

$$A_{YP} = A + Y + P (A_Y = A + Y)$$

(where $Y_P$ denotes a rotation of the $Y_P$ pulley, $A_{YP}$ denotes a rotation of the $A_{YP}$ pulley, A denotes a rotation of the actuation operating pulley, Y denotes a rotation of the yaw operating pulley, and P denotes a rotation of the pitch operating pulley.)

Thus, in order to transmit the output of the operator 510 as only the Y and A components to the end tool 520, the operating force transmitter 530 extracts the following components:

$$Y = Y_P - P$$

$$A = A_{YP} - Y_P$$

To this end, the operating force transmitter 530 includes a differential pulley that receives an input of $Y_P$ and P and outputs only the difference (Y component) between $Y_P$ and P, and a differential pulley that receives an input of $A_{YP}$ and $Y_P$ and outputs only the difference (A component) between $A_{YP}$ and $Y_P$.

Herein, the first input unit 5311 of the first differential member 531 is connected with the first $Y_P$ pulley 514a (or the second $Y_P$ pulley 514b connected therewith) to rotate when the yaw operating pulley 5123 rotates and also rotate when the pitch operating pulley 5113 rotates. Also, the second input unit 5312 of the first differential member 531 is connected with the pitch operating pulley 5113 to rotate when the pitch operating pulley 5113 rotates. Also, the output unit 5313 of the first differential member 531 is connected with the yaw wire 535Y to control the yaw operation of the end tool 520.

The first input unit 5321 of the second differential member 532 is connected with the first $A_{YP}$ pulley 515a (or the second $A_{YP}$ pulley 515b connected therewith) to rotate when the actuation operating pulley 5133 rotates, rotate when the yaw operating pulley 5123 rotates, and rotate when the pitch operating pulley 5113 rotates. Also, the second input unit 5322 of the second differential member 532 is connected with the second $Y_P$ pulley 514b to rotate when the second $Y_P$ pulley 514b rotates. Also, the output unit 5323 of the second differential member 532 is connected with the actuation wire 535A to control the actuation operation of the end tool 520.

The pitch operating pulley 5113 is connected with the pitch wire 535P to control the pitch operation of the end tool 520.

First, the pitch operation will be described below.

As described above, when the user grips the pitch operating bar 5112 of the pitch operator 511 of the operator 510 and rotates the pitch operating bar 5112 around the pitch operating axis 5111 in the direction of an arrow P of FIG. 38, the pitch operating pulley 5113 rotates along with the pitch operating axis 5111. Then, the pitch pulley 523 connected with the pitch operating pulley 5113 by the pitch wire 535P, the yaw pulley 524 connected therewith, the first jaw 521, and the second jaw 522 rotate around the pitch rotating axis 420PX (see FIG. 32) to perform a pitch operation.

In this case, the pitch operation does not affect the first and second differential pulleys 531 and 532 of the operating force transmitter 530 which determine the yaw and actuation operations of the end tool 520. In more detail, when the first YP pulley 514a and the first AYP pulley 515a rotate around the pitch operating axis 5111 according to the pitch operation, the first input unit 5311 of the first differential member 531 that is connected with the second YP pulley 514b and the second input unit 5312 of the first differential member 531 that is connected with the pitch operating pulley 5113 rotate; however, since the rotations are offset in the first differential member 531, the output unit 5313 of the first differential member 531 does not rotate. Likewise, the first input unit 5321 of the second differential member 532 that is connected with the second AYP pulley 515b and the second input unit 5322 of the second differential member 532 that is connected with the second YP pulley 514b rotate; however, since the rotations are offset in the second differential member 532, the output unit 5323 of the second differential member 532 does not rotate. Thus, the pitch operation may be performed independently of the yaw operation and the actuation operation.

The yaw operation of the present embodiment will be described below.

When the user holds and rotates the yaw operating bar 5122 with the index finger in the direction of an arrow Y of FIG. 38, the yaw operating pulley 5123 connected with the yaw operating bar 5122 rotates around the yaw operating axis 5121. Then, the resulting rotating force is transmitted through the yaw operating wire 535Y2 to the first YP pulley 514a and the second YP pulley 514b connected therewith, to rotate the second YP pulley 514b. When the second YP pulley 514b rotates, the first input unit 5311 of the first differential member 531 connected therewith and the output unit 5313 of the first differential member 531 connected therewith rotate. Consequently, when the output unit 5313 of the first differential member 531 rotates, the yaw wire 535Y connected with the output unit 5313, the yaw pulley 524 connected with the yaw wire 535Y, and the first and second jaws 521 and 522 connected with the yaw pulley 524 rotate around the yaw rotating axis 420YX (see FIG. 32) to perform a yaw operation.

The actuation operation of the present embodiment will be described below.

When the user holds and rotates the actuation operating bar 5132 with the thumb finger in the direction of an arrow A of FIG. 38, the actuation operating pulley 5133 connected with the actuation operating bar 5132 rotates around the actuation operating axis 5131. Then, the resulting rotating force is transmitted through the yaw-actuation connecting wire 514W to the yaw-actuation operating pulley 514P. When the yaw-actuation operating pulley 514P rotates, the resulting rotating force is transmitted through the yaw-actuation operating wire 535AY connected therewith to the first AYP pulley 515a and the second AYP pulley 515b connected therewith to rotate the second AYP pulley 515b. When the second AYP pulley 515b rotates, the first input unit 5321 of the second differential member 532 connected therewith and the output unit 5323 of the second differential member 532 connected therewith rotate. Consequently, when the output unit 5323 of the second differential member 532 rotates, the actuation wire 535A connected with the output unit 5323 moves linearly in the direction of the arrow A of FIG. 38. Accordingly, the actuation axis 420AX (see FIG. 32) connected with the actuation wire 535A translates to perform an actuation operation of the first jaw 521 and the second jaw 522.

A case where the yaw operating pulley 5123 and the pitch operating pulley 5113 rotate together will be described below.

As described above, the first YP pulley 514a and the second YP pulley 514b connected therewith rotate along with the yaw operating pulley 5123 when the yaw operating pulley 5123 rotates, and rotate along with the pitch operating pulley 5113 when the pitch operating axis 5111 rotates. The yaw wire 535Y for performing the yaw operation of the end tool 520 is only affected by the operation of the yaw operator 512 but not by the operation of the pitch operator 511. Thus, the first input unit 5311 of the first differential member 531 is connected with the second YP pulley 514b, and the second input unit 5312 of the first differential member 531 is connected with the pitch operating pulley 5113, to extract only a pure yaw operation control component from the rotation of the pitch operating pulley 5113 and the rotation of the yaw operating pulley 5123.

According to the present invention, even when the yaw operator 512 rotates along with the pitch operating axis 5111, the yaw operation of the end tool 520 may depend only on the operation of the yaw operator 512 and not be affected by the pitch operating axis 5111.

A case where the actuation operating pulley 5133, the yaw operating pulley 5123, and the pitch operating pulley 5113 rotate together will be described below.

As described above, the first AYP pulley 515a and the second AYP pulley 515b connected therewith rotate along with the actuation operating pulley 5133 when the actuation operating pulley 5133 rotates, rotate along with the yaw operating pulley 5123 when the yaw operating pulley 5123 rotates, and rotate along with the pitch operating pulley 5113 when the pitch operating axis 5111 rotates. The actuation wire 535A for performing the actuation operation of the end tool 520 is only affected by the operation of the actuation operator 513 but not by the operation of the pitch operator 511 and the operation of the yaw operator 512. Thus, the first input unit 5321 of the second differential member 532 is connected with the second AYP pulley 515b, and the second input unit 5322 of the second differential member 532 is connected with the second YP pulley 514b, to extract only a pure actuation operation control component from the rotation of the pitch operating pulley 5113, the rotation of the yaw operating pulley 5123, and the rotation of the actuation operating pulley 5133.

According to the present invention, even when the actuation operator 513 rotates along with the yaw operating pulley 5123 or the pitch operating pulley 5113, the actuation operation of the end tool 420 may depend only on the operation of the actuation operator 513 and not be affected by the yaw operating pulley 5123 or the pitch operating pulley 5113.

Thus, as described above, the pitch, yaw, and actuation operations of the operator are independently divided into the pitch, yaw, and actuation operations of the end tool. Also, even when the pitch, yaw, and actuation operations of the operator occur simultaneously or not, the pitch, yaw, and actuation operations of the operator may be independently divided into the pitch, yaw, and actuation operations of the end tool.

Any combination of various configurations of the operator described with reference to FIG. 3A, various configurations of the operating force transmitter described with reference to FIGS. 4A and 15 to 27, and various modifications described with reference to FIGS. 7 to 14 may be applied to the surgical instrument 500 according to the fifth embodiment of the present invention.

<Sixth Embodiment of Surgical Instrument>
(E1+H3+D)

Hereinafter, the surgical instrument 600 according to the sixth embodiment of the present invention will be described. In the surgical instrument 600 according to the sixth embodiment of the present invention, an end tool 620 has the configuration described with reference to FIGS. 32 to 36, and an operator 610 includes a first jaw operator and a second jaw operator that operate a first jaw and second jaw independently instead of the yaw operator and the actuation operator as in the surgical instrument 300 according to third second embodiment illustrated in FIG. 30.

Figure 39:
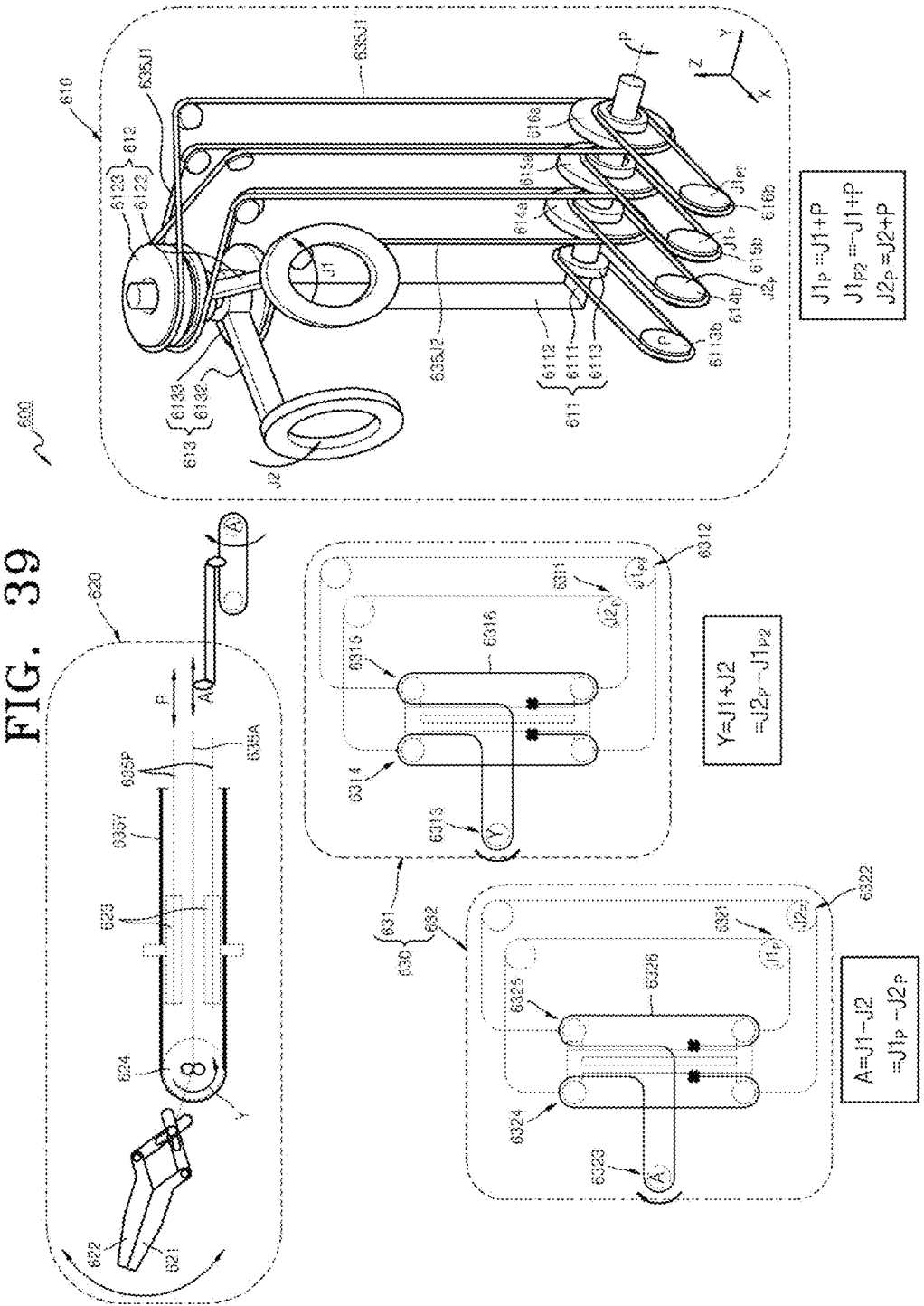
FIG. 39 is a view illustrating a surgical instrument according to a sixth embodiment of the present invention.

FIG. 39 is a view illustrating the surgical instrument 600 according to the sixth embodiment of the present invention. Referring to FIG. 39, the surgical instrument 600 according to the sixth embodiment of the present invention includes the operator 610, the end tool 620, an operating force transmitter 630, and a connector (not illustrated).

The end tool 620 includes a first jaw 621, a second jaw 622, one or more pitch pulleys 623, and one or more yaw pulleys 624, and the operating force transmitter 630 includes one or more pitch wires 635P, one or more yaw wires 635Y, and one or more actuation wires 635A. In the end tool 620, the pulley/wire for a pitch operation, the pulley/wire for a yaw operation, and the pulley/wire for an actuation operation are separately formed such that one operation does not affect other operations. Since the end tool 620 is substantially identical to the end tool 420 described with reference to FIGS. 32 to 36, a detailed description thereof will be omitted herein.

The operating force transmitter 630 includes a first differential member 631 and a second differential member 632. The first differential member 631 and the second differential member 632 each include two or more input units and one input unit, receive an input of rotating forces from the two or more input units, extract a desired rotating force from the sum of (or the difference between) the input rotating forces, and output the desired rotating force through the output unit. The first and second differential members 631 and 632 may include various differential pulleys and differential gears, such as, the differential pulley of the surgical instrument 100 according to the first embodiment illustrated in FIGS. 4A and 4B, the first modification of the differential pulley illustrated in FIG. 15, the second modification of the differential pulley illustrated in FIG. 18, and the third modification of the differential pulley illustrated in FIG. 22. That is, although the differential pulley of FIG. 21E is illustrated as the first and second differential members 631 and 632 of the surgical instrument 600 according to the sixth embodiment in FIG. 39, the present invention is not limited thereto, and various differential pulleys and differential gears may be used in the present embodiment.

Hereinafter, the operator 610 of the surgical instrument 600 according to the sixth embodiment of the present invention will be described in more detail.

Referring to FIG. 39, the operator 610 of the surgical instrument 600 according to the sixth embodiment of the present invention includes a pitch operator 611 controlling a pitch motion of the end tool 620, a first jaw operator 612 controlling a motion of the first jaw 621 of the end tool 620, and a second jaw operator 613 controlling a motion of the second jaw 622 of the end tool 620.

The pitch operator 611 includes a pitch operating axis 6111, a pitch operating bar 6112, and a pitch operating pulley 6113. Herein, the pitch operating axis 6111 may be formed in the direction parallel to the Y axis, and the pitch operating bar 6112 may be connected with the pitch operating axis 6111 to rotate along with the pitch operating axis 6111. For example, when the user grips and rotates the pitch operating bar 6112, the pitch operating axis 6111 connected with the pitch operating bar 6112 and the pitch operating pulley 6113 connected therewith rotate together therewith. Then, the resulting rotating force is transmitted to the end tool 620 through the operating force transmitter 630, so that the end tool 620 rotates in the same direction as the rotation direction of the pitch operating axis 6111. That is, when the pitch operator 611 rotates in the clockwise direction around the pitch operating axis 6111, the end tool 620 also rotates in the clockwise direction around a pitch pulley operating axis (not illustrated), and when the pitch operator 611 rotates in the counterclockwise direction around the pitch operating axis 6111, the end tool 620 also rotates in the counterclockwise direction around the pitch pulley operating axis. The pitch operating pulley 6113 is integrated with the pitch operating axis 6111 to rotate along with the pitch operating axis 6111.

The first jaw operator 612 includes a first jaw operating axis, a first jaw operating bar 6122, and a first jaw operating pulley 6123. Although it is illustrated that the first jaw operating axis is formed to extend from the pitch operating bar 6112 and the pitch operating bar 6112 is inserted into the first jaw operating pulley 6123, the present invention is not limited thereto. For example, the pitch operating bar 6112 and the first jaw operating axis may be formed as separate members on different axes. In this case, the first jaw operating axis may be formed in various directions by ergonomic design according to the structure of the hand of the user gripping the operator 610.

A first jaw operating wire 635J1 and a first additional jaw operating wire 635J1' may be connected to the first jaw operating pulley 6123. In this case, any one of the first jaw operating wire 635J1 and the first additional jaw operating wire 635J1' may be twisted one time such that the rotating force transmission directions of the first jaw operating wire 635J1 and the first additional jaw operating wire 635J1' are opposite to each other. The first jaw operating bar 6122 and the first jaw operating pulley 6123 are formed to rotate around the first jaw operating axis. For example, when the user holds and rotates the first jaw operating bar 6122 with the thumb finger, the first jaw operating pulley 6123 connected with the first jaw operating bar 6122 rotates around the first jaw operating axis. Then, the resulting rotating force is transmitted to the end tool 620 through the operating force transmitter 630, so that the first jaw 621 of the end tool 620 horizontally rotate in the same direction as the rotation direction of the first jaw operating pulley 6123.

The second jaw operator 613 includes a second jaw operating axis, a second jaw operating bar 6132, and a second jaw operating pulley 6133. Although it is illustrated that the second jaw operating axis is formed to extend from the pitch operating bar 6112 and the pitch operating bar 6112 is inserted into the second jaw operating pulley 6133, the present invention is not limited thereto. For example, the pitch operating bar 6112 and the second jaw operating axis may be formed as separate members on different axes. In this case, the second jaw operating axis may be formed in various directions by ergonomic design according to the structure of the hand of the user gripping the operator 610.

A second jaw operating wire 635J2 may be connected to the second jaw operating pulley 6133. The second jaw operating bar 6132 and the second jaw operating pulley 6133 are formed to rotate around the second jaw operating axis. For example, when the user holds and rotates the second jaw operating bar 6132 with the index finger, the second jaw operating pulley 6133 connected with the second jaw operating bar 6132 rotates around the second jaw operating axis. Then, the resulting rotating force is transmitted to the end tool 620 through the operating force transmitter 630, so that the second jaw 622 of the end tool 620 horizontally rotates in the same direction as the rotation direction of the second jaw operating pulley 6133.

The pitch operating axis 6111 is inserted into a first second jaw-pitch (J2P) pulley 614a, a first first jaw-pitch (J1P) pulley 615a, and a first J1P additional pulley 616a such that the first J2P pulley 614a, the first J1P pulley 615a, and the first J1P additional pulley 616a may rotate around the pitch operating axis 6111.

The first J2P pulley 614a and a second J2P pulley 614b connected therewith rotate along with the second jaw operating pulley 6133 when the second jaw operating pulley 6133 rotates, and rotate along with the pitch operating pulley 6113 when the pitch operating bar 6112, and the first operator 612 and the second operator 613 connected therewith rotate around the pitch operating axis 6111. That is, the first J2P pulley 614a and the second J2P pulley 614b may be considered as pulleys that reflect the rotations of the second jaw operating bar 6132 and the rotation of the pitch operating bar 6112 together.

In detail, when the second jaw operating bar 6132 rotates, the second jaw operating pulley 6133 connected with the second jaw operating bar 6132 rotates along with the second jaw operating bar 6132, and thus the second jaw operating wire 635J2 connected therewith moves to rotate the first J2P pulley 614a and the second J2P pulley 614b connected therewith. When the pitch operating axis 6111 and the pitch operating bar 6112 rotate in the direction of an arrow P of FIG. 39, the second jaw operating axis and the second jaw operating pulley 6133 also rotate around the pitch operating axis 6111. Then, the second jaw operating wire 635J2 rotates around the pitch operating axis 6111 in the direction of the arrow P of FIG. 39 according to the rotation of the operator 610, and the first J2P pulley 614a connected therewith also rotates accordingly. Consequently, the first J2P pulley 614a and the second J2P pulley 614b rotate when the second jaw operating pulley 6132 rotates, and rotate when the pitch operating bar 6112 rotates. This means that a second jaw operation input and a pitch operation input are added together by the first J2P pulley 614a and the second J2P pulley 614b of the operator 610 to output the sum of the second jaw operation input and the pitch operation input.

The first J1P pulley 615a and a second J1P pulley 615b connected therewith rotate along with the first jaw operating pulley 6123 when the first jaw operating bar 6122 rotates, and rotate along with the pitch operating pulley 6113 when the pitch operating bar 6112, and the first operator 612 and the second operator 613 connected therewith rotate around the pitch operating axis 6111. That is, the first J1P pulley 615a and the second J1P pulley 615b may be considered as pulleys that reflect the rotations of the first jaw operating bar 6122 and the rotation of the pitch operating bar 6112 together.

Likewise, the first J1P additional pulley 616a and a second J1P additional pulley 616b connected therewith rotate along with the first jaw operating pulley 6123 when the first jaw operating bar 6122 rotates, and rotate along with the pitch operating pulley 6113 when the pitch operating bar 6112, and the first operator 612 and the second operator 613 connected therewith rotate around the pitch operating axis 6111. That is, the first J1P additional pulley 616a and the second J1P additional pulley 616b may be considered as pulleys that reflect the rotation of the first jaw operating bar 6122 and the rotation of the pitch operating bar 6112 together.

Herein, the rotation directions of the first J1P pulley 615a and the first J1P additional pulley 616a are opposite to each other. This is because unlike the first jaw operating wire 635J1 connecting the first jaw operating pulley 6123 and the first J1P pulley 615a, the first additional jaw operating wire 635J1' connecting the first jaw operating pulley 6123 and the first J1P additional pulley 616a is twisted one time. That is, since the rotating force transmission directions of the first jaw operating wire 635J1 and the first additional jaw operating wire 635J1' are opposite to each other, the rotation directions of the first J1P pulley 615a and the first J1P additional pulley 616a are opposite to each other.

Although it is illustrated that the first J2P pulley 614a is connected to the second J2P pulley 614b, and the second J2P pulley 614b is connected to a first input unit 6311 of the first differential member 631 and a second input unit 6322 of the second differential member 632, this is merely for convenience of description, and the first J2P pulley 614a may be directly connected to the first input unit 6311 of the first differential member 631 and the second input unit 6322 of the second differential member 632, without using the second J2P pulley 614b.

Likewise, although it is illustrated that the first J1P pulley 615a is connected to the second J1P pulley 615b, and the second J1P pulley 615b is connected to a first input unit 6321 of the second differential member 632, this is merely for convenience of description, and the first J1P pulley 615a may be directly connected to the first input unit 6321 of the second differential member 632, without using the second J1P pulley 615b.

Likewise, although it is illustrated that the first J1P additional pulley 616a is connected to the second J1P additional pulley 616b, and the second J1P additional pulley 616b is connected to a second input unit 6312 of the first differential member 631, this is merely for convenience of description, and the first J1P additional pulley 616a may be directly connected to the second input unit 6312 of the first differential member 631, without using the second J1P additional pulley 616b.

Overall Operation of Sixth Embodiment

Hereinafter, an overall configuration for the pitch operation, the yaw operation, and the actuation operation of the surgical instrument 600 according to the sixth embodiment of the present invention will be summarized with reference to the above descriptions.

In the surgical instrument 600 according to the sixth embodiment of the present invention, the first differential member 631 includes the first input unit 6311, the second input unit 6312, an output unit 6313, a first differential control member 6314, a second differential control member 6315, and a differential control wire 6316, and the second differential member 632 includes the first input unit 6321, the second input unit 6322, an output unit 6323, a first differential control member 6324, a second differential control member 6325, and a differential control wire 6326.

In detail, for the configuration of the end tool 620 of the present embodiment, the operating force transmitter 630 capable of dividing the operation input of the operator 610 into a pitch operation, a yaw operation, and an actuation operation is necessary to perform the pitch, yaw, and actuation operations of the end tool 620. The pitch operator 611 includes the first jaw operator 612 and the second jaw operator 613, and divides the operation inputs thereof into a pitch operation component, a yaw operation component, and an actuation operation component. The rotation operation of the pitch operating bar may be directly connected to the pitch operation of the end tool. However, the yaw and actuation operations of the end tool 620 reconstructs the operation inputs of the first jaw and the second jaw. This may be expressed as the following equation:

$Y = J1 + J2$ (two jaws rotate in the same direction in the yaw operation)

$A = J1 - J2$ (two jaws rotate in opposite directions in the actuation operation)

To this end, the operation inputs of the two jaws are connected to the first J1P pulley 615a and the first J2P pulley 614a, and the first J1P additional pulley 616a is provided to transmit the operation input of the first jaw reversely. This may be expressed as the following equation:

$$J1_P = J1 + P$$
$$J1_{P2} = -J1 + P$$
$$J2_P = J2 + P$$

(where $J1_P$ denotes the rotation of the $J1_P$ pulley, $J1_{P2}$ denotes the rotation of the J1P additional pulley, $J2_P$ denotes the rotation of the $J2_P$ pulley, J1 denotes the rotation of the first jaw operating pulley, J2 denotes the rotation of the second jaw operating pulley, and P denotes the rotation of the pitch operating pulley.)

Thus, in order to transmit the output of the operator 610 as only the Y and A components to the end tool 620, the operating force transmitter 630 extracts the following components:

$$Y = J1 + J2 = J2_P - J1_{P2}$$

$$A = J1 - J2 = J1_P - J2_P$$

To this end, the operating force transmitter 630 includes a differential pulley that receives an input of $J2_P$ and $J1_{P2}$ and outputs only the difference (Y component) between $J2_P$ and $J1_{P2}$, and a differential pulley that receives an input of $J1_P$ and $J2_P$ and outputs only the difference (A component) between $J1_P$ and $J2_P$.

The first input unit 6311 of the first differential member 631 is connected with the first J2P pulley 614a (or the second J2P pulley 614b connected therewith) to rotate when the second jaw operating pulley 6133 rotates and also rotate when the pitch operating pulley 6113 rotates. The second input unit 6312 of the first differential member 631 is connected with the first J1P additional pulley 616a (or the second J1P additional pulley 616b connected therewith) to rotate when the first jaw operating pulley 6123 rotates and also rotate when the pitch operating pulley 6113 rotates. Also, the output unit 6313 of the first differential member 631 is connected with the yaw wire 635Y to control the yaw operation of the end tool 620.

The first input unit 6321 of the second differential member 632 is connected with the first J1P pulley 615a (or the second J1P pulley 615b connected therewith) to rotate when the first jaw operating pulley 6123 rotates and also rotate when the pitch operating pulley 6113 rotates. The second input unit 6322 of the second differential member 632 is connected with the first J2P pulley 614a (or the second J2P pulley 614b connected therewith) to rotate when the second jaw operating pulley 6133 rotates and also rotate when the pitch operating pulley 6113 rotates. Also, the output unit 6323 of the second differential member 632 is connected with the actuation wire 635A to control the actuation operation of the end tool 620.

The pitch operating pulley 6113 is connected with the pitch wire 635P to control the pitch operation of the end tool 620.

First, the pitch operation will be described below.

As described above, when the user grips the pitch operating bar 6112 of the pitch operator 611 of the operator 610 and rotates the pitch operating bar 6112 around the pitch operating axis 6111 in the direction of an arrow P of FIG. 39, the pitch operating pulley 6113 rotates along with the pitch operating axis 6111. Then, the pitch pulley 623 connected with the pitch operating pulley 6113 by the pitch wire 635P, the yaw pulley 624 connected therewith, the first jaw 621, and the second jaw 622 rotate around the pitch rotating axis 420PX (see FIG. 32) to perform a pitch operation.

In this case, the pitch operation does not affect the first and second differential pulleys 631 and 632 of the operating force transmitter 630 which determine the yaw and actuation operations of the end tool 620. In more detail, when the first J2P pulley 614a, the first J1P pulley 615a, and the first J1P additional pulley 616a rotate around the pitch operating axis 6111 according to the pitch operation, the first input unit 6311 of the first differential member 631 that is connected with the second J2P pulley 614b and the second input unit 6312 of the first differential member 631 that is connected with the second J1P additional pulley 616b rotate; however, since the rotations are offset in the first differential member 631, the output unit 6313 of the first differential member 631 does not rotate. Likewise, the first input unit 6321 of the second differential member 632 that is connected with the second J1P pulley 615b and the second input unit 6322 of the second differential member 632 that is connected with the second J2P pulley 614b rotate; however, since the rotations are offset in the second differential member 632, the output unit 6323 of the second differential member 632 does not rotate. Thus, the pitch operation may be performed independently of the yaw operation and the actuation operation.

The yaw operation and the actuation operation of the present embodiment will be described below.

For a yaw operation, the user holds and rotates the first jaw operating bar 6122 with the thumb finger in the direction of an arrow J1 of FIG. 39, and holds and rotates the second jaw operating bar 6132 with the index finger in the direction of an arrow J2 of FIG. 39 (that is, rotates the first jaw operating bar 6122 and the second jaw operating bar 6132 in the same direction). For an actuation operation, the user rotates the first jaw operating bar 6122 in a direction opposite to the direction of the arrow J1 of FIG. 39, and rotates the second jaw operating bar 6132 in the direction of the arrow J2 of FIG. 39 (that is, rotates the first jaw operating bar 6122 and the second jaw operating bar 6132 in opposite directions).

Then, the first jaw operating pulley 6123 connected with the first jaw operating bar 6122 rotates around the first jaw operating axis (i.e., the pitch operating bar), and the resulting rotating force is transmitted through the first jaw operating wire 635J1 to the first J1P pulley 615a and the second J1P pulley 615b connected therewith, to rotate the second J1P pulley 615b. When the second J1P pulley 615b rotates, the first input unit 6321 of the second differential member 632 connected therewith and the output unit 6323 of the second differential member 632 connected therewith rotate. In addition, the rotating force of the first jaw operating pulley 6123 is transmitted through the first additional jaw operating wire 635J1' to the first J1P additional pulley 616a and the second J1P additional pulley 616b connected therewith, to rotate the second J1P additional pulley 616b. When the second J1P additional pulley 616b rotates, the second input unit 6312 of the first differential member 631 connected therewith and the output unit 6313 of the first differential member 631 connected therewith rotate.

At the same time, the second jaw operating pulley 6133 connected with the second jaw operating bar 6132 rotates around the second jaw operating axis (i.e., the pitch operating bar), and the resulting rotating force is transmitted through the second jaw operating wire 635J2 to the first J2P pulley 614a and the second J2P pulley 614b connected therewith, to rotate the second J2P pulley 614b. When the second J2P pulley 614b rotates, the first input unit 6311 of the first differential member 631 connected therewith and the output unit 6313 of the first differential member 631 connected therewith rotate. In addition, when the second J2P pulley 614b rotates, the second input unit 6322 of the second differential member 632 connected therewith and the output unit 6323 of the second differential member 632 connected therewith rotate.

As described above, the first J2P pulley 614a and the second J2P pulley 614b connected therewith rotate along with the second jaw operating pulley 6133 when the second jaw operating pulley 6133 rotates, and rotate along with the pitch operating pulley 6113 when the pitch operating pulley 6113 rotates. The first J1P pulley 615a and the second J1P pulley 615b connected therewith rotate along with the first jaw operating pulley 6123 when the first jaw operating pulley 6123 rotates, and rotate along with the pitch operating pulley 6113 when the pitch operating pulley 6113 rotates. Likewise, the first J1P additional pulley 616a and the second J1P additional pulley 616b connected therewith rotate along with the first jaw operating pulley 6123 when the first jaw operating pulley 6123 rotates, and rotate along with the pitch operating pulley 6113 when the pitch operating pulley 6113 rotates.

Consequently, when the second J2P pulley 614b and the second J1P additional pulley 616b are connected respectively to the two input units of the first differential member 631, only a pure yaw operation control component may be extracted from the rotation of the pitch operating pulley 6113, the rotation of the first jaw operating pulley 6123, and the rotation of the second jaw operating pulley 6133.

Likewise, when the second J1P pulley 615b and the second J2P additional pulley 614b are connected respectively to the two input units of the second differential member 632, only a pure actuation operation control component may be extracted from the rotation of the pitch operating pulley 6113, the rotation of the first jaw operating pulley 6123, and the rotation of the second jaw operating pulley 6133.

Consequently, for a yaw operation, when the first jaw operating bar 6122 is rotated in the direction of the arrow J1 of FIG. 39 and the second jaw operating bar 6132 is rotated in the direction of the arrow J2 of FIG. 39, the first J2P pulley 614a and the second J2P pulley 614b connected therewith rotate in the counterclockwise direction in FIG. 39, the first J1P pulley 615a and the second J1P pulley 615b connected therewith rotate in the counterclockwise direction in FIG. 39, and the first J1P additional pulley 616a and the second J1P additional pulley 616b rotate in the clockwise direction in FIG. 39. Also, the first input unit 6311 of the first differential member 631 that is connected with the second J2P pulley 614b rotates in the counterclockwise direction, and the second input unit 6312 of the first differential member 631 that is connected with the second J1P additional pulley 616b rotates in the clockwise direction. Accordingly, the output unit 6313 of the first differential member 631 rotates in the counterclockwise direction, and the yaw wire 635Y connected with the output unit 6313, the yaw pulley 624 connected with the yaw wire 635Y, and the first and second jaws 621 and 622 connected with the yaw pulley 624 rotate around the yaw rotating axis 420YX (see FIG. 32) to perform a yaw operation.

Likewise, for an actuation operation, when the first jaw operating bar 6122 is rotated in a direction opposite to the direction of the arrow J1 of FIG. 39 and the second jaw operating bar 6132 is rotated in the direction of the arrow J2 of FIG. 39, the first J2P pulley 614a and the second J2P pulley 614b connected therewith rotate in the counterclockwise direction in FIG. 39, the first J1P pulley 615a and the second J1P pulley 615b connected therewith rotate in the clockwise direction in FIG. 39, and the first J1P additional pulley 616a and the second J1P additional pulley 616b rotate in the counterclockwise direction in FIG. 39. Also, the first input unit 6321 of the second differential member 632 that is connected with the second J1P pulley 615b rotates in the clockwise direction, and the second input unit 6322 of the second differential member 632 that is connected with the second J2P pulley 614b rotates in the counterclockwise direction. Accordingly, the output unit 6323 of the second differential member 632 rotates in the clockwise direction, the actuation wire 635A connected to the output unit 6313 moves linearly in the direction of an arrow A of FIG. 39, and the actuation axis 420AX (see FIG. 32) connected with the actuation wire 635A translates, to perform an actuation operation of the first jaw 621 and the second jaw 622.

Thus, according to the present invention, the yaw operation and the actuation operation of the end tool may be extracted from the rotation of the first jaw operating pulley 6123 and the rotation of the second jaw operating pulley 6133.

Thus, as described above, the pitch, first jaw, and second jaw operations of the operator are independently divided into the pitch, yaw, and actuation operations of the end tool. Also, even when the pitch, first jaw, and second jaw operations of the operator occur simultaneously or not, the pitch, yaw, and actuation operations of the operator may be independently divided into the pitch, yaw, and actuation operations of the end tool.

Any combination of various configurations of the operator described with reference to FIG. 3A, various configurations of the operating force transmitter described with reference to FIGS. 4A and 15 to 27, and various modifications described with reference to FIGS. 7 to 14 may be applied to the surgical instrument 600 according to the sixth embodiment of the present invention.

<End Tools of Seventh to Ninth Embodiments of Surgical Instrument> (E2)

Hereinafter, surgical instruments 700, 800, and 900 according to seventh, eighth, and ninth embodiments of the present invention will be described. The surgical instruments 700, 800, and 900 according to the seventh, eighth, and ninth embodiments of the present invention are substantially identical to the surgical instruments 100, 200, and 300 according to the first, second, and third embodiments of the present invention and are different from the surgical instruments 100, 200, and 300 according to the first, second, and third embodiments of the present invention in terms of the configuration of an end tool. Thus, the configuration of the end tool applied in common to the seventh, eighth, and ninth embodiments will be described first.

Figure 40:
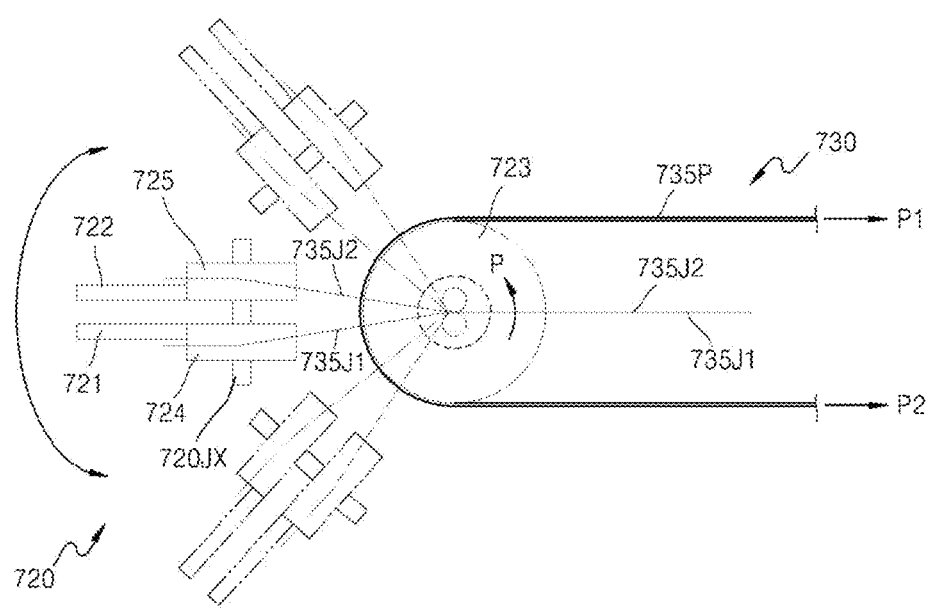
FIG. 40 is an XZ-plane side view of an end tool included in a surgical instrument 700 according to a seventh embodiment of the present invention.
Figure 41:
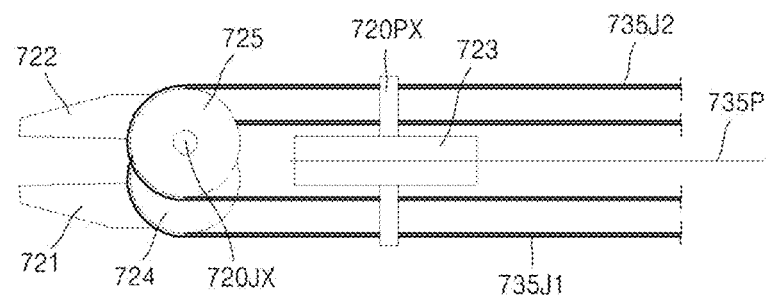
FIG. 41 is an XY-plane plan view of the end tool of FIG. 40.
Figure 42:
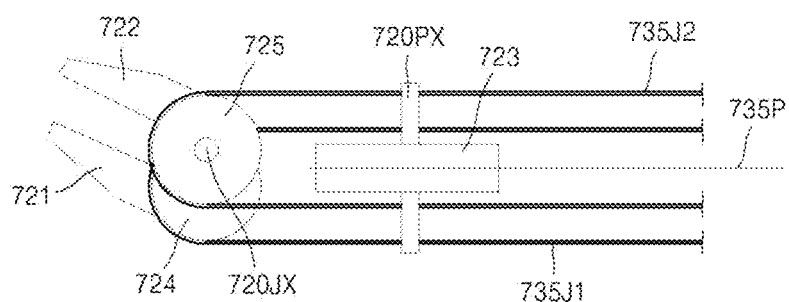
FIG. 42 is a plan view illustrating a yaw motion of the end tool of FIG. 41.
Figure 43:
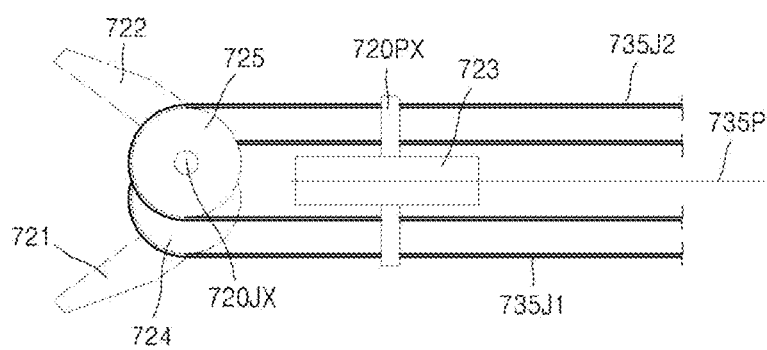
FIG. 43 is a plan view illustrating an actuation motion of the end tool of FIG. 41.

FIGS. 40 to 43 are schematic views illustrating an end tool included in a surgical instrument 700 according to a seventh embodiment of the present invention. FIG. 40 is an XZ-plane side view of the end tool, FIG. 41 is an XY-plane plan view of the end tool, FIG. 42 is a plan view illustrating a yaw motion of the end tool of FIG. 41, and FIG. 43 is a plan view illustrating an actuation motion of the end tool of FIG. 41. Although FIGS. 41 to 43 schematically illustrate that the first jaw and the second jaw rotate around different axes, the present invention is not limited thereto, and the first jaw and the second jaw may rotate around the same axis.

Referring to FIGS. 40 to 43, an end tool 720 included in the surgical instrument 700 according to the seventh embodiment of the present invention includes a first jaw 721, a second jaw 722, a pitch pulley 723, a first jaw pulley 724, and a second jaw pulley 725. An operating force transmitter 730 included in the surgical instrument 700 according to the seventh embodiment of the present invention includes a pitch wire 735P, a first jaw wire 735J1, and a second jaw wire 735J2.

In the present embodiments, a pitch operation is performed by the rotation of the pitch wire wound around the pitch pulley, the two jaw wires are formed to intersect the pitch pulley and extend toward the end tool, and the two jaw wires are wound around their respective jaw pulleys to perform rotation operations for the yaw and actuation operations of their respective jaws. Since the jaw wires are formed to intersect the pitch pulley, the jaw wires are minimally affected by the rotation of the pitch pulley according to the pitch operation.

In detail, at one end portion of a connector (not illustrated), the pitch pulley 723 is formed to rotate around a pitch rotating axis 720PX with respect to the connector. Also, on one side of the pitch pulley 723, the first jaw pulley 724 and the second jaw pulley 725 are formed around a jaw rotating axis 720JX. Thus, the pitch pulley 723 may rotate around the pitch rotating axis 720PX, and the first jaw pulley 724 and the second jaw pulley 725 coupled therewith rotate along with the pitch pulley 723.

The first jaw 721 is coupled with the first jaw pulley 724 to rotate along with the first jaw pulley 724, and the second jaw 722 is coupled with the second jaw pulley 725 to rotate along with the second jaw pulley 725.

In the end tool 720 of the surgical instrument 700 according to the seventh embodiment of the present invention, the pulley/wire for a pitch operation, the pulley/wire for an operation of the first jaw, and the pulley/wire for an operation of the second jaw are separately formed such that one operation does not affect other operations. This will be described below in more detail.

First, the pitch operation of the present embodiment will be described below.

The pitch wire 735P of the operating force transmitter 730 for a pitch operation of the end tool 720 connects a pitch operator (not illustrated) of an operator (not illustrated) and the pitch pulley 723 of the end tool 720. Thus, when the pitch operator rotates around a pitch operating axis (not illustrated) in the counterclockwise direction in FIG. 40, the pitch wire 735P connected therewith moves in the direction of an arrow P2 of FIG. 40. Accordingly, the pitch pulley 723 connected with the pitch wire 735P, the first jaw pulley 724 connected therewith, the first jaw 721, and the second jaw 722 rotate around the pitch rotating axis 720PX in the direction of an arrow P of FIG. 40 to perform a pitch operation. On the other hand, when the pitch operator rotates around the pitch operating axis in the clockwise direction in FIG. 40, the pitch wire 735P connected therewith moves in the direction of an arrow P1 of FIG. 40. Accordingly, the pitch pulley 723 connected with the pitch wire 735P, the first jaw pulley 724 connected therewith, the first jaw 721, and the second jaw 722 rotate around the pitch rotating axis 720PX in a direction opposite to the direction of the arrow P of FIG. 40 to perform a pitch operation.

The yaw operation and the actuation operation of the present embodiment will be described below.

The first jaw wire 735J1 of the operating force transmitter 730 for the operation of the first jaw 721 of the end tool 720 connects a yaw operator (not illustrated), an actuation operator (not illustrated), or a first jaw operator (not illustrated) of an operator (not illustrated) and the first jaw pulley 724 of the end tool 720. Accordingly, when the yaw operator, the actuation operator, or the first jaw operator of the operator rotates, the first jaw wire 735J1 connected therewith, the first jaw pulley 724 connected therewith, and the first jaw 721 rotate around the jaw rotating axis 720JX.

The second jaw wire 735J2 of the operating force transmitter 730 for the operation of the second jaw 722 of the end tool 720 connects a yaw operator (not illustrated), an actuation operator (not illustrated), or a second jaw operator (not illustrated) of an operator (not illustrated) and the second jaw pulley 725 of the end tool 720. Accordingly, when the yaw operator, the actuation operator, or the second jaw operator of the operator rotates, the second jaw wire 735J2 connected therewith, the second jaw pulley 725 connected therewith, and the second jaw 722 rotate around the jaw rotating axis 720JX.

As illustrated in FIG. 42, when the first jaw pulley 724 and the second jaw pulley 725 rotate around the jaw rotating axis 720JX in the same direction, a yaw operation is performed. As illustrated in FIG. 43, when the first jaw pulley 724 and the second jaw pulley 725 rotate around the jaw rotating axis 720JX in opposite directions, an actuation operation is performed.

<Seventh Embodiment of Surgical Instrument>
(E2+H1+D)

Hereinafter, the surgical instrument 700 according to the seventh embodiment of the present invention will be described. In the surgical instrument 700 according to the seventh embodiment of the present invention, the end tool 720 has the configuration described with reference to FIGS. 40 to 43, and an operator 710 has a yaw operator and an actuation operator formed independently of each other as in the surgical instrument 100 according to the first embodiment of the present invention (illustrated in FIG. 2), so that a rotation of a yaw operating axis and a rotation of an actuation operating axis are performed independently of each other.

Figure 44:
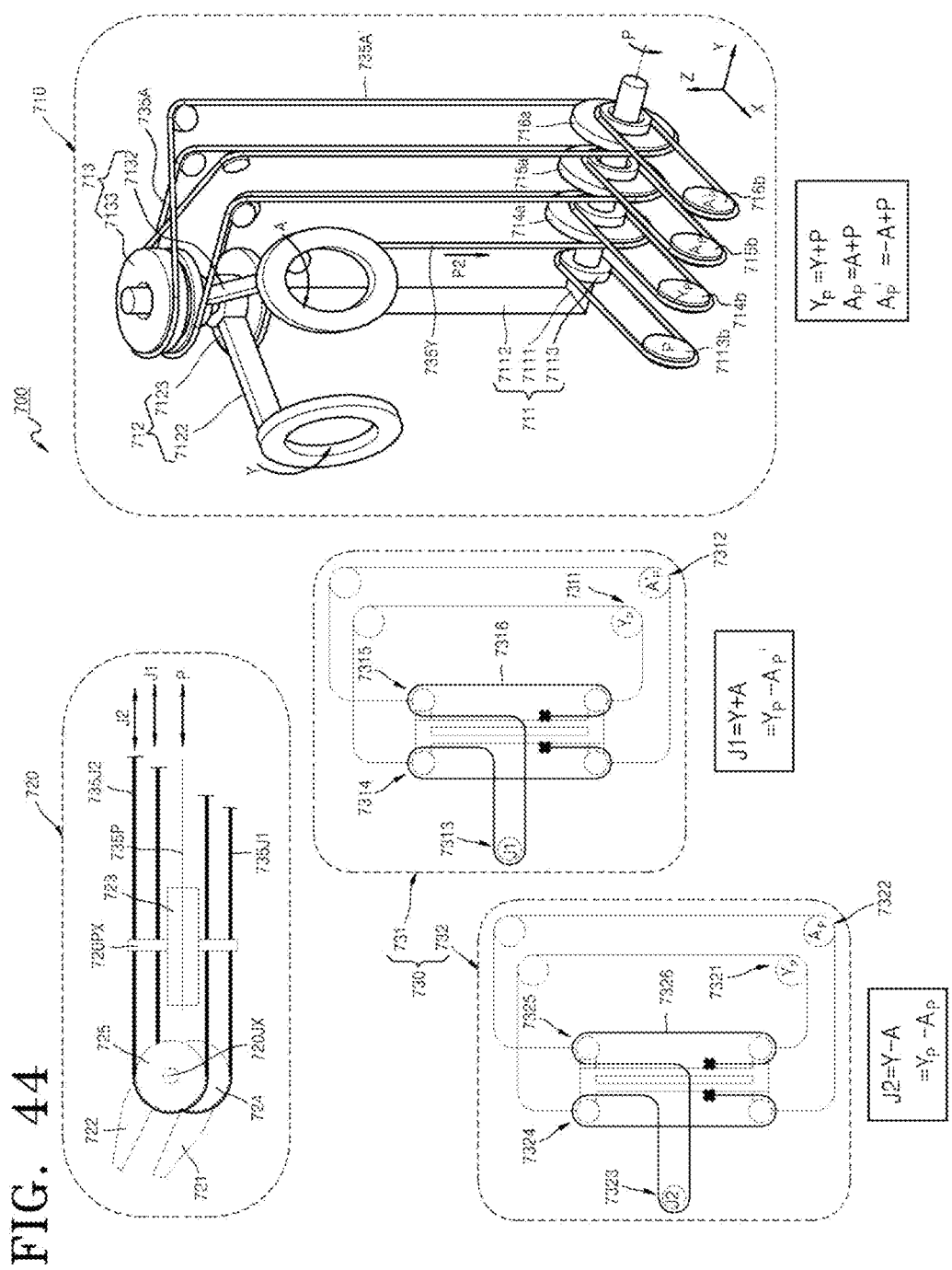
FIG. 44 is a view illustrating a surgical instrument according to a seventh embodiment of the present invention.

FIG. 44 is a view illustrating the surgical instrument 700 according to the seventh embodiment of the present invention. Referring to FIG. 44, the surgical instrument 700 according to the seventh embodiment of the present invention includes the operator 710, the end tool 720, an operating force transmitter 730, and a connector (not illustrated).

The end tool 720 includes the first jaw 721, the second jaw 722, the pitch pulley 723, the first jaw pulley 724, and the second jaw pulley 725, and the operating force transmitter 730 includes the pitch wire 735P, the first jaw wire 735J1, and the second jaw wire 735J2. In the end tool 720, the pulley/wire for a pitch operation, the pulley/wire for an operation of the first jaw, and the pulley/wire for an operation of the second jaw are separately formed such that one operation does not affect other operations. The end tool 720 is the same as described above with reference to FIGS. 40 to 43 and thus a detailed description thereof will be omitted herein.

The operating force transmitter 730 includes a first differential member 731 and a second differential member 732. The first differential member 731 and the second differential member 732 each include two or more input units and one input unit, receive an input of rotating forces from the two or more input units, extract a desired rotating force from the sum of (or the difference between) the input rotating forces, and output the desired rotating force through the output unit. The first and second differential members 731 and 732 may include various differential pulleys and differential gears, such as, the differential pulley of the surgical instrument 100 according to the first embodiment illustrated in FIGS. 4A and 4B, the first modification of the differential pulley illustrated in FIG. 15, the second modification of the differential pulley illustrated in FIG. 18, and the third modification of the differential pulley illustrated in FIG. 22. That is, although the differential pulley of FIG. 21E is illustrated as the first and second differential members 731 and 732 of the surgical instrument 700 according to the seventh embodiment in FIG. 44, the present invention is not limited thereto, and various differential pulleys and differential gears may be used in the present embodiment.

Hereinafter, the operator 710 of the surgical instrument 700 according to the seventh embodiment of the present invention will be described in more detail.

Referring to FIG. 44, the operator 710 of the surgical instrument 700 according to the seventh embodiment of the present invention includes a pitch operator 711 controlling a pitch motion of the end tool 720, a yaw operator 712 controlling a yaw motion of the end tool 720, and an actuation operator 713 controlling an actuation motion of the end tool 720.

The pitch operator 711 includes a pitch operating axis 7111, a pitch operating bar 7112, and a pitch operating pulley 7113. Herein, the pitch operating axis 7111 may be formed in a direction parallel to the Y axis, and the pitch operating bar 7112 may be connected with the pitch operating axis 7111 to rotate along with the pitch operating axis 7111. For example, when the user grips and rotates the pitch operating bar 7112, the pitch operating axis 7111 connected with the pitch operating bar 7112 and the pitch operating pulley 7113 connected therewith rotate together. Then, the resulting rotating force is transmitted to the end tool 720 through the operating force transmitter 730, so that the end tool 720 rotates in the same direction as the rotation direction of the pitch operating axis 7111. That is, when the pitch operator 711 rotates in the clockwise direction around the pitch operating axis 7111, the end tool 720 also rotates in the clockwise direction around a pitch pulley operating axis (not illustrated), and when the pitch operator 711 rotates in the counterclockwise direction around the pitch operating axis 7111, the end tool 720 also rotates in the counterclockwise direction around the pitch pulley operating axis. The pitch operating pulley 7113 is integrated with the pitch operating axis 7111 to rotate along with the pitch operating axis 7111.

The yaw operator 712 includes a yaw operating axis, a yaw operating bar 7122, and a yaw operating pulley 7123. Although it is illustrated that the yaw operating axis is formed to extend from the pitch operating bar 7112 and the pitch operating bar 7112 is inserted into the yaw operating pulley 7123, the present invention is not limited thereto. For example, the pitch operating bar 7112 and the yaw operating axis may be formed as separate members on different axes. In this case, the yaw operating axis may be formed in various directions by ergonomic design according to the structure of the hand of the user gripping the operator 710.

A yaw operating wire 735Y may be connected to the yaw operating pulley 7123. The yaw operating bar 7122 and the yaw operating pulley 7123 are formed to rotate around the yaw operating axis. For example, when the user holds and rotates the yaw operating bar 7122 with the index finger, the yaw operating pulley 7123 connected with the yaw operating bar 7122 rotates around the yaw operating axis. Then, the resulting rotating force is transmitted to the end tool 720 through the operating force transmitter 730, so that the first and second jaws 721 and 722 of the end tool 720 horizontally rotate in the same direction as the rotation direction of the yaw operating pulley 7123.

The actuation operator 713 includes an actuation operating axis, an actuation operating bar 7132, and an actuation operating pulley 7133. Herein, the actuation operating axis may be formed to extend from the pitch operating bar 7112, and may be formed in various directions by ergonomic design according to the structure of the hand of the user gripping the operator 710. An actuation operating wire 735A and an actuation additional operating wire 735A' may be connected to the actuation operating pulley 7133. In this case, any one of the actuation operating wire 735A and the actuation additional operating wire 735A' may be twisted one time such that the rotating force transmission directions of the actuation operating wire 735A and the actuation additional operating wire 735A' are opposite to each other. The actuation operating axis is formed to extend from the pitch operating bar 7112 and may be formed in the direction parallel to the Z axis or in various directions by ergonomic design according to the structure of the hand of the user gripping the operator 710. The actuation operating bar 7132 and the actuation operating pulley 7133 are formed to rotate around the actuation operating axis. For example, when the user holds and rotates the actuation operating bar 7132 with the thumb finger, the actuation operating pulley 7133 connected with the actuation operating bar 7132 rotates around the actuation operating axis. Then, the resulting rotating force is transmitted to the end tool 720 through the operating force transmitter 730, so that the first and second jaws 721 and 722 of the end tool 720 perform an actuation operation.

The pitch operating axis 7111 is inserted into a first YP pulley 714a, a first AP pulley 715a, and a first AP additional pulley 716a such that the first YP pulley 714a, the first AP pulley 715a, and the first AP additional pulley 716a may rotate around the pitch operating axis 7111.

When the yaw operating pulley 7123 rotates, the first YP pulley 714a and a second YP pulley 714b connected therewith rotate along with the yaw operating pulley 7123; and when the pitch operating bar 7112 and the yaw operator 712 and the actuation operator 713 connected therewith rotate together around the pitch operating axis 7111, the first YP pulley 714a and the second YP pulley 714b connected therewith rotate along with the pitch operating pulley 7113. That is, the first YP pulley 714a and the second YP pulley 714b may be considered as pulleys that reflect the rotations of the yaw operating bar 7122 and the rotation of the pitch operating bar 7112 together.

In detail, when the yaw operating bar 7122 rotates, the yaw operating pulley 7123 connected with the yaw operating bar 7122 rotates along with the yaw operating bar 7122, and thus the yaw operating wire 735Y moves to rotate the first YP pulley 714a and the second YP pulley 714b connected therewith. When the pitch operating axis 7111 and the pitch operating bar 7112 rotate in the direction of an arrow P of FIG. 44, the yaw operating axis and the yaw operating pulley 7123 also rotate around the pitch operating axis 7111. Then, the yaw operating wire 735Y rotates around the pitch operating axis 7111 in the direction of the arrow P of FIG. 44 according to the rotation of the operator 710, and the first YP pulley 714a connected therewith also rotates accordingly. Consequently, the first YP pulley 714a and the second YP pulley 714b rotate when the yaw operating pulley 7123 rotates, and also rotate when the pitch operating pulley 7113 rotates. This means that a yaw operation input and a pitch operation input are added together by the first YP pulley 714a and the second YP pulley 714b of the operator 710 to output the sum of the yaw operation input and the pitch operation input.

When the actuation operating bar 7132 rotates, the first AP pulley 715a and a second AP pulley 715b connected therewith rotate along with the actuation operating pulley 7133; and when the actuation operating bar 7112 and the yaw operator 712 and the actuation operator 713 connected therewith rotate together around the pitch operating axis 7111, the first AP pulley 715a and the second AP pulley 715b connected therewith rotate along with the pitch operating pulley 7113. That is, the first AP pulley 715a and the second AP pulley 715b may be considered as pulleys that reflect the rotations of the actuation operating pulley 7133 and the rotation of the pitch operating pulley 7113 together.

Likewise, when the actuation operating bar 7132 rotates, the first AP additional pulley 716a and a second AP additional pulley 716b connected therewith rotate along with the actuation operating pulley 7133; and when the pitch operating bar 7112 and the yaw operator 712 and the actuation operator 713 connected therewith rotate together around the pitch operating axis 7111, the first AP additional pulley 716a and the second AP additional pulley 716b connected therewith rotate along with the pitch operating pulley 7113. That is, the first AP additional pulley 716a and the second AP additional pulley 716b may be considered as pulleys that reflect the rotations of the actuation operating bar 7132 and the rotation of the pitch operating bar 7112 together.

Herein, the rotation directions of the first AP pulley 715a and the first AP additional pulley 716a are opposite to each other. This is because unlike the actuation operating wire 735A connecting the actuation operating pulley 7133 and the first AP pulley 715a, the actuation additional operating wire 735A' connecting the actuation operating pulley 7133 and the first AP additional pulley 716a is twisted one time. That is, since the rotating force transmission directions of the actuation operating wire 735A and the actuation additional operating wire 735A' are opposite to each other, the rotation directions of the first AP pulley 715a and the first AP additional pulley 716a are opposite to each other.

Although it is illustrated that the first YP pulley 714a is connected to the second YP pulley 714b, and the second YP pulley 714b is connected to a first input unit 7311 of the first differential member 731 and a first input unit 7321 of the second differential member 732, this is merely for convenience of description, and the first YP pulley 714a may be directly connected to the first input unit 7311 of the first differential member 731 and first input unit 7321 of the second differential member 732, without using the second YP pulley 714b.

Likewise, although it is illustrated that the first AP pulley 715a is connected to the second AP pulley 715b, and the second AP pulley 715b is connected to the first input unit 7321 of the second differential member 732, this is merely for convenience of description, and the first AP pulley 715a may be directly connected to the first input unit 7321 of the second differential member 732, without using the second AP pulley 715b.

Also, although it is illustrated that the first AP additional pulley 716a is connected to the second AP additional pulley 716b, and the second AP additional pulley 716b is connected to the first input unit 7311 of the first differential member 731, this is merely for convenience of description, and the first AP additional pulley 716a may be directly connected to the first input unit 7311 of the first differential member 731, without using the second AP additional pulley 716b.

Overall Operation of Seventh Embodiment

Hereinafter, an overall configuration for the pitch operation, the yaw operation, and the actuation operation of the surgical instrument 700 according to the seventh embodiment of the present invention will be summarized with reference to the above descriptions.

In the surgical instrument 700 according to the seventh embodiment of the present invention, the first differential member 731 includes the first input unit 7311, a second input unit 7312, an output unit 7313, a first differential control member 7314, a second differential control member 7315, and a differential control wire 7316, and the second differential member 732 includes the first input unit 7321, a second input unit 7322, an output unit 7323, a first differential control member 7324, a second differential control member 7325, and a differential control wire 7326.

For the configuration of the end tool 720 of the present embodiment, the operating force transmitter 730 capable of dividing the operation input of the operator 710 into a pitch operation, a first jaw operation, and a second jaw operation is necessary to perform the pitch, yaw, and actuation operations of the end tool 720. The rotation operation of the pitch operating bar may be directly connected to the pitch operation of the end tool. However, since the end tool needs to include the operation component of the first jaw and the operation component of the second jaw but the input of the operator is the yaw component and the actuation component, the operation component of the first jaw and the operation component of the second jaw have to include the yaw component and the actuation component as follows: This may be expressed as the following equation:

$J1=Y+A$ (the first jaw rotates in the same direction in both the yaw operation and the actuation operation.)

$J2=Y-A$ (the second jaw rotates in the same direction in the yaw operation and rotates in an opposite direction in the actuation operation.)

To this end, the yaw operator 712 and the actuation operator 713 of the operator 710 are connected to the first YP pulley 714a and the first AP pulley 715a, and the first AP additional pulley 716a is provided to transmit the actuation operation input reversely. This may be expressed as the following equation:

$$Y_P = Y + P$$
$$A_P = A + P$$
$$A_{P'} = -A + P$$

Thus, in order to transmit the output of the operator 710 as only the components of the first and second jaws to the end tool 720, the operating force transmitter 730 extracts the following components:

$$J1 = Y + A = Y_P - A_{P'}$$
$$J2 = Y - A = Y_P - A_P$$

To this end, the operating force transmitter 730 includes a differential pulley that receives an input of YP and AP' and outputs only the difference (J1 component) between YP and AP', and a differential pulley that receives an input of YP and AP and outputs only the difference (J2 component) between YP and AP.

(where Y denotes the rotation of the yaw operating pulley, A denotes the rotation of the actuation operating pulley, YP denotes the rotation of the YP pulley, AP denotes the rotation of the AP pulley, AP' denotes the rotation of the AP additional pulley, J1 denotes the rotation of the first jaw operating pulley, and J2 denotes the rotation of the second jaw operating pulley.)

This will be described below in more detail.

The first input unit 7311 of the first differential member 731 is connected with the first YP pulley 714a (or the second YP pulley 714b connected therewith) to rotate when the yaw operating pulley 7123 rotates and also rotate when the pitch operating pulley 7113 rotates. The second input unit 7312 of the first differential member 731 is connected with the first AP additional pulley 716a (or the second AP additional pulley 716b connected therewith) to rotate when the actuation operating pulley 7133 rotates and also rotate when the pitch operating pulley 7113 rotates. Also, the output unit 7313 of the first differential member 731 is connected with the first jaw wire 735J1 to control the operation of the first jaw 721 of the end tool 720.

The first input unit 7321 of the second differential member 732 is connected with the first YP pulley 714a (or the second YP pulley 714b connected therewith) to rotate when the yaw operating pulley 7123 rotates and also rotate when the pitch operating pulley 7113 rotates. The second input unit 7322 of the second differential member 732 is connected with the first AP pulley 715a (or the second AP pulley 715b connected therewith) to rotate when the actuation operating pulley 7133 rotates and also rotate when the pitch operating pulley 7113 rotates. Also, the output unit 7323 of the second differential member 732 is connected with the second jaw wire 735J2 to control the operation of the second jaw 722 of the end tool 720.

The pitch operating pulley 7113 is connected with the pitch wire 735P to control the pitch operation of the end tool 720.

First, the pitch operation will be described below.

As described above, when the user grips the pitch operating bar 7112 of the pitch operator 711 of the operator 710 and rotates the pitch operating bar 7112 around the pitch operating axis 7111 in the direction of the arrow P of FIG. 44, the pitch operating pulley 7113 rotates along with the pitch operating axis 7111. Then, the pitch pulley 723 connected with the pitch operating pulley 7113 by the pitch wire 735P, the first jaw pulley 724 connected therewith, the second jaw pulley 725, the first jaw 721, and the second jaw 722 rotate around the pitch rotating axis 720PX (see FIG. 40) to perform a pitch operation.

In this case, the pitch operation does not affect the output units of the first and second differential pulleys 731 and 732 of the operating force transmitter 730 which determine the operations of the first and second jaws 721 and 722 of the end tool 720. In more detail, when the first YP pulley 714a, the first AP pulley 715a, and the first AP additional pulley 716a rotate around the pitch operating axis 7111 according to the pitch operation, the first input unit 7311 of the first differential member 731 that is connected with the second YP pulley 714b and the second input unit 7312 of the first differential member 731 that is connected with the second AP additional pulley 716b rotate; however, since the rotations are offset in the first differential member 731, the output unit 7313 of the first differential member 731 does not rotate. Likewise, the first input unit 7321 of the second differential member 732 that is connected with the second YP pulley 714b and the second input unit 7322 of the second differential member 732 that is connected with the second AP pulley 715b rotate; however, since the rotations are offset in the second differential member 732, the output unit 7323 of the second differential member 732 does not rotate. Thus, the pitch operation may be performed independently of the yaw operation and the actuation operation.

The yaw operation and the actuation operation of the present embodiment will be described below.

For a yaw operation, the user holds the yaw operating bar 7122 with the index finger and rotates the yaw operating bar 7122 in the direction of an arrow Y of FIG. 44.

Then, the yaw operating pulley 7123 connected with the yaw operating bar 7122 rotates around the yaw operating axis (i.e., the pitch operating bar), and the resulting rotating force is transmitted through the yaw operating wire 735Y to the first YP pulley 714a and the second YP pulley 714b connected therewith, to rotate the second YP pulley 714b. When the second YP pulley 714b rotates, the first input unit 7311 of the first differential member 731 connected therewith and the output unit 7313 of the first differential member 731 connected therewith rotate. In addition, when the second YP pulley 714b rotates, the first input unit 7321 of the second differential member 732 connected therewith and the output unit 7323 of the second differential member 732 connected therewith rotate.

For an actuation operation, the user holds the actuation operating bar 7132 with the thumb finger and rotates the actuation operating bar 7132 in the direction of an arrow A of FIG. 44.

Then, the actuation operating pulley 7133 connected with the actuation operating bar 7132 rotates around the actuation operating axis (i.e., the pitch operating bar), and the resulting rotating force is transmitted through the actuation operating wire 735A to the first AP pulley 715a and the second AP pulley 715b connected therewith, to rotate the second AP pulley 715b. When the second AP pulley 715b rotates, the second input unit 7322 of the second differential member 732 that is connected therewith and the output unit 7323 of the second differential member 732 connected therewith rotate. In addition, the rotating force of the actuation operating pulley 7133 is transmitted through the actuation additional operating wire 735A' to the first AP additional pulley 716a and the second AP additional pulley 716b connected therewith, to rotate the second AP additional pulley 716b. When the second AP additional pulley 716b rotates, the second input unit 7312 of the first differential member 731 that is connected therewith and the output unit 7313 of the first differential member 731 connected therewith rotate.

As described above, the second YP pulley 714a and the second YP pulley 714b connected therewith rotate along with the yaw operating pulley 7123 when the yaw operating pulley 7123 rotates, and rotate along with the pitch operating pulley 7113 when the pitch operating pulley 7113 rotates. The first AP pulley 715a and the second AP pulley 715b connected therewith rotate along with the actuation operating pulley 7133 when the actuation operating pulley 7133 rotates, and rotate along with the pitch operating pulley 7113 when the pitch operating pulley 7113 rotates. Likewise, the first AP pulley 716a and the second AP pulley 716b connected therewith rotate along with the actuation operating pulley 7133 when the actuation operating pulley 7133 rotates, and rotate along with the pitch operating pulley 7113 when the pitch operating pulley 7113 rotates.

Referring to the above equation, when the second YP pulley 714b and the second AP additional pulley 716b are connected respectively to the two input units of the first differential member 731, only a pure operation control component of the first jaw 721 may be extracted from the rotation of the pitch operating pulley 7113, the rotation of the yaw operating pulley 7123, and the rotation of the actuation operating pulley 7133.

Likewise, when the second YP pulley 714b and the second AP pulley 715b are connected respectively to the two input units of the second differential member 732, only a pure operation control component of the second jaw 722 may be extracted from the rotation of the pitch operating pulley 7113, the rotation of the yaw operating pulley 7123, and the rotation of the actuation operating pulley 7133.

Consequently, for a yaw operation, when the yaw operating bar 7122 is rotated in the direction of the arrow Y of FIG. 44, the first YP pulley 714a and the second YP pulley 714b connected therewith rotate in the counterclockwise direction in FIG. 44. Then, the first input unit 7311 of the first differential member 731 that is connected with the second YP pulley 714b rotates in the counterclockwise direction. Accordingly, the output unit 7313 of the first differential member 731 rotates in the counterclockwise direction, and the first jaw wire 735J1 connected with the output unit 7313, the first jaw pulley 724 connected with the first jaw wire 735J1, and the first jaw 721 connected with the first jaw pulley 724 rotate around the jaw rotating axis 720JX (see FIG. 40) in the counterclockwise direction. Likewise, the first input unit 7321 of the second differential member 732 that is connected with the second YP pulley 714b rotates in the counterclockwise direction. Accordingly, the output unit 7323 of the second differential member 732 rotates in the counterclockwise direction, and the second jaw wire 735J2 connected with the output unit 7323, the second jaw pulley 725 connected with the second jaw wire 735J2, and the second jaw 722 connected with the second jaw pulley 725 rotate around the jaw rotating axis 720JX (see FIG. 40) in the counterclockwise direction. In this manner, the first jaw 721 and the second jaw 722 rotate in the same direction to perform a yaw operation.

Similarly, for an actuation operation, when the actuation operating bar 7132 is rotated in the direction of the arrow A of FIG. 44, the first AP pulley 715a and the second AP pulley 715b connected therewith rotate in the clockwise direction in FIG. 44, and the first AP additional pulley 716a and the second AP additional pulley 716b rotate in the counterclockwise direction in FIG. 44. Then, the second input unit 7322 of the second differential member 732 that is connected with the second AP pulley 715b rotates in the clockwise direction. Accordingly, the output unit 7323 of the second differential member 732 rotates in the counterclockwise direction, and the second jaw wire 735J2 connected with the output unit 7323, the second jaw pulley 725 connected with the second jaw wire 735J2, and the second jaw 722 connected with the second jaw pulley 725 rotate around the jaw rotating axis 720JX (see FIG. 40) in the counterclockwise direction. Likewise, the second input unit 7312 of the first differential member 731 that is connected with the second AP additional pulley 716b rotates in the counterclockwise direction. Accordingly, the output unit 7313 of the first differential member 731 rotates in the clockwise direction, and the first jaw wire 735J1 connected with the output unit 7313, the first jaw pulley 724 connected with the first jaw wire 735J1, and the first jaw 721 connected with the first jaw pulley 724 rotate around the jaw rotating axis 720JX (see FIG. 40) in the clockwise direction. In this manner, the first jaw 721 and the second jaw 722 rotate in opposite directions to perform an actuation operation.

Thus, according to the present invention, the pitch operation of the end tool, the rotation operation of the first jaw, and the rotation operation of the second jaw may be extracted respectively from the rotation of the pitch operating pulley 7113, the rotation of the yaw operating pulley 7123, and the rotation of the actuation operating pulley 7133. Accordingly, even when the pitch, yaw, and actuation operations of the operator occur simultaneously or not, the pitch, yaw, and actuation operations of the operator may be independently divided into the pitch operation component of the end tool, the rotation operation component of the first jaw, and the rotation operation component of the second jaw.

Any combination of various configurations of the operator described with reference to FIG. 3A, various configurations of the operating force transmitter described with reference to FIGS. 4A and 15 to 27, and various modifications described with reference to FIGS. 7 to 14 may be applied to the surgical instrument 700 according to the seventh embodiment of the present invention.

<Eighth Embodiment of Surgical Instrument>
(E2+H2+D)

Hereinafter, the surgical instrument 800 according to the eighth embodiment of the present invention will be described. In the surgical instrument 800 according to the eighth embodiment of the present invention, an end tool 820 has the configuration described with reference to FIGS. 40 to 43, and an actuation operator formed is formed on an yaw operator such that the actuation operator rotates together when the yaw operator rotates, as in the surgical instrument 200 according to the second embodiment illustrated in FIG. 28.

Figure 45:
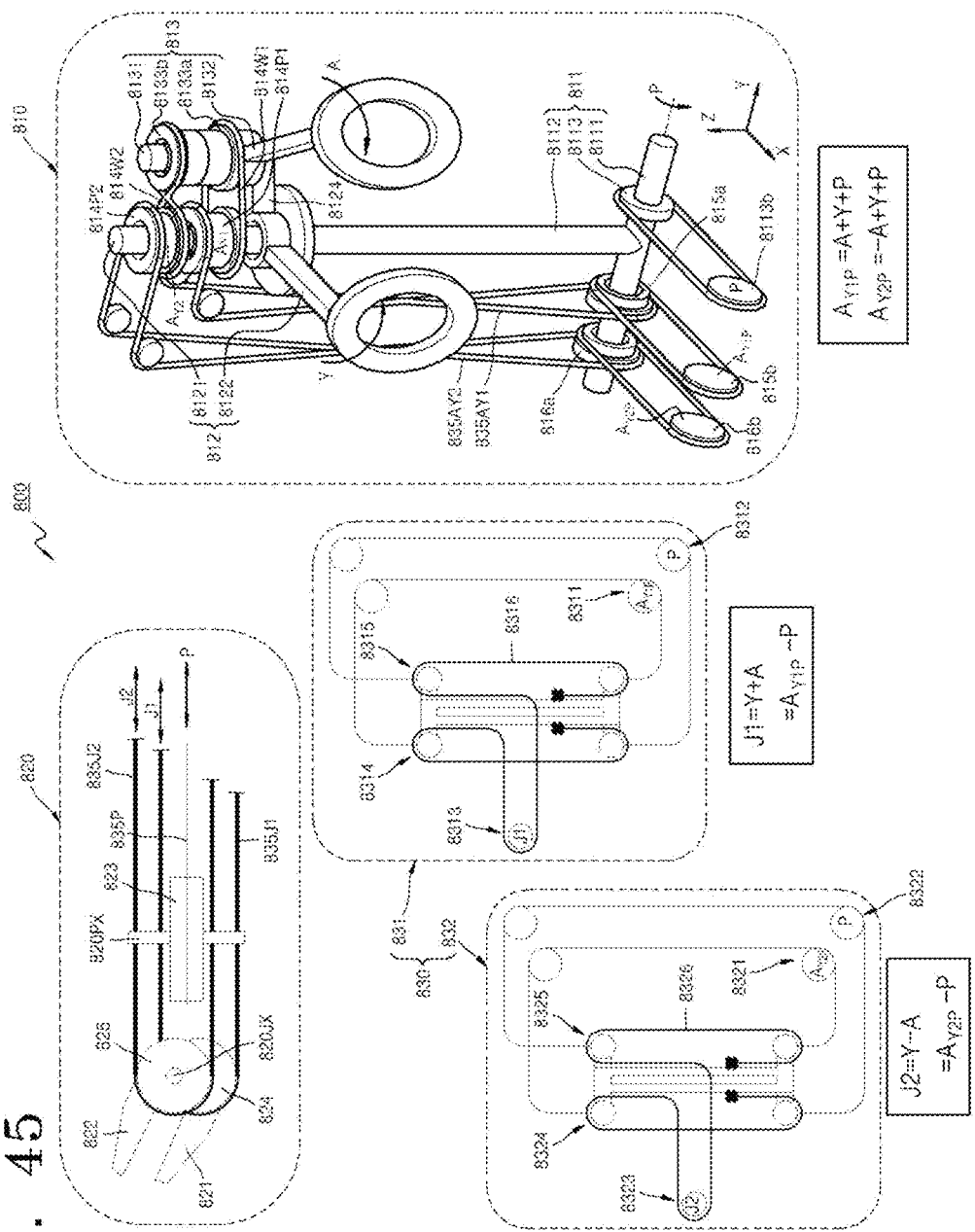
FIG. 45 is a view illustrating a surgical instrument according to an eighth embodiment of the present invention.

FIG. 45 is a view illustrating the surgical instrument 800 according to the eighth embodiment of the present invention. Referring to FIG. 45, the surgical instrument 800 according to the eighth embodiment of the present invention includes an operator 810, the end tool 820, an operating force transmitter 830, and a connector (not illustrated).

The end tool 820 includes a first jaw 821, a second jaw 822, a pitch pulley 823, a first jaw pulley 824, and a second jaw pulley 825, and the operating force transmitter 830 includes a pitch wire 835P, a first jaw wire 835J1, and a second jaw wire 835J2. In the end tool 820, the pulley/wire for a pitch operation, the pulley/wire for an operation of the first jaw, and the pulley/wire for an operation of the second jaw are separately formed such that one operation does not affect other operations. Since the end tool 820 is substantially identical to the end tool 720 described with reference to FIGS. 40 to 43, a detailed description thereof will be omitted herein.

The operating force transmitter 830 includes a first differential member 831 and a second differential member 832. The first differential member 831 and the second differential member 832 each include two or more input units and one input unit, receive an input of rotating forces from the two or more input units, extract a desired rotating force from the sum of (or the difference between) the input rotating forces, and output the desired rotating force through the output unit. The first and second differential members 831 and 832 may include various differential pulleys and differential gears, such as, the differential pulley of the surgical instrument 100 according to the first embodiment illustrated in FIGS. 4A and 4B, the first modification of the differential pulley illustrated in FIG. 15, the second modification of the differential pulley illustrated in FIG. 18, and the third modification of the differential pulley illustrated in FIG. 22. That is, although the differential pulley of FIG. 21E is illustrated as the first and second differential members 831 and 832 of the surgical instrument 800 according to the eighth embodiment in FIG. 44, the present invention is not limited thereto, and various differential pulleys and differential gears may be used in the present embodiment.

Hereinafter, the operator 810 of the surgical instrument 800 according to the eighth embodiment of the present invention will be described in more detail.

Referring to FIG. 45, the operator 810 of the surgical instrument 800 according to the eighth embodiment of the present invention includes a pitch operator 811 controlling a pitch motion of the end tool 820, a yaw operator 812 controlling a yaw motion of the end tool 820, and an actuation operator 813 controlling an actuation motion of the end tool 820.

The pitch operator 811 includes a pitch operating axis 8111, a pitch operating bar 8112, and a pitch operating pulley 8113. Herein, the pitch operating axis 8111 may be formed in the direction parallel to the Y axis, and the pitch operating bar 8112 may be connected with the pitch operating axis 8111 to rotate along with the pitch operating axis 8111. For example, when the user grips and rotates the pitch operating bar 8112, the pitch operating axis 8111 connected with the pitch operating bar 8112 and the pitch operating pulley 8113 connected therewith rotate together therewith. Then, the resulting rotating force is transmitted to the end tool 820 through the operating force transmitter 830, so that the end tool 820 rotates in the same direction as the rotation direction of the pitch operating axis 8111. That is, when the pitch operator 811 rotates in the clockwise direction around the pitch operating axis 8111, the end tool 820 also rotates in the clockwise direction around a pitch pulley operating axis (not illustrated), and when the pitch operator 811 rotates in the counterclockwise direction around the pitch operating axis 8111, the end tool 820 also rotates in the counterclockwise direction around the pitch pulley operating axis. The pitch operating pulley 8113 is integrated with the pitch operating axis 8111 to rotate along with the pitch operating axis 8111.

The yaw operator 812 includes a yaw operating axis 8121 and a yaw operating bar 8122. Although it is illustrated that the yaw operating axis 8121 is formed to extend from the pitch operating bar 8112, the present invention is not limited thereto. For example, the pitch operating bar 8112 and the yaw operating axis 8121 may be formed as separate members on different axes. In this case, the yaw operating axis 8121 may be formed in various directions by ergonomic design according to the structure of the hand of the user gripping the operator 810.

When the pitch operator 811 rotates, a coordinate system of the yaw operator 812 may change relatively. The yaw operating bar 8122 is formed to rotate around the yaw operating axis 8121. For example, when the user holds and rotates the yaw operating bar 8122 with the index finger, the yaw operating bar 8122 rotates around the yaw operating axis 8122. Then, the resulting rotating force is transmitted to the end tool 820 through a first yaw-actuation operating wire 835AY1 and a second yaw-actuation operating wire 835AY2, so that the first and second jaws 821 and 822 of the end tool 820 horizontally rotate in the same direction as the rotation direction of the yaw operator 812.

The actuation operator 813 includes an actuation operating axis 8131, an actuation operating bar 8132, a first actuation operating pulley 8133a, and a second actuation operating pulley 8133b. Herein, the actuation operating bar 8132, the first actuation operating pulley 8133a, and the second actuation operating pulley 8133b are formed to rotate around the actuation operating axis 8131. For example, when the user holds and rotates the actuation operating bar 8132 with the thumb finger, the first actuation operating pulley 8133a and the second actuation operating pulley 8133b connected with the actuation operating bar 8132 rotate around the actuation operating axis 8131. Then, the resulting rotating force is transmitted to the end tool 820 through the operating force transmitter 830, so that the first and second jaws 821 and 822 of the end tool 820 perform an actuation operation. In this case, the actuation operator 813 may be formed in various directions by ergonomic design according to the structure of the hand of the user gripping the operator 810.

The actuation operator 813 is formed on a yaw-actuation connector 8124 extending from the yaw operator 812. Thus, when the yaw operating bar 8122 of the yaw operator 812 rotates, the actuation operator 813 also rotates along with the yaw operating bar 8122. A first yaw-actuation operating pulley 814P1 and a second yaw-actuation operating pulley 814P2 are formed to rotate around the yaw operating axis 8121. The first actuation operating pulley 8133a and the first yaw-actuation operating pulley 814P1 are connected by a first yaw-actuation connecting wire 814W1, and the first yaw-actuation operating wire 835AY1 is connected to the first yaw-actuation operating pulley 814P1. Likewise, the second actuation operating pulley 8133b and the second yaw-actuation operating pulley 814P2 are connected by a second yaw-actuation connecting wire 814W2, and the second yaw-actuation operating wire 835AY2 is connected to the second yaw-actuation operating pulley 814P2.

Thus, when the yaw operating bar 8122 rotates, the yaw-actuation connector 8124 extending therefrom and the actuation operator 813 rotate around the yaw operating axis 8121, the first yaw-actuation connecting wire 814W1 connected to the first actuation operating pulley 8133a and the second yaw-actuation connecting wire 814W2 connected to the second actuation operating pulley 8133b also rotate around the yaw operating axis 8121, and consequently, the first yaw-actuation operating pulley 814P1 and the second yaw-actuation operating pulley 814P2 rotate around the yaw operating axis 8121.

Consequently, the first yaw-actuation operating pulley 814P1 and the second yaw-actuation operating pulley 814P2 are formed to rotate when the yaw operator 812 rotates and also rotate when the actuation operator 813 rotates.

The pitch operating axis 8111 is inserted into a first actuation-yaw-pitch (AY1P) pulley 815a and a first actuation-yaw-pitch (AY2P) pulley 816a such that the first AY1P pulley 815a and the first AY2P pulley 816a rotate around the pitch operating axis 8111; and the first AY1P pulley 815a and the first AY2P pulley 816a are connected to the first yaw-actuation operating pulley 814P and the second yaw-actuation operating pulley 814P2 by the first yaw-actuation operating wire 835AY1 and the second yaw-actuation operating wire 835AY2, respectively.

The first AY1P pulley 815a and a second AY1P pulley 815b connected therewith rotate along with the actuation operator 813 when the actuation operator 813 rotates, rotate along with the yaw operator 812 when the yaw operator 812 rotates, and rotate along with the pitch operator 811 when the pitch operator 811 rotates. That is, the first AY1P pulley 815a and the second AY1P pulley 815b may be considered as pulleys that reflect the rotation of the actuation operator 813, the rotation of the yaw operator 812, and the rotations of the pitch operator 811 together.

In detail, when the actuation operating bar 8132 rotates, the first actuation operating pulley 8133a connected with the actuation operating bar 8132 rotates along with the first actuation operating bar 8132, and thus the first yaw-actuation connecting wire 814W1 moves to rotate the first yaw-actuation operating pulley 814P1. When the first yaw-actuation operating pulley 814P1 rotates, the first yaw-actuation operating wire 835AY1 connected therewith rotates to rotate the first AY1P pulley 815a and the second AY1P pulley 815b connected therewith. When the yaw operating bar 8122 rotates, the actuation operator 813 connected with the yaw operating bar 8122 rotates along with the yaw operating bar 8122, and thus the first actuation operating pulley 8133a of the actuation operator 813 and the first yaw-actuation connecting wire 814W1 connected therewith rotate around the yaw operating axis 8121 to rotate the first yaw-actuation operating pulley 814P1. When the first yaw-actuation operating pulley 814P1 rotates, the first yaw-actuation operating wire 835AY1 connected therewith rotates to rotate the first AY1P pulley 815a and the second AY1P pulley 815b connected therewith. When the pitch operating axis 8111 and the pitch operating bar 8112 rotate in the direction of an arrow P of FIG. 45, the actuation operator 813 also rotate around the pitch operating axis 8111. Then, the first yaw-actuation operating wire 835AY1 rotates according to the rotation of the operator 810, and the first AY1P pulley 815a connected therewith also rotates accordingly. Consequently, the first AY1P pulley 815a and the second AY1P pulley 815b rotate when the actuation operator 813 rotates, rotate when the yaw operator 812 rotates, and rotate when the pitch operator 811 rotates.

Likewise, when the first AY2P pulley 816a and a second AY2P pulley 815b connected therewith rotate along with the actuation operator 816 when the actuation operator 813 rotates, rotate along with the yaw operator 812 when the yaw operator 812 rotates, and rotate along with the pitch operator 811 when the pitch operator 811 rotates. That is, the first AY2P pulley 816a and the second AY2P pulley 816b may be considered as pulleys that reflect the rotations of the actuation operator 813, the rotation of the yaw operator 812, and the rotation of the pitch operator 811 together.

Although it is illustrated that the first AY1P pulley 815a is connected to the second AY1P pulley 815b, and the second AY1P pulley 815b is connected to a first input unit 8311 of the first differential member 831, this is merely for convenience of description, and the first AY1P pulley 815a may be directly connected to the first input unit 8311 of the first differential member 831, without using the second AY1P pulley 815b.

Likewise, although it is illustrated that the first AY2P pulley 816a is connected to the second AY2P pulley 816b, and the second AY2P pulley 816b is connected to a first input unit 8321 of the second differential member 832, this is merely for convenience of description, and the first AY2P pulley 816a may be directly connected to the first input unit 8321 of the second differential member 832, without using the second AY2P pulley 816b.

Likewise, although it is illustrated that the pitch operating pulley 8113 is connected to a second pitch operating pulley 8113b, and the second pitch operating pulley 8113b is connected to a second input unit 8312 of the first differential member 831 and a second input unit 8322 of the second differential member 832, this is merely for convenience of description, and the pitch operating pulley 8113 may be directly connected to the second input unit 8312 of the first differential member 831 and the second input unit 8322 of the second differential member 832, without using the second pitch operating pulley 8113b.

Overall Operation of Eighth Embodiment

Hereinafter, an overall configuration for the pitch operation, the yaw operation, and the actuation operation of the surgical instrument 800 according to the eighth embodiment of the present invention will be summarized with reference to the above descriptions.

In the surgical instrument 800 according to the eighth embodiment of the present invention, the first differential member 831 includes the first input unit 8311, the second input unit 8312, an output unit 8313, a first differential control member 8314, a second differential control member 8315, and a differential control wire 8316, and the second differential member 832 includes the first input unit 8321, the second input unit 8322, an output unit 8323, a first differential control member 8324, a second differential control member 8325, and a differential control wire 8326.

For the configuration of the end tool 820 of the present embodiment, the operating force transmitter 830 capable of dividing the operation input of the operator 810 into a pitch operation, a first jaw operation, and a second jaw operation is necessary to perform the pitch, yaw, and actuation operations of the end tool 820. The rotation operation of the pitch operating bar may be directly connected to the pitch operation of the end tool 820. However, since the end tool 820 needs to include the operation component of the first jaw and the operation component of the second jaw but the input of the operator 810 is the yaw component and the actuation component, the operation component of the first jaw and the operation component of the second jaw have to include the yaw component and the actuation component as follows:

J1=Y+A (the first jaw rotates in the same direction in both the yaw operation and the actuation operation.)

J2=Y−A (the second jaw rotates in the same direction in the yaw operation and rotates in an opposite direction in the actuation operation.)

Particularly, in the present embodiment, since the actuation operator 813 is disposed on the yaw operator 812, the output of the operator 810 is the sum of the yaw operation input, the actuation operation input, and the pitch operation input. As described above, the output of the operator 810 may be expressed as the following equation:

$$A_{Y1P} = A_{Y1} + P = A + Y + P$$
$$A_{Y2P} = A_{Y2} + P = -A + Y + P$$

Thus, in order to transmit the output of the operator 810 as only the components of the first and second jaws to the end tool 820, the operating force transmitter 830 extracts the following components:

$$J1 = Y + A = A_{Y1P} - P$$
$$J2 = Y - A = A_{Y2P} - P$$

To this end, the operating force transmitter 830 includes a differential pulley that receives an input of $A_{Y1P}$ and P and outputs only the difference (J1 component) between $A_{Y1P}$ and P, and a differential pulley that receives an input of $A_{Y2P}$ and P and outputs only the difference (J2 component) between $A_{Y2P}$ and P.

(where Y denotes the rotation of the yaw operating pulley, A denotes the rotation of the actuation operating pulley, $A_{Y1}$ denotes the rotation of the $A_{Y1}$ pulley, $A_{Y2}$ denotes the rotation of the $A_{Y2}$ pulley, $A_{Y1P}$ denotes the rotation of the $A_{Y1}$ pulley, $A_{Y2}$ denotes the rotation of the $A_{Y2P}$ pulley, P denotes the rotation of the pitch operating pulley, J1 denotes the rotation of the first jaw operating pulley, and J2 denotes the rotation of the second jaw operating pulley.)

This will be described below in more detail.

First, the pitch operation will be described below.

As described above, when the user grips the pitch operating bar 8112 of the pitch operator 811 of the operator 810 and rotates the pitch operating bar 8112 around the pitch operating axis 8111 in the direction of the arrow P of FIG.

45, the pitch operating pulley 8113 rotates along with the pitch operating axis 8111. Then, the pitch pulley 823 connected with the pitch operating pulley 8113 by the pitch wire 835P, the first jaw pulley 824 connected therewith, the second jaw pulley 825, the first jaw 821, and the second jaw 822 rotate around a pitch rotating axis 820PX to perform a pitch operation.

In this case, the pitch operation does not affect the output units of the first and second differential pulleys 831 and 832 of the operating force transmitter 830, which determine the operations of the first and second jaws 821 and 822 of the end tool 820. In more detail, when the first AY1P pulley 815a and the first AY2P pulley 816a rotate around the pitch operating axis 8111 according to the pitch operation, the first input unit 8311 of the first differential member 831 that is connected with the second AY1P pulley 815b and the second input unit 8312 of the first differential member 831 that is connected with the pitch operating pulley 8113 rotate; however, since the rotations are offset in the first differential member 831, the output unit 8313 of the first differential member 831 does not rotate. Likewise, the first input unit 8321 of the second differential member 832 that is connected with the second AY2P pulley 816b and the second input unit 8322 of the second differential member 832 that is connected with the pitch operating pulley 8113 rotate; however, since the rotations are offset in the second differential member 832, the output unit 8323 of the second differential member 832 does not rotate. Thus, the pitch operation may be performed independently of the yaw operation and the actuation operation.

The yaw operation and the actuation operation of the present embodiment will be described below.

In the surgical instrument 800, the first differential member 831 includes the first input unit 8311, the second input unit 8312, the output unit 8313, the first differential control member 8314, the second differential control member 8315, and the differential control wire 8316, and the second differential member 832 includes the first input unit 8321, the second input unit 8322, the output unit 8323, the first differential control member 8324, the second differential control member 8325, and the differential control wire 8326.

The first input unit 8311 of the first differential member 831 is connected with the second AY1P pulley 815b to rotate when the actuation operator 813 rotates, rotate when the yaw operator 812 rotates, and rotate when the pitch operator 811 rotates. Also, the second input unit 8312 of the first differential member 831 is connected with the second pitch operating pulley 8113b to rotate when the pitch operator 811 rotates. Also, the output unit 8313 of the first differential member 831 is connected with the first jaw wire 835J1 to control the operation of the first jaw 821 of the end tool 820.

The first input unit 8321 of the second differential member 832 is connected with the second AY2P pulley 816b to rotate when the actuation operator 816 rotates, rotate when the yaw operator 812 rotates, and rotate when the pitch operator 811 rotates. Also, the second input unit 8322 of the second differential member 832 is connected with the second pitch operating pulley 8113b to rotate when the pitch operator 811 rotates. Also, the output unit 8323 of the second differential member 832 is connected with the second jaw wire 835J2 to control the operation of the second jaw 822 of the end tool 820.

As described above, the first AY1P pulley 815a, the second AY1P pulley 815b connected therewith, the first AY2P pulley 816a, and the second AY2P pulley 816b connected therewith rotate along with the actuation operator 813 when the actuation operator 813 rotates, rotate along with the yaw operator 812 when the yaw operator 812 rotates, and rotate along with the pitch operator 811 when the pitch operator 811 rotates.

Referring to the above equation, when the second AY1P pulley 815b and the pitch operating pulley 8113 are connected respectively to the two input units of the first differential member 831, only a pure operation control component of the first jaw 821 may be extracted from the rotation of the pitch operator 811, the rotation of the yaw operator 812, and the rotation of the actuation operator 813.

Similarly, when the second AY2P pulley 816b and the pitch operating pulley 8113 are connected respectively to the two input units of the second differential member 832, only a pure operation control component of the second jaw 822 may be extracted from the rotation of the pitch operator 811, the rotation of the yaw operator 812, and the rotation of the actuation operator 813.

Consequently, for a yaw operation, when the user holds and rotates the yaw operating bar 8122 with the index finger in the direction of an arrow Y of FIG. 45, the actuation operator 813 connected with the yaw operator 812 rotates around the yaw operating axis 8121. Then, the resulting rotating force is transmitted to the first AY1P pulley 815a and the second AY1P pulley 815b connected therewith through the first yaw-actuation connecting wire 814W1, the first yaw-actuation operating pulley 814P1, and the first yaw-actuation operating wire 835AY1, to rotate the second AY1P pulley 815b in the counterclockwise direction. Then, the first input unit 8311 of the first differential member 831 that is connected with the second AY1P pulley 815b rotates in the counterclockwise direction, and thus the output unit 8313 of the first differential member 831 rotates in the counterclockwise direction. Then, the first jaw wire 835J1 connected with the output unit 8313, the first jaw pulley 824 connected therewith, and the first jaw 821 connected therewith rotate around a jaw rotating axis 820JX in the counterclockwise direction.

At the same time, when the yaw operating bar 8122 is rotated in the direction of the arrow Y of FIG. 45, the actuation operator 813 connected with the yaw operator 812 rotates around the yaw operating axis 8121. Then, the resulting rotating force is transmitted to the first AY2P pulley 816a and the second AY2P pulley 816b connected therewith through the second yaw-actuation connecting wire 814W2, the second yaw-actuation operating pulley 814P2, and the second yaw-actuation operating wire 835AY2, to rotate the second AY2P pulley 816b in the counterclockwise direction. Then, the first input unit 8321 of the second differential member 832 that is connected with the second AY2P pulley 816b rotates in the counterclockwise direction, and thus the output unit 8323 of the second differential member 832 rotates in the counterclockwise direction. Then, the second jaw wire 835J2 connected with the output unit 8323, the second jaw pulley 825 connected therewith, and the second jaw 822 connected therewith rotate around the jaw rotating axis 820JX in the counterclockwise direction.

Consequently, when the yaw operator 812 rotates in the direction of the arrow Y of FIG. 45, the first jaw 821 and the second jaw 822 rotate around the jaw rotating axis 820JX in the same direction to perform a yaw operation.

The actuation operation of the present embodiment will be described below.

For an actuation operation, when the user holds and rotates the actuation operating bar 8132 with the thumb finger in the direction of an arrow A of FIG. 45, the actuation operator 813 rotates around the actuation operating axis 8131. Then, the resulting rotating force is transmitted to the first AY1P pulley 815a and the second AY1P pulley 815b connected therewith through the first yaw-actuation connecting wire 814W1, the first yaw-actuation operating pulley 814P1, and the first yaw-actuation operating wire 835AY1, to rotate the second AY1P pulley 815b in the clockwise direction. Then, the first input unit 8311 of the first differential member 831 that is connected with the second AY1P pulley 815b rotates in the clockwise direction, and thus the output unit 8313 of the first differential member 831 rotates in the clockwise direction. Then, the first jaw wire 835J1 connected with the output unit 8313, the first jaw pulley 824 connected therewith, and the first jaw 821 connected therewith rotate around the jaw rotating axis 820JX in the clockwise direction.

At the same time, when the actuation operating bar 8132 is rotated in the direction of the arrow A of FIG. 45, the actuation operator 813 rotates around the actuation operating axis 8131. Then, the resulting rotating force is transmitted to the first AY2P pulley 816a and the second AY2P pulley 816b connected therewith through the second yaw-actuation connecting wire 814W2, the second yaw-actuation operating pulley 814P2, and the second yaw-actuation operating wire 835AY2, to rotate the second AY2P pulley 816b in the counterclockwise direction. Then, the first input unit 8321 of the second differential member 832 that is connected with the second AY2P pulley 816b rotates in the counterclockwise direction, and thus the output unit 8323 of the second differential member 832 rotates in the counterclockwise direction. Then, the second jaw wire 835J2 connected with the output unit 8323, the second jaw pulley 825 connected therewith, and the second jaw 822 connected therewith rotate around the jaw rotating axis 820JX in the counterclockwise direction.

Consequently, when the yaw operator 812 rotates in the direction of the arrow A of FIG. 45, the first jaw 821 and the second jaw 822 rotate around the jaw rotating axis 820JX in opposite directions to perform an actuation operation.

Thus, according to the present invention, the pitch operation of the end tool, the rotation operation of the first jaw, and the rotation operation of the second jaw may be extracted respectively from the rotation of the pitch operator 811, the rotation of the yaw operator 812, and the rotation of the actuation operator 813. Accordingly, even when the pitch, yaw, and actuation operations of the operator occur simultaneously or not, the pitch, yaw, and actuation operations of the operator may be independently divided into the pitch operation component of the end tool, the rotation operation component of the first jaw, and the rotation operation component of the second jaw.

Any combination of various configurations of the operator described with reference to FIG. 3A, various configurations of the operating force transmitter described with reference to FIGS. 4A and 15 to 27, and various modifications described with reference to FIGS. 7 to 14 may be applied to the surgical instrument 800 according to the eighth embodiment of the present invention.

<Modification of Operator of Eighth Embodiment of Surgical Instrument> (E2+H2+D4)

Figure 46:
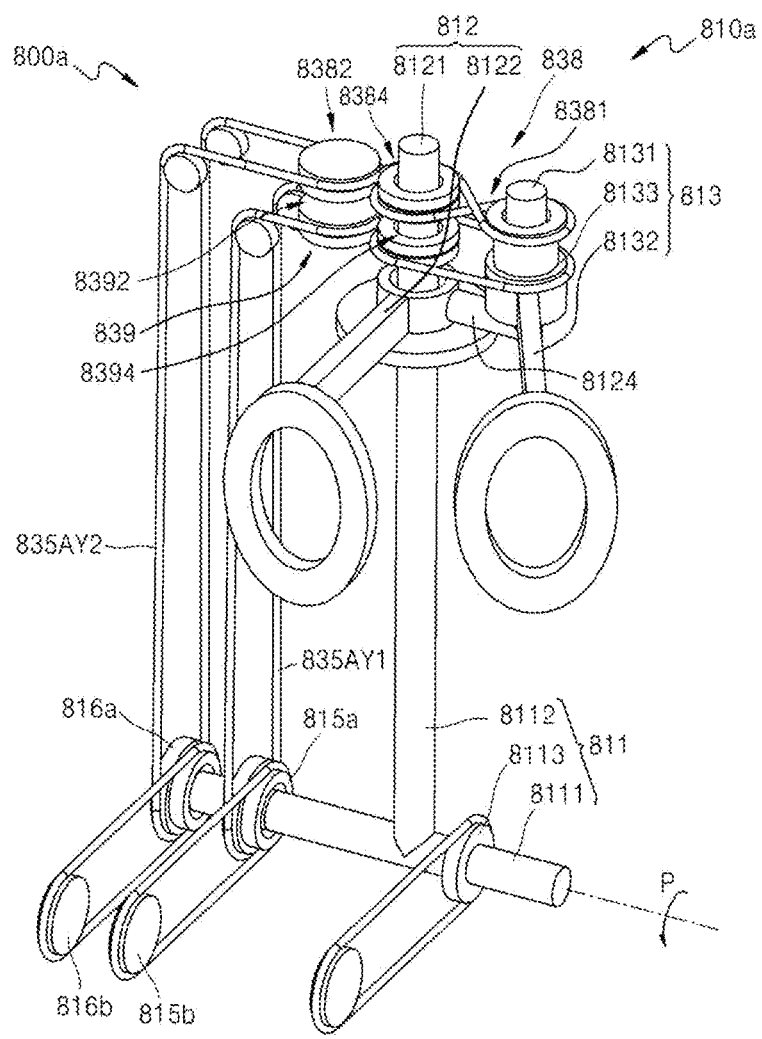
FIG. 46 is a view illustrating a surgical instrument according to a modification of a differential pulley of the eighth embodiment illustrated in FIG. 45.

FIG. 46 is a view illustrating a surgical instrument 800a according to a modification of the operator of the eighth embodiment illustrated in FIG. 45. Since the surgical instrument 800a according to a modification of the operator of the eighth embodiment of the present invention is similar to the surgical instrument 800 (see FIG. 45) according to the eighth embodiment of the present invention and is different from the surgical instrument 100 in terms of the configuration of the operator, the configuration of the operator will be mainly described below.

Referring to FIG. 46, an operator 810a of the surgical instrument 800a according to a modification of the operator 810 of the eighth embodiment of the present invention uses the third modification of the differential pulley illustrated in FIGS. 22 and 23.

In detail, in the operator 810 of the eighth embodiment, the actuation operator 813 is disposed on the yaw operator 812. The sum of the actuation operation input and the yaw operation input is output from the operator 810, and the first jaw and the second jaw of the end tool 820 need the sum of and the difference between the yaw operation input and the actuation operation input in the eighth embodiment. Therefore, a differential pulley capable of outputting the sum of the yaw operation and the actuation operation may be used in the configuration of the operator.

However, in the configuration of the operator 810 of the eighth embodiment, since the actuation operator 813 is disposed on the yaw operator 812, the third modification (see FIGS. 22 and 23) of the differential pulley in which one input unit is not independent of but is formed on another input unit may be used.

Referring to FIG. 46, the third modification (see FIGS. 22 and 23) of the differential pulley including a yaw input unit and an actuation input unit may be applied to the operator 810 such that the operator 810 is modified to have the output of AYP=A+Y+P, AYP2=−A+Y+P.

Since the modification of the eighth embodiment are the same in other configurations except for the configuration of the operator 810a, it may also use the other configurations of the eight embodiment.

That is, as described above, an operating force transmitter 830 of the surgical instrument 800a according to the this modification includes a first differential pulley 838 and a second differential pulley 839, and the first differential pulley 838 includes a first input unit 8381, a second input unit 8382, an output unit, and a connector 8384. The output unit of the first differential pulley 838 may be substantially identical to the first AY2P pulley 816a. The second differential pulley 839 includes a first input unit 8391, a second input unit 8392, an output unit, and a connector 8394. The output unit of the second differential pulley 839 may be substantially identical to the first AY1P pulley 815a.

By the first differential pulley 838 and the second differential pulley 839, when one of two or more input units rotates, only the output unit may be rotated without other input units rotating, and when two or more input units rotate simultaneously, a single rotating force equal to the sum or (the difference between) the rotating forces of two input units may be output through the output unit.

<Ninth Embodiment of Surgical Instrument> (E2+H3+D)

Hereinafter, a surgical instrument 900 according to a ninth embodiment of the present invention will be described. In the surgical instrument 900 according to the ninth embodiment of the present invention, an end tool 920 has the configuration described with reference to FIGS. 40 to 43, and an operator 910 includes a first jaw operator and a second jaw operator that operate a first jaw and second jaw independently instead of a yaw operator and an actuation operator as in the surgical instrument 300 according to third second embodiment illustrated in FIG. 30.

Figure 47:
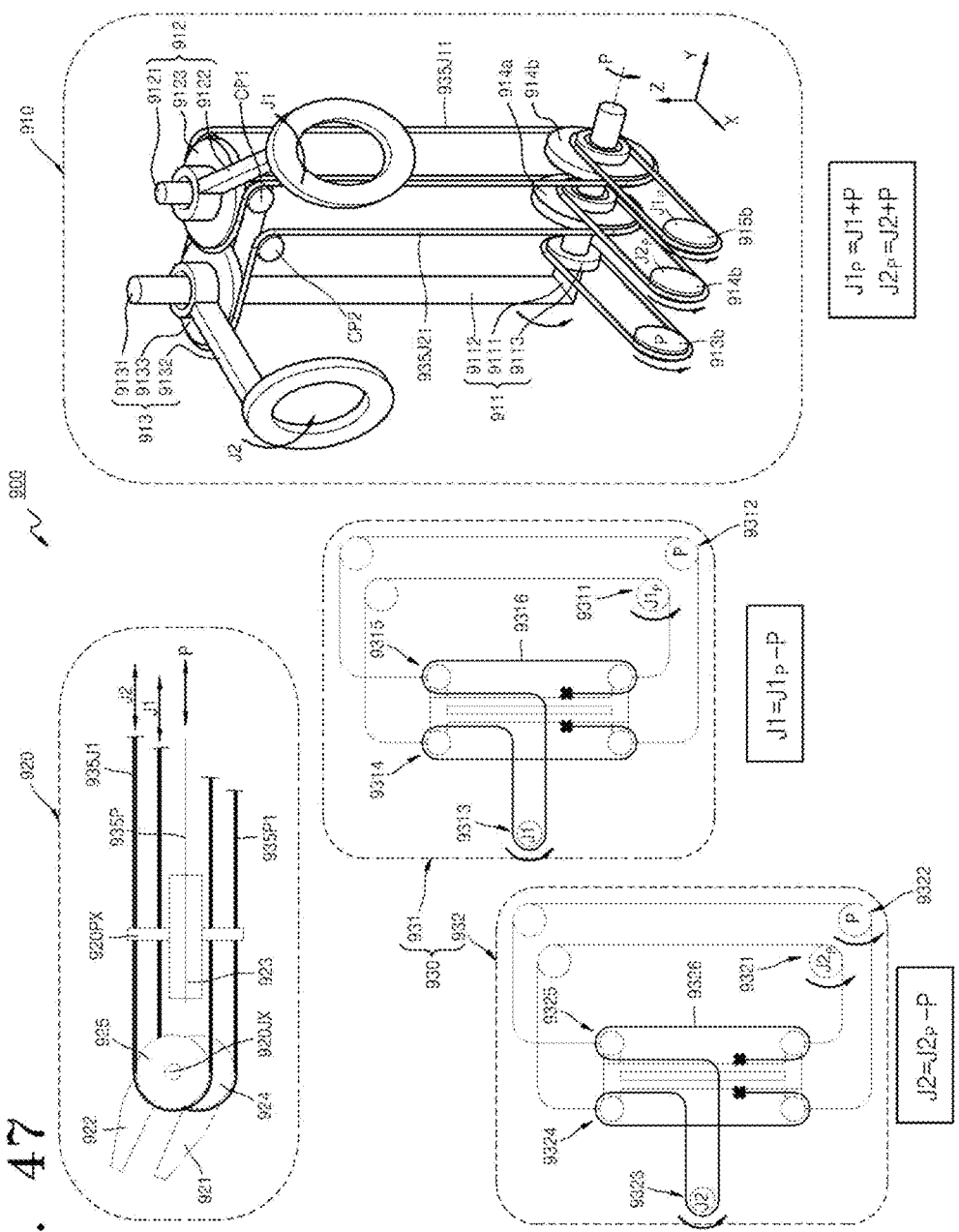
FIG. 47 is a view illustrating a surgical instrument according to a ninth embodiment of the present invention.

FIG. 47 is a view illustrating the surgical instrument 900 according to the ninth embodiment of the present invention. Referring to FIG. 47, the surgical instrument 900 according to the ninth embodiment of the present invention includes an operator 910, an end tool 920, an operating force transmitter 930, and a connector (not illustrated).

The end tool 920 includes a first jaw 921, a second jaw 922, a pitch pulley 923, a first jaw pulley 924, and a second jaw pulley 925, and the operating force transmitter 930 includes a pitch wire 935P, a first jaw wire 935J1, and a second jaw wire 935J2. In the end tool 920, the pulley/wire for a pitch operation, the pulley/wire for an operation of the first jaw, and the pulley/wire for an operation of the second jaw are separately formed such that one operation does not affect other operations. Since the end tool 920 is substantially identical to the end tool 720 described with reference to FIGS. 40 to 43, a detailed description thereof will be omitted herein.

The operating force transmitter 930 includes a first differential member 931 and a second differential member 932. The first differential member 931 and the second differential member 932 includes two or more input units and one input unit, receives an input of rotating forces from the two or more input units, extracts a desired rotating force from the sum of (or the difference between) the input rotating forces, and outputs the desired rotating force through the output unit. The first and second differential members 931 and 932 may include various differential pulleys and differential gears, such as, the differential pulley of the surgical instrument 100 according to the first embodiment illustrated in FIGS. 4A and 4B, the first modification of the differential pulley illustrated in FIG. 15, the second modification of the differential pulley illustrated in FIG. 18, and the third modification of the differential pulley illustrated in FIG. 22. That is, although the differential pulley of FIG. 21E is illustrated as the first and second differential members 931 and 932 of the surgical instrument 900 according to the ninth embodiment in FIG. 47, the present invention is not limited thereto, and various differential pulleys and differential gears may be used in the present embodiment.

Hereinafter, the operator 910 of the surgical instrument 900 according to the ninth embodiment of the present invention will be described in more detail.

Referring to FIG. 47, the operator 910 of the surgical instrument 900 according to the ninth embodiment of the present invention includes a pitch operator 911 controlling a pitch motion of the end tool 920, a first jaw operator 912 controlling a motion of the first jaw 921 of the end tool 920, and a second jaw operator 913 controlling a motion of the second jaw 922 of the end tool 920.

The pitch operator 911 includes a pitch operating axis 9111, a pitch operating bar 9112, and a pitch operating pulley 9113. Herein, the pitch operating axis 9111 may be formed in the direction parallel to the Y axis, and the pitch operating bar 9112 may be connected with the pitch operating axis 9111 to rotate along with the pitch operating axis 9111. The pitch operating pulley 9113 is integrated with the pitch operating axis 9111 to rotate along with the pitch operating axis 9111.

The first jaw operator 912 includes a first jaw operating axis 9121, a first jaw operating bar 9122, and a first jaw operating pulley 9123. A first jaw operating wire 935J11 may be connected to the first jaw operating pulley 9123. In this case, the first jaw operating axis 9121 may be formed in various directions by ergonomic design according to the structure of the hand of the user gripping the operator 910. The first jaw operating bar 9122 and the first jaw operating pulley 9123 are formed to rotate around the first jaw operating axis 9121. For example, when the user holds and rotates the first jaw operating bar 9122 with the thumb finger, the first jaw operating pulley 9123 connected with the first jaw operating bar 9122 rotates around the first jaw operating axis 9121. Then, the resulting rotating force is transmitted to the end tool 920 through the operating force transmitter 930, so that the first jaw 921 of the end tool 920 horizontally rotates in the same direction as the rotation direction of the first jaw operating pulley 9123.

The second jaw operator 913 includes a second jaw operating axis 9131, a second jaw operating bar 9132, and a second jaw operating pulley 9133. Although it is illustrated that the second jaw operating axis 9131 is formed to extend from the pitch operating bar 9112, the present invention is not limited thereto. For example, the pitch operating bar 9112 and the second jaw operating axis 9131 may be formed as separate members on different axes. In this case, the second jaw operating axis 9131 may be formed in various directions by ergonomic design according to the structure of the hand of the user gripping the operator 910. A second jaw operating wire 935J21 may be connected to the second jaw operating pulley 9133. The second jaw operating bar 9132 and the second jaw operating pulley 9133 are formed to rotate around the second jaw operating axis 9131. For example, when the user holds and rotates the second jaw operating bar 9132 with the index finger, the second jaw operating pulley 9133 connected with the second jaw operating bar 9132 rotates around the second jaw operating axis 9131. Then, the resulting rotating force is transmitted to the end tool 920 through the operating force transmitter 930, so that the second jaw 922 of the end tool 920 horizontally rotates in the same direction as the rotation direction of the second jaw operating pulley 9133.

The pitch operating axis 9111 is inserted into a first second yaw-pitch (Y2P) pulley 914a and a first first actuation-pitch (J1P) pulley 915a such that the first Y2P pulley 914a and the first J1P pulley 915a rotate around the pitch operating axis 9111.

The first J2P pulley 914a and a second J2P pulley 914b connected therewith rotate along with the second jaw operating pulley 9133 when the second jaw operating pulley 9133 rotates, and rotate along with the pitch operating pulley 9113 when the pitch operating pulley 9113 rotates. That is, the first J2P pulley 914a and the second J2P pulley 914b may be considered as pulleys that reflect the rotations of the second jaw operating pulley 9133 and the rotation of the pitch operating pulley 9113 together.

In detail, when the second jaw operating bar 9132 rotates, the second jaw operating pulley 9133 connected with the second jaw operating bar 9132 rotates along with the second jaw operating bar 9132, and thus the second jaw operating wire 935J21 connected therewith moves to rotate the first J2P pulley 914a and the second J2P pulley 914b connected therewith. When the pitch operating axis 9111 and the pitch operating bar 9112 rotate in the direction of an arrow P of FIG. 47, the second jaw operating axis 9131 and the second jaw operating pulley 9133 also rotate around the pitch operating axis 9111. Then, the second jaw operating wire 935J21 rotates around the pitch operating axis 9111 in the direction of the arrow P of FIG. 47 according to the rotation of the operator 910, and the first J2P pulley 914a connected therewith also rotates accordingly. Consequently, the first J2P pulley 914a and the second J2P pulley 914b rotate when the second jaw operating pulley 9133 rotates, and rotate when the pitch operating pulley 9113 rotates.

Likewise, the first J1P pulley 915a and a second J1P pulley 915b connected therewith rotate along with the first jaw operating pulley 9123 when the first jaw operating pulley 9123 rotates, and rotate along with the pitch operating pulley 9113 when the pitch operating pulley 9113 rotates. That is, the first J1P pulley 915a and the second J1P pulley 915b may be considered as pulleys that reflect the rotation of the first jaw operating pulley 9123 and the rotations of the pitch operating pulley 9113 together.

Although it is illustrated that the first J2P pulley 914a is connected to the second J2P pulley 914b, and the second J2P pulley 914b is connected to a first input unit 9321 of the second differential member 932, this is merely for convenience of description, and the first J2P pulley 914a may be directly connected to the first input unit 9321 of the second differential member 932, without using the second J2P pulley 914b.

Likewise, although it is illustrated that the first J1P pulley 915a is connected to the second J1P pulley 915b, and the second J1P pulley 915b is connected to a first input unit 9311 of the first differential member 931, this is merely for convenience of description, and the first J1P pulley 915a may be directly connected to the first input unit 9311 of the first differential member 931, without using the second J1P pulley 915b.

Likewise, although it is illustrated that the pitch operating pulley 9113 is connected to a second pitch operating pulley 913b, and the second pitch operating pulley 913b is connected to a second input unit 9312 of the first differential member 931 and a second input unit 9322 of the second differential member 932, this is merely for convenience of description, and the pitch operating pulley 9113 may be directly connected to the second input unit 9312 of the first differential member 931 and the second input unit 9322 of the second differential member 932, without using the second pitch operating pulley 913b.

Overall Operation of Ninth Embodiment

Hereinafter, an overall configuration for the pitch operation, the yaw operation, and the actuation operation of the surgical instrument 900 according to the ninth embodiment of the present invention will be summarized with reference to the above descriptions.

In the surgical instrument 900 according to the ninth embodiment of the present invention, the first differential member 931 includes a first input unit 9311, a second input unit 9312, an output unit 9313, a first differential control member 9314, a second differential control member 9315, and a differential control wire 9316, and the second differential member 932 includes the first input unit 9321, the second input unit 9322, an output unit 9323, a first differential control member 9324, a second differential control member 9325, and a differential control wire 9326.

For the configuration of the end tool 920 of the present embodiment, the operating force transmitter 930 capable of dividing the operation input of the operator 910 into a pitch operation, a first jaw operation, and a second jaw operation is necessary to perform the pitch, yaw, and actuation operations of the end tool 920. The rotation operation of the pitch operating bar may be directly connected to the pitch operation of the end tool. The operator includes the first jaw operator and the second jaw operator, and the output of the operator may be expressed as the following equation:

$$J1P = J1 + P$$
$$J2P = J2 + P$$

Thus, in order to transmit the output of the operator 910 as only the components of the first and second jaws to the end tool 920, the operating force transmitter 930 extracts the following components:

$$J1 = J1P - P$$
$$J2 = J2P - P$$

To this end, the operating force transmitter 930 includes a differential pulley that receives an input of J1P and P and outputs only the difference (J1 component) between J1P and P, and a differential pulley that receives an input of J2P and P and outputs only the difference (J2 component) between J2P and P.

(where J1P denotes the rotation of the J1P pulley, J2P denotes the rotation of the J2P pulley, J1 denotes the rotation of the first jaw operating pulley, J2 denotes the rotation of the second jaw operating pulley, and P denotes the rotation of the pitch operating pulley.)

The first input unit 9311 of the first differential member 931 is connected with the second J1P pulley 915b to rotate when the first jaw operating pulley 9123 rotates and also rotate when the pitch operating pulley 9113 rotates. Also, the second input unit 9312 of the first differential member 931 is connected with the pitch operating pulley 9113 to rotate when the pitch operating pulley 9113 rotates. Also, the output unit 9313 of the first differential member 931 is connected with the first jaw wire 935J1 to control the operation of the first jaw 921 of the end tool 920.

The first input unit 9321 of the second differential member 932 is connected with the second J2P pulley 914b to rotate when the second jaw operating pulley 9133 rotates and also rotate when the pitch operating pulley 9113 rotates. Also, the second input unit 9322 of the second differential member 932 is connected with the pitch operating pulley 9113 to rotate when the pitch operating pulley 9113 rotates. Also, the output unit 9323 of the second differential member 932 is connected with the second jaw wire 935J2 to control the operation of the second jaw 922 of the end tool 920.

The pitch operating pulley 9113 is connected with the pitch wire 935P to control the pitch operation of the end tool 920.

First, the pitch operation will be described below.

As described above, when the user grips the pitch operating bar 9112 of the pitch operator 911 of the operator 910 and rotates the pitch operating bar 9112 around the pitch operating axis 9111 in the direction of an arrow P (pitch) of FIG. 47, the pitch operating pulley 9113 rotates along with the pitch operating axis 9111. Then, the pitch pulley 923 connected with the pitch operating pulley 9113 by the pitch wire 935P, the first jaw pulley 924 connected therewith, the second jaw pulley 925, the first jaw 921, and the second jaw 922 rotate around a pitch rotating axis 920PX to perform a pitch operation.

In this case, the first J2P pulley 914a and the first J1P pulley 915a rotate around the pitch operating axis 9111. Then, the first input unit 9311 of the first differential member 931 that is connected with the second J1P pulley 915b and the second input unit 9312 of the first differential member 931 that is connected with the pitch operating pulley 9113 rotate; however, since the rotations are offset in the first differential member 931, the output unit 9313 of the first differential member 931 does not rotate. Likewise, the first input unit 9321 of the second differential member 932 that is connected with the second J2P pulley 914b and the second input unit 9322 of the second differential member 932 that is connected with the pitch operating pulley 9113 rotate; however, since the rotations are offset in the second differential member 932, the output unit 9323 of the second differential member 932 does not rotate. Thus, the pitch operation may be performed independently of the yaw operation and the actuation operation.

The yaw operation and the actuation operation of the present embodiment will be described below.

For a yaw operation, the user holds and rotates the first jaw operating bar 9122 with the thumb finger in the direction of an arrow J1 of FIG. 47, and holds and rotates the second jaw operating bar 9132 with the index finger in the direction of an arrow J2 of FIG. 47 (that is, rotates the first jaw operating bar 9122 and the second jaw operating bar 9132 in the same direction). For an actuation operation, the user rotates the first jaw operating bar 9122 in a direction opposite to the direction of the arrow J1 of FIG. 47, and rotates the second jaw operating bar 9132 in the direction of the arrow J2 of FIG. 47 (that is, rotates the first jaw operating bar 9122 and the second jaw operating bar 9132 in opposite directions).

Then, the first jaw operating pulley 9123 connected with the first jaw operating bar 9122 rotates around the first jaw operating axis 9121, and the resulting rotating force is transmitted through the first jaw operating wire 935J11 to the first J1P pulley 915a and the second J1P pulley 915b connected therewith, to rotate the second J1P pulley 915b. When the second J1P pulley 915b rotates, the first input unit 9311 of the first differential member 931 connected therewith and the output unit 9313 of the first differential member 931 connected therewith rotate.

At the same time, the second jaw operating pulley 9133 connected with the second jaw operating bar 9132 rotates around the second jaw operating axis 9131, and the resulting rotating force is transmitted through the second jaw operating wire 935J21 to the first J2P pulley 914a and the second J2P pulley 914b connected therewith, to rotate the second J2P pulley 914b. When the second J2P pulley 914b rotates, the first input unit 9321 of the second differential member 932 connected therewith and the output unit 9323 of the second differential member 932 connected therewith rotate.

As described above, the first J2P pulley 914a and the second J2P pulley 914b connected therewith rotate along with the second jaw operating pulley 9133 when the second jaw operating pulley 9133 rotates, and rotate along with the pitch operating pulley 9113 when the pitch operating pulley 9113 rotates. The first J1P pulley 915a and the second J1P pulley 915b connected therewith rotate along with the first jaw operating pulley 9123 when the first jaw operating pulley 9123 rotates, and rotate along with the pitch operating pulley 9113 when the pitch operating pulley 9113 rotates.

Consequently, when the second J1P pulley 915b and the pitch operating pulley 9113 are connected respectively to the two input units of the first differential member 931, only a pure operation control component of the first jaw 921 may be extracted from the rotation of the pitch operating pulley 9113 and the rotation of the first jaw operating pulley 9123.

Similarly, when the second J2P pulley 914b and the pitch operating pulley 9113 are connected respectively to the two input units of the second differential member 932, only a pure operation control component of the second jaw 922 may be extracted from the rotation of the pitch operating pulley 9113 and the rotation of the second jaw operating pulley 9133.

Consequently, for a yaw operation, when the first jaw operating bar 9122 is rotated in the direction of the arrow J1 of FIG. 47 and the second jaw operating bar 9132 is rotated in the direction of the arrow J2 of FIG. 47, the first J2P pulley 914a and the second J2P pulley 914b connected therewith rotate in the counterclockwise direction in FIG. 47 and the first J1P pulley 915a and the second J1P pulley 915b rotate in the counterclockwise direction in FIG. 47. Then, the first input unit 9311 of the first differential member 931 connected with the second J1P pulley 915b rotates in the counterclockwise direction. Accordingly, the output unit 9313 of the first differential member 931 rotates in the counterclockwise direction, and the first jaw wire 935J1 connected with the output unit 9313, the first jaw pulley 924 connected with the first jaw wire 935J1, and the first jaw 921 connected with the first jaw pulley 924 rotate around a jaw rotating axis 920JX in the counterclockwise direction. Likewise, the first input unit 9321 of the second differential member 932 connected with the second J2P pulley 914b rotates in the counterclockwise direction. Accordingly, the output unit 9323 of the second differential member 932 rotates in the counterclockwise direction, and the second jaw wire 935J2 connected with the output unit 9323, the second jaw pulley 925 connected with the second jaw wire 935J2, and the second jaw 922 connected with the second jaw pulley 925 rotate around the jaw rotating axis 920JX in the counterclockwise direction. In this manner, the first jaw 921 and the second jaw 922 rotate in the same direction to perform a yaw operation.

Similarly, for an actuation operation, when the first jaw operating bar 9122 is rotated in the direction of the arrow J1 of FIG. 47 and the second jaw operating bar 9132 is rotated in the direction of the arrow J2 of FIG. 47, the first J2P pulley 914a and the second J2P pulley 914b connected therewith rotate in the counterclockwise direction in FIG. 47 and the first J1P pulley 915a and the second J1P pulley 915b rotate in the counterclockwise direction in FIG. 47. Then, the first input unit 9311 of the first differential member 931 that is connected with the second J1P pulley 915b rotates in the clockwise direction. Accordingly, the output unit 9313 of the first differential member 931 rotates in the clockwise direction, and the first jaw wire 935J1 connected with the output unit 9313, the first jaw pulley 924 connected with the first jaw wire 935J1, and the first jaw 921 connected with the first jaw pulley 924 rotate around the jaw rotating axis 920JX in the clockwise direction. Likewise, the first input unit 9321 of the second differential member 932 that is connected with the second $J2_P$ pulley 914b rotates in the counterclockwise direction. Accordingly, the output unit 9323 of the second differential member 932 rotates in the counterclockwise direction, and the second jaw wire 935J2 connected with the output unit 9323, the second jaw pulley 925 connected with the second jaw wire 935J2, and the second jaw 922 connected with the second jaw pulley 925 rotate around the jaw rotating axis 920JX in the counterclockwise direction. In this manner, the first jaw 921 and the second jaw 922 rotate in opposite directions to perform an actuation operation.

Thus, according to the present invention, the yaw operation and the actuation operation of the end tool may be extracted respectively from the rotation of the first jaw operating pulley 9123 and the rotation of the second jaw operating pulley 9133.

According to the present invention, the pitch operation of the end tool, the rotation operation of the first jaw, and the rotation operation of the second jaw may be extracted respectively from the rotation of the pitch operating pulley 9113, the rotation of the first jaw operating pulley 9123, and the rotation of the second jaw operating pulley 9133. Thus, even when the pitch, first jaw, and second jaw operations of the operator occur simultaneously or not, the pitch, yaw, and actuation operations of the operator may be independently divided into the pitch operation component of the end tool, the rotation operation component of the first jaw, and the rotation operation component of the second jaw.

Any combination of various configurations of the operator described with reference to FIG. 3A, various configurations of the operating force transmitter described with reference to FIGS. 4A and 15 to 27, and various modifications described with reference to FIGS. 7 to 14 may be applied to the surgical instrument 900 according to the ninth embodiment of the present invention.

While the present invention has been described with reference to exemplary embodiments thereof, it will be understood by those of ordinary skill in the art that various changes in form and details may be made therein without departing from the spirit and scope of the invention as defined by the appended claims. The exemplary embodiments should be considered in descriptive sense only and not for purposes of limitation. Therefore, the scope of the invention is defined not by the detailed description of the invention but by the appended claims, and all differences within the scope will be construed as being included in the present invention.

INDUSTRIAL APPLICABILITY

The present invention relates to surgical instruments and may be applied to surgical instruments that may be manually operated to perform laparoscopic operations or various surgical operations.

The invention claimed is:

1. An end tool for a surgical instrument, the end tool comprising:
   a first jaw and a second jaw configured to operate independently of each other; and
   an end tool control member including:
   a first pulley coupled with the first jaw and rotatable around a first axis;
   a second pulley and a fourth pulley each being rotatable around an end tool pitch operating axis making a first predetermined angle with the first axis, the second pulley and the fourth pulley being arranged on both sides of the end tool pitch operating axis to face each other;
   a third pulley and a fifth pulley each being rotatable around a second axis making a second predetermined angle with the first axis, the third pulley and the fifth pulley facing each other;
   a sixth pulley coupled with the second jaw and facing the first pulley;
   a seventh pulley and a ninth pulley each being rotatable around the end tool pitch operating axis making the first predetermined angle with the first axis, the seventh pulley and the ninth pulley being arranged on both sides of the end tool pitch operating axis to face each other;
   a eighth pulley and a tenth pulley each being rotatable around a third axis making a third predetermined angle with the first axis, the eighth pulley and the tenth pulley facing each other;
   a first jaw operating wire, at least a portion of the first jaw operating wire being configured to sequentially contact the third pulley, the second pulley, the first pulley, the fourth pulley, and the fifth pulley to rotate the first pulley, the second pulley, the third pulley, the fourth pulley, and the fifth pulley; and
   a second jaw operating wire, at least a portion of the second jaw operating wire being configured to sequentially contact the eighth pulley, the seventh pulley, the sixth pulley, the ninth pulley, and the tenth pulley to rotate the sixth pulley, the seventh pulley, the eighth pulley, the ninth pulley, and the tenth pulley,
   wherein the end tool control member further includes a pitch pulley that is configured to rotate around the end tool pitch operating axis making the first predetermined angle with the first axis, and a pitch wire that is wound around the pitch pulley, the pitch wire being configured to transmit a pitch motion of an operator to the pitch pulley,
   wherein the end tool control member further includes a wire guide disposed between the first axis and the end tool pitch operating axis to contact at least a portion of one of the first jaw operating wire and the second jaw operating wire,
   wherein based on a first plane extending between the first pulley and the second pulley and being perpendicular to the first axis, the first jaw operating wire is configured to:
   contact the third pulley on one side of the first plane,
   contact the second pulley on another side of the first plane,
   contact the fourth pulley on the one side of the first plane, and
   contact the fifth pulley on the another side of the first plane,
   wherein based on the first plane extending between the first pulley and the second pulley and being perpendicular to the first axis, the second jaw operating wire is configured to:
   contact the eighth pulley on the one side of the first plane,
   contact the seventh pulley on the another side of the first plane,
   contact the ninth pulley on the one side of the first plane, and
   contact the tenth pulley on the another side of the first plane.

2. The end tool of claim 1,
   wherein with respect to a second plane being perpendicular to the first axis and including a rotating axis of each of the third pulley, the second pulley, the fourth pulley, and the fifth pulley, the first jaw operating wire is configured to sequentially contact an upper side of the third pulley, a lower side of the second pulley, an upper side of the fourth pulley, and a lower side of the fifth pulley, and
   wherein with respect to a third plane being perpendicular to the first axis and including a rotating axis of each of the eighth pulley, the seventh pulley, the ninth pulley, and the tenth pulley, the second jaw operating wire is configured to sequentially contact a lower side of the eighth pulley, an upper side of the seventh pulley, a lower side of the ninth pulley, and an upper side of the tenth pulley.

3. The end tool of claim 1,
wherein with respect to a fourth plane that is perpendicular to the first axis and passes through a center of the third pulley, the first jaw operating wire is configured to enter from one side, either an upper side or a lower side, of the fourth plane, and
wherein with respect to a fifth plane that is perpendicular to the first axis and passes through a center of the fifth pulley, the first jaw operating wire, after entering from the one side of the fourth plane, is configured to exit from another side, either an upper side or a lower side, of the fifth plane, which is a side relatively opposite to the one side from which the first jaw operating wire enters.

4. The end tool of claim 3,
wherein the first jaw operating wire, after entering from the one side of the fourth plane, is configured to pass through a sixth plane passing through a center of the first axis and a center of the second pulley.

5. The end tool of claim 1,
wherein with respect to a seventh plane that is perpendicular to the first axis and passes through a center of the eighth pulley, the second jaw operating wire is configured to enter from one side, either an upper side or a lower side, of the seventh plane, and
wherein with respect to an eighth plane that is perpendicular to the first axis and passes through a center of the tenth pulley, the second jaw operating wire, after entering from the one side of the seventh plane, is configured to exit from another side, either an upper side or a lower side, of the eighth plane, which is a side relatively opposite to the one side from which the second jaw operating wire enters.

6. The end tool of claim 5,
wherein the second jaw operating wire, after entering from the one side of the seventh plane, is configured to pass through a plane passing through a center of the first axis and the center of the eighth pulley.

7. An end tool for a surgical instrument, the end tool comprising:
a first jaw and a second jaw configured to operate independently of each other; and
an end tool control member including:
a first pulley coupled with the first jaw and rotatable around a first axis;
a second pulley and a fourth pulley each being rotatable around an end tool pitch operating axis making a first predetermined angle with the first axis, the second pulley and the fourth pulley being arranged on both sides of the end tool pitch operating axis to face each other;
a third pulley and a fifth pulley each being rotatable around a second axis making a second predetermined angle with the first axis, the third pulley and the fifth pulley facing each other;
a sixth pulley coupled with the second jaw and facing the first pulley;
a seventh pulley and a ninth pulley each being rotatable around the end tool pitch operating axis making the first predetermined angle with the first axis, the seventh pulley and the ninth pulley being arranged on both sides of the end tool pitch operating axis to face each other;
an eighth pulley and a tenth pulley each being rotatable around a third axis making a third predetermined angle with the first axis, the eighth pulley and the tenth pulley facing each other;
a first jaw operating wire, at least a portion of the first jaw operating wire being configured to sequentially contact the third pulley, the second pulley, the first pulley, the fourth pulley, and the fifth pulley to rotate the first pulley, the second pulley, the third pulley, the fourth pulley, and the fifth pulley; and
a second jaw operating wire, at least a portion of the second jaw operating wire being configured to sequentially contact the eighth pulley, the seventh pulley, the sixth pulley, the ninth pulley, and the tenth pulley to rotate the sixth pulley, the seventh pulley, the eighth pulley, the ninth pulley, and the tenth pulley,
wherein based on one plane extending between the first pulley and the second pulley and being perpendicular to the first axis, the first jaw operating wire or the second jaw operating wire is configured to enter the end tool control member from one side of the one plane and exit from the one side of the one plane,
wherein based on the one plane extending between the first pulley and the second pulley and being perpendicular to the first axis, the first jaw operating wire is further configured to:
contact the third pulley on one side of the one plane,
contact the second pulley on another side of the one plane,
contact the fourth pulley on the one side of the one plane, and
contact the fifth pulley on the another side of the one plane, and
wherein based on the one plane extending between the first pulley and the second pulley and being perpendicular to the first axis, the second jaw operating wire is further configured to:
contact the eighth pulley on the one side of the one plane,
contact the seventh pulley on the another side of the one plane,
contact the ninth pulley on the one side of the one plane, and
contact the tenth pulley on the another side of the one plane.

8. The end tool of claim 7,
wherein based on the one plane, the first jaw operating wire is configured to:
contact the third pulley on the one side of the one plane,
sequentially contact the second pulley, the first pulley, and the fourth pulley on another side of the one plane, and
contact the fifth pulley on the one side of the one plane.

9. The end tool of claim 7,
wherein based on the one plane, the second jaw operating wire is configured to:
contact the eighth pulley on another side of the one plane,
sequentially contact the seventh pulley, the sixth pulley, and the ninth pulley on the one side of the one plane, and
contact the tenth pulley on the another side of the one plane.

10. The end tool of claim 7,
wherein the first jaw operating wire and the second jaw operating wire are only wires that are configured to control a pitch motion, a yaw motion, and an actuation motion of the end tool.

11. The end tool of claim 10,
wherein the pitch motion of the end tool is performed when opposite sides of a wire of one or more of the first jaw operating wire and the second jaw operating wire, which is wound around the end tool, are pulled simultaneously.

12. The end tool of claim 10,
wherein the yaw motion or the actuation motion of the end tool is performed when one side of a wire of one or more of the first jaw operating wire and the second jaw operating wire, which is wound around the end tool, is pulled and another side of the wire is pushed.

13. The end tool of claim 7, further comprising
a pitch pulley configured to rotate around the end tool pitch operating axis of each of the second pulley and the fourth pulley.

14. An end tool for a surgical instrument, the end tool comprising:
a first jaw and a second jaw configured to operate independently of each other; and
an end tool control member including:
a first pulley coupled with the first jaw and rotatable around a first axis;
a second pulley and a fourth pulley each being rotatable around an end tool pitch operating axis making a first predetermined angle with the first axis, the second pulley and the fourth pulley being arranged on both sides of the end tool pitch operating axis to face each other;
a third pulley and a fifth pulley each being rotatable around a second axis making a second predetermined angle with the first axis, the third pulley and the fifth pulley facing each other;
a sixth pulley coupled with the second jaw and facing the first pulley;
a seventh pulley and a ninth pulley each being rotatable around the end tool pitch operating axis making the first predetermined angle with the first axis, the seventh pulley and the ninth pulley being arranged on both sides of the end tool pitch operating axis to face each other;
an eighth pulley and a tenth pulley each being rotatable around a third axis making a third predetermined angle with the first axis, the eighth pulley and the tenth pulley facing each other;
a first jaw operating wire, at least a portion of the first jaw operating wire being configured to sequentially contact the third pulley, the second pulley, the first pulley, the fourth pulley, and the fifth pulley to rotate the first pulley, the second pulley, the third pulley, the fourth pulley, and the fifth pulley; and
a second jaw operating wire, at least a portion of the second jaw operating wire being configured to sequentially contact the eighth pulley, the seventh pulley, the sixth pulley, the ninth pulley, and the tenth pulley to rotate the sixth pulley, the seventh pulley, the eighth pulley, the ninth pulley, and the tenth pulley,
wherein with respect to one plane being perpendicular to the first axis and including a rotating axis of each of the third pulley, the second pulley, the fourth pulley, and the fifth pulley, the first jaw operating wire is configured to sequentially contact an upper side of the third pulley, a lower side of the second pulley, a lower side of the fourth pulley, and an upper side of the fifth pulley, and
with respect to another plane being perpendicular to the first axis and including a rotating axis of each of the eighth pulley, the seventh pulley, the ninth pulley, and the tenth pulley, the second jaw operating wire is configured to sequentially contact a lower side of the eighth pulley, an upper side of the seventh pulley, an upper side of the ninth pulley, and a lower side of the tenth pulley,
wherein based on the one plane extending between the first pulley and the second pulley and being perpendicular to the first axis, the first jaw operating wire is further configured to:
contact the third pulley on one side of the one plane,
contact the second pulley on another side of the one plane,
contact the fourth pulley on the one side of the one plane, and
contact the fifth pulley on the another side of the one plane,
wherein based on the another plane extending between the first pulley and the second pulley and being perpendicular to the first axis, the second jaw operating wire is further configured to:
contact the eighth pulley on the one side of the another plane,
contact the seventh pulley on the another side of the another plane,
contact the ninth pulley on the one side of the another plane, and
contact the tenth pulley on the another side of another plane.

15. The end tool of claim 14, further comprising
a pitch pulley configured to rotate around the end tool pitch operating axis of each of the second pulley and the fourth pulley.

* * * * *